US007271248B2

(12) United States Patent
Hardiman et al.

(10) Patent No.: US 7,271,248 B2
(45) Date of Patent: Sep. 18, 2007

(54) HUMAN RECEPTOR PROTEINS; RELATED REAGENTS AND METHODS

(75) Inventors: Gerard T. Hardiman, San Diego, CA (US); Fernando L. Rock, La Honda, CA (US); J. Fernando Bazan, Palo Alto, CA (US); Robert A. Kastelein, Redwood City, CA (US); Stephen W. K. Ho, Sunnyvale, CA (US); Yong-Jun Liu, Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 220 days.

(21) Appl. No.: 10/975,909

(22) Filed: Oct. 28, 2004

(65) Prior Publication Data

US 2005/0112659 A1 May 26, 2005

Related U.S. Application Data

(60) Division of application No. 09/950,041, filed on Sep. 10, 2001, now abandoned, which is a continuation-in-part of application No. 09/728,540, filed on Nov. 28, 2000, now abandoned, and a continuation-in-part of application No. 09/073,363, filed on May 6, 1998, now abandoned.

(60) Provisional application No. 60/207,558, filed on May 25, 2000, provisional application No. 60/076,947, filed on Mar. 5, 1998, provisional application No. 60/072,212, filed on Jan. 22, 1998, provisional application No. 60/044,293, filed on May 7, 1997.

(51) Int. Cl.
*C07K 16/00* (2006.01)
*C07K 16/28* (2006.01)
*A61K 39/00* (2006.01)

(52) U.S. Cl. ............................. 530/387.1; 530/387.3; 530/388.1; 530/388.15

(58) Field of Classification Search .................. None
See application file for complete search history.

(56) References Cited

U.S. PATENT DOCUMENTS

| 5,350,836 A | 9/1994 | Kopchick et al. |
| 5,853,977 A | 12/1998 | Dalie et al. |

FOREIGN PATENT DOCUMENTS

| WO | WO98/02557 | 1/1998 |
| WO | WO98/50547 | 11/1998 |
| WO | WO99/20756 | 4/1999 |
| WO | WO 00/24776 | 5/2000 |
| WO | WO 01/62922 | 8/2001 |

OTHER PUBLICATIONS

DataBase: A-Geneseq, Accession No. AAW86361, Ruben SM [WO9850547, Mar. 15, 1998].*
DataBase: PIR-80, Accession No. O00206, Medzhitove et al Jul. 1997.*
Golenbock et al, Nature Immunology, Apr. 2001. vol. 2, No. 4, pp. 286-288.*
M.D. Adams, et al., *GenBank*, Accession No. AA381849, Apr. 21, 1997. Definition: "EST94973 Activated T-cells I *Homo sapiens* cDNA 5' and similar to similar to *H. sapiens* hypothetical protein (GP:D13637_), mRNA sequence."
Mark D. Adams, et al., *Nature*, 377:3-17, Sep. 28, 1995, "Initial assessment of human gene diversity and expression patterns based upon 83 million nucleotides of cDNA sequence".
James W. Baumgartner, et al., *J. Biological Chemistry*, 269(46):29094-29101, 1994. "The Role of the WSXWS Equivalent Motif in Growth Hormone Receptor Function".
Marcia P. Belvin, et al., *Annu. Rev. Cell Dev. Biol.*, 12:393-416, 1996. "A Conserved Signaling Pathway: The *Drosophilia* Toll-Dorsal Pathway".
Irwin M. Chalken and William V. Williams, *TIBTECH*, 14:369-375, 1996. "Identifying structure-function relationships in four-helix bundle cytokines: towads de novo mimetics design".
Charles A. Dinarello, *Blood*, 87(6):2095-2147, Mar. 15, 1996. "Biologic Basis for Interleukin-1 in Disease".
Charles A. Dinarello, *Blood*, 77(8):1627-1652, Apr. 15, 1991. "Interleukin-1 and Interleukin-1 Antagonism".
Charles A. Dinarello, *The FASEB Journal*, 8:1314-1325, Dec. 1994. "The interleukin-1 family: 10 years of discovery".
David G. George, et al., *Macromolecular Sequencing and Synthesis Selected Methods and Application*, Ch. 12, pp. 127-149, 1988. "Current Methods in Sequence Comparison and Analysis".
I.R. Gibbons, et al., *Proc. Natl. Acad. Sci. USA*, 88:8563-8567, Oct. 1991. "A PCR procedure to determine the sequence of large polypeptides by rapid walking through a cDNA library".
Thomas J. Gonda and Richard J. D'Andrea, *Blood*, 89(2):355-369. "Activating Mutations in Cytokine Receptors: Implications for Receptor Function and Role in Disease".
Gary Hardiman, et al., *Oncogene*, 13:2467-2475, 1996. "Modular characterization and molecular analysis of human *MyD88*".
M. Hibi, et al., *GenBank*, Accession No. M57230, Jan. 5, 1995. Definition: "Human membrane glycoprotein gp130 mRNA, complete cds."
L. Hillier, et al., *GenBank*, Accession No. AA042999, May 10, 1997. Definition: "zk56c03.r1 Soares_pregnant_uterus_NbHPU *Homo sapiens* cDNA clone IMAGE:486820 5', mRNA sequence."
L. Hillier, et al., *GenBank*, Accession No. AA707766, Dec. 24, 1997, Definition: "zh24d04.s1 Soares_pineal_gland_N3HPG *Homo sapiens* cDNA clone IMAGE:412999 3', mRNA sequence."
L. Hillier, et al., *GenBank*, Accession No. AA05049, May 9, 1997. Definition: "zh96c04.r1 Soares_fetal_liver_splean_1NFLS_S1 *Homo sapiens* cDNA clone IMAGE:429126 5', mRNA sequence".
L. Hillier, et al., *GenBank*, Accession No. H48602, Sep. 15, 1995. Definition: "yq80b01.r1 Soares fetal liver spleen 1NFLS *Homo sapiens* cDNA clone IMAGE:202057 5' similar to SP:TOLL_DROME P08953 Toll Protein ;, mRNA sequence".

(Continued)

*Primary Examiner*—Eileen O'Hara
*Assistant Examiner*—Fozia Hamud

(57) ABSTRACT

Nucleic acids encoding mammalian Toll-like receptors (TLRs) have been identified in human cells. Recombinantly produced TLRs are used in the preparation of antibodies that are capable of binding to the TLRs. The antibodies are advantageously used in the prevention and treatment of septic shock, inflammatory conditions, and viral infections.

12 Claims, 6 Drawing Sheets

OTHER PUBLICATIONS

L. Hillier, et al., *GenBank*, Accession No. N41021, Jan. 22, 1996. Definition: "yy53b03.s1 Soares_multiple_sclerosis_2NbHMSP *Homo sapiens* cDNA clone IMAGE:277229 3', mRNA sequence".

L. Hillier, et al., *GenBank*, Accession No. R76150, Jun. 6, 1995. Definition: "yi71d02.r1 Soares placenta Nb2HP *Homo sapiens* cDNA clone IMAGE:144675 5', mRNA sequence".

L. Hillier, et al., *GenBank*, Accession No. T60365, Feb. 13, 1995. Definition: "yb90h06.r1 Stratagene liver (#937224) *Homo sapiens* cDNA clone IMAGE:78491 5', mRNA sequence".

Dan Hultmark, *Nature*, 367:116-117, Jan. 13, 1994. "Ancient relationships".

A.D. Larsen, *GenBank*, Accession No. X55721, Feb. 6, 1991. Definition: "Human mRNA coding for granulocyte colony stimulating factor receptor 25-1."

Bruno Lemaitre, et al., *Cell*, 86:973-983, Sep. 20, 1996. "The Dorsoventral Regulatory Gene Cassette *spätzle/Toll/cactus* Controls the Potent Antifungal Response in Drosophilia Adults".

Patrick Lemaire and Laurent Kodjabachian, *Trends in Genetics*, 12(12):525-531, Dec. 1996. "The vertibrate organizer: structure and molecules".

Mark A. Lemmon and Joseph Schlessinger, *TIBS*, 19:459-463, Nov. 1994. "Regulation of signal transduction and signal diversity by receptor oligomerization".

M. Marra, et al., *GenBank*, Accession No. AA266744, Mar. 21, 1997. Definition: "mz93d07.r1 Soares mouse lymph node NbMLN Mus musculus cDNA clone IMAGE:720973 5', mRNA sequence."

M. Marra, et al., *GenBank*, Accession No. AA288480, Apr. 4, 1997. Definition: "vb16a09.r1 Soares mouse 3NbMS Mus musculus cDNA clone IMAGE:749080 5', mRNA sequence."

R. Medzhitov, et al., *GenBank*, Accession No. U93091, Nov. 30, 1998. Definition: 'Human Toll protein homolog mRNA, complete cds and LINE-1 reverse transcriptase homolog, pseudogene.

Rusian Medzhitov, et al., *Nature*, 388:394-397, Jul. 24, 1997. "A human homologue of the Drosophila Toll protein signals activation of adaptive immunity".

Donald Morisato & Kathyrn V. Anderson, *Annu. Rev. Genetics*, 29:371-399, 1995, "Signaling Pathways that Establish the Dorsal-Ventral Pattern of the *Drosphila* Embryo".

D. Muzny, et al., *GenBank*, Accession No. AC003046, AC002362, AC002363, Jan. 6, 1998. Definition: "*Homo sapiens* Xp22 PACs RPC11-263P4 and RPC11-164K3 complete sequence."

NCI-CGAP, *GenBank*, Accession No. AA740990, Feb. 7, 1998. Definition: nz05g01.s1 NCI_CGAP_GCBI *Homo sapiens* cDNA clone IMAGE:1286928 3' similar to TR:Q15399 Q15399 ORF, Complete CDs. ;, mRNA sequence.

NCI-CGAP, *GenBank*, Accession No. AA741118, Feb. 7, 1998. Definition: "nz04f11.s1 NCI_CGAP_GCBI *Homo sapiens* cDNA clone IMAGE:1286829 3', mRNA sequence."

NCI-CGAP, *GenBank*, Accession No. AA252405, Aug. 13, 1997. Definition: "zs12e09.r1 NCI_CGAP_GCBI *Homo sapiens* cDNA clone IMAGE:685000 5', mRNA sequence."

Nobuo Nomura, et al., DNA Research 1:27-35, 1994. "Prediction of the Coding Sequences of Unidentified Human Genes. I. The Codong Sequences of 40 New Genes (KIA A0001-KIA A0040) Deduced by Analysis of Randomly Sampled cDNA Clones from Human Immature Myeloid Cell Line KG-1".

N. Nomura, *GenBank*, Accession No. D13637, Jul. 10, 1997. Definition: "Human mRNA for KIAA0012 gene, complete cds."

Haruki Okamura, et al., *Nature*, 378:88-91, Nov. 12, 1995. "Cloning of a new cytokine that induces IFN-□production by T cells".

K. Okubo, *GenBank*, Accession No. C01399, Jul. 23, 1996. Definition: "HUMGS0008381 Human adult (K. Okubo) *Homo sapiens* cDNA, mRNA sequence."

Jay D. Parker, et al., *Nucleic Acids Research*, 19(11):3055-3060, Jun. 11, 1991. "Targeted gene walking polymerase chain reaction".

D.H. Presky, et al., *GenBank*, Accession No. U64198, Nov. 26, 1996. Definition: "Human Il-12 receptor beta2 mRNA, complete cds."

Fernando L. Rock, et al., *Proc. Natl. Acad. Sci. USA*, 95:588-593, Jan. 1998. "A family of human receptors structurally related to *Drosophila* Toll".

Marco Rosetto, et al., *Biochem. Biophys. Res. Com.*, 209(1):111-116, Apr. 6, 1995. "Signals from the IL-1 Receptor Homolog, Toll, Can Activate an Immune Response in *Drosophila* Hemocyte Cell Line".

J. Sambrook, et al., *Molecular Cloning*, $2_{nd}$ ., vol. 3:Chapter 17, Cold Spring Harbor Laboratory Press, 1989. "Expression of Cloned Genes in *Escherichia coli* ".

Venkatakrishna Shyamala and Giovanna Ferro-Luzzi Ames, *GENE*, 84:1-8, 1989. "Genome walking by single-specific-primer polymerase chain reaction: SSP-PCR".

P. Verhasselt, et al., *DNA Sequences—J. DNA Sequencing and Mapping*, 2:281-287, 1992. "DNA sequencing by a subcloning-walking strategy using a specific and semi-random primer in the polymerase chain reaction".

Yanshu Wang, et al., *J. Biological Chemistry*, 271(8):4468-4476, Feb. 23, 1996. "A Large Family of Putative Transmembrane Receptors Homologous to the Product of the *Drosophila* Tissue Polarity Gene *frizzled* ".

Steven A. Wasserman, *Molecular Biology of the Cell*, 4:767-771, Aug. 1993. "A Conserved Signal Transduction Pathway Regulating the Activity of the *rel* like Proteins Dorsal and NF-kB".

Iain Wilson, et al., *Current Biology*, 7(3):R175-R178, 1997. "Signaling pathways: A common theme in plants and animals?".

Takeuchi et al., "TLR6: A novel member of an expanding Toll-like receptor family", *Gene*, vol. 231, pp. 59-65 (1999).

Akira et al., "Toll-like receptors: critical proteins linking innate and acquired immunity", *Nature Immunology*, vol. 2, No. 8, pp. 675-680 (2001).

Muzny et al., *GenBank* Accession No. AC006252, "*Homo sapiens* 3p21.1 contig 9 PAC RPC15-1157M23 (Rosewell Park Cancer Institute Human PAC Library) complete sequence", Dec. 29, 1998.

Peer Bork, Powers and Pitfalls in Sequence Analysis: The 70% Hurdle, Genome Research, 10:398-400 (2000).

Peer Bork, Go hunting in sequence database but watch out the traps, Trends in Genetics, vol. 12:425-427 (Oct. 1998).

Steven E. Brenner, Errors in genome annotation, Trends in Genetics, vol. 15:132-133 (Apr. 1999).

Chaudhary et al., Cloning and Characterization of Two Toll/Interleukin-1 Receptor-Like Genes TIL3 and TIL4: Evidence for a Multi-Gene Receptor Family in Humans, Blood, vol. 91, No. 11:4020-4027 (Jun. 1998).

Chiang et al., Expression of a Novel Toll-like gene spans the parasegment boundary and contributes to hedgehog function in the adult eye of *Drosophila*, Mechanism of Development, 47:225-239 Nov. 1994).

Doercks et al., Protein annotation: detective work for function prediction, Trends in Genetics, vol. 14:248-250 (Jun. 1998).

Eldon et al., The *Drosophila* 18 wheeler is required for morphogenesis and has striking similarities to Toll, Development, 120:885-899 (Apr. 1994).

Haynes et al., Proteome analysis: Biological assay or data archive?, Electrophoresis, 19:1862-1871 (Aug. 1998).

Konopka et al., Variable expression of the translocated c-abl oncogene in Philadelphia-chromosome-positive B-lymphoid cells lines from chronic myelogenous leukemia patients, Proc. Natl. Acad. Sci, USA 83:4049-4052 (Jun. 1986).

Massague et al., The TGF-beta Family of Growth and Differentiation Factors, Cell, vol. 49:437-438 (May 1987).

Mitcham et al., T1/ST2 Signaling Establishes It as a Member of an Expanding Interleukin-1 Receptor Family, The Journal of Biological Chemistry, vol. 271:5777-5783 (Mar. 1996).

Pennica et al., WISP genes are members of the connective tissue growth factor family that are up-regulated in Wnt-1 transformed cells and aberrantly expressed in human colon tumors, vol. 95:14717-14722 (Dec. 1998).

Pilbeam et al., Comparison of the Effects of Various Lengths of Synthetic Human Parathyroid Hormone-Related Peptide (hPTHrP) of Malignancy on Bone Resorption and Formation in Organ Culture, Bone 14:717-720 (Sep. 1993).

Rock et al., EMBL assession No. U88878.1, *Homo sapiens* Toll-like receptor 2 (TLR2) MRNA, Complete cds., (Oct. 3, 1997).

Skolnick et al., From genes to protein structure and function: novel applications of computational approaches in the genomic era, Trends in Biotechnology 18:34-39 (Jan. 2000).

Smith et al., The challenges of genome sequence annotation or "The devil is in the details", Nature Biotechnology, vol. 15:1222-1223 (Nov. 1997).

Taguchi et al., Chromosomal Localization of TIL, a Gene Encoding a Protein Related to the *Drosophila* Transmembrane Receptor Toll, to Human Chromosome 4p14, Genomics 32:486-488 (Mar. 1996).

Vukicevic et al., Induction of nephrogenic mesenchyme by osteogenic protein 1 (bone morphogenetic protein7), Proc. Natl. Acad. Sci. USA, vol. 93:9021-9026 (Aug. 1996).

* cited by examiner

FIG. 2A

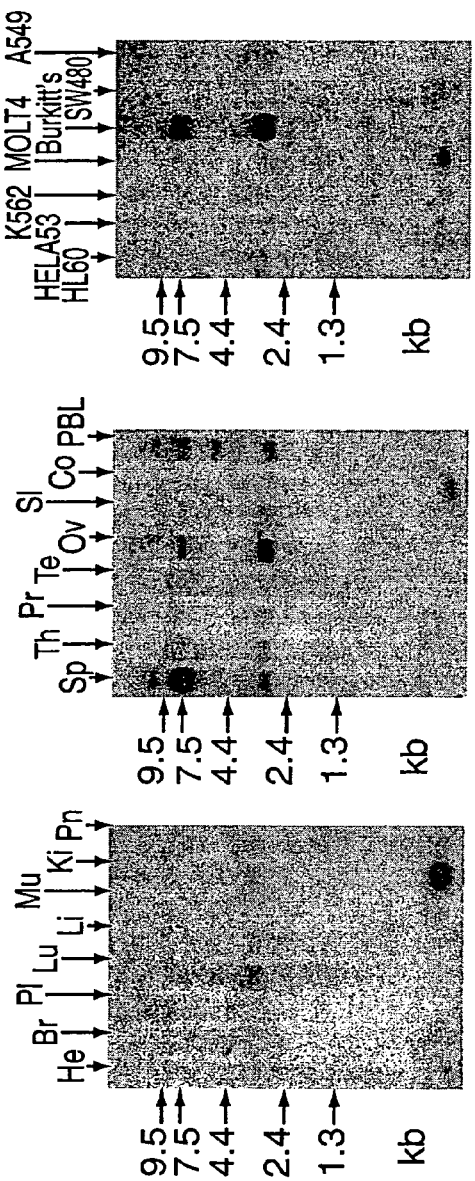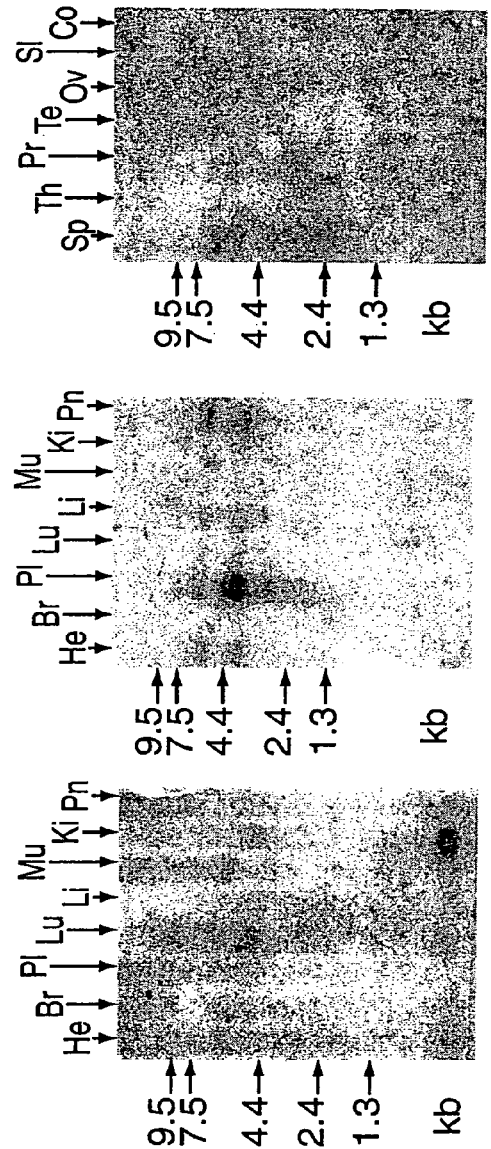

HUMAN RECEPTOR PROTEINS; RELATED REAGENTS AND METHODS

This application is a divisional of U.S. application Ser. No. 09/950,041, filed Sep. 10, 2001 now abandoned; which is a continuation-in-part of U.S. application Ser. No. 09/728,540, filed Nov. 28, 2000 now abandoned; which claims priority from both U.S. Provisional Application Ser. No. 60/207,558 and is a continuation-in-part of U.S. application Ser. No. 09/073,363, filed May 6, 1998 now abandoned; which claims priority from U.S. Provisional Application Ser. Nos. 60/044,293 filed May 7, 1997, 60/076,947 filed Mar. 5, 1998, and 60/072,212 filed Jan. 22, 1998; all of which are incorporated herein by reference.

FIELD OF THE INVENTION

The present invention relates to compositions and methods for affecting mammalian physiology, including morphogenesis or immune system function. In particular, it provides nucleic acids, proteins, and antibodies which regulate development and/or the immune system. Diagnostic and therapeutic uses of these materials are also disclosed.

BACKGROUND OF THE INVENTION

Recombinant DNA technology refers generally to techniques of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network". Recent research has provided new insights into the inner workings of this network. While it remains clear that much of the immune response does, in fact, revolve around the network-like interactions of lymphocytes, macrophages, granulocytes, and other cells, immunologists now generally hold the opinion that soluble proteins, known as lymphokines, cytokines, or monokines, play critical roles in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders.

Lymphokines apparently mediate cellular activities in a variety of ways. They have been shown to support the proliferation, growth, and/or differentiation of pluripotential hematopoietic stem cells into vast numbers of progenitors comprising diverse cellular lineages which make up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

Another important cell lineage is the mast cell (which has not been positively identified in all mammalian species), which is a granule-containing connective tissue cell located proximal to capillaries throughout the body. These cells are found in especially high concentrations in the lungs, skin, and gastrointestinal and genitourinary tracts. Mast cells play a central role in allergy-related disorders, particularly anaphylaxis as follows: when selected antigens crosslink one class of immunoglobulins bound to receptors on the mast cell surface, the mast cell degranulates and releases mediators, e.g., histamine, serotonin, heparin, and prostaglandins, which cause allergic reactions, e.g., anaphylaxis.

Research to better understand and treat various immune disorders has been hampered by the general inability to maintain cells of the immune system in vitro. Immunologists have discovered that culturing many of these cells can be accomplished through the use of T-cell and other cell supernatants, which contain various growth factors, including many of the lymphokines.

The interleukin-1 family of proteins includes the IL-1α, the IL-1β, the IL-1RA, and recently the IL-1γ (also designated Interferon-Gamma Inducing Factor, IGIF). This related family of genes have been implicated in a broad range of biological functions. See Dinarello, FASEB J. 8, 1314 (1994); Dinarello, Blood 77, 1627 (1991); and Okamura, et al., Nature 378, 88 (1995).

In addition, various growth and regulatory factors exist which modulate morphogenetic development. This includes, e.g., the Toll ligands, which signal through binding to receptors which share structural, and mechanistic, features characteristic of the IL-1 receptors. See, e.g., Lemaitre, et al., Cell 86, 973 (1996); and Belvin and Anderson, Ann. Rev. Cell & Devel. Biol. 12, 393 (1996).

From the foregoing, it is evident that the discovery and development of new soluble proteins and their receptors, including ones similar to lymphokines, should contribute to new therapies for a wide range of degenerative or abnormal conditions which directly or indirectly involve development, differentiation, or function, e.g., of the immune system and/or hematopoietic cells. In particular, the discovery and understanding of novel receptors for lymphokine-like molecules which enhance or potentiate the beneficial activities of other lymphokines would be highly advantageous. The present invention provides new receptors for ligands exhibiting similarity to interleukin-1 like compositions and related compounds, and methods for their use.

BRIEF DESCRIPTION OF THE DRAWINGS

FIGS. 2A-2C show conserved structural patterns in the signaling domains of Toll- and IL-1-like cytokine receptors, and two divergent modular proteins. FIGS. 2A-2B show a sequence alignment of the common TH domain. TLRs are labeled as in FIG. 1; the human (Hu) or mouse (Mo) IL-1 family receptors (IL-1R1-6) are sequentially numbered as earlier proposed (Hardiman, et al., Oncogene 13, 2467 (1996)); Myd88 and the sequences from tobacco (To) and flax, L. usitatissimum (Lu), represent C— and N-terminal domains, respectively, of larger, multidomain molecules. Ungapped blocks of sequence (numbered 1-10) are boxed. Triangles indicate deleterious mutations, while truncations N-terminal of the arrow eliminate bioactivity in human IL-1R1 (Heguy, et al., J. Biol. Chem. 267,2605(1992)). PHD (Rost and Sander, Proteins 19, 55 (1994)) and DSC (King and Sternberg, Protein Sci. 5, 2298 (1996)) secondary structure predictions of α-helix (H), β-strand (E), or coil (L) are marked. The amino acid shading scheme depicts chemically similar residues: hydrophobic, acidic, basic, Cys, aromatic, structure-breaking, and tiny. Diagnostic sequence patterns for IL-1Rs, TLRs, and full alignment (ALL) were derived by Consensus at a stringency of 75%. Symbols for amino acid subsets are (see internet site for detail): o, alcohol; 1, aliphatic; ●, any amino acid; a, aromatic; c, charged; h, hydrophobic; -, negative; p, polar; +, positive; s, small; u, tiny; t, turnlike. FIG. 2C shows a topology diagram of the proposed TH β/α domain fold. The parallel β-sheet (with β-strands A-E as yellow triangles) is seen at its C-terminal end; α-helices (circles labeled 1-5) link the β-strands; chain connections are to the front (visible) or back (hidden). Conserved, charged residues at the C-end of the β-sheet are noted in gray. (Asp) or as a lone black (Arg) residue (see text).

FIGS. 5A-5F depict mRNA blot analyses of Human TLRs. Human multiple tissue blots (He, heart; Br, brain; Pl, placenta; Lu, lung; Li, liver; Mu, muscle; Ki, kidney; Pn, Pancreas; Sp, spleen; Th, thymus; Pr, prostate; Te, testis; Ov, ovary, SI, small intestine; Co, colon; PBL, peripheral blood lymphocytes) and cancer cell line (promyelocytic leukemia, HL60; cervical cancer, HELAS3; chronic myelogenous leukemia, K562; lymphoblastic leukemia, Molt4; colorectal adenocarcinoma, SW480; melanoma, G361; Burkitt's Lymphoma Raji, Burkitt's; colorectal adenocarcinoma, SW480; lung carcinoma, A549) containing approximately 2 μg of poly(A)+ RNA per lane were probed with radiolabeled cDNAs encoding TLR1 (FIGS. 5A-5C), TLR2 (FIG. 5D), TLR3 (FIG. 5E), and TLR4 (FIG. 5F) as described. Blots were exposed to X-ray film for 2 days (FIGS. 5A-5C) or one week (FIGS. 5D-5F) at −70° C. with intensifying screens. An anomalous 0.3 kB species appears in some lanes; hybridization experiments exclude a message encoding a TLR cytoplasmic fragment.

SUMMARY OF THE INVENTION

Figure 1:
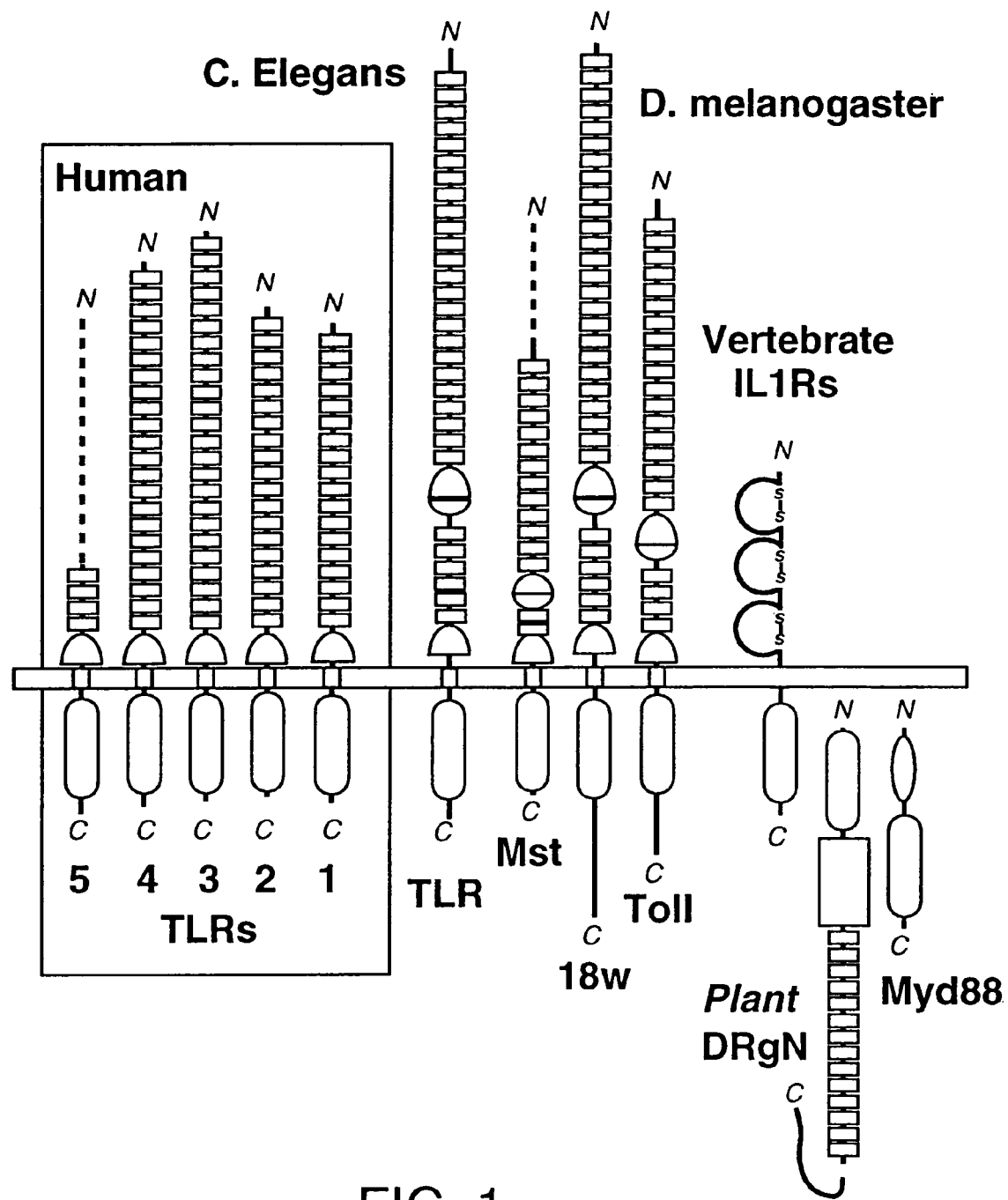
FIG. 1 shows a schematic comparison of the protein architectures of Drosophila, Caehorabditis, and human TLRs, and their relationship to vertebrate IL-1 receptors and plant disease resistance proteins. Three Drosophila (Dm) TLRs (Toll, 18w, and the Mst ORF fragment) (Morisato and Anderson, Ann. Rev. Genet. 29, 371 (1995); Chiang and Beachy, Mech. Develop. 47, 225 (1994); Mitcham, et al., J. Biol. Chem. 271, 5777 (1996); and Eldon, et al., Develop. 120, 885 (1994)) are arrayed beside four complete (TLRs 1-4) and one partial (TLR5) human (Hu) receptors. Individual LRRs in the receptor ectodomains that are flagged by PRINTS (Attwood, et al., Nucleic Acids Res. 25, 212 (1997)) are explicitly noted by boxes; 'top' and 'bottom' Cys-rich clusters that flank the C— or N-terminal ends of LRR arrays are respectively drawn by opposed half-circles. The loss of the internal Cys-rich region in TLRs 1-5 largely accounts for their smaller ectodomains (558, 570, 690, and 652 aa, respectively) when compared to the 784 and 977 aa extensions of Toll and 18w. The incomplete chains of DmMst and HuTLR5 (about 519 and 153 aa ectodomains, respectively) are represented by dashed lines. The intracellular signaling module common to TLRs, IL-1-type receptors (IL-1Rs), the intracellular protein Myd88, and the tobacco disease resistance gene N product (DRgN) is indicated below the membrane. See, e.g., Hardiman, et al., Oncogene 13, 2467(1996); and Rock, et al., Proc. Nat'l Acad. Sci. USA 95, 588 (1998). Additional domains include the trio of Ig-like modules in IL-1Rs (disulfide-linked loops); the DRgN protein features an NTPase domain (box) and Myd88 has a death domain (black oval).

The present invention is directed to nine novel related mammalian receptors, e.g., primate, human, Toll receptor like molecular structures, designated TLR2, TLR3, TLR4, TLR5, TLR7, TLR8, TLR9, and TLR10, and their biological activities. It includes nucleic acids coding for the polypeptides themselves and methods for their production and use. The nucleic acids of the invention are characterized, in part, by their homology to cloned complementary DNA (cDNA) sequences enclosed herein.

In certain embodiments, the invention provides a composition of matter selected from the group of: a substantially pure or recombinant TLR2 protein or peptide exhibiting identity over a length of at least about 12 amino acids to SEQ ID NO: 4; a natural sequence TLR2 of SEQ ID NO: 4; a fusion protein comprising TLR2 sequence; a substantially pure or recombinant TLR3 protein or peptide exhibiting identity over a length of at least about 12 amino acids to SEQ ID NO: 6; a natural sequence TLR3 of SEQ ID NO: 6; a fusion protein comprising TLR3 sequence; a substantially pure or recombinant TLR4 protein or peptide exhibiting identity over a length of at least about 12 amino acids to SEQ ID NO: 26; a natural sequence TLR4 of SEQ ID NO: 26; a fusion protein comprising TLR4 sequence; a substantially pure or recombinant TLR5 protein or peptide exhibiting identity over a length of at least about 12 amino acids to SEQ ID NO: 10; a natural sequence TLR5 of SEQ ID NO: 10; a fusion protein comprising TLR5 sequence; a substantially pure or recombinant TLR6 protein or peptide exhibiting identity over a length of at least about 12 amino acids to SEQ ID NO: 12, 28, or 30; a natural sequence TLR6 of SEQ ID NO: 12, 28, or 30; a fusion protein comprising TLR6 sequence; a substantially pure or recombinant TLR7 protein or peptide exhibiting identity over a length of at least about 12 amino acids to SEQ ID NO: 16, 18, or 37; a natural sequence TLR7 of SEQ ID NO: 16, 18, or 37; a fusion protein comprising TLR7 sequence; a substantially pure or recombinant TLR8 protein or peptide exhibiting identity over a length of at least about 12 amino acids to SEQ ID NO: 32 or 39; a natural sequence TLR8 of SEQ ID NO: 32 or 39; a fusion protein comprising TLR8 sequence; a substantially pure or recombinant TLR9 protein or peptide exhibiting identity over a length of at least about 12 amino acids to SEQ ID NO: 22 or 41; a natural sequence TLR9 of SEQ ID NO:

22 or 41; a fusion protein comprising TLR9 sequence; a substantially pure or recombinant TLR10 protein or peptide exhibiting identity over a length of at least about 12 amino acids to SEQ ID NO: 34, 43, or 45; a natural sequence TLR10 of SEQ ID NO: 34, 43, or 45; and a fusion protein comprising TLR10 sequence. Preferably, the substantially pure or isolated protein comprises a segment exhibiting sequence identity to a corresponding portion of a TLR2, TLR3, TLR4, TLR5, TLR6, TLR7, TLR8, TLR9, or TLR10, wherein said identity is over at least about 15 amino acids; preferably about 19 amino acids; or more preferably about 25 amino acids. In specific embodiments, the composition of matter: is TLR2, which comprises a mature sequence of SEQ ID NO:4; or lacks a post-translational modification; is TLR3, which comprises a mature sequence of SEQ ID NO:6; or lacks a post-translational modification; is TLR4, which: comprises a mature sequence of SEQ ID NO:8 or SEQ ID NO:26; or lacks a post-translational modification; is TLR5, which: comprises the complete sequence of SEQ ID NO:10; or lacks a post-translational; is TLR6, which comprises a mature sequence of SEQ ID NO:12, 14, 28, or 30; or lacks a post-translational modification; is TLR7, which comprises a mature sequence of SEQ ID NO:16, 18, or 37; or lacks a post-translational modification; is TLR8, which: comprises a mature sequence of SEQ ID NO:20, 32, or 39; or lacks a post-translational modification; is TLR9, which: comprises the complete sequence of SEQ ID NO:22.or SEQ ID NO:41; or lacks a post-translational; is TLR10, which comprises a mature sequence of SEQ ID NO:24, 34, 43, or 45; or lacks a post-translational modification; or the composition of matter may be a protein or peptide which: is from a warm blooded animal selected from a mammal, including a primate, such as a human; comprises at least one polypeptide segment of SEQ ID NO: 4, 6, 26, 10, 12, 28, 30, 16, 18, 32, 22, or 34; exhibits aplurality of portions exhibiting said identity; is a natural allelic variant of TLR2, TLR3, TLR4, TLR5, TLR6, TLR7, TLR8, TLR9, or TLR10; has a length at least about 30 amino acids; exhibits at least two non-overlapping epitopes which are specific for a primate TLR2, TLR3, TLR4, TLR5, TLR6, TLR7, TLR8, TLR9, or TLR10; exhibits sequence identity over a length of at least about 35 amino acids to a primate TLR2, TLR3, TLR4, TLR5, TLR6, TLR7, TLR8, TLR9, or TLR10; further exhibits at least two non-overlapping epitopes which are specific for a primate TLR2, TLR3, TLR4, TLR5, TLR6, TLR7, TLR8, TLR9, or TLR10; exhibits identity over, a length of at least about 20 amino acids to a rodent TLR6; is glycosylated; has a molecular weight of at least 100 kD with natural glycosylation; is a synthetic polypeptide; is conjugated to another chemical moiety; is a 5-fold or less substitution from natural sequence; or is a deletion or insertion variant from a natural sequence. In specific embodiments, the TLR, antigenic fragment of TLR, antibody to TLR, antibody fragment to TLR, antibody to a TLR ligand also includes an immobilized form. Immobilization may be by conjugation or attachment to a bead, to a magnetic bead, to a slide, or to a container. Immobilization may be to cyanogen bromide-activated SEPHAROSE by methods well known in the art, or adsorbed to polyolefin surfaces, with or without glutaraldehyde cross-linking.

Other embodiments include a composition comprising: a sterile TLR2 protein or peptide; or the TLR2 protein or peptide and a carrier, wherein the carrier is: an aqueous compound, including water, saline, and/or buffer; and/or formulated for oral, rectal, nasal, topical, or parenteral administration; a sterile TLR3 protein or peptide; or the TLR3 protein or peptide and a carrier, wherein the carrier is: an aqueous compound, including water, saline, and/or buffer; and/or formulated for oral, rectal, nasal, topical, or parenteral administration; a sterile TLR4 protein or peptide; or the TLR4 protein or peptide and a carrier, wherein the carrier is: an aqueous compound, including water, saline, and/or buffer; and/or formulated for oral, rectal, nasal, topical, or parenteral administration; a sterile TLR5 protein or peptide; or the TLR5 protein or peptide and a carrier, wherein the carrier is: an aqueous compound, including water, saline, and/or buffer; and/or formulated for oral, rectal, nasal, topical, or parenteral administration; a sterile TLR6 protein or peptide; or the TLR6 protein or peptide and a carrier, wherein the carrier is: an aqueous compound, including water, saline, and/or buffer; and/or formulated for oral, rectal, nasal, topical, or parenteral administration; a sterile TLR7 protein or peptide; or the TLR7 protein or peptide and a carrier, wherein the carrier is: an aqueous compound, including water, saline, and/or buffer; and/or formulated for oral, rectal, nasal, topical, or parenteral administration; a sterile TLR8 protein or peptide; or the TLR8 protein or peptide; and a carrier, wherein the carrier is: an aqueous compound, including water, saline, and/or buffer; and/or formulated for oral, rectal, nasal, topical, or parenteral administration; a sterile TLR9 protein or peptide; or the TLR9 protein or peptide and a carrier, wherein the carrier is: an aqueous compound, including water, saline, and/or buffer; and/or formulated for oral, rectal, nasal, topical, or parenteral administration; a sterile TLR10 protein or peptide; or the TLR10 protein or peptide and a carrier, wherein the carrier is: an aqueous compound, including water, saline, and/or buffer; and/or formulated for oral, rectal, nasal, topical, or parenteral administration.

In certain fusion protein embodiments, the invention provides a fusion protein comprising: mature protein sequence of SEQ ID NO: 4, 6, 8, 10, 12, 14, 16, 18, 20, 22, 24, 26, 28, 30, 32, 34, 37, 39, 41, 43, or 45; a detection or purification tag, including a FLAG, His6, or Ig sequence; or sequence of another receptor protein.

Various kit embodiments include a kit comprising a TLR protein or polypeptide, and: a compartment comprising the protein or polypeptide; and/or instructions for use or disposal of reagents in the kit.

Binding compound embodiments include those comprising an antigen binding site from an antibody, which specifically binds to a natural TLR2, TLR3, TLR4, TLR5, TLR6, TLR7, TLR8, TLR9, or TLR10 protein, wherein: the protein is a primate protein; the binding compound is an Fv, Fab, or Fab2 fragment; the binding compound is conjugated to another chemical moiety; or the antibody: is raised against a peptide sequence of a mature polypeptide of SEQ ID NO: 4, 6, 8, 10, 12, 14, 16, 18, 20, 22, 24, 26, 28, 30, 32, 34, 37, 39, 41, 43, or 45; is raised against a mature TLR2, TLR3, TLR4, TLR5, TLR6, TLR7, TLR8, TLR9, or TLR10; is raised to a purified human TLR2, TLR3, TLR4, TLR5, TLR6, TLR7, TLR8, TLR9, or TLR10; is immunoselected; is a polyclonal antibody; binds to a denatured TLR2, TLR3, TLR4, TLR5, TLR6, TLR7, TLR8, TLR9, or TLR10; exhibits a Kd to antigen of at least 30 µM; is attached to a solid substrate, including a bead or plastic membrane; is in a sterile composition; or is detectably labeled, including a radioactive or fluorescent label. A binding composition kit often comprises the binding compound, and: a compartment comprising said binding compound; and/or instructions for use or disposal of reagents in the kit. Often the kit is capable of making a qualitative or quantitative analysis.

Methods are provided, e.g., of making an antibody, comprising immunizing an immune system with an immunogenic amount of a primate TLR2, TLR3, TLR4, TLR5, TLR6, TLR7, TLR8, TLR9, or TLR10, thereby causing said antibody to be produced; or producing an antigen:antibody complex, comprising contacting such an antibody with a mammalian TLR2, TLR3, TLR4, TLR5, TLR6, TLR7, TLR8, TLR9, or TLR10 protein or peptide, thereby allowing said complex to form.

Other compositions include a composition comprising: a sterile binding compound, or the binding compound and a carrier, wherein the carrier is: an aqueous compound, including water, saline, and/or buffer; and/or formulated for oral, rectal, nasal, topical, or parenteral administration.

Nucleic acid embodiments include an isolated or recombinant nucleic acid encoding a TLR2-10 protein or peptide or fusion protein, wherein: the TLR is from a mammal; or the nucleic acid: encodes an antigenic peptide sequence of SEQ ID NO: 4, 6, 8, 10, 12, 14, 16, 18, 20, 22, 24, 26, 28, 30, 32, 34, 37, 39, 41, 43, or 45; encodes a plurality of antigenic peptide sequences of SEQ ID NO: 4, 6, 8, 10, 12, 14, 16, 18, 20, 22, 24, 26, 28, 30, 32, 34, 37, 39, 41, 43, or 45; comprises at least 17 contiguous nucleotides from SEQ ID NO: 3, 5, 7, 9, 11, 13, 15, 17, 19, 21, 23, 25, 27, 29, 31, 33, 35, 36, 38, 40, 42, or 44; exhibits at least about 80% identity to a natural cDNA encoding said segment; is an expression vector; further comprises an origin of replication; is from a natural source; comprises a detectable label such as a radioactive label, a fluorescent label, or an immunogenic label; comprises synthetic nucleotide sequence; is less than 6 kb, preferably less than 3 kb; is from a mammal, including a primate; comprises a natural fill length coding sequence; is a hybridization probe for a gene encoding said TLR; or is a PCR primer, PCR product, or mutagenesis primer. A cell, tissue, or organ comprising such a recombinant nucleic acid is also provided. Preferably, the cell is: a prokaryotic cell; a eukaryotic cell; a bacterial cell; a yeast cell; an insect cell; a mammalian cell; a mouse cell; a primate cell; or a human cell. Kits are provided comprising such nucleic acids, and: a compartment comprising said nucleic acid; a compartment further comprising a primate TLR2, TLR3, TLR4, or TLR5 protein or polypeptide; and/or instructions for use or disposal of reagents in the kit. Often, the kit is capable of making a qualitative or quantitative analysis.

Other embodiments include a nucleic acid which: hybridizes under wash conditions of 30° C. and less than 2M salt to SEQ ID NO: 3; hybridizes under wash conditions of 30° C. and less than 2 M salt to SEQ ID NO: 5; hybridizes under wash conditions of 30° C. and less than 2M salt to SEQ ID NO: 7; hybridizes under wash conditions of 30° C. and less than 2 M salt to SEQ ID NO: 9; hybridizes under wash conditions of 30° C. and less than 2 M salt to SEQ ID NO: 11, 13, 27, or 29; hybridizes under wash conditions of 30° C. and less than 2 M salt to SEQ ID NO: 15, 17, or 36; hybridizes under wash conditions of 30° C. and less than 2 M salt to SEQ ID NO: 19, 31, or 38; hybridizes under wash conditions of 30° C. and less than 2 M salt to SEQ ID NO: 21 or 40; hybridizes under wash conditions of 30° C. and less than 2 M salt to SEQ ID NO: 23, 33, 42, or 44; exhibits at least about 85% identity over a stretch of at least about 30 nucleotides to a primate TLR2; exhibits at least about 85% identity over a stretch of at least about 30 nucleotides to a primate TLR3; exhibits at least about 85% identity over a stretch of at least about 30 nucleotides to a primate TLR4; or exhibits at least about 85% identity over a stretch of at least about 30 nucleotides to a primate TLR5. Preferably, such nucleic acid will have such properties, wherein: wash conditions are at 45° C. and/or 500 mM salt; or the identity is at least 90% and/or the stretch is at least 55 nucleotides.

More preferably, the wash conditions are at 55° C. and/or 150 mM salt; or the identity is at least 95% and/or the stretch is at least 75 nucleotides.

Also provided are methods of producing a ligand:receptor complex, comprising contacting a substantially pure primate TLR2, TLR3, TLR4, TLR5, TLR6, TLR7, TLR8, TLR9, or TLR10, including a recombinant or synthetically produced protein, with candidate Toll ligand; thereby allowing said complex to form.

The invention also provides a method of modulating physiology or development of a cell or tissue culture cells comprising contacting the cell with an agonist or antagonist of a mammalian TLR2, TLR3, TLR4, TLR5, TLR6, TLR7, TLR8, TLR9, or TLR10. Preferably, the cell is a pDC2 cell with the agonist or antagonist of TLR10.

Abbreviations: TLR, Toll-like receptor; DTLR, DNAX Toll-like receptor; IL-1R, interleukin-1 receptor; TH, Toll homology; LRR, leucine-rich repeat; EST, expressed sequence tag; STS, sequence tagged site; FISH, fluorescence in situ hybridization; GMCSF, granulocyte-macrophage colony-stimulating factor; NIPC or IPC, natural interferon producing cells.

DETAILED DESCRIPTION OF THE PREFERRED EMBODIMENTS

OUTLINE

I. General

II. Activities

III. Nucleic Acids
   A. encoding fragments, sequence, probes
   B. mutations, chimeras, fusions
   C. making nucleic acids
   D. vectors, cells comprising IV. Proteins, Peptides
   A. fragments, sequence, immunogens, antigens
   B. muteins
   C. agonists/antagonists, functional equivalents
   D. making proteins
   E. soluble receptors V. Making Nucleic Acids, Proteins
   A. synthetic
   B. recombinant
   C. natural sources VI. Antibodies
   A. polyclonals
   B. monoclonal
   C. fragments; Kd
   D. anti-idiotypic antibodies
   E. hybridoma cell lines VII. Kits and Methods to Quantify TLRs 2-10
   A. ELISA
   B. assay mRNA encoding
   C. qualitative/quantitative
   D. kits VIII. Therapeutic Compositions, Methods
   A. combination compositions
   B. unitdose
   C. administration IX. Ligands

I. General

The present invention provides the amino acid sequence and DNA sequence of mammalian, herein primate Toll like receptor molecules (TLR) having particular defined properties, both structural and biological. These have been designated herein as TLR2, TLR3, TLR4, TLR5, TLR6, TLR7, TLR8, TLR9, and TLR10, respectively, and increase the number of members of the human Toll like receptor family from 1 to 10. Various cDNAs encoding these molecules were obtained from primate, e.g., human, cDNA sequence libraries. Other primate or other mammalian counterparts would also be desired.

Some of the standard methods applicable are described or referenced, e.g., in Maniatis, et al., Molecular Cloning, A Laboratory Manual, Cold Spring Harbor Laboratory, Cold Spring Harbor Press (1982); Sambrook, et al., Molecular Cloning: A Laboratory Manual, (2d ed.), vols. 1-3, CSH Press, NY (1989); and Ausubel, et al., Current Protocols in Molecular Biology, Greene/Wiley, New York (1987); each of which is incorporated herein by reference.

A complete nucleotide (SEQ ID NO: 1) and corresponding amino acid sequence (SEQ. ID NO: 2) of a human TLR1 coding segment is shown in the indicated sequence listings. See also Nomura, et al., DNA Res. 1,27 (1994). A complete nucleotide (SEQ ID NO: 3) and corresponding amino acid sequence (SEQ ID NO: 4) of a human TLR2 coding segment is also shown, as indicated. A complete nucleotide (SEQ ID NO: 5) and corresponding amino acid sequence (SEQ ID NO: 6) of a human TLR3 coding segment are shown, as indicated. A complete nucleotide (SEQ ID NO: 7) and corresponding amino acid sequence (SEQ ID NO: 8) of a human TLR4 coding segment are also shown, in the indicated sequence listings. See also SEQ ID NO: 25 and 26. A partial nucleotide (SEQ ID NO: 9) and corresponding amino acid sequence (SEQ ID NO: 10) of a human TLR5 coding segment are shown in the indicated sequence listings. A complete nucleotide (SEQ ID NO: 11) and corresponding amino acid sequence (SEQ ID NO: 12) of a human TLR6 coding segment are shown, along with partial sequence of a mouse TLR6 (SEQ ID NO: 13, 14, 27, 28, 29, and 30), as indicated. Partial nucleotide (SEQ ID NO: 15 and 17) and corresponding amino acid sequence (SEQ ID NO: 16 and 18) of a human TLR7 coding segment are shown in the indicated sequence listings, while full length sequences are provided in SEQ ID NO: 36 and 37. Partial nucleotide (SEQ ID NO: 19) and corresponding amino acid sequence (SEQ ID NO: 20) of a human TLR8 coding segment is shown, with supplementary sequence (SEQ ID NO: 31, 32, 38, and 39). Partial nucleotide (SEQ ID NO: 21) and corresponding amino acid sequence (SEQ ID NO: 22) of a human TLR9 coding segment is shown in the indicated sequence listings. See also SEQ ID NO: 40 and 41. Partial nucleotide (SEQ ID NO: 23) and corresponding amino acid sequence (SEQ ID NO: 24) of a human TLR10 coding segment is shown as indicated, along with supplementary sequences (SEQ ID NO: 33, 34, 42, and 43) and rodent, e.g., mouse, sequence (SEQ ID NO: 35, 44, and 45).

Transmembrane segments correspond approximately to 802-818 (791-823) of primate TLR7 SEQ ID NO: 37; 559-575 (550-586) of TLR8 SEQ ID NO: 39; 553-569 (549-582) of TLR9 SEQ ID NO: 41; 796-810 (790-814) of TLR10 SEQ ID NO: 43; and 481-497 (475-503) of TLR10 SEQ ID NO: 45.

As used herein, the term Toll like receptor 2 (TLR2) shall be used to describe a protein comprising a protein or peptide segment having or sharing the amino acid sequence shown in SEQ ID NO: 4, or a substantial fragment thereof. Similarly, with a TLR3 and SEQ ID NO: 6; TLR4 and SEQ ID NO: 8; TLR5 and SEQ ID NO: 9; TLR6 and SEQ ID NO: 12; TLR7 and SEQ ID NO: 37; TLR8 and SEQ ID NO: 20; TLR9 and SEQ ID NO: 22; and TLR10 and SEQ ID NO: 24. Rodent, e.g., mouse, TLR11 sequence is provided, e.g., in EST AA739083; TLR13 in ESTAI019567; TLR14 in ESTs AI390330 and AA244663.

The invention also includes a protein variations of the respective TLR allele whose sequence is provided, e.g., a mutein agonist or antagonist. Typically, such agonists or antagonists will exhibit less than about 10% sequence differences, and thus will often have between 1- and 11-fold substitutions, e.g., 2-, 3-, 5-, 7-fold, and others. It also encompasses allelic and other variants, e.g., natural polymorphic, of the protein described. Typically, it will bind to its corresponding biological receptor with high affinity, e.g., at least about 100 nM, usually better than about 30 nM, preferably better than about 10 nM, and more preferably at better than about 3 nM. The term shall also be used herein to refer to related naturally occurring forms, e.g., alleles, polymorphic variants, and metabolic variants of the mammalian protein.

This invention also encompasses proteins or peptides having substantial amino acid sequence identity with the amino acid sequence in Table 2. It will include sequence variants with relatively few substitutions, e.g., preferably less than about 3-5. Similar features apply to the other TLR sequences provided in Tables 3, 4, 5, 6, 7, 8, 9, or 10.

A substantial polypeptide "fragment", or "segment", is a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. Sequences of segments of different proteins can be compared to one another over appropriate length stretches.

Amino acid sequence homology, or sequence identity, is determined by optimizing residue matches, if necessary, by introducing gaps as required. See, e.g., Needleham, et al., J. Mol. Biol. 48,443 (1970); Sankoff, et al., Chapter One in Time Warps, String Edits, and Macromolecules: The Theory and Practice of Sequence Comparison, Addison-Wesley, Reading, Mass. (1983); and software packages from IntelliGenetics, Mountain View, Calif.; GCG WISCONSIN PACKAGE (Accelrys, Inc., San Diego, Calif.); and the NCBI (NIH); each of which is incorporated herein by reference. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine,.arginine; and phenylalanine, tyrosine. Homologous amino acid sequences are intended to include natural allelic and interspecies variations in the cytokine sequence. Typical homologous proteins or peptides will have from 50-100% homology (if gaps can be introduced), to 60-100% homology (if conservative substitutions are included) with an amino acid sequence segment of SEQ ID NO: 4, 6, 8, 10, 12, 14, 16, 18, 20, 22, 24, 26, 28, 30, 32, 34, 37, 39, 41, 43, or 45. Homology measures will be at least about 70%, generally at least 76%, more generally at least 81%, often at least 85%, more often at least 88%, typically at least 90%, more typically at least 92%, usually at least 94%, more usually at least 95%, preferably at least 96%, and more preferably at least 97%, and in particularly preferred embodiments, at least 98% or more. The degree of homology will vary with the length of the compared segments. Homologous proteins or peptides, such as the allelic variants, will share most biological activities with the embodiments described in SEQ ID NO. 4, 6, 8, 10, 12, 14, 16, 18, 20, 22, 24, 26, 28, 30, 32, 34, 37, 39, 41, 43, or 45. Particularly interesting regions of comparison, at the amino acid or nucleotide levels, correspond to those within each of the blocks 1-10, or intrablock regions, corresponding to those indicated in FIGS. 2A-2B.

As used herein, the term "biological activity" is used to describe, without limitation, effects on inflammatory responses, innate immunity, and/or morphogenic development by respective ligands. For example, these receptors should, like IL-1 receptors, mediate phosphatase or phosphorylase activities, which activities are easily measured by standard procedures. See, e.g., Hardie, et al., The Protein Kinase FactBook vols. I and II, Academic Press, San Diego, Calif. (1995); Hanks, et al., Meth. Enzymol. 200, 38(1991); Hunter, et al., Cell 70, 375 (1992); Lewin, Cell 61, 743 (1990); Pines, et al., Cold Spring Harbor Symp. Quant. Biol. 56, 449 (1991); and Parker, et al., Nature 363, 736 (1993). The receptors exhibit biological activities much like regulatable enzymes, regulated by ligand binding. However, the enzyme turnover number is more close to an enzyme than a receptor complex. Moreover, the numbers of occupied receptors necessary to induce such enzymatic activity is less than most receptor systems, and may number closer to dozens per cell, in contrast to most receptors which will trigger at numbers in the thousands per cell. The receptors, or portions thereof, may be useful as phosphate labeling enzymes to label general or specific substrates.

The terms ligand, agonist, antagonist, and analog of, e.g., a TLR, include molecules that modulate the characteristic cellular responses to Toll ligand like proteins, as well as molecules possessing the more standard structural binding competition features of ligand-receptor interactions, e.g., where the receptor is a natural receptor or an antibody. The cellular responses likely are mediated through binding of various Toll ligands to cellular receptors related to, but possibly distinct from, the type I or type II IL-1 receptors. See, e.g., Belvin and Anderson, Ann. Rev. Cell Dev. Biol. 12, 393 (1996); Morisato and Anderson, Ann. Rev. Genetics 29, 371 (1995) and Hultmark, Nature 367, 116 (1994).

Also, a ligand is a molecule which serves either as a natural ligand to which said receptor, or an analog thereof, binds, or a molecule which is a functional analog of the natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman, et al., Goodman & Gilman's: The Pharmacological Bases of Therapeutics, Pergamon Press, New York (1990).

Rational drug design may also be based upon structural studies of the molecular shapes of a receptor or antibody and other effectors or ligands. Effectors may be other proteins which mediate other functions in response to ligand binding, or other proteins which normally interact with the receptor. One means for determining which sites interact with specific other proteins is a physical structure determination, e.g., x-ray crystallography or 2 dimensional-NMR techniques. These will provide guidance as to which amino acid residues form molecular contact regions. For a detailed description of protein structural determination, see, e.g., Blundell and Johnson, Protein Crystallography, Academic Press, New York (1976), which is hereby incorporated herein by reference.

II. Activities

The Toll like receptor proteins will have a number of different biological activities, e.g., in phosphate metabolism, being added to or removed from specific substrates, typically proteins. Such will generally result in modulation of an inflammatory function, other innate immunity response, or a morphological effect. The TLR2, 3, 4, 5, 6, 7, 8, 9, or 10 proteins are homologous to other Toll like receptor proteins, but each have structural differences. For example, a human TLR2 gene coding sequence probably has about 70% identity with the nucleotide coding sequence of mouse TLR2. At the amino acid level, there is also likely to be reasonable identity.

The biological activities of the TLRs will be related to addition or removal of phosphate moieties to substrates, typically in a specific manner, but occasionally in a non specific manner. Substrates may be identified, or conditions for enzymatic activity may be assayed by standard methods, e.g., as described in Hardie, et al., The Protein Kinase FactBook vols. I and II, Academic Press, San Diego, Calif. (1995); Hanks, et al., Meth. Enzymol. 200, 38 (1991); Hunter, et al., Cell 70, 375 (1992); Lewin, Cell 61, 743 (1990); Pines, et al., Cold Spring Harbor Symp. Quant. Biol. 56, 449 (1991); and Parker, et al., Nature 363, 736 (1993).

III. Nucleic Acids

This invention contemplates use of isolated nucleic acid or fragments, e.g., which encode these or closely related proteins, or fragments thereof, e.g., to encode a corresponding polypeptide, preferably one which is biologically active. In addition, this invention covers isolated or recombinant DNA which encodes such proteins or polypeptides having characteristic sequences of the respective TLRs, individually or as a group. Typically, the nucleic acid is capable of hybridizing, under appropriate conditions, with a nucleic acid sequence segment shown in SEQ ID NO: 3, 5, 7, 9, 11, 13, 15, 17, 19, 21, 23, 25, 27, 29, 31, 33, 35, 36, 38, 40, 42, or 44, but preferably not with a corresponding segment of SEQ ID NO: 1. Said biologically active protein or polypeptide can be a full length protein, or fragment, and will typically have a segment of amino acid sequence highly homologous to one shown in SEQ ID NO: 4, 6, 8, 10, 12, 14, 16, 18, 20, 22, 24, 26, 28, 30, 32, 34, 37, 39, 41, 43, or 45. Further, this invention covers the use of isolated or recombinant nucleic acid, or fragments thereof, which encode proteins having fragments which are equivalent to the TLR2-10 proteins. The isolated nucleic acids can have the respective regulatory sequences in the 5' and 3' flanks, e.g., promoters, enhancers, poly-A addition signals, and others from the natural gene.

An "isolated" nucleic acid is a nucleic acid, e.g., an RNA, DNA, or a mixed polymer, which is substantially pure, e.g., separated from other components which naturally accompany a native sequence, such as ribosomes, polymerases, and flanking genomic sequences from the originating species. The term embraces a nucleic acid sequence which has been removed from its naturally occurring environment, and includes recombinant or cloned DNA isolates, which are thereby distinguishable from naturally occurring compositions, and chemically synthesized analogs or analogs biologically synthesized by heterologous systems. A substantially pure molecule includes isolated forms of the molecule, either completely or substantially pure.

An isolated nucleic acid will generally be a homogeneous composition of molecules, but will, in some embodiments, contain heterogeneity, preferably minor. This heterogeneity is typically found at the polymer ends or portions not critical to a desired biological function or activity.

A "recombinant" nucleic acid is typically defined either by its method of production or its structure. In reference to its method of production, e.g., a product made by a process, the process is use of recombinant nucleic acid techniques, e.g., involving human intervention in the nucleotide sequence. Typically this intervention involves in vitro manipulation, although under certain circumstances it may involve more classical animal breeding techniques. Alternatively, it can be a nucleic acid made by generating a sequence comprising fusion of two fragments which are not naturally contiguous to each other, but is meant to exclude products of nature, e.g., naturally occurring mutants as found in their natural state. Thus, for example, products made by transforming cells with any unnaturally occurring vector is encompassed, as are nucleic acids comprising sequence derived using any synthetic oligonucleotide process. Such a process is often done to replace a codon with a redundant codon encoding the same or a conservative amino acid, while typically introducing or removing a restriction enzyme sequence recognition site. Alternatively, the process is performed to join together nucleic acid segments of desired functions to generate a single genetic entity comprising a desired combination of functions not found in the commonly available natural forms, e.g., encoding a fusion protein. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. This will include a dimeric repeat. Specifically included are synthetic nucleic acids which, by genetic code redundancy, encode equivalent polypeptides to fragments of TLR2-5 and fusions of sequences from various different related molecules, e.g., other IL-1 receptor family members.

A "fragment" in a nucleic acid context is a contiguous segment of at least about 17 nucleotides, generally at least 21 nucleotides, more generally at least 25 nucleotides, ordinarily at least 30 nucleotides, more ordinarily at least 35 nucleotides, often at least 39 nucleotides, more often at least 45 nucleotides, typically at least 50 nucleotides, more typically at least 55 nucleotides, usually at least 60 nucleotides, more usually at least 66 nucleotides, preferably at least 72 nucleotides, more preferably at least 79 nucleotides, and in particularly preferred embodiments will be at least 85 or more nucleotides. Typically, fragments of different genetic sequences can be compared to one another over appropriate length stretches, particularly defined segments such as the domains described below.

A nucleic acid which codes for a TLR2-10 will be particularly useful to identify genes, mRNA, and cDNA species which code for itself or closely related proteins, as well as DNAs which code for polymorphic, allelic, or other genetic variants, e.g., from different individuals or related species. Preferred probes for such screens are those regions of the interleukin which are conserved between different polymorphic variants or which contain nucleotides which lack specificity, and will preferably be full length or nearly so. In other situations, polymorphic variant specific sequences will be more useful.

This invention further covers recombinant nucleic acid molecules and fragments having a nucleic acid sequence identical to or highly homologous to the isolated DNA set forth herein. In particular, the sequences will often be operably linked to DNA segments which control transcription, translation, and DNA replication. These additional segments typically assist in expression of the desired nucleic acid segment.

Homologous, or highly identical, nucleic acid sequences, when compared to one another or Table 2-10 sequences, exhibit significant similarity. The standards for homology in nucleic acids are either measures for homology generally used in the art by sequence comparison or based upon hybridization conditions. Comparative hybridization conditions are described in greater detail below.

Substantial identity in the nucleic acid sequence comparison context means either that the segments, or their complementary strands, when compared, are identical when optimally aligned, with appropriate nucleotide insertions or deletions, in at least about 60% of the nucleotides, generally at least 66%, ordinarily at least 71%, often at least 76%, more often at least 80%, usually at least 84%, more usually at least 88%, typically at least 91%, more typically at least about 93%, preferably at least about 95%, more preferably at least about 96 to 98% or more, and in particular embodiments, as high at about 99% or more of the nucleotides, including, e.g., segments encoding structural domains such as the segments described below. Alternatively, substantial identity will exist when the segments will hybridize under selective hybridization conditions, to a strand or its complement, typically using a sequence derived from Tables 2-10. Typically, selective hybridization will occur when there is at least about 55% homology over a stretch of at least about 14 nucleotides, more typically at least about 65%, preferably at least about 75%, and more preferably at least about 90%. See, Kanehisa, Nucl. Acids Res. 12, 203 (1984), which is incorporated herein by reference. The length of homology comparison, as described, may be over longer stretches, and in certain embodiments will be over a stretch of at least about 17 nucleotides, generally at least about 20 nucleotides, ordinarily at least about 24 nucleotides, usually at least about 28 nucleotides, typically at least about 32 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters typically controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 500 mM, usually less than about 400 mM, more usually less than about 300 mM, typically less than-about 200 mM, preferably less than about 100 mM, and more preferably less than about 80 mM, even down to less than about 20 mM. However, the combination of parameters is much more important than the measure of any single parameter. See, e.g., Wetmur and Davidson, J. Mol. Biol. 31, 349 (1968), which is hereby incorporated herein by reference.

Alternatively, for sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman, Adv. Appl. Math. 2,482 (1981), by the homology alignment algorithm of Needlman and Wunsch, J. Mol. Biol. 48, 443 (1970), by the search for similarity method of Pearson and Lipman, Proc. Nat'l Acad. Sci. USA 85, 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng and Doolittle, J. Mol. Evol. 35, 351 (1987). The method used is similar to the method described by Higgins and Sharp, CABIOS 5, 151 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test-sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al., J. Mol. Biol. 215, 403 (1990). Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, Proc. Nat'l Acad. Sci. USA 89, 10915 (1989)) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul, Proc. Nat'l Acad. Sci. USA 90, 5873 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules hybridize to each other under stringent conditions, as described below.

The isolated DNA can be readily modified by nucleotide substitutions, nucleotide deletions, nucleotide insertions, and inversions of nucleotide stretches. These modifications result in novel DNA sequences which encode this protein or its derivatives. These modified sequences can be used to produce mutant proteins (muteins) or to enhance the expression of variant species. Enhanced expression may involve gene amplification, increased transcription, increased translation, and other mechanisms. Such mutant TLR-like derivatives include predetermined or site-specific mutations of the protein or its fragments, including silent mutations using genetic code degeneracy. "Mutant TLR" as used herein encompasses a polypeptide otherwise falling within the homology definition of the TLR as set forth above, but having an amino acid sequence which differs from that of other TLR-like proteins as found in nature, whether by way of deletion, substitution, or insertion. In particular, "site specific mutant TLR" encompasses a protein having substantial homology with a protein of Tables 2-10, and typically shares most of the biological activities or effects of the forms disclosed herein.

Although site specific mutation sites are predetermined, mutants need not be site specific. Mammalian TLR mutagenesis can be achieved by making amino acid insertions or deletions in the gene, coupled with expression. Substitutions, deletions, insertions, or any combinations may be generated to arrive at a final construct. Insertions include amino- or carboxy-terminal fusions. Random mutagenesis can be conducted at a target codon and the expressed mammalian TLR mutants can then be screened for the desired activity. Methods for making substitution mutations at predetermined sites in DNA having a known sequence are well known in the art, e.g., by M13 primer mutagenesis. See also Sambrook, et al. (1989) and Ausubel, et al. (1987 and periodic Supplements).

The mutations in the DNA normally should not place coding sequences out of reading frames and preferably will not create complementary regions that could hybridize to produce secondary mRNA structure such as loops or hairpins.

The phosphoramidite method described by Beaucage and Carruthers, Tetra. Letts. 22, 1859 (1981), will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Polymerase chain reaction (PCR) techniques can often be applied in mutagenesis. Alternatively, mutagenesis primers are commonly used methods for generating defined mutations at predetermined sites. See, e.g., Innis, et al., PCR Protocols: A Guide to Methods and Applications, Academic Press, San Diego, Calif. (1990); and Dieffenbach and Dveksler, PCR Primer: A Laboratory Manual, Cold Spring Harbor Press, CSH, N.Y. (1995).

IV. Proteins and Peptides

As described above, the present invention encompasses primate TLR2-10, e.g., whose sequences are disclosed in SEQ ID NO: 4, 6, 8, 10, 12, 14, 16, 18, 20, 22, 24, 26, 28, 30, 32, 34, 37, 39, 41, 43, or 45, and described above. Allelic and other variants are also contemplated, including, e.g., fusion proteins combining portions of such sequences with others, including epitope tags and functional domains.

The present invention also provides recombinant proteins, e.g., heterologous fusion proteins using segments from these rodent proteins. A heterologous fusion protein is a fusion of proteins or segments which are naturally not normally fused in the same manner. Thus, the fusion product of a TLR with an IL-1 receptor is a continuous protein molecule having sequences fused in a typical peptide linkage, typically made as a single translation product and exhibiting properties, e.g., sequence or antigenicity, derived from each source peptide. A similar concept applies to heterologous nucleic acid sequences.

In addition, new constructs may be made from combining similar functional or structural domains from other related proteins, e.g., IL-1 receptors or other TLRs, including species variants. For example, ligand-binding or other segments may be "swapped" between different new fusion polypeptides or fragments. See, e.g., Cunningham, et al., Science 243, 1330 (1989); and O'Dowd, et al., J. Biol. Chem. 263,15985 (1988), each of which is incorporated herein by reference. Thus, new chimeric polypeptides exhibiting new combinations of specificities will result from the functional linkage of receptor-binding specificities. For example, the ligand binding domains from other related receptor molecules may be added or substituted for other domains of this or related proteins. The resulting protein will often have hybrid function and properties. For example, a fusion protein may include a targeting domain which may serve to provide sequestering of the fusion protein to a particular subcellular organelle.

Candidate fusion partners and sequences can be selected from various sequence data bases, e.g., GenBank, c/o IntelliGenetics, Mountain View, Calif.; and BCG, University of Wisconsin Biotechnology Computing Group, Madison, Wis., which are each incorporated herein by reference.

The present invention particularly provides muteins which bind Toll ligands, and/or which are affected in signal transduction. Structural alignment of human TLR1-10 with other members of the IL-1 family show conserved features/ residues. See, e.g., FIG. 3A. Alignment of the human TLR sequences with other members of the IL-1 family indicates various structural and functionally shared features. See also, Bazan, et al., Nature 379, 591 (1996); Lodi, et al., Science 263, 1762 (1994); Sayle and Milner-White, TIBS 20, 374 (1995); and Gronenberg, et al., Protein Engineering 4, 263 (1991).

The IL-1α and IL-1β ligands bind an IL-1 receptor type I as the primary receptor and this complex then forms a high affinity receptor complex with the IL-1 receptor type III. Such receptor subunits are probably shared with the new IL-1 family members.

Similar variations in other species counterparts of TLR2-10 sequences, e.g., in the corresponding regions, should provide similar interactions with ligand or substrate. Substitutions with either mouse sequences or human sequences are particularly preferred. Conversely, conservative substitutions away from the ligand binding interaction regions will probably preserve most signaling activities.

"Derivatives" of the primate TLR2-10 include amino acid sequence mutants, glycosylation variants, metabolic derivatives and covalent or aggregative conjugates with other chemical moieties. Covalent derivatives can be prepared by linkage of functionalities to groups which are found in the TLR amino acid side chains or at the N— or C-termini, e.g., by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g.; lysine or arginine. Acyl groups are selected from the group of alkyl-moieties including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the receptors or fragments thereof with other proteins of polypeptides. These derivatives can be synthesized in recombinant culture such as N— or C-terminal fusions or by the use of agents known in the art for their usefulness in cross-linking proteins through reactive side groups. Preferred derivatization sites with cross-linking agents are at free amino groups, carbohydrate moieties, and cysteine residues.

Fusion polypeptides between the receptors and other homologous or heterologous proteins are also provided. Homologous polypeptides may be fusions between different receptors, resulting in, for instance, a hybrid protein exhibiting binding specificity for multiple different Toll ligands, or a receptor which may have broadened or weakened specificity of substrate effect. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired ligand may be easily determined. See, e.g., Dull, et al., U.S. Pat. No. 4,859,609, which is hereby incorporated herein by reference. Other gene fusion partners include glutathione-S-transferase (GST), bacterial β-galactosidase, trpE, Protein A, B-lactamase, alpha amylase, alcohol dehydrogenase, and yeast alpha mating factor. See, e.g., Godowski, et al., Science 241, 812 (1988).

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will-be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook, et al., Molecular Cloning: A Laboratory Manual (2d ed.), Vols. 1-3, Cold Spring Harbor Laboratory (1989), and Ausubel, et al., Current Protocols in Molecular Biology, Greene/Wiley, New York (1987), which are each incorporated herein by reference. Techniques for synthesis of polypeptides are described, for example, in Merrifield, J. Amer. Chem. Soc. 85, 2149 (1963); Merrifield, Science 232, 341 (1986); and Atherton, et al., Solid Phase Peptide Synthesis: A Practical Approach, IRL Press, Oxford (1989); each of which is incorporated herein by reference. See also Dawson, et al., Science 266, 776 (1994) for methods to make larger polypeptides.

This invention also contemplates the use of derivatives of a TLR2-10 other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of a receptor or other binding molecule, e.g., an antibody. For example, a Toll ligand can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of a TLR receptor, antibodies, or other similar molecules. The ligand can also be labeled with a detectable group, for example radioiodinated by the chloramine T procedure, covalently bound to rare earth chelates, or conjugated to another fluorescent moiety for use in diagnostic assays.

Soluble Toll-like receptors (sTLR) as used in the context of the present invention refers to a protein, or a substantially equivalent analog, having an amino acid sequence corresponding to the extracellular region of native TLR2, TLR3, TLR4, TLR5, TLR6, TLR7, TLR8, TLR9, or TLR10. Soluble TLRs may be constructed by deleting terminal or internal residues or sequences. Particularly preferred sequences include those in which the transmembrane region and intracellular domain of a TLR-are deleted or substituted with hydrophilic residues to facilitate secretion of the receptor into the cell culture medium. Software programs can be used for predicting the transmembrane, extracellular, and cytosolic domains of a polypeptide. These software programs can be found in the GCG WISCONSIN PACKAGE (Accelrys, Inc., San Diego, Calif.) and in the LASERGENE sequence analysis software (DNAStar, Inc., Madison, Wis.). The resulting water-soluble protein is referred to as a soluble TLR molecule, where this TLR retains its ability to bind its ligand, e.g., bacterial lipopolysaccharide, endotoxin, peptidoglycan, lipoteichoic acid, and unmethylated CpG oligonucleotides.

When administered in therapeutic formulations, soluble TLRs circulate in the body and bind to its ligand or ligands, where the ligands may be soluble, intracellular, intercellular, or occurring as part of a microbe or fungus. When the soluble TLR binds to the ligand, the ligand is prevented from interacting with its natural TLR, and thereby prevented from relaying a signal to the cell.

DNA constructs coding for soluble TLRs can be inserted in appropriate expression vectors, expressed in cultured cells or microorganisms, and expressed. The expressed soluble TLR can be assayed for the ability to bind the above mentioned ligands (See, e.g., U.S. Pat. No. 5,767,065, issued to Mosley, et al.; U.S. Pat. No. 5,712,155, issued to Smith, et al.)

V. Making Nucleic Acids and Protein

DNA which encodes the protein or fragments thereof can be obtained by chemical synthesis, screening cDNA libraries, or by screening genomic libraries prepared from a wide variety of cell lines or tissue samples. Natural sequences can be isolated using standard methods and the sequences provided herein, e.g., in Tables 2-10. Other species counterparts can be identified by hybridization techniques, or by various PCR techniques, combined with or by searching in sequence databases, e.g., GenBank.

This DNA can be expressed in a wide variety of host cells for the synthesis of a full-length receptor or fragments which can in turn, for example, be used to generate polyclonal or monoclonal antibodies; for binding studies; for construction and expression of modified ligand binding or kinase/phosphatase domains; and for structure/function studies. Variants or fragments can be expressed in host cells that are transformed or transfected with appropriate expression vectors. These molecules can be substantially free of protein or cellular contaminants, other than those derived from the recombinant host, and therefore are particularly useful in pharmaceutical compositions when combined with a pharmaceutically acceptable carrier and/or diluent. The protein, or portions thereof, may be expressed as fusions with other proteins.

Expression vectors are typically self-replicating DNA or RNA constructs containing the desired receptor gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention include those which contain DNA which encodes a protein, as described, or a fragment thereof encoding a biologically active equivalent polypeptide. The DNA can be under the control of a viral promoter and can encode a selection marker. This invention further contemplates use of such expression vectors which are capable of expressing eukaryotic cDNA coding for such a protein in a prokaryotic or eukaryotic host, where the vector is compatible with the host and where the eukaryotic cDNA coding for the receptor is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of the protein encoding portion or its fragments into the host DNA by recombination.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al., Cloning Vectors: A Laboratory Manual, Elsevier, N.Y. (1985), and Rodriquez, et al. (eds.) Vectors: A Survey of Molecular Cloning Vectors and Their Uses, Buttersworth, Boston (1988), which are incorporated herein by reference.

Transformed cells are cells, preferably mammalian, that have been transformed or transfected with receptor vectors constructed using recombinant DNA techniques. Transformed host cells usually express the desired protein or its fragments, but for purposes of cloning, amplifying, and manipulating its DNA, do not need to express the subject protein. This invention further contemplates culturing transformed cells in a nutrient medium, thus permitting the receptor to accumulate in the cell membrane. The protein can be recovered, either from the culture or, in certain instances, from the culture medium.

For purposes of this invention, nucleic sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., E. coli and B. subtilis. Lower eukaryotes include yeasts, e.g., S. cerevisiae and Pichia, and species of the genus Dictyostelium. Higher eukaryotes include established-tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, E. coli and its vectors will be used generically to include equivalent vectors used in other prokaryotes. A representative vector for amplifying DNA is pBR322 or many of its derivatives. Vectors that can be used to express the receptor or its fragments include, but are not limited to, such vectors as those containing the lac promoter (pUC-series); trp promoter (pBR322-trp); Ipp promoter (the pIN-series); lambda-pP or pR promoters (pOTS); .or hybrid promoters such as. ptac (pDR540). See Brosius, et al., "Expression Vectors Employing Lambda-, trp-, lac-, and Ipp-derived Promoters", in Vectors: A Survey of Molecular Cloning Vectors and Their Uses, (eds. Rodriguez and Denhardt), Buttersworth, Boston, Chapter 10, pp. 205-236 (1988), which is incorporated herein by reference.

Lower eukaryotes, e.g., yeasts and Dictyostelium, may be transformed with TLR sequence containing vectors. For purposes of this invention, the most common lower eukaryotic host is the baker's yeast, Saccharomyces cerevisiae. It will be used to generically represent lower eukaryotes although a number of other strains and species are also available. Yeast vectors typically consist of a replication origin (unless of the integrating type), a selection gene, a promoter, DNA encoding the receptor or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are normally the preferred host cells for expression of the functionally active interleukin protein. In principle, any higher eukaryotic tissue culture cell line is workable, e.g., insect baculovirus expression systems, whether from an invertebrate or vertebrate source. However, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al., Mol. Cell Biol. 5, 1136 (1985); pMClneo PolyA, see Thomas, et al., Cell 51, 503 (1987); and a baculovirus vector such as pAC 373 or pAC 610.

For secreted proteins, an open reading frame usually encodes a polypeptide that consists of a mature or secreted product covalently linked at its N-terminus to a signal peptide. The signal peptide is cleaved prior to secretion of the mature, or active, polypeptide. The cleavage site can be predicted with a high degree of accuracy from empirical rules, e.g., von-Heijne, Nucleic Acids Research 14, 4683 (1986), and the precise amino acid composition of the signal peptide does not appear to be critical to its function, e.g., Randall, et al., Science 243, 1156 (1989); Kaiser, et al., Science 235, 312 (1987).

It will often be desired to express these polypeptides in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the receptor gene may be co-transformed with one or more genes encoding mammalian or other glycosylating enzymes. Using this approach, certain mammalian glycosylation patterns will be achievable in prokaryote or other cells.

The source of TLR can be a eukaryotic or prokaryotic host expressing recombinant TLR, such as is described above. The source can also be a cell line such as mouse Swiss 3T3 fibroblasts, but other mammalian cell lines are also contemplated by this invention, with the preferred cell line being from the human species.

Now that the sequences are known, the primate TLRs, fragments, or derivatives thereof can be prepared by conventional processes for synthesizing peptides. These include processes such as are described in Stewart and Young, Solid Phase Peptide Synthesis, Pierce Chemical Co., Rockford, Ill. (1984); Bodanszky and Bodanszky, The Practice of Peptide Synthesis, Springer-Verlag, New York; and Bodanszky (1984) The Principles of Peptide Synthesis, Springer-Verlag, New York; all of each which are incorporated herein by reference. For example, an azide process, an acid chloride process, an acid anhydride process, a mixed anhydride process, an active ester process (e.g., p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes. Similar techniques can be used with partial TLR sequences.

The TLR proteins, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction typically must be protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonylhydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al., J. Am. Chem. Soc. 85, 2149 (1963), which is incorporated herein by reference.

The prepared protein and fragments thereof can be isolated and purified from the reaction mixture by means of peptide separation, for example, by extraction, precipitation, electrophoresis, various forms of chromatography, and the like. The receptors of this invention can be obtained in varying degrees of purity depending upon-desired uses. Purification can be accomplished by use of the protein purification techniques disclosed herein, see below, or by the use of the antibodies herein described in methods of immunoabsorbant affinity chromatography. This immunoabsorbant affinity chromatography is carried out by first linking the antibodies to a solid support and then contacting the linked antibodies with solubilized lysates of appropriate cells, lysates of other cells expressing the receptor, or lysates or supernatants of cells producing the protein as a result of DNA techniques, see below.

Generally, the purified protein will be at least about 40% pure, ordinarily at least about 50% pure, usually at least about 60% pure, typically at least about 70% pure, more typically at least about 80% pure, preferable at least about 90% pure and more preferably at least about 95% pure, and in particular embodiments, 97%-99% or more. Purity will usually be on a weight basis, but can also be on a molar basis. Different assays will be applied as appropriate.

The present invention further relates to variants of the nucleic acid molecules of the present invention, which encode portions, analogs or derivatives of a TLR, and to variants of a TLR polypeptide. Variants may occur naturally, such as a natural allelic variant. By an "allelic variant" is intended one of several alternate forms of a gene occupying a given locus on a chromosome of an organism (Lewin, Genes II, John Wiley and Sons, New York (1985)). Non-naturally occurring variants may be produced using art-known mutagenesis techniques. Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Some contemplated examples of conservative substitutions include substitution of a hydrophobic residue such as isoleucine, valine, leucine or methionine for another hydrophobic residue. Also, a polar residue such as arginine, lysine, glutamic acid, aspartic acid, glutamine, asparagine, and the like, can be conservatively substituted for another member of this group. Still another aspect of a polypeptide incorporating conservative substitutions occurs when a substituted amino acid residue replaces an unsubstituted parent amino acid residue. The variations may include silent substitutions, additions and deletions, which do not alter the properties and activities of the TLR or portions thereof.

VI. Antibodies

The term "antibody" is used in the broadest sense and specifically covers monoclonal antibodies, antibody compositions with polyepitopic specificity, bispecific antibodies, and single-chain molecules, as well as antibody fragments (e.g., Fab, F(ab')$_2$, and Fv), so long as they antagonize the biological activity of TLR2, TLR3, TLR4, TLR5, TLR6, TLR7, TLR8, TLR9, or TLR10.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352, 624(1991) and Marks et al., J. Mol. Biol., 222, 581(1991), for example.

Monoclonal antibodies include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81, 6851(1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit-having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321, 522 (1986); Reichmann et al., Nature, 332, 323(1988); and Presta, Curr. Op. Struct. Biol., 2, 593 (1992). The humanized antibody includes a Primatized™ antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds., Springer-Verlag, New York, pp. 269-315(1994).

Antibodies can be raised to the various TLR proteins and fragments thereof, both in naturally occurring native forms and in their recombinant forms, the difference being that antibodies to the active receptor are more likely to recognize epitopes which are only present in the native conformations. Denatured antigen detection can also be useful in, e.g., Western analysis.

A TLR of this invention can be used as an immunogen for the production of antisera or antibodies specific, e.g., capable of distinguishing between various Toll-like receptors or various fragments thereof. The purified TLR can be used to screen monoclonal antibodies or antigen-binding fragments prepared by immunization with various forms of impure preparations containing the protein.

The purified TLR can also be used as a reagent to detect antibodies generated in response to the presence of elevated levels of expression, or immunological disorders which lead to antibody production to the endogenous receptor.

Additionally, TLR fragments may also serve as immunogens to produce the antibodies of the present invention, as described immediately below. For example, this invention contemplates antibodies having binding affinity to or being raised against the amino acid sequences shown in SEQ ID NOS: 4, 6, 8, 10, 12, 14, 16, 18, 20, 22, 24, 26, 28, 30, 32, 34, 37, 39, 41, 43, or 45, fragments thereof, or various homologous peptides. In particular, this invention contemplates antibodies having binding affinity to, or having been raised against, specific fragments which are predicted to be, or actually are, exposed at the exterior protein surface of the native TLR.

The blocking of physiological response to the receptor ligands may result from the inhibition of binding of the ligand to the receptor, likely through competitive inhibition. Thus, in vitro assays of the present invention will often use antibodies or antigen binding segments of these antibodies, or fragments attached to solid phase substrates. These assays will also allow for the diagnostic determination of the effects of either ligand binding region mutations and modifications, or other mutations and modifications, e.g., which affect signaling or enzymatic function.

This invention also contemplates the use of competitive drug screening assays, e.g., where antibodies to the receptor (or antibody fragments) compete with a test compound for binding to a ligand or other antibody. The invention also contemplates use of water-soluble versions of the Toll-like receptors for drug screening. In this manner, the neutralizing antibodies or fragments can be used to detect the presence of a polypeptide which shares one or more binding sites to a receptor and can also be used to occupy binding sites on a receptor that might otherwise bind a ligand.

Preferred antibodies will exhibit properties of both affinity and selectivity. High affinity is generally preferred, while selectivity will allow distinction between various embodiment subsets. In particular, it will be desirable to possess antibody preparations characterized to bind, e.g., various specific combinations of related members while not binding others. Such various combinatorial subsets are specifically enabled, e.g., these reagents may be generated or selected using standard methods of immunoaffinity, selection, etc.

Antibodies, including binding fragments and single chain versions, against predetermined fragments of the protein can be raised by immunization of animals with conjugates of the fragments with immunogenic proteins. Monoclonal antibodies are prepared from cells secreting the desired antibody.

These antibodies can be screened for binding to normal or defective protein, or screened for agonistic or antagonistic activity. These monoclonal antibodies will usually bind with at least a $K_D$ of about 1 mM, more usually at least about 300 µM, typically at least about 100 µM, more typically at least about 30 µM, preferably at least about 10 µM, and more preferably at least about 3 µM or better.

The antibodies, including antigen binding fragments, of this invention can have significant diagnostic or therapeutic value. They can be potent antagonists that bind to the receptor and inhibit binding to ligand or inhibit the ability of the receptor to elicit a biological response, e.g., act on its substrate. They can also be agonists that bind to the receptor, and initiate signals that are similar to those stimulated to the receptor's ligand under physiological conditions. Antibodies to a Toll-like receptor can also be coupled to toxins or radionuclides to produce a conjugate, where the conjugate can be used for inhibiting or killing cells bearing a Toll-like receptor. Further, these antibodies can be conjugated to drugs or other therapeutic agents, either directly or indirectly by means of a linker.

The antibodies of this invention can also be useful in diagnostic applications. As capture or non-neutralizing antibodies, they might bind to the receptor without inhibiting ligand or substrate binding. As neutralizing antibodies, they can be useful in competitive binding assays.

They will also be useful in detecting or quantifying ligand. They may be used as reagents for Western blot analysis, or for immunoprecipitation or immunopurification of the respective protein.

Protein fragments may be joined to other materials, particularly polypeptides, as fused or covalently joined polypeptides to be used as immunogens. Mammalian TLR and its fragments may be fused or covalently linked to a variety of immunogens, such as keyhole limpet hemocyanin, bovine serum albumin, tetanus toxoid, etc. See Microbiology, Hoeber Medical Division, Harper and Row, (1969); Landsteiner, Specificity of Serological Reactions, Dover Publications, New York (1962); and Williams, et al., Methods in Immunology and Immunochemistry, Vol. 1, Academic Press, New York (1967); each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.), Basic and Clinical Immunology (4th ed.), Lange Medical Publications, Los Altos, Calif., and references cited therein; Harlow and Lane (1988) Antibodies: A Laboratory Manual, CSH Press; Goding, Monoclonal Antibodies: Principles and Practice (2d ed) Academic Press, New York (1986); and particularly in Kohler and Milstein, Nature 256, 495 (1975), which discusses one method of generating monoclonal antibodies. Each of these references is incorporated herein by reference.

Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al., Science 246, 1275 (1989); and Ward, et al., Nature 341, 544 (1989), each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant or chimeric immunoglobulins may be produced, see Cabilly, U.S. Pat. No. 4,816,567; or made in transgenic mice, see Mendez, et al., Nature Genetics 15, 146 (1997). These references are incorporated herein by reference.

The antibodies of this invention can also be used for affinity chromatography in isolating the TLRs. Columns can be prepared where the antibodies are linked to a solid support, e.g., particles, such as AGAROSE, SEPHADEX, or the like, where a cell lysate may be passed through the column, the column washed, followed by increasing concentrations of a mild denaturant, whereby the purified protein will be released. The protein may be used to purify antibody.

The antibodies may also be used to screen expression libraries for particular expression products. Usually the antibodies used in such a procedure will be labeled with a moiety allowing easy detection of presence of antigen by antibody binding.

Antibodies raised against a TLR will also be used to raise anti-idiotypic antibodies. These will be useful in detecting or diagnosing various immunological conditions related to expression of the protein or cells which express the protein. They also will be useful as agonists or antagonists of the ligand, which may be competitive inhibitors or substitutes for naturally occurring ligands.

A TLR protein that specifically binds to or that is specifically immunoreactive with an antibody generated against a defined immunogen, such as an immunogen consisting of the amino acid sequence of SEQ ID NO: 4, 6, 8, 10, 12, 14, 16, 18, 20, 22, or 24, is typically determined in an immunoassay. The inmunuoassay typically uses a polyclonal antiserum which was raised, e.g., to aprotein of SEQ ID NO: 4, 6, 8, 10, 12, 14, 16, 18, 20, 22, or 24. This antiserum is selected to have low crossreactivity against other IL-1R family members, e.g., TLR1, preferably from the same species, and any such crossreactivity is removed by immunoabsorption prior to use in the immunoassay.

In order to produce antisera for use in an immunoassay, the protein of SEQ ID NO: 4, 6, 8, 10, 12, 14, 16, 18, 20, 22, or 24, or a combination thereof, is isolated as described herein. For example, recombinant protein may be produced in a mammalian cell line. An appropriate host, e.g., an inbred strain of mice such as Balb/c, is immunized with the selected protein, typically using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other IL-1R family members, e.g., mouse TLRs or human TLR1, using a competitive binding immunoassay such as the one described in Harlow and Lane, supra, at pages 570-573. Preferably at least two TLR family members are used in this determination in conjunction with either or some of the human TLR2-10. These IL-1R family members can be produced as recombinant proteins and isolated using standard molecular biology and protein chemistry techniques as described herein.

Immunoassays in the competitive binding format can be used for the crossreactivity determinations. For example, the proteins of SEQ ID NO: 4, 6, 8, 10, 12, 14, 16, 18, 20, 22, and/or 24, or various fragments thereof, can be immobilized to a solid support. Proteins added to the assay compete with the binding of the antisera to the immobilized antigen. The ability of the above proteins to compete with the binding of the antisera to the immobilized protein is compared to the protein of SEQ ID NO: 4, 6, 8, 10, 12, 14, 16, 18, 20, 22, and/or 24. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein (e.g., the IL-1R like protein of SEQ ID NO: 4, 6, 8, 10, 12, 14, 16, 18, 20, 22, and/or 24). In order to make this comparison; the two proteins are each assayed at a wide range of concentrations and the amount of each protein required to inhibit 50% of the binding of the antisera to the immobilized protein is determined. If the amount of the second protein required is less than twice the amount of the protein of the selected protein or proteins that is required, then the second protein is said to specifically bind to an antibody generated to the immunogen.

It is understood that these TLR proteins are members of a family of homologous proteins that comprise at least 10 so far identified genes. For a particular gene product, such as the TLR2-10, the term refers not only to the amino acid sequences disclosed herein, but also to other proteins that are allelic, non-allelic or species variants. It also understood that the terms include nonnatural mutations introduced by deliberate mutation using conventional recombinant technology such as single site mutation, or by excising short sections of DNA encoding the respective proteins, or by substituting new amino acids, or adding new amino acids. Such minor alterations must substantially maintain the immunoidentity of the original molecule and/or its biological activity. Thus, these alterations include proteins that are specifically immunoreactive with a designated naturally occurring IL-1R related protein, for example, the TLR proteins shown in SEQ ID NO: 4, 6, 8, 10, 12, 14, 16, 18, 20, 22, or 24. The biological properties of the altered proteins can be determined by expressing the protein in an appropriate cell line and measuring the appropriate effect upon lymphocytes. Particular protein modifications considered minor would include conservative substitution of amino acids with similar chemical properties, as described above for the IL-1R family as a whole. By aligning a protein optimally with the protein of TLR2-10 and by using the conventional immunoassays described herein to determine immunoidentity, one can determine the protein compositions of the invention.

VII. Kits and Quantitation

Both naturally occurring and recombinant forms of the IL-1R like molecules of this invention are particularly useful in kits and assay methods. For example, these methods would also be applied to screening for binding activity, e.g., ligands for these proteins. Several methods of automating assays have been developed in recent years so as to permit screening of tens of thousands of compounds per year. See, e.g., a BIOMEK automated workstation, Beckman Instruments, Palo Alto, Calif., and Fodor, et al., Science 251, 767 (1991), which is incorporated herein by reference. The latter describes means for testing binding by a plurality of defined polymers synthesized on a solid substrate. The development of suitable assays to screen for a ligand or agonist/antagonist homologous proteins can be greatly facilitated by the availability of large amounts of purified, soluble TLRs in an active state such as is provided by this invention.

Purified TLR can be coated directly onto plates for use in the aforementioned ligand screening techniques. However, non-neutralizing antibodies to these proteins can be used as capture antibodies to immobilize the respective receptor on the solid phase, useful, e.g., in diagnostic uses.

This invention also contemplates use of TLR2-10, fragments thereof, peptides, and their fusion products in a variety of diagnostic kits and methods for detecting the presence of the protein or its ligand. Alternatively, or additionally, antibodies against the molecules may be incorporated into the kits and methods. Typically the kit will have a compartment containing either a defined TLR peptide or gene segment or a reagent which recognizes one or the other. Typically, recognition reagents, in the case of peptide, would be a receptor or antibody, or in the case of a gene segment, would usually be a hybridization probe.

A preferred kit for determining the concentration of, e.g., TLR4, a sample would typically comprise a labeled compound, e.g., ligand or antibody, having known binding affinity for TLR4, a source of TLR4 (naturally occurring or recombinant) as a positive control, and a means for separating the bound from free labeled compound, for example a solid phase for immobilizing the TLR4 in the test sample. Compartments containing reagents, and instructions, will normally be provided.

Antibodies, including antigen binding fragments, specific for mammalian TLR or a peptide fragment, or receptor fragments are useful in diagnostic applications to detect the presence of elevated levels of ligand and/or its fragments. Diagnostic assays may be homogeneous (without a separation step between free reagent and antibody-antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA) and the like. For example, unlabeled antibodies can be employed by using a second antibody which is labeled and which recognizes the antibody to TLR4 or to a particular fragment thereof. These assays have also been extensively discussed in the literature. See, e.g., Harlow and Lane, Antibodies: A Laboratory Manual, CSH. (1988), and Coligan, Current Protocols In Immunology, Greene/Wiley, New York (1991).

Anti-idiotypic antibodies may have similar use to serve as agonists or antagonists of TLR4. These should be useful as therapeutic reagents under appropriate circumstances.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled ligand is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent, and will contain instructions for proper use and disposal of reagents. Desirably, the reagents are provided as a dry lyophilized powder, where the reagents may be reconstituted in an aqueous medium having appropriate concentrations for performing the assay.

The aforementioned constituents of the diagnostic assays may be used without modification or may be modified in a variety of ways. For example, labeling may be achieved by covalently or non-covalently joining a moiety which directly or indirectly provides a detectable signal. In any of these assays, a test compound, TLR, or antibodies thereto can be labeled either directly or indirectly. Possibilities for direct labeling include label groups: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free ligand, or alternatively the bound from the free test compound. The TLR can be immobilized on various matrixes followed by washing. Suitable matrices include plastic such as an ELISA plate, filters, and beads. Methods of immobilizing the receptor to a matrix include, without limitation, direct adhesion to plastic, use of a capture antibody, chemical coupling, and biotin-avidin. The last step in this approach involves the precipitation of antibody/antigen complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al., Clin. Chem. 30, 1457 (1984), and the double antibody magnetic particle separation as described in U.S. Pat. No. 4,659,678, each of which is incorporated herein by reference.

The methods for linking protein or fragments to various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a TLR. These sequences can be used as probes for detecting levels of the respective TLR in patients suspected of having an immunological disorder. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}P$. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al., Progress in Growth Factor Res. 1, 89 (1989).

VIII. Therapeutic Utility

This invention provides reagents with significant therapeutic value. The TLRs (naturally occurring or recombinant), fragments thereof, mutein receptors, and antibodies, along with compounds identified as having binding affinity to the receptors or antibodies, should be useful in the treatment of conditions exhibiting abnormal expression of the receptors of their ligands. Such abnormality will typically be manifested by immunological disorders. Additionally, this invention should provide therapeutic value in various diseases or disorders associated with abnormal expression or abnormal triggering of response to the ligand. The Toll ligands have been suggested to be involved in morphologic development, e.g., dorso-ventral polarity determination, and immune responses, particularly the primitive innate responses. See, e.g., Sun, et al., Eur. J. Biochem. 196, 247 (1991); Hultmark, Nature 367, 116 (1994).

Recombinant TLRs, muteins, agonist or antagonist antibodies thereto, or antibodies can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile, e.g., filtered, and placed into dosage forms as by lyophilization in dosage vials or storage in stabilized aqueous preparations. This invention also contemplates use of antibodies or binding fragments thereof which are not complement binding.

Ligand screening using TLR or fragments thereof can be performed to identify molecules having binding affinity to the receptors. Subsequent biological assays can then be utilized to determine if a putative ligand can provide competitive binding, which can block intrinsic stimulating activity. Receptor fragments can be used as a blocker or antagonist in that it blocks the activity of ligand. Likewise, a compound having intrinsic stimulating activity can activate the receptor and is thus an agonist in that it simulates the activity of ligand, e.g., inducing signaling. This invention further contemplates the therapeutic use of antibodies to TLRs as antagonists.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al., Goodman and Gilman's: The Pharmacological Bases of Therapeutics, 8th Ed., Pergamon Press (1990); which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the Merck Index, Merck & Co., Rahway, New Jersey. Because of the likely high affinity binding, or turnover numbers, between a putative ligand and its receptors, low dosages of these reagents would be initially expected to be effective. And the signaling pathway suggests extremely low amounts of ligand may have effect. Thus, dosage ranges would ordinarily be expected to be in amounts lower than 1 mM concentrations, typically less than about 10 µM concentrations, usually less than about 100 nM, preferably less than about 10 pM (picomolar), and most preferably less than about 1 fM (femtomolar), with an appropriate carrier. Slow release formulations, or slow release apparatus will often be utilized for continuous administration.

TLRs, fragments thereof, and antibodies or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al., Goodman and Gilman's: The Pharmacological Bases of Therapeutics, 8th Ed., Pergamon Press (1990); and Avis, et al., Pharmaceutical Dosage Forms: Parenteral Medications, Dekker, N.Y. (1993); Lieberman, et al., Pharmaceutical Dosage Forms: Tablets Dekker, N.Y. (1990); and Lieberman, et al., Pharmaceutical Dosage Forms: Disperse Systems Dekker, N.Y. (1990). The therapy of this invention may be combined with or used in association with other therapeutic agents, particularly agonists or antagonists of other IL-1 family members.

IX. Ligands

The description of the Toll-like receptors herein provide means to identify ligands, as described above. Such ligand should bind specifically to the respective receptor with reasonably high affinity. Various constructs are made available which allow either labeling of the receptor to detect its ligand. For example, directly labeling TLR, fusing onto it markers for secondary labeling, e.g., FLAG or other epitope tags, etc., will allow detection of receptor. This can be histological, as an affinity method for biochemical purification, or labeling or selection in an expression cloning approach. A two-hybrid selection system may also be applied making appropriate constructs with the available TLR sequences. See, e.g., Fields and Song, Nature 340, 245 (1989).

Generally, descriptions of TLRs will be analogously applicable to individual specific embodiments directed to TLR2, TLR3, TLR4, TLR5, TLR6, TLR7, TLR8, TLR9, and/or TLR10 reagents and compositions.

The broad scope of this invention is best understood with reference to the following examples, which are not intended to limit the inventions to the specific embodiments.

X. Isolation and Culture of Cells.

Blood $CD11C^+$ immature dendritic cells, plasmacytoid pre-dendritic cells, and $CD14^+CD16^-$ monocytes were isolated from human peripheral blood, according to Rissoan, et al., Science 283, 1183 (1999) and Grouard, et al., J. Exp. Med. 185, 1101 (1997). The purity of each cell population was over 99%. Monocytes were cultured for five days in RPMI 1640 (BioWhittaker, Walkersville, Md.) supplemented with 10% fetal calf serum (BioWhittaker, Walkersville, Md.), 2 mM L-glutamine, 10 mM HEPES, 1 mM sodium pyruvate, 0.055 mM 2-mercaptoethanol, penicillin G, and streptomycin (Invitrogen Life Technologies, Carlsbad, Calif.), in the presence of 50 ng/ml GM-CSF (Schering-Plough, Kenilworth, N.J.)and 200 U/ml IL-4 (Schering-Plough, Kenilworth, N.J.). The resulting monocyte-derived immature dendritic cells were washed and cultured for 24 h with human CD40L-transfected L cells (irratiated at 5,500 rad) to obtain mature dendric cells type 1 (Rissoan, et al., Science 283, 1183 (1999)). Plasmacytoid pre-dendritic cells were cultured for five days with 10 ng/ml IL-3 (R & D Systems). The resulting plasmacytoid pre-dendritic cells-derived immature dendritic cells were washed and cultured for 24 h, with CD40L-transfected cells to obtain pre-dendritic cell-derived dendritic cells. To induce the maturation of immature dendritic cells, the cells were cultured for 24 h with CD40L-transfected L cells.

To induce cytokine production, cells were cultured for 24 h at two times $10^4/0.2$ ml in round-bottom 96-well culture plates in the presence of 0.01 mg/ml peptidoglycan from *S. aureus* (Fluka, Milwaukee, Wis.), 0.01 mg/ml lipQteichoic acid (LTA) from *S. aureus* (Sigma, St. Louis, Mo.), 0.01 mg/ml LPS from *S. minnesota* serotype Re595 (Sigma, St. Louis, Mo.), 0.05 mg/ml Poly I:C (Sigma, St. Louis, Mo.), 0.005 mM (0.046 mg/ml) phosphodiester CpG oligodeoxynucleotide (AAC-30) (Yamamoto, et al, Jpn. J. Cancer Res. 85, 775 (1994)). AAC-30 was added at 0, 4, and 16 h to compensate for degradation by DNase activity in the medium.

XI. Reverse Transcription Polymerase Chain Reaction (RT-PCR)

Reverse transcription polymerase chain reaction for the detection of mRNA coding for Toll-like receptors was as follows. RNA was isolated with the acid guanidinium thiocyanate-phenol-chloroform method (Chomczynski and Sacchi, Anal. Biochem. 162, 156 (1987)). Contaminating DNA was removed by digestion with 5 U deoxyribonuclease I (Boehringer Mannheim) for 30 min at 37° C. Reverse transcription was carried out with random hexamers (Promega, Madison, Wis.) for priming and SUPERSCRIPT II (Invitrogen Life Technologies, Carlsbad, Calif.). The PCR reaction volume was 0.05 ml, containing 0.5 μM of each primer, 40 nM of each deoxynucleoside triphosphate, and 1.25 U AMPLITAQ (Perkin Elmer, Foster City, Calif.). Primers used are shown in Table 1.

TABLE 1

Sequence of PCR primers.

Reverse transcriptase PCR primers.
Forward primers/Reverse primers

TLR#

| | | |
|---|---|---|
| 1 | CGTAAAACTGGAAGCTTTGCAAGA | (SEQ ID NO: 46) |
| | CCTTGGGCCATTCCAAATAAGTCC | (SEQ ID NO: 47) |
| 2 | GGCCAGCAAATTACCTGTGTG | (SEQ ID NO: 48) |
| | CCAGGTAGGTCTTGGTGTTCA | (SEQ ID NO: 49) |
| 3 | ATTGGGTCTGGGAACATTTCTCTTC | (SEQ ID NO: 50) |
| | GTGAGATTTAAACATTCCTCTTCGC | (SEQ ID NO: 51) |
| 4 | CTGCAATGGATCAAGGACCA | (SEQ ID NO: 52) |
| | TCCCACTCCAGGTAAGTGTT | (SEQ ID NO: 53) |
| 5 | CATTGTATGCACTGTCACTC | (SEQ ID NO: 54) |
| | CCACCACCATGATGAGAGCA | (SEQ ID NO: 55) |
| 6 | TAGGTCTCATGACGAAGGAT | (SEQ ID NO: 56) |
| | GGCCACTGCAAATAAGTCCG | (SEQ ID NO: 57) |
| 7 | AGTGTCTAAAGAACCTGG | (SEQ ID NO: 58) |
| | CTTGGCCTTACAGAAATG | (SEQ ID NO: 59) |
| 8 | CAGAATAGCAGGCGTAACACATCA | (SEQ ID NO: 60) |
| | AATGTCACAGGTGCATTCAAAGGG | (SEQ ID NO: 61) |
| 9 | TTATGGACTTCCTGCTGGAGGTGC | (SEQ ID NO: 62) |
| | CTGCGTTTTGTCGAAGACCA | (SEQ ID NO: 63) |
| 10 | CAATCTAGAGAAGGAAGATGGTCC | (SEQ ID NO: 64) |
| | GCCCTTATAAACTTGTGAAGGTGT | (SEQ ID NO: 65) |

β-actin

| | | |
|---|---|---|
| | ATCTGGCACCACACCTTCTACAATGAGCTGCG | (SEQ ID NO: 66) |
| | CGTCATACTCCTGCTTGCTGATCCACATCTGC | (SEQ ID NO: 67) |

Real time PCR primers.
Forward primers/Reverse primers

Toll like receptor

| | | |
|---|---|---|
| 2 | GGCCAGCAAATTACCTGTGTG | (SEQ ID NO: 68) |
| | AGGCGGACATCCTGAACCT | (SEQ ID NO: 69) |
| 4 | CTGCAATGGATCAAGGACCA | (SEQ ID NO: 70) |
| | TTATCTGAAGGTGTTGCACATTCC | (SEQ ID NO: 71) |
| 7 | TTACCTGGATGGAAACCAGCTACT | (SEQ ID NO: 72) |
| | TCAAGGCTGAGAAGCTGTAAGCTA | (SEQ ID NO: 73) |
| 9 | TGAAGACTTCAGGCCCAACTG | (SEQ ID NO: 74) |
| | TGCACGGTCACCAGGTTGT | (SEQ ID NO: 75) |

A GENEAMP PCR System 9700 (Perkin Elmer/Applied Biosystems, Foster City, Calif.) was used with an initial denaturation step of 94° C. for 5 min, followed by 35 cycles of 94° C. for 30 sec, 55° C. for 30 sec, 72° C. for 1 min, and a final elongation step of 72° C. for 7 min. PCR products were separated on a 3% agarose gel containing ethidium bromide. A 1-kb DNA ladder standard (Invitrogen Life Technologies, Carlsbad, Calif.) was used as a size marker.

XII. Real-Time Quantitative Reverse Transcription PCR

RNA was isolated with the acid guanidinium thiocyanate-phenol-chloroform method (Chomczynski and Sacchi, Anal. Biochem. 162, 156 (1987)). The reverse transcription was performed with SUPERSCRIPT II (Invitrogen Life Technologies, Carlsbad, Calif.). cDNA was analyzed for the expression of Toll like receptor genes by the fluorogenic 5'-nuclease PCR assay (Rissoan, et al., Science 283, 1183

(1999)) using a Perkin-Elmer ABI Prism 7700 Sequence Detection System (Applied Biosystems, Foster City, Calif.). Reactions were incubated for 2 min at 50° C., denatured for 10 min at 95° C., and subjected to 40 two-step amplification cycles with annealing/extension at 60° C. for 1 min, followed by denaturation at 95° C. for 15 sec. The primers used are shown in Table 1. Values are expressed as arbitrary units (relative to ubiquitin X 1,000).

XIII. Quantitation of Cytokines by ELISA

ELISA kits from the following companies were used to analyze cytokine production: TNF-α and IL-6 (R & D Systems, Minneapolis, Minn.), IL-12 and IFN-α (Biosource International, Camarillo, Calif.).

EXAMPLES

Example I

General Methods

Some of the standard methods are described or referenced, e.g., in Maniatis, et al., Molecular Cloning, A Laboratory Manual, Cold Spring Harbor Laboratory, Cold Spring Harbor Press (1982); Sambrook, et al., Molecular Cloning: A Laboratory Manual, (2d ed.), vols. 1-3, CSH Press, NY (1989); Ausubel, et al., Current Protocols in Molecular Biology, Greene/Wiley, New York (1987). Methods for protein purification include such methods as ammonium sulfate precipitation, column chromatography, electrophoresis, centrifugation, crystallization, and others. See, e.g., Deutscher, "Guide to Protein Purification" in Methods in Enzymology, vol. 182 (1990), and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli, Chemische Industrie 12, 69 (1989); Hochuli, "Purification of Recombinant Proteins with Metal Chelate Absorbent" in Setlow (ed.) Genetic Engineering, Principle and Methods 12, 87 (1990), Plenum Press, N.Y.; and Crowe, et al., QIAexpress: The High Level Expression and Protein Purification System QUIAGEN, Inc., Chatsworth, Calif. (1992).

Standard immunological techniques and assays are described, e.g., in Hertzenberg, et al., Weir's Handbook of Experimental Immunology vols. 1-4, Blackwell Science (1996); Coligan (1991) Current Protocols in Immunology Wiley/Greene, NY; and Methods in Enzymology volumes. 70, 73, 74, 84, 92, 93, 108, 116, 121, 132, 150,. 162, and 163.

Assays for vascular biological activities are well known in the art. They will cover angiogenic and angiostatic activities in tumor, or other tissues, e.g., arterial smooth muscle proliferation (see, e.g., Koyoma, et al., Cell 87, 1069 (1996), monocyte. adhesion to vascular epithelium (see McEvoy, et al., J. Exp. Med. 185:2069 (1997), Ross, Nature 362, 801 (1993); Rekhter and Gordon, Am. J. Pathol. 147, 668 (1995); Thyberg, et al., Atherosclerosis 10, 966 (1990); and Gumbiner, Cell 84, 345 (1996).

Assays for neural cell biological activities are described, e.g., in Wouterlood, Neuroscience Protocols modules 10, Elsevier; Methods in Neurosciences Academic Press (1995); and Neuromethods Humana Press, Totowa, N.J. Methodology of developmental systems is described in Meisami, Handbook of Human Growth and Developmental Biology CRC Press (1988).

Computer sequence analysis is performed, e.g., using available software programs, including the GCG WISCONSIN PACKAGE (Accelrys, Inc., San Diego, Calif.). Public sequence databases were also used, e.g., from GenBank, NCBI, EMBO, and others. Determination of transmembrane and other important motifs may be predicted using such bioinformatics tools.

Many techniques that have been used, as they relate to interleukin-10 receptors, may also be applied to the Toll-like receptors, e.g., U.S. Pat. Nos. 5,789,192, issued to Moore, et al., U.S. Pat. No. 5,985,828, issued to Moore, et al., and U.S. Pat. No. 5,863,796, issued to Moore, et al., which are incorporated herein by reference for all purposes.

Example II

Novel Family of Human Receptors

The discovery of sequence homology between the cytoplasmic domains of *Drosophila* Toll and human interleukin-1 (IL-1) receptors suggests that both molecules are used in signaling pathways that involve Rel-type transcription factors. This conserved signaling scheme governs an evolutionarily ancient immune response in both insects and vertebrates. We report the molecular cloning of a novel class of putative human receptors with a protein architecture that is closely similar to *Drosophila* Toll in both intra- and extra-cellular segments. Five human Toll-like receptors, designated TLRs 1-5, are likely the direct homologs of the fly molecule, and as such could constitute an important and unrecognized component of innate immunity in humans; intriguingly, the evolutionary retention of TLRs in vertebrates may indicate another role, akin to Toll in the dorsoventralization of the *Drosophila* embryo, as regulators of early morphogenetic patterning. Multiple tissue mRNA blots indicate markedly different patterns of expression for the human TLRs. Using fluorescence in situ hybridization and Sequence-Tagged Site database analyses, we also show that the cognate TLR genes reside on chromosomes 4 (TLRs 1, 2, and 3), 9 (TLR4), and 1 (TLR5). Structure prediction of the aligned Toll-homology (TH) domains from varied insect and human TLRs, vertebrate IL-1 receptors, and MyD88 factors, and plant disease resistance proteins, recognizes a parallel β/α fold with an acidic active site; a similar structure notably recurs in a class of response regulators broadly involved in transducing sensory information in bacteria.

The study of the Toll receptors of invertebrates and the Toll-like receptors of mammal, has revealed a family of receptors and signaling pathways that has been maintained during evolution (DeRobertis and Sasai, Nature 380, 37 (1996); Arendt and Nübler-Jung, Mech. Develop. 61, 7 (1997); Miklos and Rubin, Cell 86, 521 (1996); Chothia, Develop. 1994 Suppl., 27 (1994); Banfi, et al., Nature Genet. 13, 167 (1996)). The study of the Toll-like receptors, as they are used in the mammalian immune system and mammalian development, may be made easier by a knowlege of the role of these receptors in more primitive animals.

A universally critical step in embryonic development is the specification of body axes, either born from innate asymmetries or triggered by external cues (DeRobertis and Sasai, Nature 380, 37 (1996); Arendt and Nübler-Jung, Mech. Develop. 61, 7 (1997)). As a model system, particular attention has been focused on the phylogenetic basis and cellular mechanisms of dorsoventral polarization (DeRobertis and Sasai, Nature 380, 37 (1996); Arendt and Nübler-Jung, Mech. Develop. 61, 7 (1997)). A prototype molecular strategy for this transformation has emerged from the *Droso*- phila embryo, where the sequential action of a small number of genes results in a ventralizing gradient of the transcription factor Dorsal (St. Johnston and Nüsslein-Volhard, Cell 68, 201 (1992); Morisato and Anderson, Ann. Rev. Genet. 29, 371 (1995)).

This signaling pathway centers on Toll, a transmembrane receptor that transduces the binding of a maternally-secreted ventral factor, Spatzle, into the cytoplasmic engagement of Tube, an accessory molecule, and the activation of Pelle, a Ser/Thr kinase that catalyzes the dissociation of Dorsal from the inhibitor Cactus and allows migration of Dorsal to ventral nuclei (Morisato and Anderson, Ann. Rev. Genet. 29, 371 (1995); Belvin and Anderson, Ann. Rev. Cell Develop. Biol. 12, 393 (1996)). The Toll pathway also controls the induction of potent antimicrobial factors in the adult fly (Lemaitre, et al., Cell 86, 973 (1996)); this role in *Drosophila* immune defense strengthens mechanistic parallels to IL-1 pathways that govern a host of immune and inflammatory responses in vertebrates (Belvin and Anderson, Ann. Rev. Cell Develop. Biol. 12, 393 (1996); Wasserman, Molec. Biol. Cell 4:767 (1993)). A Toll-related cytoplasmic domain in IL-1 receptors directs the binding of a Pelle-like kinase, IRAK, and the activation of a latent NF-κB/I-κB complex that mirrors the embrace of Dorsal and Cactus (Belvin and Anderson, Ann. Rev. Cell Develop. Biol. 12, 393 (1996); Wasserman, Molec. Biol. Cell 4, 767 (1993)).

We describe the cloning and molecular characterization of four new Toll-like molecules in humans, designated TLRs 2-5 (following Chiang and Beachy, Mech. Develop. 47, 225 (1994)), that reveal a receptor family more closely tied to Drosophila Toll homologs than to vertebrate IL-1 receptors. The TLR sequences are derived from human ESTs; these partial cDNAs were used to draw complete expression profiles in human tissues for the five TLRs, map the chromosomal locations of cognate genes, and narrow the choice of cDNA libraries for full-length cDNA retrievals. Spurred by other efforts (Banfi, et al., Nature Genet. 13, 167 (1996); and Wang, et al., J. Biol. Chem. 271, 4468 (1996)), we are assembling, by structural conservation and molecular parsimony, a biological system in humans that is the counterpart of a compelling regulatory scheme in *Drosophila*. In addition, a biochemical mechanism driving Toll signaling is suggested by the proposed tertiary fold of the Toll-homology (TH) domain, a core module shared by TLRs, a broad family of IL-1 receptors, mammalian MyD88 factors and plant disease resistance proteins. Mitcham, et al., J. Biol. Chem. 271, 5777 (1996); and Hardiman, et al., Oncogene 13, 2467 (1996). We propose that a signaling route coupling morphogenesis and primitive immunity in insects, plants, and animals (Belvin and Anderson, Ann. Rev. Cell Develop. Biol. 12, 393 (1996); and Wilson, et al., Curr. Biol. 7, 175 (1997)) may have roots in bacterial two-component pathways.

Toll-like receptor (TLR) molecules belong to the IL-1/ Toll receptor family. Ligands for TLR2 and TLR4 have been identified, and their functions are related to the host immune response to microbial antigen or injury. Takeuchi, et al., Immunity 11, 443 (1999); and Noshino, et al., J. Immunol. 162, 3749 (1999). The pattern of expression of TLRs seem to be restricted. Muzio, et al., J. Immunol. 164, 5998 (2000). With these findings that: i) TLR10 is highly expressed and restricted in pDC2s, and ii) pDC2 is the NIPC, it is likely that TLR10 will play an important role in the host's innate immune response.

Computational Analysis.

Human sequences related to insect TLRs were identified from the EST database (dbEST) at the National Center for Biotechnology Information (NCBI) using the BLAST server (Altschul, et al., Nature Genet. 6, 119 (1994)). More sensitive pattern- and profile-based methods (Bork and Gibson, Meth. Enzymol. 266, 162 (1996)) were used to isolate the signaling domains of the TLR family that are shared with vertebrate and plant proteins present in nonredundant databases.

The progressive alignment of TLR intra- or extracellular domain sequences was carried out by ClustalW (Thompson, et al., Nucleic Acids Res. 22, 4673 (1994)); this program also calculated the branching order of aligned sequences by the Neighbor-Joining algorithm (5000 bootstrap replications provided confidence values for the tree groupings).

Conserved alignment patterns, discerned at several degrees of stringency, were drawn by the Consensus program (internet URL http://www.bork.embl-heidelberg.de/ Alignment/consensus.html). The PRINTS library of protein fingerprints(http://www.biochem.ucl. ac.uk/bsm/dbbrowser/ PRINTS/PRINTS.html) (Attwood, et al., Nucleic Acids Res. 25, 212 (1997)) reliably identified the myriad leucine-rich repeats (LRRs) present in the extracellular segments of TLRs with a compound motif (PRINTS code Leurichrpt) that flexibly matches N— and C-terminal features of divergent LRRs. Two prediction algorithms whose three-state accuracy is above 72% were used to derive a consensus secondary structure for the intracellular domain alignment, as a bridge to fold recognition efforts (Fischer, et al., FASEB J. 10, 126 (1996)). Both the neural network program PHD (Rost and Sander, Proteins 19, 55 (1994)) and the statistical prediction method DSC (King and Sternberg, Protein Sci. 5, 2298 (1996)) have internet servers (URLs http://www.em-blheidelberg.de/predictprotein/phd_pred.html and http:// bonsai.lif.icnet.uk/bmm/dsc/dsc_read_align.html, respectively). The intracellular region encodes the THD region discussed, e.g., Hardiman, et al., Oncogene 13, 2467 (1996); Rock, et al., Proc. Nat'l Acad. Sci. USA 95. 588 (1998), each of which is incorporated herein by reference. This domain is very important in the mechanism of signaling by the receptors, which transfers a phosphate group to a substrate.

Cloning of Full-length Human TLR cDNAs.

PCR primers derived from the Toll-like Humrsc786 sequence (GenBank accession code D13637) (Nomura, et al., DNA Res. 1, 27 (1994)) were used to probe a human erythroleukemic, TF-1 cell line-derived cDNA library (Kitamura, et al., Blood 73, 375 (1989)) to yield the TLR1 cDNA sequence. The remaining TLR sequences were flagged from dbEST, and the relevant EST clones obtained from the I.M.A.G.E. consortium (Lennon, et al., Genomics 33, 151 (1996)) via Research Genetics (Huntsville, Ala.): CloneID #'s 80633 and 117262 (TLR2), 144675 (TLR3), 202057 (TLR4) and 277229 (TLR5). Full length cDNAs for human TLRs 2-4 were cloned by DNA hybridization screening of λgt10 phage, human adult lung, placenta, and fetal liver 5'-STRETCH PLUS cDNA libraries (Clontech), respectively; the TLR5 sequence is derived from a human multiple-sclerosis plaque EST. All positive clones were sequenced and aligned to identify individual TLR ORFs: TLR1 (2366 bp clone, 786 aa ORF), TLR2 (2600 bp, 784 aa), TLR3 (3029 bp, 904 aa), TLR4 (3811 bp, 879 aa) and TLR5 (1275 bp, 370 aa). Similar method are used for TLRs 6-10. Probes for TLR3 and TLR4 hybridizations were generated by PCR using human placenta (Stratagene, La Jolla, Calif.) and adult liver (Clontech, Palo Alto, Calif.) cDNA libraries as templates, respectively; primer pairs were derived from the respective EST sequences. PCR reactions were conducted using *T. aquaticus* TAQPLUS DNA polymerase (Stratagene, La Jolla, Calif.) under the following conditions: 1×(94° C., 2 min) 30×(55° C., 20 sec; 72° C. 30 sec; 94° C. 20 sec), 1×(72° C., 8 min). For TLR2 full-length cDNA screening, a 900 bp fragment generated by EcoRI/XbaI digestion of the first EST clone (ID #80633) was used as a probe.

Northern Blots (mRNA) and Chromosomal Localization.

Human multiple tissue (Cat #1, 2) and cancer cell line blots (Cat #7757-1), containing approximately 2 µg of poly(A)+ RNA per lane, were purchased from Clontech (Palo Alto, Calif.). For TLRs 1-4, the isolated full-length cDNAs served as probes, for TLR5 the EST clone (ID #277229) plasmid insert was used. Briefly, the probes were radiolabeled with [α-$^{32}$P] dATP using the Amersham REDIPRIME random primer labeling kit (RPN1633). Pre-hybridization and hybridizations were performed at 65° C. in 0.5 M Na$_2$HPO$_4$, 7% SDS, 0.5 M EDTA (pH 8.0). All stringency washes were conducted at 65° C. with two initial washes in 2×SSC, 0.1% SDS for 40 min followed by a subsequent wash in 0.1×SSC, 0.1% SDS for 20 min. Membranes were then exposed at −70° C. to X-Ray film (Kodak, Rochester, N.Y.) in the presence of intensifying screens. More detailed studies by cDNA library Southerns (14) were performed with selected human TLR clones to examine their expression in hemopoietic cell subsets.

Human chromosomal mapping was conducted by the method of fluorescence in situ hybridization (FISH) as described in Heng and Tsui, Meth. Molec. Biol. 33, 109 (1994), using the various full-length (TLRs 2-4) or partial (TLR5) cDNA clones as probes. These analyses were performed as a service by SeeDNA Biotech Inc. (Ontario, Canada). A search for human syndromes (or mouse defects in syntenic loci) associated with the mapped TLR genes was conducted in the Dysmorphic Human-Mouse Homology Database by internet server (http://www.hgmp.mrc.ac.uk/DHMHD/hum_chromel.html). Similar methods nare applicable to TLRs 6-10.

Conserved Architecture of Insect and Human TLR Ectodomains.

The Toll family in Drosophila comprises at least four distinct gene products: Toll, the prototype receptor involved in dorsoventral patterning of the fly embryo (Morisato and Anderson, Ann. Rev. Genet. 29, 371 (1995)) and a second named '18 Wheeler' (18w) that may also be involved in early embryonic development (Chiang and Beachy, Mech. Develop. 47, 225 (1994); Eldon, et al., Develop. 120, 885 (1994)); two additional receptors are predicted by incomplete, Toll-like ORFs downstream of the male-specific-transcript (Mst) locus (GenBank code X67703) or encoded by the 'sequence-tagged-site' (STS) Dm2245 (GenBank code G01378) (Mitcham, et al., J. Biol. Chem. 271, 5777 (1996)). The extracellular segments of Toll and 18w are distinctively composed of imperfect, ~24 amino acid LRR motifs (Chiang and Beachy, Mech. Develop. 47, 225 (1994); and Eldon, et al., Develop. 120, 885 (1994)). Similar tandem arrays of LRRs commonly form the adhesive antennae of varied cell surface molecules and their generic tertiary structure is presumed to mimic the horseshoe-shaped cradle of a ribonuclease inhibitor fold, where seventeen LRRs show a repeating β/α-hairpin, 28 residue motif (Buchanan and Gay, Prog. Biophys. Molec. Biol. 65, 1 (1996)). The specific recognition of Spatzle by Toll may follow a model proposed for the binding of cystine-knot fold glycoprotein hormones by the multi-LRR ectodomains of serpentine receptors, using the concave side of the curved β-sheet (Kajava, et al., Structure 3, 867 (1995)); intriguingly, the pattern of cysteines in Spatzle, and an orphan Drosophila ligand, Trunk, predict a similar cystine-knot tertiary structure (Belvin and Anderson, Ann. Rev. Cell Develop. Biol. 12, 393 (1996); and Casanova, et al., Genes Develop. 9, 2539 (1995)).

The 22 and 31 LRR ectodomains of Toll and 18w, respectively (the Mst ORF fragment displays 16 LRRs), are most closely related to the comparable 18, 19, 24, and 22 LRR arrays of TLRs 1-4 (the incomplete TLR5 chain presently includes four membrane-proximal LRRs) by sequence and pattern analysis (Altschul, et al., Nature Genet. 6, 119 (1994); and Bork and Gibson, Meth. Enzymol. 266, 162 (1996)) (FIG. 1). However, a striking difference in the human TLR chains is the common loss of a ~90 residue cysteine-rich region that is variably embedded in the ectodomains of Toll, 18w and the Mst ORF (distanced four, six and two LRRs, respectively, from the membrane boundary). These cysteine clusters are bipartite, with distinct 'top' (ending an LRR) and 'bottom' (stacked atop an LRR) halves (Chiang and Beachy, Mech. Develop. 47, 225 (1994); Eldon, et al., Develop. 120, 885 (1994); and Buchanan and Gay, Prog. Biophys. Molec. Biol. 65, 1 (1996)); the 'top' module recurs in both Drosophila and human TLRs as a conserved juxtamembrane spacer (FIG. 1). We suggest that the flexibly located cysteine clusters in Drosophila receptors (and other LRR proteins), when mated 'top' to 'bottom', form a compact module with paired termini that can be inserted between any pair of LRRs without altering the overall fold of TLR ectodomains; analogous 'extruded' domains decorate the structures of other proteins (Russell, Protein Engin. 7, 1407 (1994)).

Molecular Design of the TH Signaling Domain.

Sequence comparison of Toll and IL-1 type-I (IL-1R1) receptors has disclosed a distant resemblance of a ~200 amino acid cytoplasmic domain that presumably mediates signaling by similar Rel-type transcription factors (Belvin and Anderson, Ann. Rev. Cell Develop. Biol. 12, 393 (1996); Belvin and Anderson, Ann. Rev. Cell Develop. Biol. 12, 393 (1996); Wasserman, Molec. Biol. Cell 4, 767 (1993)). More recent additions to this functional paradigm include a pair of plant disease resistance proteins from tobacco and flax that feature an N-terminal TH module followed by nucleotide-binding (NTPase) and LRR segments (Wilson, et al., Curr. Biol. 7, 175 (1997)); by contrast, a 'death domain' precedes the TH chain of MyD88, an intracellular myeloid differentiation marker (Mitcham, et al., J. Biol. Chem. 271, 5777 (1996); and Hardiman, et al., Oncogene 13, 2467 (1996)) (FIG. 1). New IL-1-type receptors include IL-1R3, an accessory signaling molecule, and orphan receptors IL-1R4 (also called ST2/Fit-1/T1), IL-1R5 (IL-1R-related protein), and IL-1R6 (IL-1R-related protein-2) (Mitcham, et al., J. Biol. Chem. 271:5777 (1996);Hardiman, et al., Oncogene 13, 2467 (1996)). With the new human TLR sequences, we have sought a structural definition of this evolutionary thread by analyzing the conformation of the common TH module: ten blocks of conserved sequence comprising 128 amino acids form the minimal TH domain fold; gaps in the alignment mark the likely location of sequence and length-variable loops (FIGS. 2A-2B).

Figure 2A:
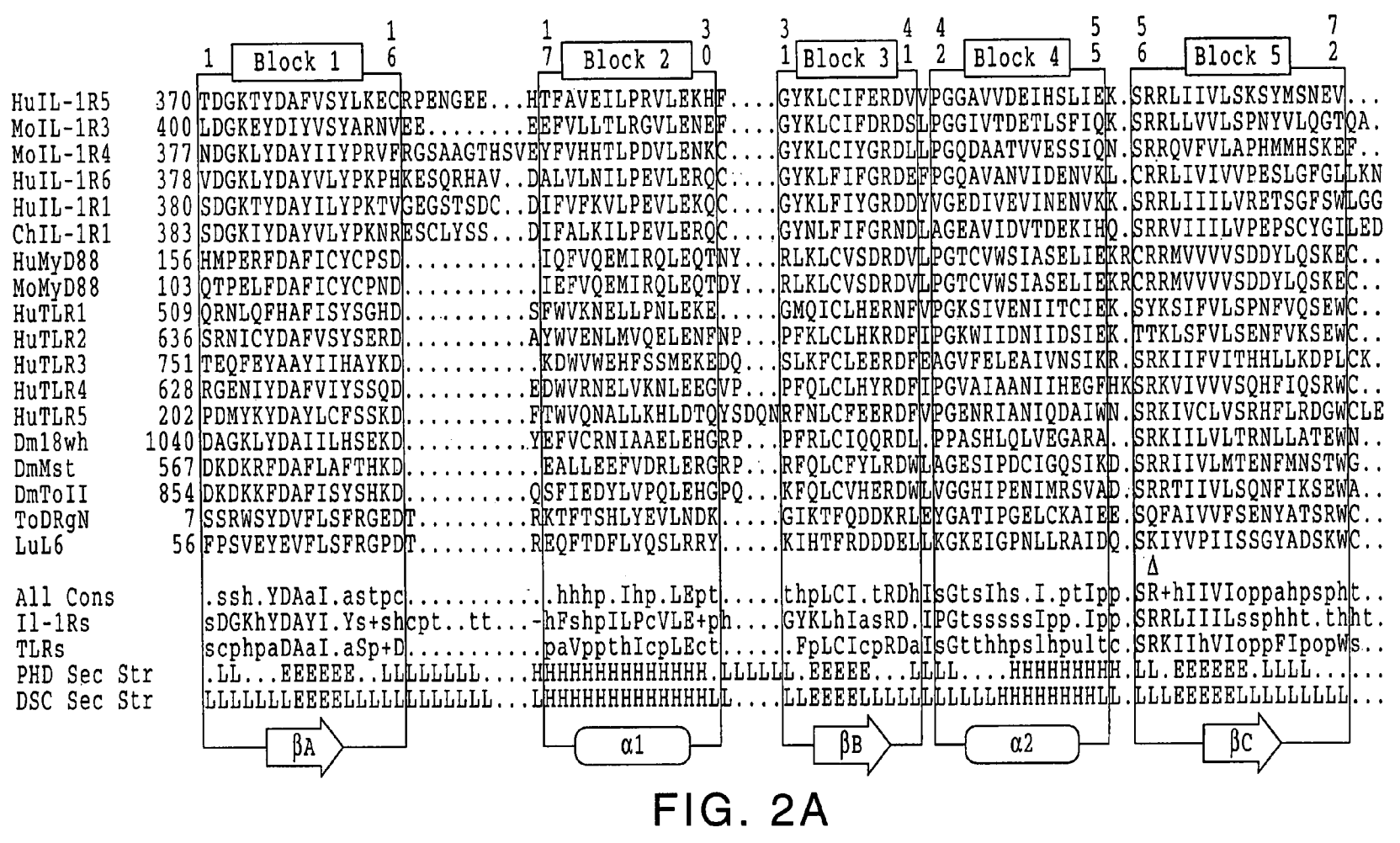
Figure 2B:
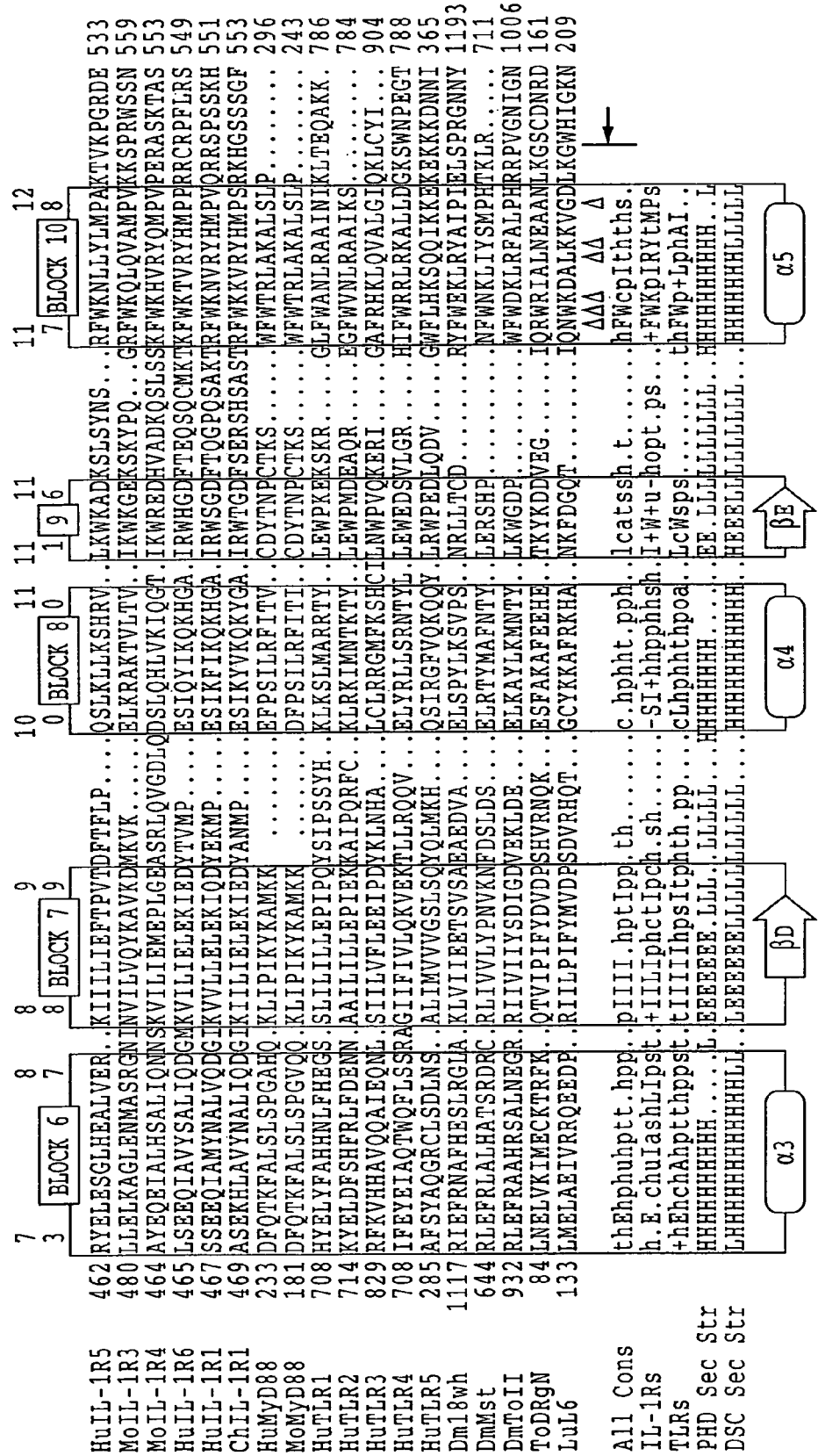

Two prediction algorithms that take advantage of the patterns of conservation and variation in multiply aligned sequences, PHD (Rost and Sander, Proteins 19, 55 (1994)) and DSC (King and Sternberg, Protein Sci. 5, 2298 (1996)), produced strong, concordant results for the TH signaling module (FIGS. 2A-2B). Each block contains a discrete secondary structural element: the imprint of alternating β-strands (labeled A-E) and α-helices (numbered 1-5) is diagnostic of a β/α-class fold with α-helices on both faces of a parallel β-sheet. Hydrophobic β-strands A, C and D are predicted to form 'interior' staves in the β-sheet, while the shorter, amphipathic β-strands B and E resemble typical 'edge' units (FIGS. 2A-2B). This assignment is consistent with a strand order of B-A-C-D-E in the core β-sheet (FIG. 2C); fold comparison ('mapping') and recognition ('threading') programs (Fischer, et al., FASEB J. 10, 126 (1996)) strongly return this doubly wound β/α topology. A surprising, functional prediction of this outline structure for the TH domain is that many of the conserved, charged residues in the multiple alignment map to the C-terminal end of the β-sheet: residue Asp16 (block numbering scheme—FIGS. 2A-2B) at the end of βA, Arg39 and Asp40 following βB, Glu75 in the first turn of α3, and the more loosely conserved Glu/Asp residues in the βD-α4 loop, or after βE (FIGS. 2A-2B). The location of four other conserved residues (Asp7, Glu28, and the Arg57-Arg/Lys58 pair) is compatible with a salt bridge network at the opposite, N-terminal end of the β-sheet (FIGS. 2A-2B). Alignment of the other TLR embodiments exhibit similar features, and peptide segments comprising these feataures, e.g., 20 amino acid segments containing them, are particularly important.

Signaling function depends on the structural integrity of the TH domain. Inactivating mutations or deletions within the module boundaries (FIGS. 2A-2B) have been catalogued for IL-1R1 and Toll (Heguy, et al., J. Biol. Chem. 267, 2605 (1992); Croston, et al., J. Biol. Chem. 270, 16514 (1995); Schneider, et al., Genes Develop. 5, 797 (1991); Norris and Manley, Genes Develop. 6, 1654 (1992); Norris and Manley, Genes Develop. 9, 358 (1995); Norris and Manley, Genes Develop. 10, 862 (1996)). The human TLR1-5 chains extending past the minimal TH domain (8, 0, 6, 22 and 18 residue lengths, respectively) are most closely similar to the stubby, 4 aa 'tail' of the Mst ORF. Toll and 18w display unrelated 102 and 207 residue tails (FIGS. 2A-2B) that may negatively regulate the signaling of the fused TH domains (Norris and Manley, Genes Develop. 9, 358 (1995); Norris and Manley, Genes Develop. 10, 862 (1996)).

Figure 3:
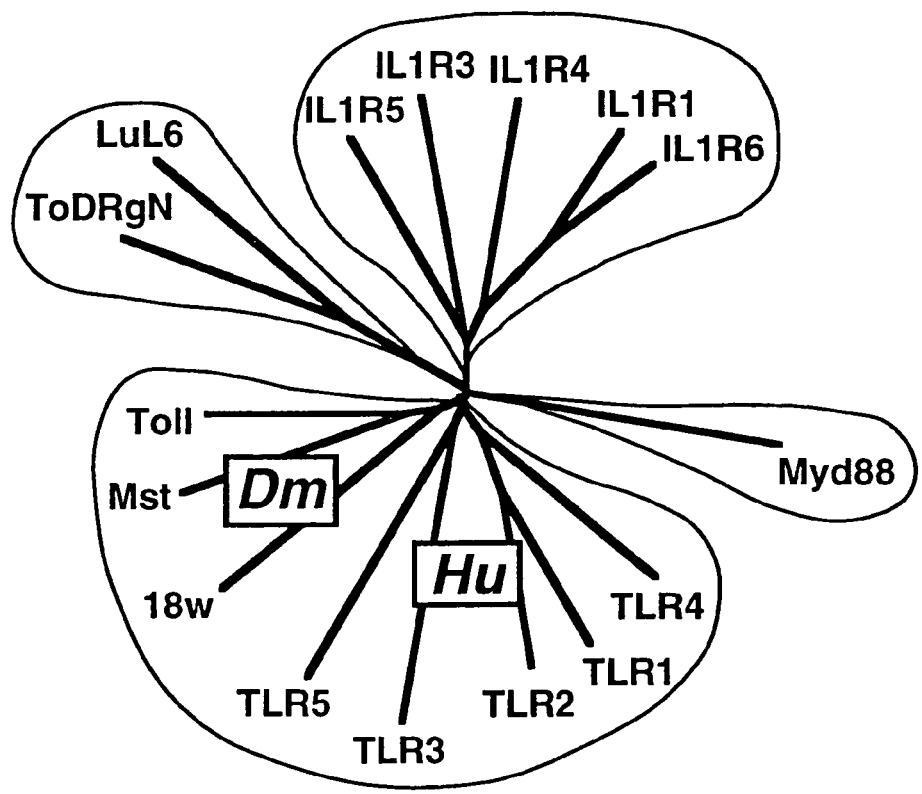
FIG. 3 shows evolution of a signaling domain superfamily. The multiple TH module alignment of FIGS. 2A-2B was used to derive a phylogenetic tree by the Neighbor-Joining method (Thompson, et al., Nucleic Acids Res. 22,4673 (1994)). Proteins labeled as in the alignment; the tree was rendered with TreeView.
Figure 4A:
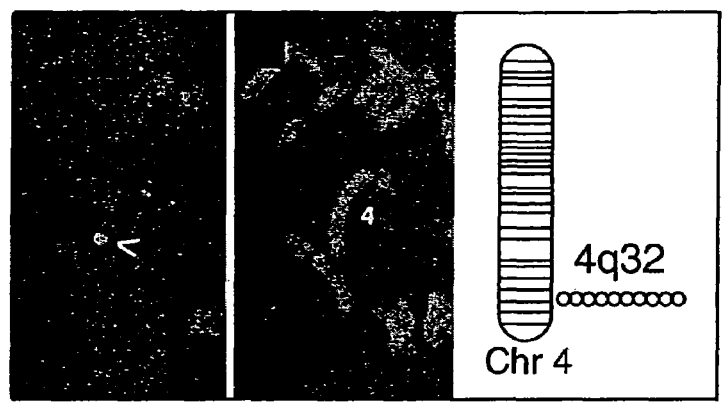
FIGS. 4A-4D depict FISH chromosomal mapping of human TLR genes. Denatured chromosomes from synchronous cultures of human lymphocytes were hybridized to biotinylated TLR cDNA probes for localization. The assignment of the FISH mapping data (left, FIGS. 4A, TLR2; 4B, TLR3; 4C, TLR4; 4D, TLR5) with chromosomal bands was achieved by superimposing FISH signals with DAPI banded chromosomes (center panels) (Heng and Tsui, Meth. Molec. Biol. 33, 109 (1994)). Analyses are summarized in the form of human chromosome ideograms (right panels).
Figure 4B:
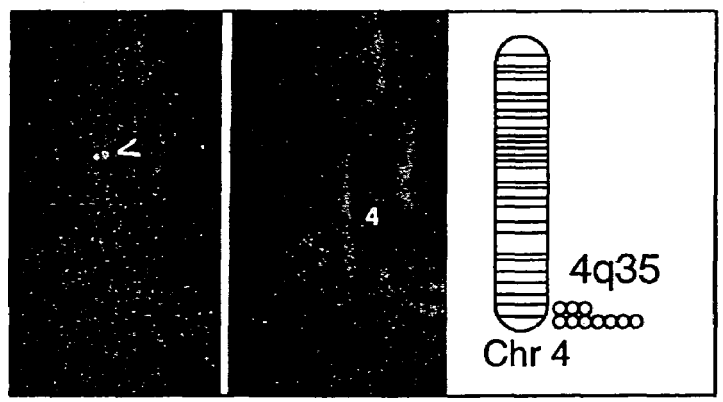
Figure 4C:
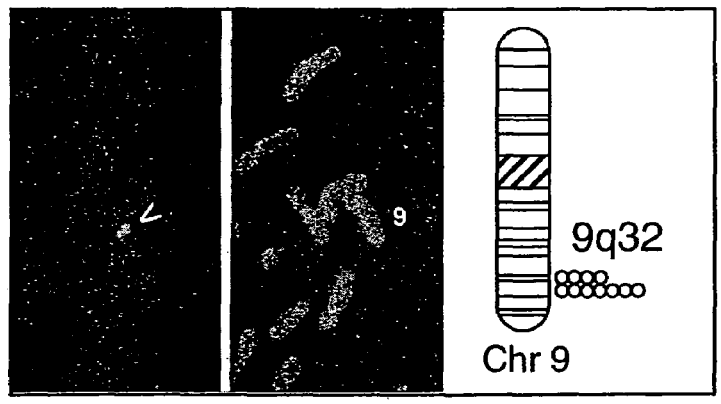
Figure 4D:
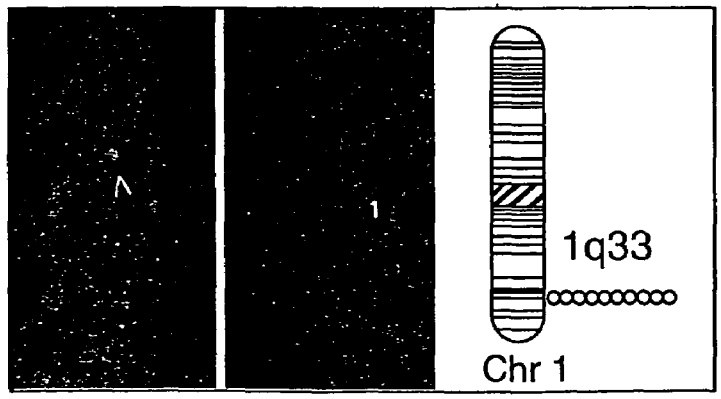

The evolutionary relationship between the disparate proteins that carry the TH domain can best be discerned by a phylogenetic tree derived from the multiple alignment (FIG. 3). Four principal branches segregate the plant proteins, the MyD88 factors, IL-1 receptors, and Toll-like molecules; the latter branch clusters the *Drosophila* and human TLRs.

Chromosomal Dispersal of Human TLR Genes.

In order to investigate the genetic linkage of the nascent human TLR gene family, we mapped the chromosomal loci of four of the five genes by FISH (FIG. 4). The TLR1 gene has previously been charted by the human genome project: an STS database locus (dbSTS accession number G06709, corresponding to STS WI-7804 or SHGC-12827) exists for the Hurnrsc786 cDNA (Nomura, et al., DNA Res. 1, 27 (1994)) and fixes the gene to chromosome 4 marker interval D4S1587-D42405 (50-56 cM) circa 4p14. This assignment has recently been corroborated by FISH analysis. Taguchi, et al., Genomics 32, 486 (1996). In the present work, we reliably assign the remaining TLR genes to loci on chromosome 4q32 (TLR2), 4q35 (TLR3), 9q32-33 (TLR4) and 1q33.3 (TLR5). During the course of this work, an STS for the parent TLR2 EST (cloneID #80633) has been generated (dbSTS accession number T57791 for STS SHGC-33147) and maps to the chromosome 4 marker interval D4S424-D4S1548 (143-153 cM) at 4q32-in accord with our findings. There is a ~50 cM gap between TLR2 and TLR3 genes on the long arm of chromosome 4.

TLR Genes are Differentially Expressed.

Both Toll and 18w have complex spatial and temporal patterns of expression in *Drosophila* that may point to functions beyond embryonic patterning (St. Johnston and Nüsslein-Volhard, Cell 68, 201 (1992); Morisato and Anderson, Ann. Rev. Genet. 29, 371 (1995); Belvin and Anderson, Ann. Rev. Cell Develop. Biol. 12, 393 (1996); Lemaitre, et al., Cell 86, 973 (1996); Chiang and Beachy, Mech. Develop. 47, 225 (1994); Eldon, et al., Develop. 120, 885 (1994)). We have examined the spatial distribution of TLR transcripts by mRNA blot analysis with varied human tissue and cancer cell lines using radiolabeled TLR cDNAs (FIG. 5). TLR1 is found to be ubiquitously expressed, and at higher levels than the other receptors. Presumably reflecting alternative splicing, 'short' 3.0 kB and 'long' 8.0 kB TLR1 transcript forms are present in ovary and spleen, respectively (FIG. 5, panels A and B). A cancer cell mRNA panel also shows the prominent overexpression of TLR1 in a Burkitt's Lymphoma Raji cell line (FIG. 5, panel C). TLR2 mRNA is less widely expressed than TLR1, with a 4.0 kB species detected in lung and a 4.4 kB transcript evident in heart, brain and muscle. The tissue distribution pattern of TLR3 echoes that of TLR2 (FIG. 5, panel E). TLR3 is also present as two major transcripts of approximately 4.0 and 6.0 kB in size, and the highest levels of expression are observed in placenta and pancreas. By contrast, TLR4 and TLR5 messages appear to be extremely tissue-specific. TLR4 was detected only in placenta as a single transcript of 7.0 kB in size. A faint 4.0 kB signal was observed for TLR5 in ovary and peripheral blood monocytes.

Components of an Evolutionarily Ancient Regulatory System.

The original molecular blueprints and divergent fates of signaling pathways can be reconstructed by comparative genomic approaches (Miklos and Rubin, Cell 86, 521 (1996); Chothia, Develop. 1994 Suppl., 27 (1994); Banfi, et al., Nature Genet. 13, 167 (1996); Wang, et al., J. Biol. Chem. 271, 4468 (1996)). We have used this logic to identify an-emergent gene family in humans, encoding five receptor paralogs at present, TLRs. 1-5, that are the direct evolutionary counterparts of a Drosophila gene family headed by Toll (FIGS. 1-3). The conserved architecture of human and fly TLRs, conserved LRR ectodomains and intracellular TH modules (FIG. 1), intimates that the robust pathway coupled to Toll in *Drosophila* (6, 7) survives in vertebrates. The best evidence borrows from a reiterated pathway: the manifold IL-1 system and its repertoire of receptor-fused TH domains, IRAK, NF-κB and I-κB homologs (Belvin and Anderson, Ann. Rev. Cell Develop. Biol. 12, 393 (1996); Wasserman, Molec. Biol. Cell 4, 767 (1993); Hardiman, et al., Oncogene 13, 2467 (1996); Cao, et al., Science 271, 1128 (1996)); a Tube-like factor has also been characterized. It is not known whether TLRs can productively couple to the IL-1R signaling machinery, or instead, a parallel set of proteins is used. Differently from IL-1 receptors, the LRR cradle of human TLRs is predicted to retain an affinity for Spatzle/Trunk-related cystine-knot factors; candidate TLR ligands (called PENs) that fit this mold have been isolated.

Biochemical mechanisms of signal transduction can be gauged by the conservation of interacting protein folds in a pathway (Miklos and Rubin, Cell 86, 521 (1996); Chothia, Develop. 1994 Suppl., 27 (1994)). At present, the Toll signaling paradigm involves some molecules whose roles are narrowly defined by their structures, actions or fates:

Pelle is a Ser/Thr kinase (phosphorylation), Dorsal is an NF-κB-like transcription factor (DNA-binding) and Cactus is an ankyrin-repeat inhibitor (Dorsal binding, degradation) (Belvin and Anderson, Ann. Rev. Cell Develop. Biol. 12, 393 (1996)). By contrast, the functions of the Toll TH domain and Tube remain enigmatic. Like other cytokine receptors (Heldin, Cell 80, 213 (1995)), ligand-mediated dimerization of Toll appears to be the triggering event: free cysteines in the juxtamembrane region of Toll create constitutively active receptor pairs (Schneider, et al., Genes Develop. 5, 797 (1991)), and chimeric Torso-Toll receptors signal as dimers (Galindo, et al., Develop. 121, 2209 (1995)); yet, severe truncations or wholesale loss of the Toll ectodomain results in promiscuous intracellular signaling (Norris and Manley, Genes Develop. 9, 358 (1995); Winans and Hashimoto, Molec. Biol. Cell 6, 587 (1995)), reminiscent of oncogenic receptors with catalytic domains (Heldin, Cell 80, 213 (1995)). Tube is membrane-localized, engages the N-terminal (death) domain of Pelle and is phosphorylated, but neither Toll-Tube or Toll-Pelle interactions are registered by two-hybrid analysis (Galindo, et al., Develop. 121, 2209 (1995); Groβhans, et al., Nature 372, 563 (1994)); this latter result suggests that the conformational 'state' of the Toll TH domain somehow affects factor recruitment (Norris and Manley, Genes Develop. 10, 862 (1996); and Galindo, et al., Develop. 121, 2209 (1995)).

Figure 2C:
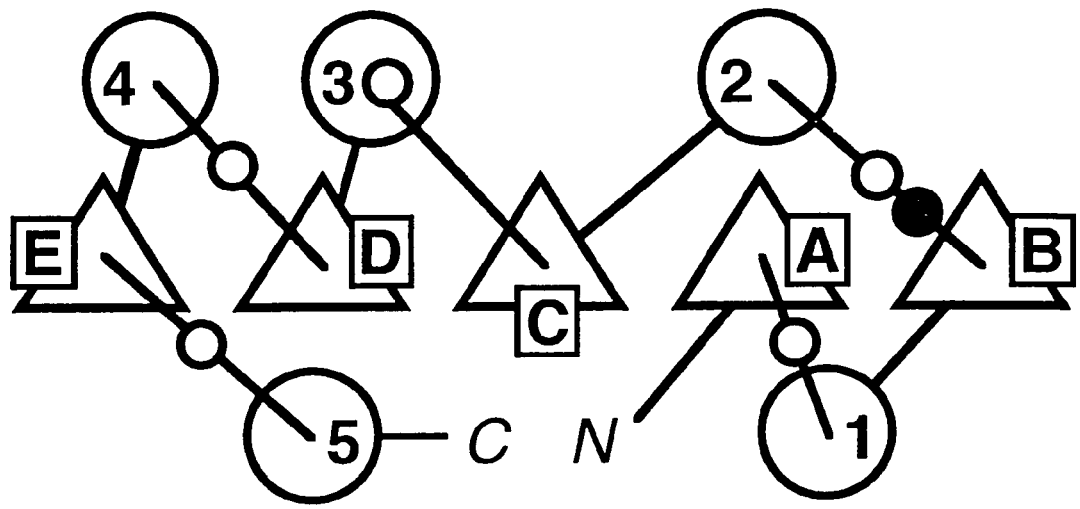

At the heart of these vexing issues is the structural nature of the Toll TH module. To address this question, we have taken advantage of the evolutionary diversity of TH sequences from insects, plants and vertebrates, incorporating the human TLR chains, and extracted the minimal, conserved protein core for structure prediction and fold recognition (FIG. 2). The strongly predicted $(\beta/\alpha)_5$ TH domain fold with its asymmetric cluster of acidic residues is topologically identical to the structures of response regulators in bacterial two-component signaling pathways (Volz, Biochemistry 32, 11741 (1993); and Parkinson, Cell 73, 857 (1993)) (FIGS. 2A-2C). The prototype chemotaxis regulator CheY transiently binds a divalent cation in an 'aspartate pocket' at the C-end of the core β-sheet; this cation provides electrostatic stability and facilitates the activating phosphorylation of an invariant Asp (Volz, Biochemistry 32, 11741 (1993)). Likewise, the TH domain may capture cations in its acidic nest, but activation, and downstream signaling, could depend on the specific binding of a negatively charged moiety: anionic ligands can overcome intensely negative binding-site potentials by locking into precise hydrogen-bond networks (Ledvina, et al., Proc. Natl. Acad. Sci. USA 93, 6786 (1996)). Intriguingly, the TH domain may not simply act as a passive scaffold for the assembly of a Tube/Pelle complex for Toll, or homologous systems in plants and vertebrates, but instead actively participate as a true conformational trigger in the signal transducing machinery. Perhaps explaining the conditional binding of a Tube/Pelle complex, Toll dimerization could promote unmasking, by regulatory receptor tails (Norris and Manley, Genes Develop. 9, 358 (1995); Norris and Manley, Genes Develop. 10, 862 (1996)), or binding by small molecule activators of the TH pocket. However, 'free' TH modules inside the cell (Norris and Manley, Genes Develop. 9, 358 (1995); Winans and Hashimoto, Molec. Biol. Cell 6, 587 (1995)) could act as catalytic, CheY-like triggers by activating and docking with errant Tube/Pelle complexes.

Morphogenetic Receptors and Immune Defense.

The evolutionary link between insect and vertebrate immune systems is stamped in DNA: genes encoding anti-microbial factors in insects display upstream motifs similar to acute phase response elements known to bind NF-κB transcription factors in mammals (Hultmark, Trends Genet. 9, 178 (1993)). Dorsal, and two Dorsal-related factors, Dif and Relish, help induce these defense proteins after bacterial challenge (Reichhart, et al., C. R. Acad. Sci. Paris 316, 1218 (1993); Ip, et al., Cell 75, 753 (1993); Dushay, et al., Proc. Natl. Acad. Sci. USA 93, 10343 (1996)); Toll, or other TLRs, likely modulate these rapid immune responses in adult *Drosophila* (Lemaitre, et al. (1996) Cell 86:973-983; Rosetto, et al., Biochem. Biophys. Res. Commun. 209, 111 (1995)). These mechanistic parallels to the IL-1 inflammatory response in vertebrates are evidence of the functional versatility of the Toll signaling pathway, and suggest an ancient synergy between embryonic patterning and innate immunity (Belvin and Anderson, Ann. Rev. Cell Develop. Biol. 12, 393 (1996); Lemaitre, et al., Cell 86, 973 (1996); Wasserman, Molec. Biol. Cell 4, 767 (1993); Wilson, et al., Curr. Biol. 7, 175 (1997); Hultmark, Trends Genet. 9, 178 (1993); Reichhart, et al., C. R. Acad. Sci. Paris 316, 1218 (1993); Ip, et al., Cell 75, 753 (1993); Dushay, et al., Proc. Natl. Acad. Sci. USA 93, 10343 (1996); Rosetto, et al., Biochem. Biophys. Res. Commun. 209, 111 (1995); Medzhitov and Janeway, Curr. Opin. Immunol. 9, 4 (1997)). The closer homology of insect and human TLR proteins invites an even stronger overlap of biological functions that supersedes the purely immune parallels to IL-1 systems, and lends potential molecular regulators to dorso-ventral and other transformations of vertebrate embryos (DeRobertis and Sasai, Nature 380, 37 (1996); Arendt and Nubler-Jung, Mech. Develop. 61, 7 (1997)).

The present description of an emergent, robust receptor family in humans mirrors the recent discovery of the vertebrate Frizzled receptors for Wnt patterning factors. Wang, et al., J. Biol. Chem. 271, 4468 (1996). As numerous other cytokine-receptor systems have roles in early development (Lemaire and Kodjabachian, Trends Genet. 12, 525 (1996)), perhaps the distinct cellular contexts of compact embryos and gangly adults simply result in familiar signaling pathways and their diffusible triggers having different biological outcomes at different times, e.g., morphogenesis versus immune defense for TLRs. For insect, plant, and human Toll-related systems (Hardiman, et al., Oncogene 13, 2467 (1996); Wilson, et al., Curr. Biol. 7, 175 (1997), these signals course through a regulatory TH domain that intriguingly resembles a bacterial transducing engine (Parkinson, Cell 73, 857 (1993)).

In particular, the TLR6 exhibits structural features which establish its membership in the family. Moreover, members of the family have been implicated in a number of significant developmental disease conditions and with function of the innate immune system. In particular, the TLR6 has been mapped to the X chromosome to a location which is a hot spot for major developmental abnormalities. See, e.g., The Sanger Center: human X chromosome website http://www.sanger.ac.uk/HGP/ChrX/index.shtml; and the Baylor College of Medicine Human Genome Sequencing website http://gc.bcm.tmc.edu:8088/cgi-bin/seq/home.

The accession number for the deposited PAC is AC003046. This accession number contains sequence from two PACs: RPC-164K3 and RPC-263P4. These two PAC sequences mapped on human chromosome Xp22 at the Baylor web site between STS markers DXS704 and DXS7166. This region is a "hot spot" for severe developmental abnormalities.

Example III

Amplification of TLR Fragment by PCR

Two appropriate primer sequences are selected (see Tables 1 through 10). RT-PCR is used on an appropriate mRNA sample selected for the presence of message to produce a partial or full length cDNA, e.g., a sample which expresses the gene. See, e.g., Innis, et al., PCR Protocols: A Guide to Methods and Applications, Academic Press, San Diego, Calif. (1990); and Dieffenbach and Dveksler, PCR Primer: A Laboratory Manual, Cold Spring Harbor Press, Cold Spring Harbor, N.Y. (1995). Such will allow determination of a useful sequence to probe for a full length gene in a cDNA library. The TLR6 is a contiguous sequence in the genome, which may suggest that the other TLRs are also. Thus, PCR on genomic DNA may yield full length contiguous sequence, and chromosome walking methodology would then be applicable. Alternatively, sequence databases will contain sequence corresponding to portions of the described embodiments, or closely related forms, e.g., alternative splicing, etc. Expression cloning techniques also may be applied on cDNA libraries.

Example IV

Tissue Distribution of TLRs

Message for each gene encoding these TLRs has been detected. See FIGS. 5A-5F. Other cells and tissues will be assayed by appropriate technology, e.g., PCR, immunoassay, hybridization, or otherwise. Tissue and organ cDNA preparations are available, e.g., from Clontech, Mountain View, Calif. Identification of sources of natural expression are useful, as described.

Southern Analysis: DNA (5 μg) from a primary amplified cDNA library is digested with appropriate restriction enzymes to release the inserts, run on a 1% agarose gel and transferred to a nylon membrane (Schleicher and Schuell, Keene, N.H.).

Samples for human mRNA isolation would typically include, e.g.: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (Ti09); T cell, TH2 clone HY935, resting (T110); T cell, TH2 clone HY935, activated with anti-CD28 and anti-CD3 for 2, 7, 12 h pooled (T111); T cells CD4+ CD45RO-T cells polarized 27 days in anti-CD28, IL-4, and anti IFN-γ, TH2 polarized, activated with anti-CD3 and anti-CD28 4 h (T116); T cell tumor lines Jurkat and Hut78, resting (T117); T cell clones, pooled AD130.2, Tc783.12, Tc783.13, Tc783.58, Tc782.69, resting (T118); T cell random γδT cell clones, resting (T119); Splenocytes, resting (B100); Splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); NK cytotoxic clone 640-A30-1, resting (K107); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFNγ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); DC 70% CD1a+, from CD34+ GM-CSF, TNFα 12 days, resting (D101); DC 70% CD1a+, from CD34+ GM-CSF, TNFα 12 days, activated with PMA and ionomycin for 1 hr (D102); DC 70% CD1a+, from CD34+ GM-CSF, TNFα 12 days, activated with PMA and ionomycin for 6 hr (D103); DC 95% CD1a+, from CD34+ GM-CSF, TNFα 12 days FACS sorted, activated with PMA and ionomycin for 1, 6 h pooled (D 104); DC 95% CD14+, ex CD34+ GM-CSF, TNFα 12 days FACS sorted, activated with PMA and ionomycin 1, 6 hr pooled (D105); DC CD1a+CD86+, from CD34+ GM-CSF, TNFα 12 days FACS sorted, activated with PMA and ionomycin for 1, 6 h pooled (D106); DC from monocytes GM-CSF, IL-4 5 days, resting (D107); DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFα, monocyte supe for 4, 16 h pooled (D110); leiomyoma L11 benign tumor (X101); normal myometrium M5 (O115); malignant leiomyosarcoma GS1 (X103); lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102); kidney fetal 28 wk male (O100); lung fetal 28 wk male (O101); liver fetal 28 wk male (O102); heart fetal 28 wk male (O103); brain fetal 28 wk male (O104); gallbladder fetal 28 wk male (O106); small intestine fetal 28 wk male (O107); adipose tissue fetal 28 wk male (O108); ovary fetal 25 wk female (O109); uterus fetal 25 wk female (O110); testes fetal 28 wk male (O111); spleen fetal 28 wk male (O112); adult placenta 28 wk (O113); and tonsil inflamed, from 12 year old (X100).

Samples for mouse mRNA isolation can include, e.g.: resting mouse fibroblastic L cell line (C200); Braf:ER (Braf fusion to estrogen receptor) transfected cells, control (C201); T cells, TH1 polarized (Mel14 bright, CD4+ cells from spleen, polarized for 7 days with IFN-γ and anti IL-4; T200); T cells, TH2 polarized (Mel14 bright, CD4+ cells from spleen, polarized for 7 days with IL-4 and anti-IFN-γ; T201); T cells, highly TH1 polarized (see Openshaw, et al., J. Exp. Med. 182, 1357 (1995); activated with anti-CD3 for 2, 6, 16 h pooled; T202); T cells, highly TH2 polarized (Openshaw, et al., J. Exp. Med. 182, 1357 (1995)); activated with anti-CD3 for 2, 6, 16 h pooled; T203); CD44-CD25+ pre T cells, sorted from thymus (T204); TH1 T cell clone D1.1, resting for 3 weeks after last stimulation with antigen (T205); TH1 T cell clone D1.1, 10 μg/ml ConA stimulated 15 h (T206); TH2 T cell clone CDC35, resting for 3 weeks after last stimulation with antigen (T207); TH2 T cell clone CDC35, 10 μg/ml ConA stimulated 15 h (T208); Mel14+ naive T cells from spleen, resting (T209); Mel14+ T cells, polarized to Th1 with IFN-γ/IL-12/anti-IL-4 for 6, 12, 24 h pooled (T210); Mel14+ T cells, polarized to Th2 with IL-4/anti-IFN-γ for 6, 13, 24 h pooled (T211); unstimulated mature B cell leukemia cell line A20 (B200); unstimulated B cell line CH12 (B201); unstimulated large B cells from spleen (B202); B cells from total spleen, LPS activated (B203); metrizamide enriched dendritic cells from spleen, resting (D200); dendritic cells from bone marrow, resting (D201); monocyte cell line RAW 264.7 activated with LPS 4 h (M200); bone-marrow macrophages derived with GM and M-CSF (M201); macrophage cell line J774, resting (M202); macrophage cell line J774+LPS+anti-IL-10 at 0.5, 1, 3, 6, 12 h pooled (M203); macrophage cell line J774+ LPS+IL-10 at 0.5, 1, 3, 5, 12 h pooled(M204); aerosol challenged mouse lung tissue, Th2 primers, aerosol OVA challenge 7, 14, 23 h pooled (see Garlisi, et al., Clinical Immunology and Immunopathology 75, 75(1995); X206); Nippostrongulus-infected lung tissue (see Coffman, et al., Science 245, 308 (1989); X200); total adult lung, normal (O200); total lung, rag-1 (Schwarz, et al., Immunodeficiency 4, 249 (1993)); O205); IL-10 K.O. spleen (see Kuhn, et al., Cell 75, 263 (1991); X201); total adult spleen, normal (O201); total spleen, rag-1 (O207); IL-10 K.O. Peyer's patches (O202); total Peyer's patches, normal (O210); IL-10 K.O. mesenteric lymph nodes (X203); total mesenteric lymph nodes, normal (O211); IL-10 K.O. colon (X203); total colon, normal (O212); NOD mouse pancreas (see Makino, et al., Jikken Dobutsu 29, 1 (1980); X205); total thymus, rag-1 (O208); total kidney, rag-1 (O209); total heart, rag-i (O202); total brain, rag-1 (O203); total testes, rag-1 (O204); total liver, rag-1 (O206); rat normal joint tissue (O300); and rat arthritic joint tissue (X300).

The TLR10 has been found to be highly expressed in precursor dendritic cell type 2 (pDC2). See, e.g., Rissoan, et al., Science 283, 1183 (1999); and Siegal, et al., Science 284, 1835 (1999). However, it is not expressed on monocytes. The restricted expression of TLR10 reinforces the suggestions of a role for the receptor in host immune defense. The pDC2 cells are natural interferon producing cells (NIPC), which produce large amounts of IFNα in response to Herpes simplex virus infection.

Example V

Cloning of Species Counterparts of TLRs

Various strategies are used to obtain species counterparts of these TLRs, preferably from other primates. One method is by cross hybridization using closely related species DNA probes. It may be useful to go into evolutionarily similar species as intermediate steps. Another method is by using specific PCR primers based on the identification of blocks of similarity or difference between particular species, e.g., human, genes, e.g., areas of highly conserved or nonconserved polypeptide or nucleotide sequence. Alternatively, antibodies may be used for expression cloning.

Example VI

Production of Mammalian TLR Protein

An appropriate, e.g., GST, fusion construct is engineered for expression, e.g., in E. coli. For example, a mouse IGIF pGex plasmid is constructed and transformed into E. coli. Freshly transformed cells are grown in LB medium containing 50 µg/ml ampicillin and induced with IPTG (Sigma, St. Louis, Mo.). After overnight induction, the bacteria are harvested and the pellets containing the TLR protein are isolated. The pellets are homogenized in TE buffer (50 mM Tris-base pH 8.0, 10 mM EDTA and 2 mM pefabloc) in 2 liters. This material is passed through a microfluidizer (Microfluidics, Newton, Mass.) three times. The fluidized supernatant is centrifuged in a Sorvall GS-3 rotor for 1 h at 13,000 rpm. The resulting supernatant containing the TLR protein is filtered and passed over a glutathione-SEPHAROSE column equilibrated in 50 mM Tris-base pH 8.0. The fractions containing the TLR-GST fusion protein are pooled and cleaved with thrombin (Enzyme Research Laboratories, Inc., South Bend, Ind.). The cleaved pool is then passed over a Q-SEPHAROSE column equilibrated in 50 mM Tris-base. Fractions containing TLR are pooled and diluted in cold distilled H20, to lower the conductivity, and passed back over a fresh Q-Sepharose column, alone or in succession with an immunoaffinity antibody column. Fractions containing the TLR protein are pooled, aliquoted, and stored in the −70° C. freezer.

Comparison of the CD spectrum with TLR1 protein may suggest that the protein is correctly folded (Hazuda, et al., J. Biol. Chem. 264, 1689 (1969)).

Example VII

Biological Assays with TLRs

Biological assays will generally be directed to the ligand binding feature of the protein or to the kinase/phosphatase activity of the receptor. The activity will typically be reversible, as are many other enzyme actions, and will mediate phosphatase or phosphorylase activities, which activities are easily measured by standard procedures. See, e.g., Hardie, et al., The Protein Kinase FactBook vols. I and II, Academic Press, San Diego (1995), Calif.; Hanks, et al., Meth. Enzymol. 200, 38 (1991); Hunter, et al., Cell 70, 375 (1992); Lewin, Cell 61, 743-752 (1990); Pines, et al. (1991) Cold Spring Harbor Symp. Quant. Biol. 56, 449 (1991); and Parker, et al., Nature 363, 736 (1993). Because of the homology of the cytoplasmic domain of the Toll receptor and the cytoplasmic domain of the IL-1 receptor, assays sensitive to IL-1 receptor activity may be suitable for measuring activity of TLRs. A review of IL-1 receptor mediated activities is available (Dinarello, Blood 87, 2095 (1996)).

Example VIII

Preparation of Antibodies Specific for TLR, e.g., TLR4

Inbred Balb/c mice are immunized intraperitoneally with recombinant forms of the protein, e.g., purified TLR4 or stable transfected NIH-3T3 cells. Animals are boosted at appropriate time points with protein, with or without additional adjuvant, to further stimulate antibody production. Serum is collected, or hybridomas produced with harvested spleens.

Alternatively, Balb/c mice are immunized with cells transformed with the gene or fragments thereof, either endogenous or exogenous cells, or with isolated membranes enriched for expression of the antigen. Serum is collected at the appropriate time, typically after numerous further administrations. Various gene therapy techniques may be useful, e.g., in producing protein in situ, for generating an immune response.

Monoclonal antibodies may be made. For example, splenocytes are fused with an appropriate fusion partner and hybridomas are selected in growth medium by standard procedures. Hybridoma supernatants are screened for the presence of antibodies which bind to the desired TLR, e.g., by ELISA or other assay. Antibodies which specifically recognize specific TLR embodiments may also be selected or prepared.

In another method, synthetic peptides or purified protein are presented to an immune system to generate monoclonal or polyclonal antibodies. See, e.g., Coligan, Current Protocols in Immunology Wiley/Greene (1991); and Harlow and Lane, Antibodies: A Laboratory Manual Cold Spring Harbor Press (1989). In appropriate situations, the binding reagent is either labeled as described above, e.g., fluorescence or otherwise, or immobilized to a substrate for panning methods. Nucleic acids may also be introduced into cells in an animal to produce the antigen, which serves to elicit an immune response. See, e.g., Wang, et al., Proc. Nat'l. Acad. Sci. 90, 4156 (1993); Barry, et al., BioTechniques 16, 616 (1994); and Xiang, et al., Immunity 2, 129 (1995).

Example IX

Production of Fusion Proteins with TLR, e.g., TLR5

Various fusion constructs are made with TLR5. This portion of the gene is fused to an epitope tag, e.g., a FLAG tag, or to a two hybrid system construct. See, e.g., Fields and Song, Nature 340, 245 (1989).

The epitope tag may be used in an expression cloning procedure with detection with anti-FLAG antibodies to detect a binding partner, e.g., ligand for the respective TLR5. The two hybrid system may also be used to isolate proteins which specifically bind to TLR5.

Example X

Chromosomal Mapping of TLRs

Chromosome spreads are prepared. In situ hybridization is performed on chromosome preparations obtained from phytohemagglutinin-stimulated lymphocytes cultured for 72 h. 5-bromodeoxyuridine is added for the final seven hours of culture (60 µg/ml of medium), to ensure a posthybridization chromosomal banding of good quality.

An appropriate fragment, e.g., a PCR fragment, amplified with the help of primers on total B cell cDNA template, is cloned into an appropriate vector. The vector is labeled by nick-translation with $^3$H. The radiolabeled probe is hybridized to metaphase spreads as described by Mattei, et al., Hum. Genet. 69, 327 (1985).

After coating with nuclear track emulsion (KODAK NTB$_2$), slides are exposed, e.g., for 18 days at 4° C. To avoid any slipping of silver grains during the banding procedure, chromosome spreads are first stained with buffered Giemsa solution and metaphase photographed.

R-banding is then performed by the fluorochrome-photolysis-Giemsa (FPG) method and metaphases rephotographed before analysis.

Alternatively, FISH can be performed, as described above. The TLR genes are located on different chromosomes. TLR2 and TLR3 are localized to human chromosome 4; TLR4 is localized to human chromosome 9, and TLR5 is localized to human chromosome 1. See FIGS. 4A-4D.

Example XI

Isolation of a Ligand for a TLR

A TLR can be used as a specific binding reagent to identify its binding partner, by taking advantage of its specificity of binding, much like an antibody would be used. A binding reagent is either labeled as described above, e.g., fluorescence or otherwise, or immobilized to a substrate for panning methods.

The binding composition is used to screen an expression library made from a cell line which expresses a binding partner, i.e., ligand, preferably membrane associated. Standard staining techniques are used to detect or sort surface expressed ligand, or surface expressing transformed cells are screened by panning. Screening of intracellular expression is performed by various staining or immunofluorescence procedures. See also McMahan, et al., EMBO J. 10, 2821 (1991).

For example, on day 0, precoat 2-chamber permanox slides with 1 ml per chamber of fibronectin, 10 ng/ml in PBS, for 30 min at room temperature. Rinse once with PBS. Then plate COS cells at 2-3×10$^5$ cells per chamber in 1.5 ml of growth media. Incubate overnight at 37° C.

On day 1 for each sample, prepare 0.5 ml of a solution of 66 µg/ml DEAE-dextran, 66 µM chloroquine, and 4 µg DNA in serum free DME. For each set, a positive control is prepared, e.g., of TLR-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde/glucose for 5 min. Wash 3× with HBSS. The slides may be stored at −80° C. after all liquid is removed. For each chamber, 0.5 ml incubations are performed as follows. Add HBSS/saponin (0.1%) with 32 µl/ml of 1 M NaN$_3$ for 20 min. Cells are then washed with HBSS/saponin 1×. Add appropriate TLR or TLR/antibody complex to cells and incubate for 30 min. Wash cells twice with HBSS/saponin. If appropriate, add first antibody for 30 min. Add second antibody, e.g., Vector anti-mouse antibody, at 1/200 dilution, and incubate for 30 min. Prepare ELISA solution, e.g., Vector Elite ABC horseradish peroxidase solution, and pre-incubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of H$_2$O$_2$ per 5 ml of glass distilled water. Carefully remove chamber and rinse slide in water. Air dry for a few minutes, then add 1 drop of Crystal Mount and a cover slip. Bake for 5 min at 85-90° C.

Evaluate positive staining of pools and progressively subclone to isolation of single genes responsible for the binding.

Alternatively, TLR reagents are used to affinity purify or sort out cells expressing a putative ligand. See, e.g., Sambrook, et al. or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of a TLR fusion construct, or by use of antibodies raised against the first antibodies. Recursive cycles of selection and amplification lead to enrichment of appropriate clones and eventual isolation of receptor expressing clones.

Phage expression libraries can be screened by mammalian TLRs. Appropriate label techniques, e.g., anti-FLAG antibodies, will allow specific labeling of appropriate clones.

Example XII

Differentiation of Pre-Dendritic Cells to Mature Myeloid Cells and Differentiation of Naive T Helper Cells to TH1 Cells; Differentiation of Pre-Dendritic Cells to Mature Lymphoid-type Cells and Differentiation of Naive T Helper Cells to TH2 Cells Dendritic cells participate in the innate immune system, as these cells contain Toll-like receptors which can respond to molecules specific to bacteria, such as bacterial lipopolysacchardise (endotoxin), lipoteichoic acid, and non-methylated CpG oligonucleotides. Two different types of precursors of dendritic cells can be found in humans. These are: (1) Peripheral blood monocytes (pDC1); and (2) $CD4^+CD3\text{-}CD11^-$ plasmacytoid cells (pDC2). Peripheral blood monocytes (pDC1) give rise to immature myeloid DCs after culturing with GMCSF and IL-4. These immature cells give rise to mature myeloid dendritic cells (DC1) after stimulation with CD40 ligand (CD40L). When the mature myeloid dendritic cells are cultured with naive T helper cells, the naive T helper cells become TH1 type cells, and produce TH1 type cytokines, such as IFN-γ (Rissoan, et al., Science 283, 1183(1999)).

$CD4^+CD3^-CD11c^-$ plasmacytoid cells give rise to immature lymphoid-type dendritic cell after culture with IL-3. These immature cells give rise to mature lymphoid-type dendritic cells after stimulation with CD40 ligand (CD40L). When the mature lymphoid-type dendritic cells are cultured with naive T helper cells, the naive T helper cells become $T_H2$ type cells which, in turn, produce TH2-type cytokines, such as IL-4 (Rissoan, et al., Science 283, 1183 (1999)).

The above description relates to two broad scenarios. The first involves peripheral blood monocytes (pDC1) and their role, after stimulation, to promote the conversion of naive T-helper cells to TH1 cells. The second scenario involves $CD4^{+CD}3^-CD11c^-$ plasmacytoid cells (pDC2) and their role, after stimulation, to promote the conversion of naive T-helper cells to TH2 cells. The above two pathways communicate with each other in a manner mediated by IL-4 (product of TH2 cells). With overproduction of IL-4, or during production of IL-4 during late stage in the immune response, this IL-4 inhibits the differentiation of $CD4^+CD3^-CD11c^-$ plasmacytoid cells (pDC2), and in this way feedback inhibits the production of TH2 type cells. With overproduction of IL-4, or during production of IL-4 during late stage in the immune response, the IL-4 stimulates the conversion of peripheral blood monocytes (pDC1) to immature myeloid dendritic cells, thus increasing the production of TH1 type cells (Rissoan, et al., Science 283, 1183 (1999)).

Example XIII

Natural Interferon Producing Cells

The following commentary concerns some of the characteristics of a line of $CD4^+CD3^-CD11c^-$ plasmacytoid cells, which have been found to be a type of "natural interferon producting cell." The plasmacytoid morphology has been shown by Siegal, et al., Science 284, 1835 (1999)).

"Natural interferon producing cells" (IPC) are specialized leucocytes that are the major source of interferon-α in response to viruses, bacteria, and tumor cells. Another characteristic of natural interferon producing cells (IPC) is that they express CD4 and Class II MHC. $CD4^{30}$ $CD3^-$ $CD11c^-$ type 2 cells have been identified as a type of IPC. $CD4^+CD3^-CD11c^-$ type 2 cells are dendritic cell precursors are cells that can respond to microbial challenge and, when challenged, can produce 200-1000 times more interferon than other blood-cells after microbial challenge (Siegal, et al., Science 284, 1835(1999)). Production of interferon-α occurs in resonse to Sendai virus, heat-killed Saureus, or UV-irradiated virus. The fact that the $CD4^+CD3^-CD11c^-$ type 2 cells produce interferon-α in the absence of other cells suggests that these cells are part of the innate immune system (Siegal, et al., Science 284, 1835(1999)).

Example XIV

Subsets of Precursors of Human Dendritic Cells

The following cell lines were studied: (1) $CD4^+CD3^-CD11c^+$ immature dendritic cells. Note that these are $CD11c^+$; (2) $CD4^+CD3^-CD11c^-$ plasmacytoid pre-dendritic cells (pDC2) (natural interferon producing cells). Note that these are $CD11c^-$; and (3) $CD14^+CD16^-$ monocytes (pDC1).

The above-mentioned cells are described by Rissoan, et al., Science 283, 1183 (1999) and by Siegal, et al., Science 284, 1835 (1999)).

The present study revealed the forms of Toll like receptors (TLRs) on the various cells lines, as well as the influences of various added factors on the expression of the various TLRs. These factors included: (1) GMCSF plus IL-4 on the TLRs; (2) CD40L; and (3) Interleukin-3 (IL-3).

$CD4^+CD3^-CD11c^+$ immature dendritic cells expressed high lveles of TLR1, 2, and 3, low levels of TLR 5, 6, 8, and 10, and undetectable levels of TLR 4, 7, and 9.

$CD4^+CD3^-CD11c^-$ plasmacytoid pre-dendritic cells (pDC2) expressed high levels of TLR 7 and 9, low levels of TLR 1, 6, adn 10, and undetectable levels of TLR 2, 3, 4, 5, and 8.

$CD14^+CD16^-$ monocytes (pDC1)expressed high levels of TLR 1, 2, 3, 5, and 8, low levels of TLR6, and undetectable levels of TLR 3, 7, 9, and 10.

The following concerns exposure of the cell types to various stimulants or factors. Where $CD14^+CD16^-$ monocytes (pDC1)are differentiated into immature dendritic cells by exposure to GMCSF plus IL-4, the initial high expression of TLR2 and TLR4 decreased dramatically, where further decline occurred with CD40L treatment. This decrease in TLR2 and TLR4 expression is consistent with the functional switch of the dendritic cell lineage from a microbial antigen recognition to antigen presentation (presentation to naive T cells).

$CD4^+CD3^-CD11c^+$ immature dendritic cells express moderate levels of TLR2 and TLR4, where expression decreases with exposure to CD40L.

$CD4^+CD3^-CD11c^-$ plasmacytoid pre-dendritic cells (pDC2), which do not express TLR2 or TLR4 at any stages of maturation.

$CD4^+CD3^-CD11c^-$ plasmacytoid pre-dendritic cells (pDC2)express TLR7 and TLR9, where expression of these two receptors progressively decreases with stimulation by IL-3 (to provoke differentiation to immature dendritic cells) and by CD40L (to provoke further differentiation to mature lymphoid dendritic cells).

Responses to peptidoglycan, lipopolysaccharide, lipoteichoic acid, unmethylated CpG oligonucleotides, and poly I:C were studied. Peptidoglycan (TLR2 ligand) stimulated $CD14^+CD16^-$ monocytes (pDC1) to produce TNF-α and IL-6. Peptidoglycan stimulated $CD4^+CD3^-CD11c^+$ immature dendritic cells to produce TNF-α, and small amounts of IL-6 and IL-12. Peptidoglycan did not stimulate $CD4^+CD3^-CD11c^-$ plasmacytoid pre-dendritic cells (pDC2)to produce any of the cytokines tested.

Lipotechoic acid (LTA), another TLR2 ligand, was tested. Its effects on the three cell lines did not exactly parallel those of peptidoglycan. LTA stimulated the monocytes to produce TNF-A and IL-6, but did not stimulate the $CD4^+CD3^-CD11c^+$ immature dendritic cells to produce detectable levels of the cytokines tested. LTA did not stimulate the plasmacytoid pre-dendritic cells.

Lipopolysaccharide (LPS) is a ligand for TLR-4. LPS stimulated monocytes to produce TNF-α and IL-6. LPS stimulated $CD4^+CD3^-CD11c^+$ immature dendritic cells to produce small amounts of IL-12p75, in two out of four human cell donors. LPS did not stimulate the plasmacytoid pre-dendritic cells to produce any of the cytokines tested.

Umnethylated CpG oligonucleotide (AAC-30) is a ligand for TLR9. AAC-30 did not stimulate monocytes or $CD4^+CD3^-CD11c^+$ immature dendritic cells to produce IFN-α, but did stimulate plasmacytoid pre-dendritic cells to produce IFN-α.

Poly I:C did not stimulate monocytes, and did not stimulate plasmacytoid pre-dendritic cells, but did stimulate $CD4^+CD3^-CD11c^+$ immature dendritic cells to produce IFN-α and IL-12p75. Although AAC-30 and poly I:C are both comprised on nucleic acid, they had dissimilar effects on the three cell lines tested.

Example XV

Treatment of Viral Diseases and Tumors

Interferon-α is used to treat a number of viral disease, including hepatitis B, hepatitis C, hepatitis D (Di Bisceglie, New Engl. J. Med. 330, 137 (1994); Hoofnagle and Di Bisceglie, New Engl. J. Med. 336, 347 (1997), and T-cell leukemia-lymphoma (Gill, et al., New Engl. J. Med. 332, 1744 (1995)). Interferon-α is also useful for treating multiple myeloma (Bataille and Harousseau, New Engl. J. Med. 336, 1657 (1997)) and chronic myeloid leukemia (Faderl, et al., New Engl. J. Med. 341, 164 (1999); Porter, et al., New Engl. J. Med. 330, 100 (1994)). Diseases and disease states that are responsive to treatment with interferon-α may be called interferon-α treatable conditions.

Activating antibodies (anti-TLR9) are contemplated, where these antibodies provoke plasmacytoid pre-dendritic cells to secrete interferon-a. The invention contemplates use of anti-TLR9 to provoke plasmacytoid pre-dendritic cells to secrete interferon-a for use in treating interferon-α responsive diseases, including those described above.

Example XVI

Treatment of Systemic Lupus Erythematosus by Anti-TLR9 or by Soluble TLR9

Systemic lupus erythematosus (SLE) is a disease involving elevated serum interferon-α. In SLE, complexes of anti-DNA (autoantibodies) and DNA are found in the bloodstream (Ronnblom and Alm, Trends in Immunol. 22, 427 (2001)). These complexes stimulate natural interferon-α producing cells, e.g., plasmacytoid pre-dendritic cells, where stimulation results in the secretion of interferon-α. This secreted interferon-α sustains the generation of more autoantibodies.

Antibodies to TLR9 are contemplated, where these antibodies are inactivating antibodies, and where the inactivating antibodies inhibit TLR9 and prevent TLR9 ligands from activating the cell to secrete interferon-α. Also contemplated is use of soluble versions of TLR9 to bind to anti-DNA/DNA complexes, thus preventing these complexes from activating TR9 (thus preventing the consequent secretion of interferon-α).

Example XVII

Treatment of Septic Shock by an Antibody to an TLR-4 or by Soluble TLR-4

Serious infections may result in a system response to the infection called sepsis. When sepsis results in hypotension and organ dysfunction, it is called septic shock (Parrillo, New Engl. J. Med. 328, 1471 (1993)). Gram-positive organisms, fungi, and endotoxin-containing gram-negative organisms can initiate a series of events resulting in sepsis and septic shock. One feature of septic shock is decreased use of oxygen by various tissues of the body. Another feature is that many vascular beds are abnormally dilated, while others are abnormally constricted, resulting in maldistribution of blood flow (Parrillo, New Engl. J. Med. 328, 1471 (1993)).

Endotoxin is a lipopolysaccharide-associated with cell membranes of gram negative microorganisms. Studies with experimental animals and with humans have shown that endotoxin causes septic shock (Parrillo, New Engl. J. Med. 328, 1471 (1993)). Endotoxin is a ligand for TLR4 (Kadowaki, et al., J. Exp. Med. (in press); Thomas, New Engl. J. Med. 342, 664 (2000); Tapping, et al., J. Immunol. 165, 5780 (2000); Supajatura, et al., J. Immunol. 167, 2250 (2001); Hoshino, et al., J. Immunol. 162, 3749 (1999)). Bacterial products have been found which are ligands for TLR2. These products, which may contribute to the pathology of septic shock, have not yet been identified (Tapping, et al., J. Immunol. 165, 5780 (2000)).

It is contemplated to use anti-TLR4 or soluble TLR4 for treating disease conditions such as sepsis, where the disease conditions involve interaction of bacterial, microbial, or fungal products with TLR-4.

Example XVIII

Treatment of Septic Shock by an Antibody to an TLR-2 or by Soluble TLR-2

Gram positive organisms can cause sepsis, where the natural products identified as causative agents have been identified as peptidoglycan, and lipoteichoic acid (Schwandner, et al., J. Biol. Chem. 274, 17406 (1999)). Capsular polysaccharide of Streptococcus, a gram positive organism, is a cause of sepsis and neonatal meningitis in Japan (Kogan, et al., J. Biol. Chem. 271, 8786 (1996)). A number of natural products have been found to stimulate TLR2, including yeast cell walls, spirochetal lipoproteins, whole mycobacteria and mycobacterial lipoarabinomannan, whole gram positive bacteria, and gram positive bacterial lipoteichoic acid, and peptidoglycan (Schwandner, et al., J. Biol. Chem. 274, 17406 (1999); Tapping, et al., J. Immunol. 165, 5780 (2000)).

It is also contemplated to use anti-TLR2 or soluble TLR2 for treating disease conditions such as sepsis, where the disease conditions involve interaction of bacterial, microbial, or fungal products with TLR-2.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. An isolated antibody or fragment thereof that specifically binds to an isolated or recombinant polypeptide comprising the amino acid sequence of SEQ ID NO: 8.

2. The antibody or fragment thereof of claim 1, wherein said antibody or fragment thereof further comprises a detectable label or purification tag.

3. The antibody or fragment thereof of claim 1, wherein said antibody or fragment thereof is attached to a solid support.

4. The antibody of claim 1, wherein said antibody is a monoclonal antibody.

5. The antibody of claim 4, wherein said antibody is a chimeric antibody.

6. The antibody of claim 4, wherein said antibody is a humanized antibody.

7. The fragment claim 1, wherein said fragment is an Fv, Fab, Fab', F(ab')$_2$, or single-chain Fv.

8. The antibody of claim 1, wherein said antibody is an antagonist antibody.

9. A hybridoma that produces the antibody of claim 1.

10. The antibody or fragment thereof of claim 1, wherein said antibody is a recombinant immunoglobulin.

11. A composition comprising the antibody or fragment thereof of claim 1.

12. A composition comprising the antibody or fragment thereof of claim 1 and a pharmaceutically acceptable carrier.

* * * * *

SEQUENCE LISTING

<160> NUMBER OF SEQ ID NOS: 45

<210> SEQ ID NO 1
<211> LENGTH: 2367
<212> TYPE: DNA
<213> ORGANISM: Homo sapiens
<220> FEATURE:
<221> NAME/KEY: CDS
<222> LOCATION: (1)..(2358)
<223> OTHER INFORMATION:
<220> FEATURE:
<221> NAME/KEY: mat_peptide
<222> LOCATION: (67)..()
<223> OTHER INFORMATION:

<400> SEQUENCE: 1

```
atg act agc atc ttc cat ttt gcc att atc ttc atg tta ata ctt cag      48
Met Thr Ser Ile Phe His Phe Ala Ile Ile Phe Met Leu Ile Leu Gln
        -20                 -15                 -10 atc aga ata caa tta tct gaa gaa agt gaa ttt tta gtt gat agg tca      96
Ile Arg Ile Gln Leu Ser Glu Glu Ser Glu Phe Leu Val Asp Arg Ser
     -5                  -1  1                   5                  10 aaa aac ggt ctc atc cac gtt cct aaa gac cta tcc cag aaa aca aca     144
Lys Asn Gly Leu Ile His Val Pro Lys Asp Leu Ser Gln Lys Thr Thr
                 15                  20                  25 atc tta aat ata tcg caa aat tat ata tct gag ctt tgg act tct gac     192
Ile Leu Asn Ile Ser Gln Asn Tyr Ile Ser Glu Leu Trp Thr Ser Asp
             30                  35                  40 atc tta tca ctg tca aaa ctg agg att ttg ata att tct cat aat aga     240
Ile Leu Ser Leu Ser Lys Leu Arg Ile Leu Ile Ile Ser His Asn Arg
         45                  50                  55 atc cag tat ctt gat atc agt gtt ttc aaa ttc aac cag gaa ttg gaa     288
Ile Gln Tyr Leu Asp Ile Ser Val Phe Lys Phe Asn Gln Glu Leu Glu
     60                  65                  70 tac ttg gat ttg tcc cac aac aag ttg gtg aag att tct tgc cac cct     336
Tyr Leu Asp Leu Ser His Asn Lys Leu Val Lys Ile Ser Cys His Pro
75                  80                  85                  90 act gtg aac ctc aag cac ttg gac ctg tca ttt aat gca ttt gat gcc     384
Thr Val Asn Leu Lys His Leu Asp Leu Ser Phe Asn Ala Phe Asp Ala
                 95                 100                 105 ctg cct ata tgc aaa gag ttt ggc aat atg tct caa cta aaa ttt ctg     432
Leu Pro Ile Cys Lys Glu Phe Gly Asn Met Ser Gln Leu Lys Phe Leu
            110                 115                 120 ggg ttg agc acc aca cac tta gaa aaa tct agt gtg ctg cca att gct     480
Gly Leu Ser Thr Thr His Leu Glu Lys Ser Ser Val Leu Pro Ile Ala
        125                 130                 135 cat ttg aat atc agc aag gtc ttg ctg gtc tta gga gag act tat ggg     528
His Leu Asn Ile Ser Lys Val Leu Leu Val Leu Gly Glu Thr Tyr Gly
    140                 145                 150
```

-continued

| | | |
|---|---|---|
| gaa aaa gaa gac cct gag ggc ctt caa gac ttt aac act gag agt ctg<br>Glu Lys Glu Asp Pro Glu Gly Leu Gln Asp Phe Asn Thr Glu Ser Leu<br>155                      160                      165                      170 | | 576 |
| cac att gtg ttc ccc aca aac aaa gaa ttc cat ttt att ttg gat gtg<br>His Ile Val Phe Pro Thr Asn Lys Glu Phe His Phe Ile Leu Asp Val<br>                      175                      180                      185 | | 624 |
| tca gtc aag act gta gca aat ctg gaa cta tct aat atc aaa tgt gtg<br>Ser Val Lys Thr Val Ala Asn Leu Glu Leu Ser Asn Ile Lys Cys Val<br>            190                      195                      200 | | 672 |
| cta gaa gat aac aaa tgt tct tac ttc cta agt att ctg gcg aaa ctt<br>Leu Glu Asp Asn Lys Cys Ser Tyr Phe Leu Ser Ile Leu Ala Lys Leu<br>        205                      210                      215 | | 720 |
| caa aca aat cca aag tta tca agt ctt acc tta aac aac att gaa aca<br>Gln Thr Asn Pro Lys Leu Ser Ser Leu Thr Leu Asn Asn Ile Glu Thr<br>220                      225                      230 | | 768 |
| act tgg aat tct ttc att agg atc ctc caa cta gtt tgg cat aca act<br>Thr Trp Asn Ser Phe Ile Arg Ile Leu Gln Leu Val Trp His Thr Thr<br>235                      240                      245                      250 | | 816 |
| gta tgg tat ttc tca att tca aac gtg aag cta cag ggt cag ctg gac<br>Val Trp Tyr Phe Ser Ile Ser Asn Val Lys Leu Gln Gly Gln Leu Asp<br>                      255                      260                      265 | | 864 |
| ttc aga gat ttt gat tat tct ggc act tcc ttg aag gcc ttg tct ata<br>Phe Arg Asp Phe Asp Tyr Ser Gly Thr Ser Leu Lys Ala Leu Ser Ile<br>        270                      275                      280 | | 912 |
| cac caa gtt gtc agc gat gtg ttc ggt ttt ccg caa agt tat atc tat<br>His Gln Val Val Ser Asp Val Phe Gly Phe Pro Gln Ser Tyr Ile Tyr<br>285                      290                      295 | | 960 |
| gaa atc ttt tcg aat atg aac atc aaa aat ttc aca gtg tct ggt aca<br>Glu Ile Phe Ser Asn Met Asn Ile Lys Asn Phe Thr Val Ser Gly Thr<br>300                      305                      310 | | 1008 |
| cgc atg gtc cac atg ctt tgc cca tcc aaa att agc ccg ttc ctg cat<br>Arg Met Val His Met Leu Cys Pro Ser Lys Ile Ser Pro Phe Leu His<br>315                      320                      325                      330 | | 1056 |
| ttg gat ttt tcc aat aat ctc tta aca gac acg gtt ttt gaa aat tgt<br>Leu Asp Phe Ser Asn Asn Leu Leu Thr Asp Thr Val Phe Glu Asn Cys<br>                      335                      340                      345 | | 1104 |
| ggg cac ctt act gag ttg gag aca ctt att tta caa atg aat caa tta<br>Gly His Leu Thr Glu Leu Glu Thr Leu Ile Leu Gln Met Asn Gln Leu<br>        350                      355                      360 | | 1152 |
| aaa gaa ctt tca aaa ata gct gaa atg act aca cag atg aag tct ctg<br>Lys Glu Leu Ser Lys Ile Ala Glu Met Thr Thr Gln Met Lys Ser Leu<br>            365                      370                      375 | | 1200 |
| caa caa ttg gat att agc cag aat tct gta agc tat gat gaa aag aaa<br>Gln Gln Leu Asp Ile Ser Gln Asn Ser Val Ser Tyr Asp Glu Lys Lys<br>380                      385                      390 | | 1248 |
| gga gac tgt tct tgg act aaa agt tta tta agt tta aat atg tct tca<br>Gly Asp Cys Ser Trp Thr Lys Ser Leu Leu Ser Leu Asn Met Ser Ser<br>395                      400                      405                      410 | | 1296 |
| aat ata ctt act gac act att ttc aga tgt tta cct ccc agg atc aag<br>Asn Ile Leu Thr Asp Thr Ile Phe Arg Cys Leu Pro Pro Arg Ile Lys<br>                      415                      420                      425 | | 1344 |
| gta ctt gat ctt cac agc aat aaa ata aag agc att cct aaa caa gtc<br>Val Leu Asp Leu His Ser Asn Lys Ile Lys Ser Ile Pro Lys Gln Val<br>        430                      435                      440 | | 1392 |
| gta aaa ctg gaa gct ttg caa gaa ctc aat gtt gct ttc aat tct tta<br>Val Lys Leu Glu Ala Leu Gln Glu Leu Asn Val Ala Phe Asn Ser Leu<br>            445                      450                      455 | | 1440 |
| act gac ctt cct gga tgt ggc agc ttt agc agc ctt tct gta ttg atc<br>Thr Asp Leu Pro Gly Cys Gly Ser Phe Ser Ser Leu Ser Val Leu Ile<br>460                      465                      470 | | 1488 |

```
att gat cac aat tca gtt tcc cac cca tca gct gat ttc ttc cag agc       1536
Ile Asp His Asn Ser Val Ser His Pro Ser Ala Asp Phe Phe Gln Ser
475                 480                 485                 490 tgc cag aag atg agg tca ata aaa gca ggg gac aat cca ttc caa tgt       1584
Cys Gln Lys Met Arg Ser Ile Lys Ala Gly Asp Asn Pro Phe Gln Cys
                495                 500                 505 acc tgt gag ctc gga gaa ttt gtc aaa aat ata gac caa gta tca agt       1632
Thr Cys Glu Leu Gly Glu Phe Val Lys Asn Ile Asp Gln Val Ser Ser
510                 515                 520 gaa gtg tta gag ggc tgg cct gat tct tat aag tgt gac tac ccg gaa       1680
Glu Val Leu Glu Gly Trp Pro Asp Ser Tyr Lys Cys Asp Tyr Pro Glu
        525                 530                 535 agt tat aga gga acc cta cta aag gac ttt cac atg tct gaa tta tcc       1728
Ser Tyr Arg Gly Thr Leu Leu Lys Asp Phe His Met Ser Glu Leu Ser
540                 545                 550 tgc aac ata act ctg ctg atc gtc acc atc gtt gcc acc atg ctg gtg       1776
Cys Asn Ile Thr Leu Leu Ile Val Thr Ile Val Ala Thr Met Leu Val
555                 560                 565                 570 ttg gct gtg act gtg acc tcc ctc tgc atc tac ttg gat ctg ccc tgg       1824
Leu Ala Val Thr Val Thr Ser Leu Cys Ile Tyr Leu Asp Leu Pro Trp
                575                 580                 585 tat ctc agg atg gtg tgc cag tgg acc cag acc cgg cgc agg gcc agg       1872
Tyr Leu Arg Met Val Cys Gln Trp Thr Gln Thr Arg Arg Arg Ala Arg
                590                 595                 600 aac ata ccc tta gaa gaa ctc caa aga aat ctc cag ttt cat gca ttt       1920
Asn Ile Pro Leu Glu Glu Leu Gln Arg Asn Leu Gln Phe His Ala Phe
            605                 610                 615 att tca tat agt ggg cac gat tct ttc tgg gtg aag aat gaa tta ttg       1968
Ile Ser Tyr Ser Gly His Asp Ser Phe Trp Val Lys Asn Glu Leu Leu
620                 625                 630 cca aac cta gag aaa gaa ggt atg cag att tgc ctt cat gag aga aac       2016
Pro Asn Leu Glu Lys Glu Gly Met Gln Ile Cys Leu His Glu Arg Asn
635                 640                 645                 650 ttt gtt cct ggc aag agc att gtg gaa aat atc atc acc tgc att gag       2064
Phe Val Pro Gly Lys Ser Ile Val Glu Asn Ile Ile Thr Cys Ile Glu
                655                 660                 665 aag agt tac aag tcc atc ttt gtt ttg tct ccc aac ttt gtc cag agt       2112
Lys Ser Tyr Lys Ser Ile Phe Val Leu Ser Pro Asn Phe Val Gln Ser
                670                 675                 680 gaa tgg tgc cat tat gaa ctc tac ttt gcc cat cac aat ctc ttt cat       2160
Glu Trp Cys His Tyr Glu Leu Tyr Phe Ala His His Asn Leu Phe His
            685                 690                 695 gaa gga tct aat agc tta atc ctg atc ttg ctg gaa ccc att ccg cag       2208
Glu Gly Ser Asn Ser Leu Ile Leu Ile Leu Leu Glu Pro Ile Pro Gln
700                 705                 710 tac tcc att cct agc agt tat cac aag ctc aaa agt ctc atg gcc agg       2256
Tyr Ser Ile Pro Ser Ser Tyr His Lys Leu Lys Ser Leu Met Ala Arg
715                 720                 725                 730 agg act tat ttg gaa tgg ccc aag gaa aag agc aaa cgt ggc ctt ttt       2304
Arg Thr Tyr Leu Glu Trp Pro Lys Glu Lys Ser Lys Arg Gly Leu Phe
                735                 740                 745 tgg gct aac tta agg gca gcc att aat att aag ctg aca gag caa gca       2352
Trp Ala Asn Leu Arg Ala Ala Ile Asn Ile Lys Leu Thr Glu Gln Ala
                750                 755                 760 aag aaa tagtctaga                                                     2367
Lys Lys

<210> SEQ ID NO 2
<211> LENGTH: 786
```

```
<212> TYPE: PRT
<213> ORGANISM: Homo sapiens

<400> SEQUENCE: 2

Met Thr Ser Ile Phe His Phe Ala Ile Ile Phe Met Leu Ile Leu Gln
        -20                 -15                 -10

Ile Arg Ile Gln Leu Ser Glu Glu Ser Glu Phe Leu Val Asp Arg Ser
     -5                  -1   1                   5                  10

Lys Asn Gly Leu Ile His Val Pro Lys Asp Leu Ser Gln Lys Thr Thr
                    15                  20                  25

Ile Leu Asn Ile Ser Gln Asn Tyr Ile Ser Glu Leu Trp Thr Ser Asp
            30                  35                  40

Ile Leu Ser Leu Ser Lys Leu Arg Ile Leu Ile Ile Ser His Asn Arg
        45                  50                  55

Ile Gln Tyr Leu Asp Ile Ser Val Phe Lys Phe Asn Gln Glu Leu Glu
    60                  65                  70

Tyr Leu Asp Leu Ser His Asn Lys Leu Val Lys Ile Ser Cys His Pro
75                  80                  85                  90

Thr Val Asn Leu Lys His Leu Asp Leu Ser Phe Asn Ala Phe Asp Ala
                95                  100                 105

Leu Pro Ile Cys Lys Glu Phe Gly Asn Met Ser Gln Leu Lys Phe Leu
                110                 115                 120

Gly Leu Ser Thr Thr His Leu Glu Lys Ser Ser Val Leu Pro Ile Ala
            125                 130                 135

His Leu Asn Ile Ser Lys Val Leu Leu Val Leu Gly Glu Thr Tyr Gly
        140                 145                 150

Glu Lys Glu Asp Pro Glu Gly Leu Gln Asp Phe Asn Thr Glu Ser Leu
155                 160                 165                 170

His Ile Val Phe Pro Thr Asn Lys Glu Phe His Phe Ile Leu Asp Val
                175                 180                 185

Ser Val Lys Thr Val Ala Asn Leu Glu Leu Ser Asn Ile Lys Cys Val
            190                 195                 200

Leu Glu Asp Asn Lys Cys Ser Tyr Phe Leu Ser Ile Leu Ala Lys Leu
        205                 210                 215

Gln Thr Asn Pro Lys Leu Ser Ser Leu Thr Leu Asn Asn Ile Glu Thr
220                 225                 230

Thr Trp Asn Ser Phe Ile Arg Ile Leu Gln Leu Val Trp His Thr Thr
235                 240                 245                 250

Val Trp Tyr Phe Ser Ile Ser Asn Val Lys Leu Gln Gly Gln Leu Asp
                255                 260                 265

Phe Arg Asp Phe Asp Tyr Ser Gly Thr Ser Leu Lys Ala Leu Ser Ile
                270                 275                 280

His Gln Val Val Ser Asp Val Phe Gly Phe Pro Gln Ser Tyr Ile Tyr
            285                 290                 295

Glu Ile Phe Ser Asn Met Asn Ile Lys Asn Phe Thr Val Ser Gly Thr
    300                 305                 310

Arg Met Val His Met Leu Cys Pro Ser Lys Ile Ser Pro Phe Leu His
315                 320                 325                 330

Leu Asp Phe Ser Asn Asn Leu Leu Thr Asp Thr Val Phe Glu Asn Cys
                335                 340                 345

Gly His Leu Thr Glu Leu Glu Thr Leu Ile Leu Gln Met Asn Gln Leu
            350                 355                 360

Lys Glu Leu Ser Lys Ile Ala Glu Met Thr Thr Gln Met Lys Ser Leu
        365                 370                 375
```

```
Gln Gln Leu Asp Ile Ser Gln Asn Ser Val Ser Tyr Asp Glu Lys Lys
    380                 385                 390

Gly Asp Cys Ser Trp Thr Lys Ser Leu Leu Ser Leu Asn Met Ser Ser
395                 400                 405                 410

Asn Ile Leu Thr Asp Thr Ile Phe Arg Cys Leu Pro Pro Arg Ile Lys
                415                 420                 425

Val Leu Asp Leu His Ser Asn Lys Ile Lys Ser Ile Pro Lys Gln Val
            430                 435                 440

Val Lys Leu Glu Ala Leu Gln Glu Leu Asn Val Ala Phe Asn Ser Leu
        445                 450                 455

Thr Asp Leu Pro Gly Cys Gly Ser Phe Ser Ser Leu Ser Val Leu Ile
    460                 465                 470

Ile Asp His Asn Ser Val Ser His Pro Ser Ala Asp Phe Phe Gln Ser
475                 480                 485                 490

Cys Gln Lys Met Arg Ser Ile Lys Ala Gly Asp Asn Pro Phe Gln Cys
                495                 500                 505

Thr Cys Glu Leu Gly Glu Phe Val Lys Asn Ile Asp Gln Val Ser Ser
            510                 515                 520

Glu Val Leu Glu Gly Trp Pro Asp Ser Tyr Lys Cys Asp Tyr Pro Glu
        525                 530                 535

Ser Tyr Arg Gly Thr Leu Leu Lys Asp Phe His Met Ser Glu Leu Ser
    540                 545                 550

Cys Asn Ile Thr Leu Leu Ile Val Thr Ile Val Ala Thr Met Leu Val
555                 560                 565                 570

Leu Ala Val Thr Val Thr Ser Leu Cys Ile Tyr Leu Asp Leu Pro Trp
                575                 580                 585

Tyr Leu Arg Met Val Cys Gln Trp Thr Gln Thr Arg Arg Arg Ala Arg
            590                 595                 600

Asn Ile Pro Leu Glu Glu Leu Gln Arg Asn Leu Gln Phe His Ala Phe
        605                 610                 615

Ile Ser Tyr Ser Gly His Asp Ser Phe Trp Val Lys Asn Glu Leu Leu
    620                 625                 630

Pro Asn Leu Glu Lys Glu Gly Met Gln Ile Cys Leu His Glu Arg Asn
635                 640                 645                 650

Phe Val Pro Gly Lys Ser Ile Val Glu Asn Ile Ile Thr Cys Ile Glu
                655                 660                 665

Lys Ser Tyr Lys Ser Ile Phe Val Leu Ser Pro Asn Phe Val Gln Ser
            670                 675                 680

Glu Trp Cys His Tyr Glu Leu Tyr Phe Ala His His Asn Leu Phe His
        685                 690                 695

Glu Gly Ser Asn Ser Leu Ile Leu Ile Leu Leu Glu Pro Ile Pro Gln
    700                 705                 710

Tyr Ser Ile Pro Ser Ser Tyr His Lys Leu Lys Ser Leu Met Ala Arg
715                 720                 725                 730

Arg Thr Tyr Leu Glu Trp Pro Lys Glu Lys Ser Lys Arg Gly Leu Phe
                735                 740                 745

Trp Ala Asn Leu Arg Ala Ala Ile Asn Ile Lys Leu Thr Glu Gln Ala
            750                 755                 760

Lys Lys

<210> SEQ ID NO 3
<211> LENGTH: 2355
<212> TYPE: DNA
```

<213> ORGANISM: Homo sapiens
<220> FEATURE:
<221> NAME/KEY: CDS
<222> LOCATION: (1)..(2352)
<223> OTHER INFORMATION:
<220> FEATURE:
<221> NAME/KEY: mat_peptide
<222> LOCATION: (67)..()
<223> OTHER INFORMATION:

<400> SEQUENCE: 3

```
atg cca cat act ttg tgg atg gtg tgg gtc ttg ggg gtc atc atc agc      48
Met Pro His Thr Leu Trp Met Val Trp Val Leu Gly Val Ile Ile Ser
    -20             -15                 -10 ctc tcc aag gaa gaa tcc tcc aat cag gct tct ctg tct tgt gac cgc      96
Leu Ser Lys Glu Glu Ser Ser Asn Gln Ala Ser Leu Ser Cys Asp Arg
 -5              -1  1                   5                      10 aat ggt atc tgc aag ggc agc tca gga tct tta aac tcc att ccc tca     144
Asn Gly Ile Cys Lys Gly Ser Ser Gly Ser Leu Asn Ser Ile Pro Ser
                15                  20                  25 ggg ctc aca gaa gct gta aaa agc ctt gac ctg tcc aac aac agg atc     192
Gly Leu Thr Glu Ala Val Lys Ser Leu Asp Leu Ser Asn Asn Arg Ile
            30                  35                  40 acc tac att agc aac agt gac cta cag agg tgt gta aac ctc cag gct     240
Thr Tyr Ile Ser Asn Ser Asp Leu Gln Arg Cys Val Asn Leu Gln Ala
        45                  50                  55 ctg gtg ctg aca tcc aat gga att aac aca ata gag gaa gat tct ttt     288
Leu Val Leu Thr Ser Asn Gly Ile Asn Thr Ile Glu Glu Asp Ser Phe
    60                  65                  70 tct tcc ctg ggc agt ctt gaa cat tta gac tta tcc tat aat tac tta     336
Ser Ser Leu Gly Ser Leu Glu His Leu Asp Leu Ser Tyr Asn Tyr Leu
75                  80                  85                  90 tct aat tta tcg tct tcc tgg ttc aag ccc ctt tct tct tta aca ttc     384
Ser Asn Leu Ser Ser Ser Trp Phe Lys Pro Leu Ser Ser Leu Thr Phe
                95                 100                 105 tta aac tta ctg gga aat cct tac aaa acc cta ggg gaa aca tct ctt     432
Leu Asn Leu Leu Gly Asn Pro Tyr Lys Thr Leu Gly Glu Thr Ser Leu
            110                 115                 120 ttt tct cat ctc aca aaa ttg caa atc ctg aga gtg gga aat atg gac     480
Phe Ser His Leu Thr Lys Leu Gln Ile Leu Arg Val Gly Asn Met Asp
        125                 130                 135 acc ttc act aag att caa aga aaa gat ttt gct gga ctt acc ttc ctt     528
Thr Phe Thr Lys Ile Gln Arg Lys Asp Phe Ala Gly Leu Thr Phe Leu
    140                 145                 150 gag gaa ctt gag att gat gct tca gat cta cag agc tat gag cca aaa     576
Glu Glu Leu Glu Ile Asp Ala Ser Asp Leu Gln Ser Tyr Glu Pro Lys
155                 160                 165                 170 agt ttg aag tca att cag aac gta agt cat ctg atc ctt cat atg aag     624
Ser Leu Lys Ser Ile Gln Asn Val Ser His Leu Ile Leu His Met Lys
                175                 180                 185 cag cat att tta ctg ctg gag att ttt gta gat gtt aca agt tcc gtg     672
Gln His Ile Leu Leu Leu Glu Ile Phe Val Asp Val Thr Ser Ser Val
            190                 195                 200 gaa tgt ttg gaa ctg cga gat act gat ttg gac act ttc cat ttt tca     720
Glu Cys Leu Glu Leu Arg Asp Thr Asp Leu Asp Thr Phe His Phe Ser
        205                 210                 215 gaa cta tcc act ggt gaa aca aat tca ttg att aaa aag ttt aca ttt     768
Glu Leu Ser Thr Gly Glu Thr Asn Ser Leu Ile Lys Lys Phe Thr Phe
    220                 225                 230 aga aat gtg aaa atc acc gat gaa agt ttg ttt cag gtt atg aaa ctt     816
Arg Asn Val Lys Ile Thr Asp Glu Ser Leu Phe Gln Val Met Lys Leu
235                 240                 245                 250
```

-continued

| | |
|---|---|
| ttg aat cag att tct gga ttg tta gaa tta gag ttt gat gac tgt acc<br>Leu Asn Gln Ile Ser Gly Leu Leu Glu Leu Glu Phe Asp Asp Cys Thr<br>              255                          260                        265 | 864 |
| ctt aat gga gtt ggt aat ttt aga gca tct gat aat gac aga gtt ata<br>Leu Asn Gly Val Gly Asn Phe Arg Ala Ser Asp Asn Asp Arg Val Ile<br>          270                          275                        280 | 912 |
| gat cca ggt aaa gtg gaa acg tta aca atc cgg agg ctg cat att cca<br>Asp Pro Gly Lys Val Glu Thr Leu Thr Ile Arg Arg Leu His Ile Pro<br>              285                        290                        295 | 960 |
| agg ttt tac tta ttt tat gat ctg agc act tta tat tca ctt aca gaa<br>Arg Phe Tyr Leu Phe Tyr Asp Leu Ser Thr Leu Tyr Ser Leu Thr Glu<br>300                        305                        310 | 1008 |
| aga gtt aaa aga atc aca gta gaa aac agt aaa gtt ttt ctg gtt cct<br>Arg Val Lys Arg Ile Thr Val Glu Asn Ser Lys Val Phe Leu Val Pro<br>315                        320                        325                        330 | 1056 |
| tgt tta ctt tca caa cat tta aaa tca tta gaa tac ttg gat ctc agt<br>Cys Leu Leu Ser Gln His Leu Lys Ser Leu Glu Tyr Leu Asp Leu Ser<br>              335                        340                        345 | 1104 |
| gaa aat ttg atg gtt gaa gaa tac ttg aaa aat tca gcc tgt gag gat<br>Glu Asn Leu Met Val Glu Glu Tyr Leu Lys Asn Ser Ala Cys Glu Asp<br>          350                          355                        360 | 1152 |
| gcc tgg ccc tct cta caa act tta att tta agg caa aat cat ttg gca<br>Ala Trp Pro Ser Leu Gln Thr Leu Ile Leu Arg Gln Asn His Leu Ala<br>              365                        370                        375 | 1200 |
| tca ttg gaa aaa acc gga gag act ttg ctc act ctg aaa aac ttg act<br>Ser Leu Glu Lys Thr Gly Glu Thr Leu Leu Thr Leu Lys Asn Leu Thr<br>380                        385                        390 | 1248 |
| aac att gat atc agt aag aat agt ttt cat tct atg cct gaa act tgt<br>Asn Ile Asp Ile Ser Lys Asn Ser Phe His Ser Met Pro Glu Thr Cys<br>395                        400                        405                        410 | 1296 |
| cag tgg cca gaa aag atg aaa tat ttg aac tta tcc agc aca cga ata<br>Gln Trp Pro Glu Lys Met Lys Tyr Leu Asn Leu Ser Ser Thr Arg Ile<br>              415                        420                        425 | 1344 |
| cac agt gta aca ggc tgc att ccc aag aca ctg gaa att tta gat gtt<br>His Ser Val Thr Gly Cys Ile Pro Lys Thr Leu Glu Ile Leu Asp Val<br>              430                        435                        440 | 1392 |
| agc aac aac aat ctc aat tta ttt tct ttg aat ttg ccg caa ctc aaa<br>Ser Asn Asn Asn Leu Asn Leu Phe Ser Leu Asn Leu Pro Gln Leu Lys<br>                445                        450                        455 | 1440 |
| gaa ctt tat att tcc aga aat aag ttg atg act cta cca gat gcc tcc<br>Glu Leu Tyr Ile Ser Arg Asn Lys Leu Met Thr Leu Pro Asp Ala Ser<br>460                        465                        470 | 1488 |
| ctc tta ccc atg tta cta gta ttg aaa atc agt agg aat gca ata act<br>Leu Leu Pro Met Leu Leu Val Leu Lys Ile Ser Arg Asn Ala Ile Thr<br>475                        480                        485                        490 | 1536 |
| acg ttt tct aag gag caa ctt gac tca ttt cac aca ctg aag act ttg<br>Thr Phe Ser Lys Glu Gln Leu Asp Ser Phe His Thr Leu Lys Thr Leu<br>              495                        500                        505 | 1584 |
| gaa gct ggt ggc aat aac ttc att tgc tcc tgt gaa ttc ctc tcc ttc<br>Glu Ala Gly Gly Asn Asn Phe Ile Cys Ser Cys Glu Phe Leu Ser Phe<br>                510                        515                        520 | 1632 |
| act cag gag cag caa gca ctg gcc aaa gtc ttg att gat tgg cca gca<br>Thr Gln Glu Gln Gln Ala Leu Ala Lys Val Leu Ile Asp Trp Pro Ala<br>              525                        530                        535 | 1680 |
| aat tac ctg tgt gac tct cca tcc cat gtg cgt ggc cag cag gtt cag<br>Asn Tyr Leu Cys Asp Ser Pro Ser His Val Arg Gly Gln Gln Val Gln<br>540                        545                        550 | 1728 |
| gat gtc cgc ctc tcg gtg tcg gaa tgt cac agg aca gca ctg gtg tct<br>Asp Val Arg Leu Ser Val Ser Glu Cys His Arg Thr Ala Leu Val Ser | 1776 |

```
                555           560           565           570
ggc atg tgc tgt gct ctg ttc ctg ctg atc ctg ctc acg ggg gtc ctg        1824
Gly Met Cys Cys Ala Leu Phe Leu Leu Ile Leu Leu Thr Gly Val Leu
                    575               580               585 tgc cac cgt ttc cat ggc ctg tgg tat atg aaa atg atg tgg gcc tgg        1872
Cys His Arg Phe His Gly Leu Trp Tyr Met Lys Met Met Trp Ala Trp
            590               595               600 ctc cag gcc aaa agg aag ccc agg aaa gct ccc agc agg aac atc tgc        1920
Leu Gln Ala Lys Arg Lys Pro Arg Lys Ala Pro Ser Arg Asn Ile Cys
        605               610               615 tat gat gca ttt gtt tct tac agt gag cgg gat gcc tac tgg gtg gag        1968
Tyr Asp Ala Phe Val Ser Tyr Ser Glu Arg Asp Ala Tyr Trp Val Glu
    620               625               630 aac ctt atg gtc cag gag ctg gag aac ttc aat ccc ccc ttc aag ttg        2016
Asn Leu Met Val Gln Glu Leu Glu Asn Phe Asn Pro Pro Phe Lys Leu
635               640               645               650 tgt ctt cat aag cgg gac ttc att cct ggc aag tgg atc att gac aat        2064
Cys Leu His Lys Arg Asp Phe Ile Pro Gly Lys Trp Ile Ile Asp Asn
                655               660               665 atc att gac tcc att gaa aag agc cac aaa act gtc ttt gtg ctt tct        2112
Ile Ile Asp Ser Ile Glu Lys Ser His Lys Thr Val Phe Val Leu Ser
            670               675               680 gaa aac ttt gtg aag agt gag tgg tgc aag tat gaa ctg gac ttc tcc        2160
Glu Asn Phe Val Lys Ser Glu Trp Cys Lys Tyr Glu Leu Asp Phe Ser
        685               690               695 cat ttc cgt ctt ttt gaa gag aac aat gat gct gcc att ctc att ctt        2208
His Phe Arg Leu Phe Glu Glu Asn Asn Asp Ala Ala Ile Leu Ile Leu
    700               705               710 ctg gag ccc att gag aaa aaa gcc att ccc cag cgc ttc tgc aag ctg        2256
Leu Glu Pro Ile Glu Lys Lys Ala Ile Pro Gln Arg Phe Cys Lys Leu
715               720               725               730 cgg aag ata atg aac acc aag acc tac ctg gag tgg ccc atg gac gag        2304
Arg Lys Ile Met Asn Thr Lys Thr Tyr Leu Glu Trp Pro Met Asp Glu
                735               740               745 gct cag cgg gaa gga ttt tgg gta aat ctg aga gct gcg ata aag tcc        2352
Ala Gln Arg Glu Gly Phe Trp Val Asn Leu Arg Ala Ala Ile Lys Ser
            750               755               760 tag                                                                     2355

<210> SEQ ID NO 4
<211> LENGTH: 784
<212> TYPE: PRT
<213> ORGANISM: Homo sapiens

<400> SEQUENCE: 4

Met Pro His Thr Leu Trp Met Val Trp Val Leu Gly Val Ile Ile Ser
        -20                 -15                 -10

Leu Ser Lys Glu Glu Ser Ser Asn Gln Ala Ser Leu Ser Cys Asp Arg
 -5                  -1  1                   5                  10

Asn Gly Ile Cys Lys Gly Ser Ser Gly Ser Leu Asn Ser Ile Pro Ser
                15                  20                  25

Gly Leu Thr Glu Ala Val Lys Ser Leu Asp Leu Ser Asn Asn Arg Ile
            30                  35                  40

Thr Tyr Ile Ser Asn Ser Asp Leu Gln Arg Cys Val Asn Leu Gln Ala
        45                  50                  55

Leu Val Leu Thr Ser Asn Gly Ile Asn Thr Ile Glu Glu Asp Ser Phe
    60                  65                  70

Ser Ser Leu Gly Ser Leu Glu His Leu Asp Leu Ser Tyr Asn Tyr Leu
```

-continued

```
            75                  80                  85                  90
Ser Asn Leu Ser Ser Ser Trp Phe Lys Pro Leu Ser Ser Leu Thr Phe
                    95                 100                 105
Leu Asn Leu Leu Gly Asn Pro Tyr Lys Thr Leu Gly Glu Thr Ser Leu
                110                 115                 120
Phe Ser His Leu Thr Lys Leu Gln Ile Leu Arg Val Gly Asn Met Asp
            125                 130                 135
Thr Phe Thr Lys Ile Gln Arg Lys Asp Phe Ala Gly Leu Thr Phe Leu
        140                 145                 150
Glu Glu Leu Glu Ile Asp Ala Ser Asp Leu Gln Ser Tyr Glu Pro Lys
155                 160                 165                 170
Ser Leu Lys Ser Ile Gln Asn Val Ser His Leu Ile Leu His Met Lys
                175                 180                 185
Gln His Ile Leu Leu Glu Ile Phe Val Asp Val Thr Ser Ser Val
                190                 195                 200
Glu Cys Leu Glu Leu Arg Asp Thr Asp Leu Asp Thr Phe His Phe Ser
            205                 210                 215
Glu Leu Ser Thr Gly Glu Thr Asn Ser Leu Ile Lys Lys Phe Thr Phe
        220                 225                 230
Arg Asn Val Lys Ile Thr Asp Glu Ser Leu Phe Gln Val Met Lys Leu
235                 240                 245                 250
Leu Asn Gln Ile Ser Gly Leu Leu Glu Leu Glu Phe Asp Asp Cys Thr
                255                 260                 265
Leu Asn Gly Val Gly Asn Phe Arg Ala Ser Asp Asn Asp Arg Val Ile
            270                 275                 280
Asp Pro Gly Lys Val Glu Thr Leu Thr Ile Arg Arg Leu His Ile Pro
        285                 290                 295
Arg Phe Tyr Leu Phe Tyr Asp Leu Ser Thr Leu Tyr Ser Leu Thr Glu
        300                 305                 310
Arg Val Lys Arg Ile Thr Val Glu Asn Ser Lys Val Phe Leu Val Pro
315                 320                 325                 330
Cys Leu Leu Ser Gln His Leu Lys Ser Leu Glu Tyr Leu Asp Leu Ser
                335                 340                 345
Glu Asn Leu Met Val Glu Glu Tyr Leu Lys Asn Ser Ala Cys Glu Asp
                350                 355                 360
Ala Trp Pro Ser Leu Gln Thr Leu Ile Leu Arg Gln Asn His Leu Ala
            365                 370                 375
Ser Leu Glu Lys Thr Gly Glu Thr Leu Leu Thr Leu Lys Asn Leu Thr
            380                 385                 390
Asn Ile Asp Ile Ser Lys Asn Ser Phe His Ser Met Pro Glu Thr Cys
395                 400                 405                 410
Gln Trp Pro Glu Lys Met Lys Tyr Leu Asn Leu Ser Ser Thr Arg Ile
                415                 420                 425
His Ser Val Thr Gly Cys Ile Pro Lys Thr Leu Glu Ile Leu Asp Val
            430                 435                 440
Ser Asn Asn Asn Leu Asn Leu Phe Ser Leu Asn Leu Pro Gln Leu Lys
            445                 450                 455
Glu Leu Tyr Ile Ser Arg Asn Lys Leu Met Thr Leu Pro Asp Ala Ser
        460                 465                 470
Leu Leu Pro Met Leu Leu Val Leu Lys Ile Ser Arg Asn Ala Ile Thr
475                 480                 485                 490
Thr Phe Ser Lys Glu Gln Leu Asp Ser Phe His Thr Leu Lys Thr Leu
                495                 500                 505
```

-continued

```
Glu Ala Gly Gly Asn Asn Phe Ile Cys Ser Cys Glu Phe Leu Ser Phe
            510                 515                 520

Thr Gln Glu Gln Gln Ala Leu Ala Lys Val Leu Ile Asp Trp Pro Ala
        525                 530                 535

Asn Tyr Leu Cys Asp Ser Pro Ser His Val Arg Gly Gln Gln Val Gln
    540                 545                 550

Asp Val Arg Leu Ser Val Ser Glu Cys His Arg Thr Ala Leu Val Ser
555                 560                 565                 570

Gly Met Cys Cys Ala Leu Phe Leu Leu Ile Leu Leu Thr Gly Val Leu
                575                 580                 585

Cys His Arg Phe His Gly Leu Trp Tyr Met Lys Met Trp Ala Trp
            590                 595                 600

Leu Gln Ala Lys Arg Lys Pro Arg Lys Ala Pro Ser Arg Asn Ile Cys
        605                 610                 615

Tyr Asp Ala Phe Val Ser Tyr Ser Glu Arg Asp Ala Tyr Trp Val Glu
    620                 625                 630

Asn Leu Met Val Gln Glu Leu Glu Asn Phe Asn Pro Pro Phe Lys Leu
635                 640                 645                 650

Cys Leu His Lys Arg Asp Phe Ile Pro Gly Lys Trp Ile Ile Asp Asn
                655                 660                 665

Ile Ile Asp Ser Ile Glu Lys Ser His Lys Thr Val Phe Val Leu Ser
            670                 675                 680

Glu Asn Phe Val Lys Ser Glu Trp Cys Lys Tyr Glu Leu Asp Phe Ser
        685                 690                 695

His Phe Arg Leu Phe Glu Glu Asn Asn Asp Ala Ala Ile Leu Ile Leu
    700                 705                 710

Leu Glu Pro Ile Glu Lys Lys Ala Ile Pro Gln Arg Phe Cys Lys Leu
715                 720                 725                 730

Arg Lys Ile Met Asn Thr Lys Thr Tyr Leu Glu Trp Pro Met Asp Glu
                735                 740                 745

Ala Gln Arg Glu Gly Phe Trp Val Asn Leu Arg Ala Ala Ile Lys Ser
            750                 755                 760
```

<210> SEQ ID NO 5
<211> LENGTH: 2715
<212> TYPE: DNA
<213> ORGANISM: Homo sapiens
<220> FEATURE:
<221> NAME/KEY: CDS
<222> LOCATION: (1)..(2712)
<223> OTHER INFORMATION:
<220> FEATURE:
<221> NAME/KEY: mat_peptide
<222> LOCATION: (64)..()
<223> OTHER INFORMATION:

<400> SEQUENCE: 5

```
atg aga cag act ttg cct tgt atc tac ttt tgg ggg ggc ctt ttg ccc    48
Met Arg Gln Thr Leu Pro Cys Ile Tyr Phe Trp Gly Gly Leu Leu Pro
    -20                 -15                 -10 ttt ggg atg ctg tgt gca tcc tcc acc acc aag tgc act gtt agc cat    96
Phe Gly Met Leu Cys Ala Ser Ser Thr Thr Lys Cys Thr Val Ser His
 -5          -1   1                 5                  10 gaa gtt gct gac tgc agc cac ctg aag ttg act cag gta ccc gat gat   144
Glu Val Ala Asp Cys Ser His Leu Lys Leu Thr Gln Val Pro Asp Asp
                15                  20                  25 cta ccc aca aac ata aca gtg ttg aac ctt acc cat aat caa ctc aga   192
Leu Pro Thr Asn Ile Thr Val Leu Asn Leu Thr His Asn Gln Leu Arg
```

```
                    30                  35                  40
aga tta cca gcc gcc aac ttc aca agg tat agc cag cta act agc ttg       240
Arg Leu Pro Ala Ala Asn Phe Thr Arg Tyr Ser Gln Leu Thr Ser Leu
        45                  50                  55 gat gta gga ttt aac acc atc tca aaa ctg gag cca gaa ttg tgc cag       288
Asp Val Gly Phe Asn Thr Ile Ser Lys Leu Glu Pro Glu Leu Cys Gln
60                  65                  70                  75 aaa ctt ccc atg tta aaa gtt ttg aac ctc cag cac aat gag cta tct       336
Lys Leu Pro Met Leu Lys Val Leu Asn Leu Gln His Asn Glu Leu Ser
                    80                  85                  90 caa ctt tct gat aaa acc ttt gcc ttc tgc acg aat ttg act gaa ctc       384
Gln Leu Ser Asp Lys Thr Phe Ala Phe Cys Thr Asn Leu Thr Glu Leu
        95                  100                 105 cat ctc atg tcc aac tca atc cag aaa att aaa aat aat ccc ttt gtc       432
His Leu Met Ser Asn Ser Ile Gln Lys Ile Lys Asn Asn Pro Phe Val
                110                 115                 120 aag cag aag aat tta atc aca tta gat ctg tct cat aat ggc ttg tca       480
Lys Gln Lys Asn Leu Ile Thr Leu Asp Leu Ser His Asn Gly Leu Ser
        125                 130                 135 tct aca aaa tta gga act cag gtt cag ctg gaa aat ctc caa gag ctt       528
Ser Thr Lys Leu Gly Thr Gln Val Gln Leu Glu Asn Leu Gln Glu Leu
140                 145                 150                 155 cta tta tca aac aat aaa att caa gcg cta aaa agt gaa gaa ctg gat       576
Leu Leu Ser Asn Asn Lys Ile Gln Ala Leu Lys Ser Glu Glu Leu Asp
                160                 165                 170 atc ttt gcc aat tca tct tta aaa aaa tta gag ttg tca tcg aat caa       624
Ile Phe Ala Asn Ser Ser Leu Lys Lys Leu Glu Leu Ser Ser Asn Gln
        175                 180                 185 att aaa gag ttt tct cca ggg tgt ttt cac gca att gga aga tta ttt       672
Ile Lys Glu Phe Ser Pro Gly Cys Phe His Ala Ile Gly Arg Leu Phe
                190                 195                 200 ggc ctc ttt ctg aac aat gtc cag ctg ggt ccc agc ctt aca gag aag       720
Gly Leu Phe Leu Asn Asn Val Gln Leu Gly Pro Ser Leu Thr Glu Lys
        205                 210                 215 cta tgt ttg gaa tta gca aac aca agc att cgg aat ctg tct ctg agt       768
Leu Cys Leu Glu Leu Ala Asn Thr Ser Ile Arg Asn Leu Ser Leu Ser
220                 225                 230                 235 aac agc cag ctg tcc acc acc agc aat aca act ttc ttg gga cta aag       816
Asn Ser Gln Leu Ser Thr Thr Ser Asn Thr Thr Phe Leu Gly Leu Lys
                240                 245                 250 tgg aca aat ctc act atg ctc gat ctt tcc tac aac aac tta aat gtg       864
Trp Thr Asn Leu Thr Met Leu Asp Leu Ser Tyr Asn Asn Leu Asn Val
        255                 260                 265 gtt ggt aac gat tcc ttt gct tgg ctt cca caa cta gaa tat ttc ttc       912
Val Gly Asn Asp Ser Phe Ala Trp Leu Pro Gln Leu Glu Tyr Phe Phe
                270                 275                 280 cta gag tat aat aat ata cag cat ttg ttt tct cac tct ttg cac ggg       960
Leu Glu Tyr Asn Asn Ile Gln His Leu Phe Ser His Ser Leu His Gly
285                 290                 295 ctt ttc aat gtg agg tac ctg aat ttg aaa cgg tct ttt act aaa caa      1008
Leu Phe Asn Val Arg Tyr Leu Asn Leu Lys Arg Ser Phe Thr Lys Gln
300                 305                 310                 315 agt att tcc ctt gcc tca ctc ccc aag att gat gat ttt tct ttt cag      1056
Ser Ile Ser Leu Ala Ser Leu Pro Lys Ile Asp Asp Phe Ser Phe Gln
                320                 325                 330 tgg cta aaa tgt ttg gag cac ctt aac atg gaa gat aat gat att cca      1104
Trp Leu Lys Cys Leu Glu His Leu Asn Met Glu Asp Asn Asp Ile Pro
        335                 340                 345 ggc ata aaa agc aat atg ttc aca gga ttg ata aac ctg aaa tac tta      1152
```

```
                                                    -continued

Gly Ile Lys Ser Asn Met Phe Thr Gly Leu Ile Asn Leu Lys Tyr Leu
        350                 355                 360 agt cta tcc aac tcc ttt aca agt ttg cga act ttg aca aat gaa aca       1200
Ser Leu Ser Asn Ser Phe Thr Ser Leu Arg Thr Leu Thr Asn Glu Thr
365                 370                 375 ttt gta tca ctt gct cat tct ccc tta cac ata ctc aac cta acc aag       1248
Phe Val Ser Leu Ala His Ser Pro Leu His Ile Leu Asn Leu Thr Lys
380                 385                 390                 395 aat aaa atc tca aaa ata gag agt gat gct ttc tct tgg ttg ggc cac       1296
Asn Lys Ile Ser Lys Ile Glu Ser Asp Ala Phe Ser Trp Leu Gly His
            400                 405                 410 cta gaa gta ctt gac ctg ggc ctt aat gaa att ggg caa gaa ctc aca       1344
Leu Glu Val Leu Asp Leu Gly Leu Asn Glu Ile Gly Gln Glu Leu Thr
            415                 420                 425 ggc cag gaa tgg aga ggt cta gaa aat att ttc gaa atc tat ctt tcc       1392
Gly Gln Glu Trp Arg Gly Leu Glu Asn Ile Phe Glu Ile Tyr Leu Ser
        430                 435                 440 tac aac aag tac ctg cag ctg act agg aac tcc ttt gcc ttg gtc cca       1440
Tyr Asn Lys Tyr Leu Gln Leu Thr Arg Asn Ser Phe Ala Leu Val Pro
        445                 450                 455 agc ctt caa cga ctg atg ctc cga agg gtg gcc ctt aaa aat gtg gat       1488
Ser Leu Gln Arg Leu Met Leu Arg Arg Val Ala Leu Lys Asn Val Asp
460                 465                 470                 475 agc tct cct tca cca ttc cag cct ctt cgt aac ttg acc att ctg gat       1536
Ser Ser Pro Ser Pro Phe Gln Pro Leu Arg Asn Leu Thr Ile Leu Asp
            480                 485                 490 cta agc aac aac aac ata gcc aac ata aat gat gac atg ttg gag ggt       1584
Leu Ser Asn Asn Asn Ile Ala Asn Ile Asn Asp Asp Met Leu Glu Gly
            495                 500                 505 ctt gag aaa cta gaa att ctc gat ttg cag cat aac aac tta gca cgg       1632
Leu Glu Lys Leu Glu Ile Leu Asp Leu Gln His Asn Asn Leu Ala Arg
        510                 515                 520 ctc tgg aaa cac gca aac cct ggt ggt ccc att tat ttc cta aag ggt       1680
Leu Trp Lys His Ala Asn Pro Gly Gly Pro Ile Tyr Phe Leu Lys Gly
525                 530                 535 ctg tct cac ctc cac atc ctt aac ttg gag tcc aac ggc ttt gac gag       1728
Leu Ser His Leu His Ile Leu Asn Leu Glu Ser Asn Gly Phe Asp Glu
540                 545                 550                 555 atc cca gtt gag gtc ttc aag gat tta ttt gaa cta aag atc atc gat       1776
Ile Pro Val Glu Val Phe Lys Asp Leu Phe Glu Leu Lys Ile Ile Asp
            560                 565                 570 tta gga ttg aat aat tta aac aca ctt cca gca tct gtc ttt aat aat       1824
Leu Gly Leu Asn Asn Leu Asn Thr Leu Pro Ala Ser Val Phe Asn Asn
            575                 580                 585 cag gtg tct cta aag tca ttg aac ctt cag aag aat ctc ata aca tcc       1872
Gln Val Ser Leu Lys Ser Leu Asn Leu Gln Lys Asn Leu Ile Thr Ser
            590                 595                 600 gtt gag aag aag gtt ttc ggg cca gct ttc agg aac ctg act gag tta       1920
Val Glu Lys Lys Val Phe Gly Pro Ala Phe Arg Asn Leu Thr Glu Leu
        605                 610                 615 gat atg cgc ttt aat ccc ttt gat tgc acg tgt gaa agt att gcc tgg       1968
Asp Met Arg Phe Asn Pro Phe Asp Cys Thr Cys Glu Ser Ile Ala Trp
620                 625                 630                 635 ttt gtt aat tgg att aac gag acc cat acc aac atc cct gag ctg tca       2016
Phe Val Asn Trp Ile Asn Glu Thr His Thr Asn Ile Pro Glu Leu Ser
            640                 645                 650 agc cac tac ctt tgc aac act cca cct cac tat cat ggg ttc cca gtg       2064
Ser His Tyr Leu Cys Asn Thr Pro Pro His Tyr His Gly Phe Pro Val
            655                 660                 665
```

```
aga ctt ttt gat aca tca tct tgc aaa gac agt gcc ccc ttt gaa ctc    2112
Arg Leu Phe Asp Thr Ser Ser Cys Lys Asp Ser Ala Pro Phe Glu Leu
            670                 675                 680 ttt ttc atg atc aat acc agt atc ctg ttg att ttt atc ttt att gta    2160
Phe Phe Met Ile Asn Thr Ser Ile Leu Leu Ile Phe Ile Phe Ile Val
        685                 690                 695 ctt ctc atc cac ttt gag ggc tgg agg ata tct ttt tat tgg aat gtt    2208
Leu Leu Ile His Phe Glu Gly Trp Arg Ile Ser Phe Tyr Trp Asn Val
700                 705                 710                 715 tca gta cat cga gtt ctt ggt ttc aaa gaa ata gac aga cag aca gaa    2256
Ser Val His Arg Val Leu Gly Phe Lys Glu Ile Asp Arg Gln Thr Glu
                720                 725                 730 cag ttt gaa tat gca gca tat ata att cat gcc tat aaa gat aag gat    2304
Gln Phe Glu Tyr Ala Ala Tyr Ile Ile His Ala Tyr Lys Asp Lys Asp
            735                 740                 745 tgg gtc tgg gaa cat ttc tct tca atg gaa aag gaa gac caa tct ctc    2352
Trp Val Trp Glu His Phe Ser Ser Met Glu Lys Glu Asp Gln Ser Leu
        750                 755                 760 aaa ttt tgt ctg gaa gaa agg gac ttt gag gcg ggt gtt ttt gaa cta    2400
Lys Phe Cys Leu Glu Glu Arg Asp Phe Glu Ala Gly Val Phe Glu Leu
765                 770                 775 gaa gca att gtt aac agc atc aaa aga agc aga aaa att att ttt gtt    2448
Glu Ala Ile Val Asn Ser Ile Lys Arg Ser Arg Lys Ile Ile Phe Val
780                 785                 790                 795 ata aca cac cat cta tta aaa gac cca tta tgc aaa aga ttc aag gta    2496
Ile Thr His His Leu Leu Lys Asp Pro Leu Cys Lys Arg Phe Lys Val
            800                 805                 810 cat cat gca gtt caa caa gct att gaa caa aat ctg gat tcc att ata    2544
His His Ala Val Gln Gln Ala Ile Glu Gln Asn Leu Asp Ser Ile Ile
        815                 820                 825 ttg gtt ttc ctt gag gag att cca gat tat aaa ctg aac cat gca ctc    2592
Leu Val Phe Leu Glu Glu Ile Pro Asp Tyr Lys Leu Asn His Ala Leu
            830                 835                 840 tgt ttg cga aga gga atg ttt aaa tct cac tgc atc ttg aac tgg cca    2640
Cys Leu Arg Arg Gly Met Phe Lys Ser His Cys Ile Leu Asn Trp Pro
        845                 850                 855 gtt cag aaa gaa cgg ata ggt gcc ttt cgt cat aaa ttg caa gta gca    2688
Val Gln Lys Glu Arg Ile Gly Ala Phe Arg His Lys Leu Gln Val Ala
860                 865                 870                 875 ctt gga tcc aaa aac tct gta cat taa                                2715
Leu Gly Ser Lys Asn Ser Val His
                880
```

<210> SEQ ID NO 6
<211> LENGTH: 904
<212> TYPE: PRT
<213> ORGANISM: Homo sapiens

<400> SEQUENCE: 6

```
Met Arg Gln Thr Leu Pro Cys Ile Tyr Phe Trp Gly Gly Leu Leu Pro
        -20                 -15                 -10

Phe Gly Met Leu Cys Ala Ser Ser Thr Thr Lys Cys Thr Val Ser His
 -5                  -1   1                   5                  10

Glu Val Ala Asp Cys Ser His Leu Lys Leu Thr Gln Val Pro Asp Asp
                15                  20                  25

Leu Pro Thr Asn Ile Thr Val Leu Asn Leu Thr His Asn Gln Leu Arg
            30                  35                  40

Arg Leu Pro Ala Ala Asn Phe Thr Arg Tyr Ser Gln Leu Thr Ser Leu
        45                  50                  55
```

-continued

```
Asp Val Gly Phe Asn Thr Ile Ser Lys Leu Glu Pro Glu Leu Cys Gln
 60              65                  70                  75

Lys Leu Pro Met Leu Lys Val Leu Asn Leu Gln His Asn Glu Leu Ser
             80                  85                  90

Gln Leu Ser Asp Lys Thr Phe Ala Phe Cys Thr Asn Leu Thr Glu Leu
         95                 100                 105

His Leu Met Ser Asn Ser Ile Gln Lys Ile Lys Asn Pro Phe Val
            110                 115                 120

Lys Gln Lys Asn Leu Ile Thr Leu Asp Leu Ser His Asn Gly Leu Ser
        125                 130                 135

Ser Thr Lys Leu Gly Thr Gln Val Gln Leu Glu Asn Leu Gln Glu Leu
140                 145                 150                 155

Leu Leu Ser Asn Asn Lys Ile Gln Ala Leu Lys Ser Glu Glu Leu Asp
                160                 165                 170

Ile Phe Ala Asn Ser Ser Leu Lys Lys Leu Glu Leu Ser Ser Asn Gln
                175                 180                 185

Ile Lys Glu Phe Ser Pro Gly Cys Phe His Ala Ile Gly Arg Leu Phe
        190                 195                 200

Gly Leu Phe Leu Asn Asn Val Gln Leu Gly Pro Ser Leu Thr Glu Lys
        205                 210                 215

Leu Cys Leu Glu Leu Ala Asn Thr Ser Ile Arg Asn Leu Ser Leu Ser
220                 225                 230                 235

Asn Ser Gln Leu Ser Thr Thr Ser Asn Thr Thr Phe Leu Gly Leu Lys
                240                 245                 250

Trp Thr Asn Leu Thr Met Leu Asp Leu Ser Tyr Asn Asn Leu Asn Val
                255                 260                 265

Val Gly Asn Asp Ser Phe Ala Trp Leu Pro Gln Leu Glu Tyr Phe Phe
                270                 275                 280

Leu Glu Tyr Asn Asn Ile Gln His Leu Phe Ser His Ser Leu His Gly
        285                 290                 295

Leu Phe Asn Val Arg Tyr Leu Asn Leu Lys Arg Ser Phe Thr Lys Gln
300                 305                 310                 315

Ser Ile Ser Leu Ala Ser Leu Pro Lys Ile Asp Asp Phe Ser Phe Gln
                320                 325                 330

Trp Leu Lys Cys Leu Glu His Leu Asn Met Glu Asp Asn Asp Ile Pro
                335                 340                 345

Gly Ile Lys Ser Asn Met Phe Thr Gly Leu Ile Asn Leu Lys Tyr Leu
        350                 355                 360

Ser Leu Ser Asn Ser Phe Thr Ser Leu Arg Thr Leu Thr Asn Glu Thr
        365                 370                 375

Phe Val Ser Leu Ala His Ser Pro Leu His Ile Leu Asn Leu Thr Lys
380                 385                 390                 395

Asn Lys Ile Ser Lys Ile Glu Ser Asp Ala Phe Ser Trp Leu Gly His
                400                 405                 410

Leu Glu Val Leu Asp Leu Gly Leu Asn Glu Ile Gly Gln Glu Leu Thr
                415                 420                 425

Gly Gln Glu Trp Arg Gly Leu Glu Asn Ile Phe Glu Ile Tyr Leu Ser
            430                 435                 440

Tyr Asn Lys Tyr Leu Gln Leu Thr Arg Asn Ser Phe Ala Leu Val Pro
        445                 450                 455

Ser Leu Gln Arg Leu Met Leu Arg Arg Val Ala Leu Lys Asn Val Asp
460                 465                 470                 475

Ser Ser Pro Ser Pro Phe Gln Pro Leu Arg Asn Leu Thr Ile Leu Asp
```

```
                         480             485             490
Leu Ser Asn Asn Asn Ile Ala Asn Ile Asn Asp Asp Met Leu Glu Gly
                495                 500                 505
Leu Glu Lys Leu Glu Ile Leu Asp Leu Gln His Asn Asn Leu Ala Arg
                510                 515                 520
Leu Trp Lys His Ala Asn Pro Gly Pro Ile Tyr Phe Leu Lys Gly
                525                 530                 535
Leu Ser His Leu His Ile Leu Asn Leu Glu Ser Asn Gly Phe Asp Glu
540                 545                 550                 555
Ile Pro Val Glu Val Phe Lys Asp Leu Phe Glu Leu Lys Ile Ile Asp
                560                 565                 570
Leu Gly Leu Asn Asn Leu Asn Thr Leu Pro Ala Ser Val Phe Asn Asn
                575                 580                 585
Gln Val Ser Leu Lys Ser Leu Asn Leu Gln Lys Asn Leu Ile Thr Ser
                590                 595                 600
Val Glu Lys Lys Val Phe Gly Pro Ala Phe Arg Asn Leu Thr Glu Leu
                605                 610                 615
Asp Met Arg Phe Asn Pro Phe Asp Cys Thr Cys Glu Ser Ile Ala Trp
620                 625                 630                 635
Phe Val Asn Trp Ile Asn Glu Thr His Thr Asn Ile Pro Glu Leu Ser
                640                 645                 650
Ser His Tyr Leu Cys Asn Thr Pro Pro His Tyr His Gly Phe Pro Val
                655                 660                 665
Arg Leu Phe Asp Thr Ser Ser Cys Lys Asp Ser Ala Pro Phe Glu Leu
                670                 675                 680
Phe Phe Met Ile Asn Thr Ser Ile Leu Leu Ile Phe Ile Phe Ile Val
                685                 690                 695
Leu Leu Ile His Phe Glu Gly Trp Arg Ile Ser Phe Tyr Trp Asn Val
700                 705                 710                 715
Ser Val His Arg Val Leu Gly Phe Lys Glu Ile Asp Arg Gln Thr Glu
                720                 725                 730
Gln Phe Glu Tyr Ala Ala Tyr Ile Ile His Ala Tyr Lys Asp Lys Asp
                735                 740                 745
Trp Val Trp Glu His Phe Ser Ser Met Glu Lys Glu Asp Gln Ser Leu
                750                 755                 760
Lys Phe Cys Leu Glu Glu Arg Asp Phe Glu Ala Gly Val Phe Glu Leu
                765                 770                 775
Glu Ala Ile Val Asn Ser Ile Lys Arg Ser Arg Lys Ile Ile Phe Val
780                 785                 790                 795
Ile Thr His His Leu Leu Lys Asp Pro Leu Cys Lys Arg Phe Lys Val
                800                 805                 810
His His Ala Val Gln Gln Ala Ile Glu Gln Asn Leu Asp Ser Ile Ile
                815                 820                 825
Leu Val Phe Leu Glu Glu Ile Pro Asp Tyr Lys Leu Asn His Ala Leu
                830                 835                 840
Cys Leu Arg Arg Gly Met Phe Lys Ser His Cys Ile Leu Asn Trp Pro
                845                 850                 855
Val Gln Lys Glu Arg Ile Gly Ala Phe Arg His Lys Leu Gln Val Ala
860                 865                 870                 875
Leu Gly Ser Lys Asn Ser Val His
                880
```

<210> SEQ ID NO 7

<211> LENGTH: 2400
<212> TYPE: DNA
<213> ORGANISM: Homo sapiens
<220> FEATURE:
<221> NAME/KEY: CDS
<222> LOCATION: (1)..(2397)
<223> OTHER INFORMATION:

<400> SEQUENCE: 7

| | | | | | | | | | | | | | | | | |
|---|---|---|---|---|---|---|---|---|---|---|---|---|---|---|---|---|
| atg | gag | ctg | aat | ttc | tac | aaa | atc | ccc | gac | aac | ctc | ccc | ttc | tca | acc | 48 |
| Met | Glu | Leu | Asn | Phe | Tyr | Lys | Ile | Pro | Asp | Asn | Leu | Pro | Phe | Ser | Thr | |
| 1 | | | | 5 | | | | | 10 | | | | | 15 | | |
| aag | aac | ctg | gac | ctg | agc | ttt | aat | ccc | ctg | agg | cat | tta | ggc | agc | tat | 96 |
| Lys | Asn | Leu | Asp | Leu | Ser | Phe | Asn | Pro | Leu | Arg | His | Leu | Gly | Ser | Tyr | |
| | | | 20 | | | | | 25 | | | | | 30 | | | |
| agc | ttc | ttc | agt | ttc | cca | gaa | ctg | cag | gtg | ctg | gat | tta | tcc | agg | tgt | 144 |
| Ser | Phe | Phe | Ser | Phe | Pro | Glu | Leu | Gln | Val | Leu | Asp | Leu | Ser | Arg | Cys | |
| | | 35 | | | | | 40 | | | | | 45 | | | | |
| gaa | atc | cag | aca | att | gaa | gat | ggg | gca | tat | cag | agc | cta | agc | cac | ctc | 192 |
| Glu | Ile | Gln | Thr | Ile | Glu | Asp | Gly | Ala | Tyr | Gln | Ser | Leu | Ser | His | Leu | |
| | 50 | | | | | 55 | | | | | 60 | | | | | |
| tct | acc | tta | ata | ttg | aca | gga | aac | ccc | atc | cag | agt | tta | gcc | ctg | gga | 240 |
| Ser | Thr | Leu | Ile | Leu | Thr | Gly | Asn | Pro | Ile | Gln | Ser | Leu | Ala | Leu | Gly | |
| 65 | | | | | 70 | | | | | 75 | | | | | 80 | |
| gcc | ttt | tct | gga | cta | tca | agt | tta | cag | aag | ctg | gtg | gct | gtg | gag | aca | 288 |
| Ala | Phe | Ser | Gly | Leu | Ser | Ser | Leu | Gln | Lys | Leu | Val | Ala | Val | Glu | Thr | |
| | | | | 85 | | | | | 90 | | | | | 95 | | |
| aat | cta | gca | tct | cta | gag | aac | ttc | ccc | att | gga | cat | ctc | aaa | act | ttg | 336 |
| Asn | Leu | Ala | Ser | Leu | Glu | Asn | Phe | Pro | Ile | Gly | His | Leu | Lys | Thr | Leu | |
| | | | 100 | | | | | 105 | | | | | 110 | | | |
| aaa | gaa | ctt | aat | gtg | gct | cac | aat | ctt | atc | caa | tct | ttc | aaa | tta | cct | 384 |
| Lys | Glu | Leu | Asn | Val | Ala | His | Asn | Leu | Ile | Gln | Ser | Phe | Lys | Leu | Pro | |
| | | 115 | | | | | 120 | | | | | 125 | | | | |
| gag | tat | ttt | tct | aat | ctg | acc | aat | cta | gag | cac | ttg | gac | ctt | tcc | agc | 432 |
| Glu | Tyr | Phe | Ser | Asn | Leu | Thr | Asn | Leu | Glu | His | Leu | Asp | Leu | Ser | Ser | |
| | 130 | | | | | 135 | | | | | 140 | | | | | |
| aac | aag | att | caa | agt | att | tat | tgc | aca | gac | ttg | cgg | gtt | cta | cat | caa | 480 |
| Asn | Lys | Ile | Gln | Ser | Ile | Tyr | Cys | Thr | Asp | Leu | Arg | Val | Leu | His | Gln | |
| 145 | | | | | 150 | | | | | 155 | | | | | 160 | |
| atg | ccc | cta | ctc | aat | ctc | tct | tta | gac | ctg | tcc | ctg | aac | cct | atg | aac | 528 |
| Met | Pro | Leu | Leu | Asn | Leu | Ser | Leu | Asp | Leu | Ser | Leu | Asn | Pro | Met | Asn | |
| | | | | 165 | | | | | 170 | | | | | 175 | | |
| ttt | atc | caa | cca | ggt | gca | ttt | aaa | gaa | att | agg | ctt | cat | aag | ctg | act | 576 |
| Phe | Ile | Gln | Pro | Gly | Ala | Phe | Lys | Glu | Ile | Arg | Leu | His | Lys | Leu | Thr | |
| | | | 180 | | | | | 185 | | | | | 190 | | | |
| tta | aga | aat | aat | ttt | gat | agt | tta | aat | gta | atg | aaa | act | tgt | att | caa | 624 |
| Leu | Arg | Asn | Asn | Phe | Asp | Ser | Leu | Asn | Val | Met | Lys | Thr | Cys | Ile | Gln | |
| | | 195 | | | | | 200 | | | | | 205 | | | | |
| ggt | ctg | gct | ggt | tta | gaa | gtc | cat | cgt | ttg | gtt | ctg | gga | gaa | ttt | aga | 672 |
| Gly | Leu | Ala | Gly | Leu | Glu | Val | His | Arg | Leu | Val | Leu | Gly | Glu | Phe | Arg | |
| | 210 | | | | | 215 | | | | | 220 | | | | | |
| aat | gaa | gga | aac | ttg | gaa | aag | ttt | gac | aaa | tct | gct | cta | gag | ggc | ctg | 720 |
| Asn | Glu | Gly | Asn | Leu | Glu | Lys | Phe | Asp | Lys | Ser | Ala | Leu | Glu | Gly | Leu | |
| 225 | | | | | 230 | | | | | 235 | | | | | 240 | |
| tgc | aat | ttg | acc | att | gaa | gaa | ttc | cga | tta | gca | tac | tta | gac | tac | tac | 768 |
| Cys | Asn | Leu | Thr | Ile | Glu | Glu | Phe | Arg | Leu | Ala | Tyr | Leu | Asp | Tyr | Tyr | |
| | | | | 245 | | | | | 250 | | | | | 255 | | |
| ctc | gat | gat | att | att | gac | tta | ttt | aat | tgt | ttg | aca | aat | gtt | tct | tca | 816 |
| Leu | Asp | Asp | Ile | Ile | Asp | Leu | Phe | Asn | Cys | Leu | Thr | Asn | Val | Ser | Ser | |
| | | | 260 | | | | | 265 | | | | | 270 | | | |
| ttt | tcc | ctg | gtg | agt | gtg | act | att | gaa | agg | gta | aaa | gac | ttt | tct | tat | 864 |

```
                Phe Ser Leu Val Ser Val Thr Ile Glu Arg Val Lys Asp Phe Ser Tyr
                            275                 280                 285 aat ttc gga tgg caa cat tta gaa tta gtt aac tgt aaa ttt gga cag                912
Asn Phe Gly Trp Gln His Leu Glu Leu Val Asn Cys Lys Phe Gly Gln
        290                 295                 300 ttt ccc aca ttg aaa ctc aaa tct ctc aaa agg ctt act ttc act tcc                960
Phe Pro Thr Leu Lys Leu Lys Ser Leu Lys Arg Leu Thr Phe Thr Ser
305                 310                 315                 320 aac aaa ggt ggg aat gct ttt tca gaa gtt gat cta cca agc ctt gag               1008
Asn Lys Gly Gly Asn Ala Phe Ser Glu Val Asp Leu Pro Ser Leu Glu
                325                 330                 335 ttt cta gat ctc agt aga aat ggc ttg agt ttc aaa ggt tgc tgt tct               1056
Phe Leu Asp Leu Ser Arg Asn Gly Leu Ser Phe Lys Gly Cys Cys Ser
            340                 345                 350 caa agt gat ttt ggg aca acc agc cta aag tat tta gat ctg agc ttc               1104
Gln Ser Asp Phe Gly Thr Thr Ser Leu Lys Tyr Leu Asp Leu Ser Phe
        355                 360                 365 aat ggt gtt att acc atg agt tca aac ttc ttg ggc tta gaa caa cta               1152
Asn Gly Val Ile Thr Met Ser Ser Asn Phe Leu Gly Leu Glu Gln Leu
370                 375                 380 gaa cat ctg gat ttc cag cat tcc aat ttg aaa caa atg agt gag ttt               1200
Glu His Leu Asp Phe Gln His Ser Asn Leu Lys Gln Met Ser Glu Phe
385                 390                 395                 400 tca gta ttc cta tca ctc aga aac ctc att tac ctt gac att tct cat               1248
Ser Val Phe Leu Ser Leu Arg Asn Leu Ile Tyr Leu Asp Ile Ser His
                405                 410                 415 act cac acc aga gtt gct ttc aat ggc atc ttc aat ggc ttg tcc agt               1296
Thr His Thr Arg Val Ala Phe Asn Gly Ile Phe Asn Gly Leu Ser Ser
            420                 425                 430 ctc gaa gtc ttg aaa atg gct ggc aat tct ttc cag gaa aac ttc ctt               1344
Leu Glu Val Leu Lys Met Ala Gly Asn Ser Phe Gln Glu Asn Phe Leu
        435                 440                 445 cca gat atc ttc aca gag ctg aga aac ttg acc ttc ctg gac ctc tct               1392
Pro Asp Ile Phe Thr Glu Leu Arg Asn Leu Thr Phe Leu Asp Leu Ser
450                 455                 460 cag tgt caa ctg gag cag ttg tct cca aca gca ttt aac tca ctc tcc               1440
Gln Cys Gln Leu Glu Gln Leu Ser Pro Thr Ala Phe Asn Ser Leu Ser
465                 470                 475                 480 agt ctt cag gta cta aat atg agc cac aac aac ttc ttt tca ttg gat               1488
Ser Leu Gln Val Leu Asn Met Ser His Asn Asn Phe Phe Ser Leu Asp
                485                 490                 495 acg ttt cct tat aag tgt ctg aac tcc ctc cag gtt ctt gat tac agt               1536
Thr Phe Pro Tyr Lys Cys Leu Asn Ser Leu Gln Val Leu Asp Tyr Ser
            500                 505                 510 ctc aat cac ata atg act tcc aaa aaa cag gaa cta cag cat ttt cca               1584
Leu Asn His Ile Met Thr Ser Lys Lys Gln Glu Leu Gln His Phe Pro
        515                 520                 525 agt agt cta gct ttc tta aat ctt act cag aat gac ttt gct tgt act               1632
Ser Ser Leu Ala Phe Leu Asn Leu Thr Gln Asn Asp Phe Ala Cys Thr
530                 535                 540 tgt gaa cac cag agt ttc ctg caa tgg atc aag gac cag agg cag ctc               1680
Cys Glu His Gln Ser Phe Leu Gln Trp Ile Lys Asp Gln Arg Gln Leu
545                 550                 555                 560 ttg gtg gaa gtt gaa cga atg gaa tgt gca aca cct tca gat aag cag               1728
Leu Val Glu Val Glu Arg Met Glu Cys Ala Thr Pro Ser Asp Lys Gln
                565                 570                 575 ggc atg cct gtg ctg agt ttg aat atc acc tgt cag atg aat aag acc               1776
Gly Met Pro Val Leu Ser Leu Asn Ile Thr Cys Gln Met Asn Lys Thr
            580                 585                 590
```

-continued

```
atc att ggt gtg tcg gtc ctc agt gtg ctt gta gta tct gtt gta gca    1824
Ile Ile Gly Val Ser Val Leu Ser Val Leu Val Val Ser Val Val Ala
            595                 600                 605 gtt ctg gtc tat aag ttc tat ttt cac ctg atg ctt ctt gct ggc tgc    1872
Val Leu Val Tyr Lys Phe Tyr Phe His Leu Met Leu Leu Ala Gly Cys
    610                 615                 620 ata aag tat ggt aga ggt gaa aac atc tat gat gcc ttt gtt atc tac    1920
Ile Lys Tyr Gly Arg Gly Glu Asn Ile Tyr Asp Ala Phe Val Ile Tyr
625                 630                 635                 640 tca agc cag gat gag gac tgg gta agg aat gag cta gta aag aat tta    1968
Ser Ser Gln Asp Glu Asp Trp Val Arg Asn Glu Leu Val Lys Asn Leu
            645                 650                 655 gaa gaa ggg gtg cct cca ttt cag ctc tgc ctt cac tac aga gac ttt    2016
Glu Glu Gly Val Pro Pro Phe Gln Leu Cys Leu His Tyr Arg Asp Phe
    660                 665                 670 att ccc ggt gtg gcc att gct gcc aac atc atc cat gaa ggt ttc cat    2064
Ile Pro Gly Val Ala Ile Ala Ala Asn Ile Ile His Glu Gly Phe His
675                 680                 685 aaa agc cga aag gtg att gtt gtg gtg tcc cag cac ttc atc cag agc    2112
Lys Ser Arg Lys Val Ile Val Val Val Ser Gln His Phe Ile Gln Ser
            690                 695                 700 cgc tgg tgt atc ttt gaa tat gag att gct cag acc tgg cag ttt ctg    2160
Arg Trp Cys Ile Phe Glu Tyr Glu Ile Ala Gln Thr Trp Gln Phe Leu
705                 710                 715                 720 agc agt cgt gct ggt atc atc ttc att gtc ctg cag aag gtg gag aag    2208
Ser Ser Arg Ala Gly Ile Ile Phe Ile Val Leu Gln Lys Val Glu Lys
            725                 730                 735 acc ctg ctc agg cag cag gtg gag ctg tac cgc ctt ctc agc agg aac    2256
Thr Leu Leu Arg Gln Gln Val Glu Leu Tyr Arg Leu Leu Ser Arg Asn
    740                 745                 750 act tac ctg gag tgg gag gac agt gtc ctg ggg cgg cac atc ttc tgg    2304
Thr Tyr Leu Glu Trp Glu Asp Ser Val Leu Gly Arg His Ile Phe Trp
755                 760                 765 aga cga ctc aga aaa gcc ctg ctg gat ggt aaa tca tgg aat cca gaa    2352
Arg Arg Leu Arg Lys Ala Leu Leu Asp Gly Lys Ser Trp Asn Pro Glu
            770                 775                 780 gga aca gtg ggt aca gga tgc aat tgg cag gaa gca aca tct atc tga    2400
Gly Thr Val Gly Thr Gly Cys Asn Trp Gln Glu Ala Thr Ser Ile
785                 790                 795
```

<210> SEQ ID NO 8
<211> LENGTH: 799
<212> TYPE: PRT
<213> ORGANISM: Homo sapiens

<400> SEQUENCE: 8

```
Met Glu Leu Asn Phe Tyr Lys Ile Pro Asp Asn Leu Pro Phe Ser Thr
1               5                   10                  15

Lys Asn Leu Asp Leu Ser Phe Asn Pro Leu Arg His Leu Gly Ser Tyr
            20                  25                  30

Ser Phe Phe Ser Phe Pro Glu Leu Gln Val Leu Asp Leu Ser Arg Cys
        35                  40                  45

Glu Ile Gln Thr Ile Glu Asp Gly Ala Tyr Gln Ser Leu Ser His Leu
    50                  55                  60

Ser Thr Leu Ile Leu Thr Gly Asn Pro Ile Gln Ser Leu Ala Leu Gly
65                  70                  75                  80

Ala Phe Ser Gly Leu Ser Ser Leu Gln Lys Leu Val Ala Val Glu Thr
                85                  90                  95

Asn Leu Ala Ser Leu Glu Asn Phe Pro Ile Gly His Leu Lys Thr Leu
```

-continued

```
                100                 105                 110
Lys Glu Leu Asn Val Ala His Asn Leu Ile Gln Ser Phe Lys Leu Pro
        115                 120                 125

Glu Tyr Phe Ser Asn Leu Thr Asn Leu Glu His Leu Asp Leu Ser Ser
        130                 135                 140

Asn Lys Ile Gln Ser Ile Tyr Cys Thr Asp Leu Arg Val Leu His Gln
145                 150                 155                 160

Met Pro Leu Leu Asn Leu Ser Leu Asp Leu Ser Leu Asn Pro Met Asn
                165                 170                 175

Phe Ile Gln Pro Gly Ala Phe Lys Glu Ile Arg Leu His Lys Leu Thr
        180                 185                 190

Leu Arg Asn Asn Phe Asp Ser Leu Asn Val Met Lys Thr Cys Ile Gln
        195                 200                 205

Gly Leu Ala Gly Leu Glu Val His Arg Leu Val Leu Gly Glu Phe Arg
        210                 215                 220

Asn Glu Gly Asn Leu Glu Lys Phe Asp Lys Ser Ala Leu Glu Gly Leu
225                 230                 235                 240

Cys Asn Leu Thr Ile Glu Glu Phe Arg Leu Ala Tyr Leu Asp Tyr Tyr
                245                 250                 255

Leu Asp Asp Ile Ile Asp Leu Phe Asn Cys Leu Thr Asn Val Ser Ser
                260                 265                 270

Phe Ser Leu Val Ser Val Thr Ile Glu Arg Val Lys Asp Phe Ser Tyr
        275                 280                 285

Asn Phe Gly Trp Gln His Leu Glu Leu Val Asn Cys Lys Phe Gly Gln
        290                 295                 300

Phe Pro Thr Leu Lys Leu Lys Ser Leu Lys Arg Leu Thr Phe Thr Ser
305                 310                 315                 320

Asn Lys Gly Gly Asn Ala Phe Ser Glu Val Asp Leu Pro Ser Leu Glu
                325                 330                 335

Phe Leu Asp Leu Ser Arg Asn Gly Leu Ser Phe Lys Gly Cys Cys Ser
                340                 345                 350

Gln Ser Asp Phe Gly Thr Thr Ser Leu Lys Tyr Leu Asp Leu Ser Phe
        355                 360                 365

Asn Gly Val Ile Thr Met Ser Ser Asn Phe Leu Gly Leu Glu Gln Leu
        370                 375                 380

Glu His Leu Asp Phe Gln His Ser Asn Leu Lys Gln Met Ser Glu Phe
385                 390                 395                 400

Ser Val Phe Leu Ser Leu Arg Asn Leu Ile Tyr Leu Asp Ile Ser His
                405                 410                 415

Thr His Thr Arg Val Ala Phe Asn Gly Ile Phe Asn Gly Leu Ser Ser
                420                 425                 430

Leu Glu Val Leu Lys Met Ala Gly Asn Ser Phe Gln Glu Asn Phe Leu
        435                 440                 445

Pro Asp Ile Phe Thr Glu Leu Arg Asn Leu Thr Phe Leu Asp Leu Ser
        450                 455                 460

Gln Cys Gln Leu Glu Gln Leu Ser Pro Thr Ala Phe Asn Ser Leu Ser
465                 470                 475                 480

Ser Leu Gln Val Leu Asn Met Ser His Asn Asn Phe Phe Ser Leu Asp
                485                 490                 495

Thr Phe Pro Tyr Lys Cys Leu Asn Ser Leu Gln Val Leu Asp Tyr Ser
        500                 505                 510

Leu Asn His Ile Met Thr Ser Lys Lys Gln Glu Leu Gln His Phe Pro
        515                 520                 525
```

```
Ser Ser Leu Ala Phe Leu Asn Leu Thr Gln Asn Asp Phe Ala Cys Thr
    530                 535                 540

Cys Glu His Gln Ser Phe Leu Gln Trp Ile Lys Asp Gln Arg Gln Leu
545                 550                 555                 560

Leu Val Glu Val Glu Arg Met Glu Cys Ala Thr Pro Ser Asp Lys Gln
                565                 570                 575

Gly Met Pro Val Leu Ser Leu Asn Ile Thr Cys Gln Met Asn Lys Thr
            580                 585                 590

Ile Ile Gly Val Ser Val Leu Ser Val Leu Val Ser Val Val Ala
        595                 600                 605

Val Leu Val Tyr Lys Phe Tyr Phe His Leu Met Leu Leu Ala Gly Cys
610                 615                 620

Ile Lys Tyr Gly Arg Gly Glu Asn Ile Tyr Asp Ala Phe Val Ile Tyr
625                 630                 635                 640

Ser Ser Gln Asp Glu Asp Trp Val Arg Asn Glu Leu Val Lys Asn Leu
                645                 650                 655

Glu Glu Gly Val Pro Pro Phe Gln Leu Cys Leu His Tyr Arg Asp Phe
                660                 665                 670

Ile Pro Gly Val Ala Ile Ala Ala Asn Ile Ile His Glu Gly Phe His
            675                 680                 685

Lys Ser Arg Lys Val Ile Val Val Ser Gln His Phe Ile Gln Ser
        690                 695                 700

Arg Trp Cys Ile Phe Glu Tyr Glu Ile Ala Gln Thr Trp Gln Phe Leu
705                 710                 715                 720

Ser Ser Arg Ala Gly Ile Ile Phe Ile Val Leu Gln Lys Val Glu Lys
                725                 730                 735

Thr Leu Leu Arg Gln Gln Val Glu Leu Tyr Arg Leu Leu Ser Arg Asn
                740                 745                 750

Thr Tyr Leu Glu Trp Glu Asp Ser Val Leu Gly Arg His Ile Phe Trp
            755                 760                 765

Arg Arg Leu Arg Lys Ala Leu Leu Asp Gly Lys Ser Trp Asn Pro Glu
770                 775                 780

Gly Thr Val Gly Thr Gly Cys Asn Trp Gln Glu Ala Thr Ser Ile
785                 790                 795

<210> SEQ ID NO 9
<211> LENGTH: 1275
<212> TYPE: DNA
<213> ORGANISM: Homo sapiens
<220> FEATURE:
<221> NAME/KEY: CDS
<222> LOCATION: (1)..(1095)
<223> OTHER INFORMATION:

<400> SEQUENCE: 9 tgt tgg gat gtt ttt gag gga ctt tct cat ctt caa gtt ctg tat ttg    48
Cys Trp Asp Val Phe Glu Gly Leu Ser His Leu Gln Val Leu Tyr Leu
1               5                   10                  15 aat cat aac tat ctt aat tcc ctt cca cca gga gta ttt agc cat ctg    96
Asn His Asn Tyr Leu Asn Ser Leu Pro Pro Gly Val Phe Ser His Leu
                20                  25                  30 act gca tta agg gga cta agc ctc aac tcc aac agg ctg aca gtt ctt   144
Thr Ala Leu Arg Gly Leu Ser Leu Asn Ser Asn Arg Leu Thr Val Leu
            35                  40                  45 tct cac aat gat tta cct gct aat tta gag atc ctg gac ata tcc agg   192
Ser His Asn Asp Leu Pro Ala Asn Leu Glu Ile Leu Asp Ile Ser Arg
        50                  55                  60
```

```
aac cag ctc cta gct cct aat cct gat gta ttt gta tca ctt agt gtc      240
Asn Gln Leu Leu Ala Pro Asn Pro Asp Val Phe Val Ser Leu Ser Val
 65                  70                  75                  80 ttg gat ata act cat aac aag ttc att tgt gaa tgt gaa ctt agc act      288
Leu Asp Ile Thr His Asn Lys Phe Ile Cys Glu Cys Glu Leu Ser Thr
                     85                  90                  95 ttt atc aat tgg ctt aat cac acc aat gtc act ata gct ggg cct cct      336
Phe Ile Asn Trp Leu Asn His Thr Asn Val Thr Ile Ala Gly Pro Pro
                100                 105                 110 gca gac ata tat tgt gtg tac cct gac tcg ttc tct ggg gtt tcc ctc      384
Ala Asp Ile Tyr Cys Val Tyr Pro Asp Ser Phe Ser Gly Val Ser Leu
            115                 120                 125 ttc tct ctt tcc acg gaa ggt tgt gat gaa gag gaa gtc tta aag tcc      432
Phe Ser Leu Ser Thr Glu Gly Cys Asp Glu Glu Glu Val Leu Lys Ser
130                 135                 140 cta aag ttc tcc ctt ttc att gta tgc act gtc act ctg act ctg ttc      480
Leu Lys Phe Ser Leu Phe Ile Val Cys Thr Val Thr Leu Thr Leu Phe
145                 150                 155                 160 ctc atg acc atc ctc aca gtc aca aag ttc cgg ggc ttc tgt ttt atc      528
Leu Met Thr Ile Leu Thr Val Thr Lys Phe Arg Gly Phe Cys Phe Ile
                165                 170                 175 tgt tat aag aca gcc cag aga ctg gtg ttc aag gac cat ccc cag ggc      576
Cys Tyr Lys Thr Ala Gln Arg Leu Val Phe Lys Asp His Pro Gln Gly
            180                 185                 190 aca gaa cct gat atg tac aaa tat gat gcc tat ttg tgc ttc agc agc      624
Thr Glu Pro Asp Met Tyr Lys Tyr Asp Ala Tyr Leu Cys Phe Ser Ser
        195                 200                 205 aaa gac ttc aca tgg gtg cag aat gct ttg ctc aaa cac ctg gac act      672
Lys Asp Phe Thr Trp Val Gln Asn Ala Leu Leu Lys His Leu Asp Thr
210                 215                 220 caa tac agt gac caa aac aga ttc aac ctg tgc ttt gaa gaa aga gac      720
Gln Tyr Ser Asp Gln Asn Arg Phe Asn Leu Cys Phe Glu Glu Arg Asp
225                 230                 235                 240 ttt gtc cca gga gaa aac cgc att gcc aat atc cag gat gcc atc tgg      768
Phe Val Pro Gly Glu Asn Arg Ile Ala Asn Ile Gln Asp Ala Ile Trp
                245                 250                 255 aac agt aga aag atc gtt tgt ctt gtg agc aga cac ttc ctt aga gat      816
Asn Ser Arg Lys Ile Val Cys Leu Val Ser Arg His Phe Leu Arg Asp
            260                 265                 270 ggc tgg tgc ctt gaa gcc ttc agt tat gcc cag ggc agg tgc tta tct      864
Gly Trp Cys Leu Glu Ala Phe Ser Tyr Ala Gln Gly Arg Cys Leu Ser
        275                 280                 285 gac ctt aac agt gct ctc atc atg gtg gtg gtt ggg tcc ttg tcc cag      912
Asp Leu Asn Ser Ala Leu Ile Met Val Val Val Gly Ser Leu Ser Gln
290                 295                 300 tac cag ttg atg aaa cat caa tcc atc aga ggc ttt gta cag aaa cag      960
Tyr Gln Leu Met Lys His Gln Ser Ile Arg Gly Phe Val Gln Lys Gln
305                 310                 315                 320 cag tat ttg agg tgg cct gag gat ctc cag gat gtt ggc tgg ttt ctt     1008
Gln Tyr Leu Arg Trp Pro Glu Asp Leu Gln Asp Val Gly Trp Phe Leu
                325                 330                 335 cat aaa ctc tct caa cag ata cta aag aaa gaa aag gaa aag aag aaa     1056
His Lys Leu Ser Gln Gln Ile Leu Lys Lys Glu Lys Glu Lys Lys Lys
            340                 345                 350 gac aat aac att ccg ttg caa act gta gca acc atc tcc taatcaaagg      1105
Asp Asn Asn Ile Pro Leu Gln Thr Val Ala Thr Ile Ser
        355                 360                 365 agcaatttcc aacttatctc aagccacaaa taactcttca ctttgtattt gcaccaagtt  1165
```

```
atcattttgg ggtcctctct ggaggttttt tttttctttt tgctactatg aaaacaacat    1225
aaatctctca attttcgtat caaaaaaaaa aaaaaaaaa tggcggccgc                1275
```

<210> SEQ ID NO 10
<211> LENGTH: 365
<212> TYPE: PRT
<213> ORGANISM: Homo sapiens

<400> SEQUENCE: 10

```
Cys Trp Asp Val Phe Glu Gly Leu Ser His Leu Gln Val Leu Tyr Leu
1               5                   10                  15

Asn His Asn Tyr Leu Asn Ser Leu Pro Pro Gly Val Phe Ser His Leu
            20                  25                  30

Thr Ala Leu Arg Gly Leu Ser Leu Asn Ser Asn Arg Leu Thr Val Leu
        35                  40                  45

Ser His Asn Asp Leu Pro Ala Asn Leu Glu Ile Leu Asp Ile Ser Arg
    50                  55                  60

Asn Gln Leu Leu Ala Pro Asn Pro Asp Val Phe Val Ser Leu Ser Val
65                  70                  75                  80

Leu Asp Ile Thr His Asn Lys Phe Ile Cys Glu Cys Glu Leu Ser Thr
                85                  90                  95

Phe Ile Asn Trp Leu Asn His Thr Asn Val Thr Ile Ala Gly Pro Pro
            100                 105                 110

Ala Asp Ile Tyr Cys Val Tyr Pro Asp Ser Phe Ser Gly Val Ser Leu
        115                 120                 125

Phe Ser Leu Ser Thr Glu Gly Cys Asp Glu Glu Val Leu Lys Ser
    130                 135                 140

Leu Lys Phe Ser Leu Phe Ile Val Cys Thr Val Thr Leu Thr Leu Phe
145                 150                 155                 160

Leu Met Thr Ile Leu Thr Val Thr Lys Phe Arg Gly Phe Cys Phe Ile
                165                 170                 175

Cys Tyr Lys Thr Ala Gln Arg Leu Val Phe Lys Asp His Pro Gln Gly
            180                 185                 190

Thr Glu Pro Asp Met Tyr Lys Tyr Asp Ala Tyr Leu Cys Phe Ser Ser
        195                 200                 205

Lys Asp Phe Thr Trp Val Gln Asn Ala Leu Leu Lys His Leu Asp Thr
    210                 215                 220

Gln Tyr Ser Asp Gln Asn Arg Phe Asn Leu Cys Phe Glu Glu Arg Asp
225                 230                 235                 240

Phe Val Pro Gly Glu Asn Arg Ile Ala Asn Ile Gln Asp Ala Ile Trp
                245                 250                 255

Asn Ser Arg Lys Ile Val Cys Leu Val Ser Arg His Phe Leu Arg Asp
            260                 265                 270

Gly Trp Cys Leu Glu Ala Phe Ser Tyr Ala Gln Gly Arg Cys Leu Ser
        275                 280                 285

Asp Leu Asn Ser Ala Leu Ile Met Val Val Gly Ser Leu Ser Gln
    290                 295                 300

Tyr Gln Leu Met Lys His Gln Ser Ile Arg Gly Phe Val Gln Lys Gln
305                 310                 315                 320

Gln Tyr Leu Arg Trp Pro Glu Asp Leu Gln Asp Val Gly Trp Phe Leu
                325                 330                 335

His Lys Leu Ser Gln Gln Ile Leu Lys Lys Glu Lys Glu Lys Lys Lys
            340                 345                 350

Asp Asn Asn Ile Pro Leu Gln Thr Val Ala Thr Ile Ser
        355                 360                 365
```

<210> SEQ ID NO 11
<211> LENGTH: 3138
<212> TYPE: DNA
<213> ORGANISM: Homo sapiens
<220> FEATURE:
<221> NAME/KEY: CDS
<222> LOCATION: (1)..(3135)
<223> OTHER INFORMATION:

<400> SEQUENCE: 11

| | | | | | | | | | | | | | | | | |
|---|---|---|---|---|---|---|---|---|---|---|---|---|---|---|---|---|
| atg | tgg | aca | ctg | aag | aga | cta | att | ctt | atc | ctt | ttt | aac | ata | atc | cta | 48 |
| Met | Trp | Thr | Leu | Lys | Arg | Leu | Ile | Leu | Ile | Leu | Phe | Asn | Ile | Ile | Leu | |
| 1 | | | | 5 | | | | | 10 | | | | | 15 | | |
| att | tcc | aaa | ctc | ctt | ggg | gct | aga | tgg | ttt | cct | aaa | act | ctg | ccc | tgt | 96 |
| Ile | Ser | Lys | Leu | Leu | Gly | Ala | Arg | Trp | Phe | Pro | Lys | Thr | Leu | Pro | Cys | |
| | | | 20 | | | | | 25 | | | | | 30 | | | |
| gat | gtc | act | ctg | gat | gtt | cca | aag | aac | cat | gtg | atc | gtg | gac | tgc | aca | 144 |
| Asp | Val | Thr | Leu | Asp | Val | Pro | Lys | Asn | His | Val | Ile | Val | Asp | Cys | Thr | |
| | | 35 | | | | | 40 | | | | | 45 | | | | |
| gac | aag | cat | ttg | aca | gaa | att | cct | gga | ggt | att | ccc | acg | aac | acc | acg | 192 |
| Asp | Lys | His | Leu | Thr | Glu | Ile | Pro | Gly | Gly | Ile | Pro | Thr | Asn | Thr | Thr | |
| | 50 | | | | | 55 | | | | | 60 | | | | | |
| aac | ctc | acc | ctc | acc | att | aac | cac | ata | cca | gac | atc | tcc | cca | gcg | tcc | 240 |
| Asn | Leu | Thr | Leu | Thr | Ile | Asn | His | Ile | Pro | Asp | Ile | Ser | Pro | Ala | Ser | |
| 65 | | | | | 70 | | | | | 75 | | | | | 80 | |
| ttt | cac | aga | ctg | gac | cat | ctg | gta | gag | atc | gat | ttc | aga | tgc | aac | tgt | 288 |
| Phe | His | Arg | Leu | Asp | His | Leu | Val | Glu | Ile | Asp | Phe | Arg | Cys | Asn | Cys | |
| | | | | 85 | | | | | 90 | | | | | 95 | | |
| gta | cct | att | cca | ctg | ggg | tca | aaa | aac | aac | atg | tgc | atc | aag | agg | ctg | 336 |
| Val | Pro | Ile | Pro | Leu | Gly | Ser | Lys | Asn | Asn | Met | Cys | Ile | Lys | Arg | Leu | |
| | | | 100 | | | | | 105 | | | | | 110 | | | |
| cag | att | aaa | ccc | aga | agc | ttt | agt | gga | ctc | act | tat | tta | aaa | tcc | ctt | 384 |
| Gln | Ile | Lys | Pro | Arg | Ser | Phe | Ser | Gly | Leu | Thr | Tyr | Leu | Lys | Ser | Leu | |
| | | 115 | | | | | 120 | | | | | 125 | | | | |
| tac | ctg | gat | gga | aac | cag | cta | cta | gag | ata | ccg | cag | ggc | ctc | ccg | cct | 432 |
| Tyr | Leu | Asp | Gly | Asn | Gln | Leu | Leu | Glu | Ile | Pro | Gln | Gly | Leu | Pro | Pro | |
| | 130 | | | | | 135 | | | | | 140 | | | | | |
| agc | tta | cag | ctt | ctc | agc | ctt | gag | gcc | aac | aac | atc | ttt | tcc | atc | aga | 480 |
| Ser | Leu | Gln | Leu | Leu | Ser | Leu | Glu | Ala | Asn | Asn | Ile | Phe | Ser | Ile | Arg | |
| 145 | | | | | 150 | | | | | 155 | | | | | 160 | |
| aaa | gag | aat | cta | aca | gaa | ctg | gcc | aac | ata | gaa | ata | ctc | tac | ctg | ggc | 528 |
| Lys | Glu | Asn | Leu | Thr | Glu | Leu | Ala | Asn | Ile | Glu | Ile | Leu | Tyr | Leu | Gly | |
| | | | | 165 | | | | | 170 | | | | | 175 | | |
| caa | aac | tgt | tat | tat | cga | aat | cct | tgt | tat | gtt | tca | tat | tca | ata | gag | 576 |
| Gln | Asn | Cys | Tyr | Tyr | Arg | Asn | Pro | Cys | Tyr | Val | Ser | Tyr | Ser | Ile | Glu | |
| | | | 180 | | | | | 185 | | | | | 190 | | | |
| aaa | gat | gcc | ttc | cta | aac | ttg | aca | aag | tta | aaa | gtg | ctc | tcc | ctg | aaa | 624 |
| Lys | Asp | Ala | Phe | Leu | Asn | Leu | Thr | Lys | Leu | Lys | Val | Leu | Ser | Leu | Lys | |
| | | 195 | | | | | 200 | | | | | 205 | | | | |
| gat | aac | aat | gtc | aca | gcc | gtc | cct | act | gtt | ttg | cca | tct | act | tta | aca | 672 |
| Asp | Asn | Asn | Val | Thr | Ala | Val | Pro | Thr | Val | Leu | Pro | Ser | Thr | Leu | Thr | |
| | 210 | | | | | 215 | | | | | 220 | | | | | |
| gaa | cta | tat | ctc | tac | aac | aac | atg | att | gca | aaa | atc | caa | gaa | gat | gat | 720 |
| Glu | Leu | Tyr | Leu | Tyr | Asn | Asn | Met | Ile | Ala | Lys | Ile | Gln | Glu | Asp | Asp | |
| 225 | | | | | 230 | | | | | 235 | | | | | 240 | |
| ttt | aat | aac | ctc | aac | caa | tta | caa | att | ctt | gac | cta | agt | gga | aat | tgc | 768 |
| Phe | Asn | Asn | Leu | Asn | Gln | Leu | Gln | Ile | Leu | Asp | Leu | Ser | Gly | Asn | Cys | |
| | | | | 245 | | | | | 250 | | | | | 255 | | |
| cct | cgt | tgt | tat | aat | gcc | cca | ttt | cct | tgt | gcg | ccg | tgt | aaa | aat | aat | 816 |

```
                Pro Arg Cys Tyr Asn Ala Pro Phe Pro Cys Ala Pro Cys Lys Asn Asn
                            260                 265                 270 tct ccc cta cag atc cct gta aat gct ttt gat gcg ctg aca gaa tta        864
Ser Pro Leu Gln Ile Pro Val Asn Ala Phe Asp Ala Leu Thr Glu Leu
        275                 280                 285 aaa gtt tta cgt cta cac agt aac tct ctt cag cat gtg ccc cca aga        912
Lys Val Leu Arg Leu His Ser Asn Ser Leu Gln His Val Pro Pro Arg
290                 295                 300 tgg ttt aag aac atc aac aaa ctc cag gaa ctg gat ctg tcc caa aac        960
Trp Phe Lys Asn Ile Asn Lys Leu Gln Glu Leu Asp Leu Ser Gln Asn
305                 310                 315                 320 ttc ttg gcc aaa gaa att ggg gat gct aaa ttt ctg cat ttt ctc ccc       1008
Phe Leu Ala Lys Glu Ile Gly Asp Ala Lys Phe Leu His Phe Leu Pro
            325                 330                 335 agc ctc atc caa ttg gat ctg tct ttc aat ttt gaa ctt cag gtc tat       1056
Ser Leu Ile Gln Leu Asp Leu Ser Phe Asn Phe Glu Leu Gln Val Tyr
            340                 345                 350 cgt gca tct atg aat cta tca caa gca ttt tct tca ctg aaa agc ctg       1104
Arg Ala Ser Met Asn Leu Ser Gln Ala Phe Ser Ser Leu Lys Ser Leu
            355                 360                 365 aaa att ctg cgg atc aga gga tat gtc ttt aaa gag ttg aaa agc ttt       1152
Lys Ile Leu Arg Ile Arg Gly Tyr Val Phe Lys Glu Leu Lys Ser Phe
370                 375                 380 aac ctc tcg cca tta cat aat ctt caa aat ctt gaa gtt ctt gat ctt       1200
Asn Leu Ser Pro Leu His Asn Leu Gln Asn Leu Glu Val Leu Asp Leu
385                 390                 395                 400 ggc act aac ttt ata aaa att gct aac ctc agc atg ttt aaa caa ttt       1248
Gly Thr Asn Phe Ile Lys Ile Ala Asn Leu Ser Met Phe Lys Gln Phe
                405                 410                 415 aaa aga ctg aaa gtc ata gat ctt tca gtg aat aaa ata tca cct tca       1296
Lys Arg Leu Lys Val Ile Asp Leu Ser Val Asn Lys Ile Ser Pro Ser
            420                 425                 430 gga gat tca agt gaa gtt ggc ttc tgc tca aat gcc aga act tct gta       1344
Gly Asp Ser Ser Glu Val Gly Phe Cys Ser Asn Ala Arg Thr Ser Val
            435                 440                 445 gaa agt tat gaa ccc cag gtc ctg gaa caa tta cat tat ttc aga tat       1392
Glu Ser Tyr Glu Pro Gln Val Leu Glu Gln Leu His Tyr Phe Arg Tyr
450                 455                 460 gat aag tat gca agg agt tgc aga ttc aaa aac aaa gag gct tct ttc       1440
Asp Lys Tyr Ala Arg Ser Cys Arg Phe Lys Asn Lys Glu Ala Ser Phe
465                 470                 475                 480 atg tct gtt aat gaa agc tgc tac aag tat ggg cag acc ttg gat cta       1488
Met Ser Val Asn Glu Ser Cys Tyr Lys Tyr Gly Gln Thr Leu Asp Leu
                485                 490                 495 agt aaa aat agt ata ttt ttt gtc aag tcc tct gat ttt cag cat ctt       1536
Ser Lys Asn Ser Ile Phe Phe Val Lys Ser Ser Asp Phe Gln His Leu
            500                 505                 510 tct ttc ctc aaa tgc ctg aat ctg tca gga aat ctc att agc caa act       1584
Ser Phe Leu Lys Cys Leu Asn Leu Ser Gly Asn Leu Ile Ser Gln Thr
            515                 520                 525 ctt aat ggc agt gaa ttc caa cct tta gca gag ctg aga tat ttg gac       1632
Leu Asn Gly Ser Glu Phe Gln Pro Leu Ala Glu Leu Arg Tyr Leu Asp
530                 535                 540 ttc tcc aac aac cgg ctt gat tta ctc cat tca aca gca ttt gaa gag       1680
Phe Ser Asn Asn Arg Leu Asp Leu Leu His Ser Thr Ala Phe Glu Glu
545                 550                 555                 560 ctt cac aaa ctg gaa gtt ctg gat ata agc agt aat agc cat tat ttt       1728
Leu His Lys Leu Glu Val Leu Asp Ile Ser Ser Asn Ser His Tyr Phe
                565                 570                 575
```

```
caa tca gaa gga att act cat atg cta aac ttt acc aag aac cta aag    1776
Gln Ser Glu Gly Ile Thr His Met Leu Asn Phe Thr Lys Asn Leu Lys
            580                 585                 590 gtt ctg cag aaa ctg atg atg aac gac aat gac atc tct tcc tcc acc    1824
Val Leu Gln Lys Leu Met Met Asn Asp Asn Asp Ile Ser Ser Ser Thr
        595                 600                 605 agc agg acc atg gag agt gag tct ctt aga act ctg gaa ttc aga gga    1872
Ser Arg Thr Met Glu Ser Glu Ser Leu Arg Thr Leu Glu Phe Arg Gly
    610                 615                 620 aat cac tta gat gtt tta tgg aga gaa ggt gat aac aga tac tta caa    1920
Asn His Leu Asp Val Leu Trp Arg Glu Gly Asp Asn Arg Tyr Leu Gln
625                 630                 635                 640 tta ttc aag aat ctg cta aaa tta gag gaa tta gac atc tct aaa aat    1968
Leu Phe Lys Asn Leu Leu Lys Leu Glu Glu Leu Asp Ile Ser Lys Asn
            645                 650                 655 tcc cta agt ttc ttg cct tct gga gtt ttt gat ggt atg cct cca aat    2016
Ser Leu Ser Phe Leu Pro Ser Gly Val Phe Asp Gly Met Pro Pro Asn
        660                 665                 670 cta aag aat ctc tct ttg gcc aaa aat ggg ctc aaa tct ttc agt tgg    2064
Leu Lys Asn Leu Ser Leu Ala Lys Asn Gly Leu Lys Ser Phe Ser Trp
    675                 680                 685 aag aaa ctc cag tgt cta aag aac ctg gaa act ttg gac ctc agc cac    2112
Lys Lys Leu Gln Cys Leu Lys Asn Leu Glu Thr Leu Asp Leu Ser His
690                 695                 700 aac caa ctg acc act gtc cct gag aga tta tcc aac tgt tcc aga agc    2160
Asn Gln Leu Thr Thr Val Pro Glu Arg Leu Ser Asn Cys Ser Arg Ser
705                 710                 715                 720 ctc aag aat ctg att ctt aag aat aat caa atc agg agt ctg acg aag    2208
Leu Lys Asn Leu Ile Leu Lys Asn Asn Gln Ile Arg Ser Leu Thr Lys
            725                 730                 735 tat ttt cta caa gat gcc ttc cag ttg cga tat ctg gat ctc agc tca    2256
Tyr Phe Leu Gln Asp Ala Phe Gln Leu Arg Tyr Leu Asp Leu Ser Ser
        740                 745                 750 aat aaa atc cag atg atc caa aag acc agc ttc cca gaa aat gtc ctc    2304
Asn Lys Ile Gln Met Ile Gln Lys Thr Ser Phe Pro Glu Asn Val Leu
    755                 760                 765 aac aat ctg aag atg ttg ctt ttg cat cat aat cgg ttt ctg tgc acc    2352
Asn Asn Leu Lys Met Leu Leu Leu His His Asn Arg Phe Leu Cys Thr
770                 775                 780 tgt gat gct gtg tgg ttt gtc tgg tgg gtt aac cat acg gag gtg act    2400
Cys Asp Ala Val Trp Phe Val Trp Trp Val Asn His Thr Glu Val Thr
785                 790                 795                 800 att cct tac ctg gcc aca gat gtg act tgt gtg ggg cca gga gca cac    2448
Ile Pro Tyr Leu Ala Thr Asp Val Thr Cys Val Gly Pro Gly Ala His
            805                 810                 815 aag ggc caa agt gtg atc tcc ctg gat ctg tac acc tgt gag tta gat    2496
Lys Gly Gln Ser Val Ile Ser Leu Asp Leu Tyr Thr Cys Glu Leu Asp
        820                 825                 830 ctg act aac ctg att ctg ttc tca ctt tcc ata tct gta tct ctc ttt    2544
Leu Thr Asn Leu Ile Leu Phe Ser Leu Ser Ile Ser Val Ser Leu Phe
    835                 840                 845 ctc atg gtg atg atg aca gca agt cac ctc tat ttc tgg gat gtg tgg    2592
Leu Met Val Met Met Thr Ala Ser His Leu Tyr Phe Trp Asp Val Trp
850                 855                 860 tat att tac cat ttc tgt aag gcc aag ata aag ggg tat cag cgt cta    2640
Tyr Ile Tyr His Phe Cys Lys Ala Lys Ile Lys Gly Tyr Gln Arg Leu
865                 870                 875                 880 ata tca cca gac tgt tgc tat gat gct ttt att gtg tat gac act aaa    2688
Ile Ser Pro Asp Cys Cys Tyr Asp Ala Phe Ile Val Tyr Asp Thr Lys
            885                 890                 895
```

-continued

```
gac cca gct gtg acc gag tgg gtt ttg gct gag ctg gtg gcc aaa ctg        2736
Asp Pro Ala Val Thr Glu Trp Val Leu Ala Glu Leu Val Ala Lys Leu
        900                 905                 910 gaa gac cca aga gag aaa cat ttt aat tta tgt ctc gag gaa agg gac        2784
Glu Asp Pro Arg Glu Lys His Phe Asn Leu Cys Leu Glu Glu Arg Asp
    915                 920                 925 tgg tta cca ggg cag cca gtt ctg gaa aac ctt tcc cag agc ata cag        2832
Trp Leu Pro Gly Gln Pro Val Leu Glu Asn Leu Ser Gln Ser Ile Gln
930                 935                 940 ctt agc aaa aag aca gtg ttt gtg atg aca gac aag tat gca aag act        2880
Leu Ser Lys Lys Thr Val Phe Val Met Thr Asp Lys Tyr Ala Lys Thr
945                 950                 955                 960 gaa aat ttt aag ata gca ttt tac ttg tcc cat cag agg ctc atg gat        2928
Glu Asn Phe Lys Ile Ala Phe Tyr Leu Ser His Gln Arg Leu Met Asp
                965                 970                 975 gaa aaa gtt gat gtg att atc ttg ata ttt ctt gag aag ccc ttt cag        2976
Glu Lys Val Asp Val Ile Ile Leu Ile Phe Leu Glu Lys Pro Phe Gln
        980                 985                 990 aag tcc aag ttc ctc cag ctc cgg  aaa agg ctc tgt ggg  agt tct gtc      3024
Lys Ser Lys Phe Leu Gln Leu Arg  Lys Arg Leu Cys Gly  Ser Ser Val
    995                 1000                 1005 ctt gag tgg cca aca aac ccg  caa gct cac cca tac  ttc tgg cag          3069
Leu Glu Trp Pro Thr Asn Pro  Gln Ala His Pro Tyr  Phe Trp Gln
1010                 1015                 1020 tgt cta aag aac gcc ctg gcc  aca gac aat cat gtg  gcc tat agt          3114
Cys Leu Lys Asn Ala Leu Ala  Thr Asp Asn His Val  Ala Tyr Ser
    1025                1030                 1035 cag gtg ttc aag gaa acg gtc  tag                                       3138
Gln Val Phe Lys Glu Thr Val
    1040            1045

<210> SEQ ID NO 12
<211> LENGTH: 1045
<212> TYPE: PRT
<213> ORGANISM: Homo sapiens

<400> SEQUENCE: 12

Met Trp Thr Leu Lys Arg Leu Ile Leu Ile Leu Phe Asn Ile Ile Leu
1               5                   10                  15

Ile Ser Lys Leu Leu Gly Ala Arg Trp Phe Pro Lys Thr Leu Pro Cys
                20                  25                  30

Asp Val Thr Leu Asp Val Pro Lys Asn His Val Ile Val Asp Cys Thr
            35                  40                  45

Asp Lys His Leu Thr Glu Ile Pro Gly Gly Ile Pro Thr Asn Thr Thr
        50                  55                  60

Asn Leu Thr Leu Thr Ile Asn His Ile Pro Asp Ile Ser Pro Ala Ser
65                  70                  75                  80

Phe His Arg Leu Asp His Leu Val Glu Ile Asp Phe Arg Cys Asn Cys
                85                  90                  95

Val Pro Ile Pro Leu Gly Ser Lys Asn Asn Met Cys Ile Lys Arg Leu
            100                 105                 110

Gln Ile Lys Pro Arg Ser Phe Ser Gly Leu Thr Tyr Leu Lys Ser Leu
        115                 120                 125

Tyr Leu Asp Gly Asn Gln Leu Leu Glu Ile Pro Gln Gly Leu Pro Pro
    130                 135                 140

Ser Leu Gln Leu Leu Ser Leu Glu Ala Asn Asn Ile Phe Ser Ile Arg
145                 150                 155                 160
```

-continued

```
Lys Glu Asn Leu Thr Glu Leu Ala Asn Ile Glu Ile Leu Tyr Leu Gly
                165                 170                 175
Gln Asn Cys Tyr Tyr Arg Asn Pro Cys Tyr Val Ser Tyr Ser Ile Glu
                180                 185                 190
Lys Asp Ala Phe Leu Asn Leu Thr Lys Leu Lys Val Leu Ser Leu Lys
                195                 200                 205
Asp Asn Asn Val Thr Ala Val Pro Thr Val Leu Pro Ser Thr Leu Thr
210                 215                 220
Glu Leu Tyr Leu Tyr Asn Asn Met Ile Ala Lys Ile Gln Glu Asp Asp
225                 230                 235                 240
Phe Asn Asn Leu Asn Gln Leu Gln Ile Leu Asp Leu Ser Gly Asn Cys
                245                 250                 255
Pro Arg Cys Tyr Asn Ala Pro Phe Pro Cys Ala Pro Cys Lys Asn Asn
                260                 265                 270
Ser Pro Leu Gln Ile Pro Val Asn Ala Phe Asp Ala Leu Thr Glu Leu
                275                 280                 285
Lys Val Leu Arg Leu His Ser Asn Ser Leu Gln His Val Pro Pro Arg
                290                 295                 300
Trp Phe Lys Asn Ile Asn Lys Leu Gln Glu Leu Asp Leu Ser Gln Asn
305                 310                 315                 320
Phe Leu Ala Lys Glu Ile Gly Asp Ala Lys Phe Leu His Phe Leu Pro
                325                 330                 335
Ser Leu Ile Gln Leu Asp Leu Ser Phe Asn Phe Glu Leu Gln Val Tyr
                340                 345                 350
Arg Ala Ser Met Asn Leu Ser Gln Ala Phe Ser Ser Leu Lys Ser Leu
                355                 360                 365
Lys Ile Leu Arg Ile Arg Gly Tyr Val Phe Lys Glu Leu Lys Ser Phe
                370                 375                 380
Asn Leu Ser Pro Leu His Asn Leu Gln Asn Leu Glu Val Leu Asp Leu
385                 390                 395                 400
Gly Thr Asn Phe Ile Lys Ile Ala Asn Leu Ser Met Phe Lys Gln Phe
                405                 410                 415
Lys Arg Leu Lys Val Ile Asp Leu Ser Val Asn Lys Ile Ser Pro Ser
                420                 425                 430
Gly Asp Ser Ser Glu Val Gly Phe Cys Ser Asn Ala Arg Thr Ser Val
                435                 440                 445
Glu Ser Tyr Glu Pro Gln Val Leu Glu Gln Leu His Tyr Phe Arg Tyr
                450                 455                 460
Asp Lys Tyr Ala Arg Ser Cys Arg Phe Lys Asn Lys Glu Ala Ser Phe
465                 470                 475                 480
Met Ser Val Asn Glu Ser Cys Tyr Lys Tyr Gly Gln Thr Leu Asp Leu
                485                 490                 495
Ser Lys Asn Ser Ile Phe Phe Val Lys Ser Ser Asp Phe Gln His Leu
                500                 505                 510
Ser Phe Leu Lys Cys Leu Asn Leu Ser Gly Asn Leu Ile Ser Gln Thr
                515                 520                 525
Leu Asn Gly Ser Glu Phe Gln Pro Leu Ala Glu Leu Arg Tyr Leu Asp
                530                 535                 540
Phe Ser Asn Asn Arg Leu Asp Leu Leu His Ser Thr Ala Phe Glu Glu
545                 550                 555                 560
Leu His Lys Leu Glu Val Leu Asp Ile Ser Ser Asn Ser His Tyr Phe
                565                 570                 575
Gln Ser Glu Gly Ile Thr His Met Leu Asn Phe Thr Lys Asn Leu Lys
```

-continued

```
                580                 585                 590
Val Leu Gln Lys Leu Met Met Asn Asp Asn Asp Ile Ser Ser Ser Thr
                595                 600                 605
Ser Arg Thr Met Glu Ser Glu Ser Leu Arg Thr Leu Glu Phe Arg Gly
            610                 615                 620
Asn His Leu Asp Val Leu Trp Arg Glu Gly Asp Asn Arg Tyr Leu Gln
625                 630                 635                 640
Leu Phe Lys Asn Leu Leu Lys Leu Glu Glu Leu Asp Ile Ser Lys Asn
                645                 650                 655
Ser Leu Ser Phe Leu Pro Ser Gly Val Phe Asp Gly Met Pro Pro Asn
            660                 665                 670
Leu Lys Asn Leu Ser Leu Ala Lys Asn Gly Leu Lys Ser Phe Ser Trp
                675                 680                 685
Lys Lys Leu Gln Cys Leu Lys Asn Leu Glu Thr Leu Asp Leu Ser His
            690                 695                 700
Asn Gln Leu Thr Thr Val Pro Glu Arg Leu Ser Asn Cys Ser Arg Ser
705                 710                 715                 720
Leu Lys Asn Leu Ile Leu Lys Asn Asn Gln Ile Arg Ser Leu Thr Lys
                725                 730                 735
Tyr Phe Leu Gln Asp Ala Phe Gln Leu Arg Tyr Leu Asp Leu Ser Ser
            740                 745                 750
Asn Lys Ile Gln Met Ile Gln Lys Thr Ser Phe Pro Glu Asn Val Leu
            755                 760                 765
Asn Asn Leu Lys Met Leu Leu Leu His His Asn Arg Phe Leu Cys Thr
770                 775                 780
Cys Asp Ala Val Trp Phe Val Trp Trp Val Asn His Thr Glu Val Thr
785                 790                 795                 800
Ile Pro Tyr Leu Ala Thr Asp Val Thr Cys Val Gly Pro Gly Ala His
                805                 810                 815
Lys Gly Gln Ser Val Ile Ser Leu Asp Leu Tyr Thr Cys Glu Leu Asp
            820                 825                 830
Leu Thr Asn Leu Ile Leu Phe Ser Leu Ser Ile Ser Val Ser Leu Phe
            835                 840                 845
Leu Met Val Met Met Thr Ala Ser His Leu Tyr Phe Trp Asp Val Trp
850                 855                 860
Tyr Ile Tyr His Phe Cys Lys Ala Lys Ile Lys Gly Tyr Gln Arg Leu
865                 870                 875                 880
Ile Ser Pro Asp Cys Cys Tyr Asp Ala Phe Ile Val Tyr Asp Thr Lys
                885                 890                 895
Asp Pro Ala Val Thr Glu Trp Val Leu Ala Glu Leu Val Ala Lys Leu
            900                 905                 910
Glu Asp Pro Arg Glu Lys His Phe Asn Leu Cys Leu Glu Glu Arg Asp
            915                 920                 925
Trp Leu Pro Gly Gln Pro Val Leu Glu Asn Leu Ser Gln Ser Ile Gln
            930                 935                 940
Leu Ser Lys Lys Thr Val Phe Val Met Thr Asp Lys Tyr Ala Lys Thr
945                 950                 955                 960
Glu Asn Phe Lys Ile Ala Phe Tyr Leu Ser His Gln Arg Leu Met Asp
                965                 970                 975
Glu Lys Val Asp Val Ile Ile Leu Ile Phe Leu Glu Lys Pro Phe Gln
            980                 985                 990
Lys Ser Lys Phe Leu Gln Leu Arg  Lys Arg Leu Cys Gly  Ser Ser Val
            995                 1000                1005
```

```
Leu Glu  Trp Pro Thr Asn Pro  Gln Ala His Pro  Tyr Phe Trp Gln
    1010             1015              1020

Cys Leu  Lys Asn Ala Leu Ala  Thr Asp Asn His  Val Ala Tyr Ser
    1025             1030              1035

Gln Val  Phe Lys Glu Thr Val
    1040             1045

<210> SEQ ID NO 13
<211> LENGTH: 180
<212> TYPE: DNA
<213> ORGANISM: Mus musculus
<220> FEATURE:
<221> NAME/KEY: CDS
<222> LOCATION: (1)..(177)
<223> OTHER INFORMATION:

<400> SEQUENCE: 13 ctt gga aaa cct ctt cag aag tct aag ttt ctt cag ctc agg aag aga        48
Leu Gly Lys Pro Leu Gln Lys Ser Lys Phe Leu Gln Leu Arg Lys Arg
1               5                   10                  15 ctc tgc agg agc tct gtc ctt gag tgg cct gca aat cca cag gct cac        96
Leu Cys Arg Ser Ser Val Leu Glu Trp Pro Ala Asn Pro Gln Ala His
            20                  25                  30 cca tac ttc tgg cag tgc ctg aaa aat gcc ctg acc aca gac aat cat       144
Pro Tyr Phe Trp Gln Cys Leu Lys Asn Ala Leu Thr Thr Asp Asn His
        35                  40                  45 gtg gct tat agt caa atg ttc aag gaa aca gtc tag                       180
Val Ala Tyr Ser Gln Met Phe Lys Glu Thr Val
    50                  55

<210> SEQ ID NO 14
<211> LENGTH: 59
<212> TYPE: PRT
<213> ORGANISM: Mus musculus

<400> SEQUENCE: 14

Leu Gly Lys Pro Leu Gln Lys Ser Lys Phe Leu Gln Leu Arg Lys Arg
1               5                   10                  15

Leu Cys Arg Ser Ser Val Leu Glu Trp Pro Ala Asn Pro Gln Ala His
            20                  25                  30

Pro Tyr Phe Trp Gln Cys Leu Lys Asn Ala Leu Thr Thr Asp Asn His
        35                  40                  45

Val Ala Tyr Ser Gln Met Phe Lys Glu Thr Val
    50                  55

<210> SEQ ID NO 15
<211> LENGTH: 990
<212> TYPE: DNA
<213> ORGANISM: Homo sapiens
<220> FEATURE:
<221> NAME/KEY: CDS
<222> LOCATION: (2)..(988)
<223> OTHER INFORMATION:

<400> SEQUENCE: 15 g aat tcc aga ctt ata aac ttg aaa aat ctc tat ttg gcc tgg aac tgc     49
  Asn Ser Arg Leu Ile Asn Leu Lys Asn Leu Tyr Leu Ala Trp Asn Cys
  1               5                   10                  15 tat ttt aac aaa gtt tgc gag aaa act aac ata gaa gat gga gta ttt       97
Tyr Phe Asn Lys Val Cys Glu Lys Thr Asn Ile Glu Asp Gly Val Phe
            20                  25                  30 gaa acg ctg aca aat ttg gag ttg cta tca cta tct ttc aat tct ctt      145
```

| | | |
|---|---|---|
| Glu Thr Leu Thr Asn Leu Glu Leu Leu Ser Leu Ser Phe Asn Ser Leu<br>35                           40                        45 | | |
| tca cat gtg cca ccc aaa ctg cca agc tcc cta cgc aaa ctt ttt ctg<br>Ser His Val Pro Pro Lys Leu Pro Ser Ser Leu Arg Lys Leu Phe Leu<br>50                         55                      60 | | 193 |
| agc aac acc cag atc aaa tac att agt gaa gaa gat ttc aag gga ttg<br>Ser Asn Thr Gln Ile Lys Tyr Ile Ser Glu Glu Asp Phe Lys Gly Leu<br>65                      70                      75                      80 | | 241 |
| ata aat tta aca tta cta gat tta agc ggg aac tgt ccg agg tgt ttc<br>Ile Asn Leu Thr Leu Leu Asp Leu Ser Gly Asn Cys Pro Arg Cys Phe<br>                      85                      90                      95 | | 289 |
| aat gcc cca ttt cca tgc gtg cct tgt gat ggt ggt gct tca att aat<br>Asn Ala Pro Phe Pro Cys Val Pro Cys Asp Gly Gly Ala Ser Ile Asn<br>                  100                    105                    110 | | 337 |
| ata gat cgt ttt gct ttt caa aac ttg acc caa ctt cga tac cta aac<br>Ile Asp Arg Phe Ala Phe Gln Asn Leu Thr Gln Leu Arg Tyr Leu Asn<br>                115                    120                    125 | | 385 |
| ctc tct agc act tcc ctc agg aag att aat gct gcc tgg ttt aaa aat<br>Leu Ser Ser Thr Ser Leu Arg Lys Ile Asn Ala Ala Trp Phe Lys Asn<br>130                        135                    140 | | 433 |
| atg cct cat ctg aag gtg ctg gat ctt gaa ttc aac tat tta gtg gga<br>Met Pro His Leu Lys Val Leu Asp Leu Glu Phe Asn Tyr Leu Val Gly<br>145                        150                        155                    160 | | 481 |
| gaa ata gcc tct ggg gca ttt tta acg atg ctg ccc cgc tta gaa ata<br>Glu Ile Ala Ser Gly Ala Phe Leu Thr Met Leu Pro Arg Leu Glu Ile<br>                165                    170                    175 | | 529 |
| ctt gac ttg tct ttt aac tat ata aag ggg agt tat cca cag cat att<br>Leu Asp Leu Ser Phe Asn Tyr Ile Lys Gly Ser Tyr Pro Gln His Ile<br>                  180                    185                    190 | | 577 |
| aat att tcc aga aac ttc tct aaa ctt ttg tct cta cgg gca ttg cat<br>Asn Ile Ser Arg Asn Phe Ser Lys Leu Leu Ser Leu Arg Ala Leu His<br>                195                    200                    205 | | 625 |
| tta aga ggt tat gtg ttc cag gaa ctc aga gaa gat gat ttc cag ccc<br>Leu Arg Gly Tyr Val Phe Gln Glu Leu Arg Glu Asp Asp Phe Gln Pro<br>210                        215                    220 | | 673 |
| ctg atg cag ctt cca aac tta tcg act atc aac ttg ggt att aat ttt<br>Leu Met Gln Leu Pro Asn Leu Ser Thr Ile Asn Leu Gly Ile Asn Phe<br>225                        230                        235                    240 | | 721 |
| att aag caa atc gat ttc aaa ctt ttc caa aat ttc tcc aat ctg gaa<br>Ile Lys Gln Ile Asp Phe Lys Leu Phe Gln Asn Phe Ser Asn Leu Glu<br>                245                    250                    255 | | 769 |
| att att tac ttg tca gaa aac aga ata tca ccg ttg gta aaa gat acc<br>Ile Ile Tyr Leu Ser Glu Asn Arg Ile Ser Pro Leu Val Lys Asp Thr<br>                  260                    265                    270 | | 817 |
| cgg cag agt tat gca aat agt tcc tct ttt caa cgt cat atc cgg aaa<br>Arg Gln Ser Tyr Ala Asn Ser Ser Ser Phe Gln Arg His Ile Arg Lys<br>                275                    280                    285 | | 865 |
| cga cgc tca aca gat ttt gag ttt gac cca cat tcg aac ttt tat cat<br>Arg Arg Ser Thr Asp Phe Glu Phe Asp Pro His Ser Asn Phe Tyr His<br>                  290                    295                    300 | | 913 |
| ttc acc cgt cct tta ata aag cca caa tgt gct gct tat gga aaa gcc<br>Phe Thr Arg Pro Leu Ile Lys Pro Gln Cys Ala Ala Tyr Gly Lys Ala<br>305                        310                        315                    320 | | 961 |
| tta gat tta agc ctc aac agt att ttc tt<br>Leu Asp Leu Ser Leu Asn Ser Ile Phe<br>                  325 | | 990 |

<210> SEQ ID NO 16
<211> LENGTH: 329
<212> TYPE: PRT

<213> ORGANISM: Homo sapiens

<400> SEQUENCE: 16

```
Asn Ser Arg Leu Ile Asn Leu Lys Asn Leu Tyr Leu Ala Trp Asn Cys
1               5                   10                  15

Tyr Phe Asn Lys Val Cys Glu Lys Thr Asn Ile Glu Asp Gly Val Phe
            20                  25                  30

Glu Thr Leu Thr Asn Leu Glu Leu Leu Ser Leu Ser Phe Asn Ser Leu
        35                  40                  45

Ser His Val Pro Pro Lys Leu Pro Ser Leu Arg Lys Leu Phe Leu
    50                  55                  60

Ser Asn Thr Gln Ile Lys Tyr Ile Ser Glu Glu Asp Phe Lys Gly Leu
65                  70                  75                  80

Ile Asn Leu Thr Leu Leu Asp Leu Ser Gly Asn Cys Pro Arg Cys Phe
                85                  90                  95

Asn Ala Pro Phe Pro Cys Val Pro Cys Asp Gly Gly Ala Ser Ile Asn
            100                 105                 110

Ile Asp Arg Phe Ala Phe Gln Asn Leu Thr Gln Leu Arg Tyr Leu Asn
        115                 120                 125

Leu Ser Ser Thr Ser Leu Arg Lys Ile Asn Ala Ala Trp Phe Lys Asn
130                 135                 140

Met Pro His Leu Lys Val Leu Asp Leu Glu Phe Asn Tyr Leu Val Gly
145                 150                 155                 160

Glu Ile Ala Ser Gly Ala Phe Leu Thr Met Leu Pro Arg Leu Glu Ile
                165                 170                 175

Leu Asp Leu Ser Phe Asn Tyr Ile Lys Gly Ser Tyr Pro Gln His Ile
            180                 185                 190

Asn Ile Ser Arg Asn Phe Ser Lys Leu Leu Ser Leu Arg Ala Leu His
        195                 200                 205

Leu Arg Gly Tyr Val Phe Gln Glu Leu Arg Glu Asp Asp Phe Gln Pro
    210                 215                 220

Leu Met Gln Leu Pro Asn Leu Ser Thr Ile Asn Leu Gly Ile Asn Phe
225                 230                 235                 240

Ile Lys Gln Ile Asp Phe Lys Leu Phe Gln Asn Phe Ser Asn Leu Glu
                245                 250                 255

Ile Ile Tyr Leu Ser Glu Asn Arg Ile Ser Pro Leu Val Lys Asp Thr
            260                 265                 270

Arg Gln Ser Tyr Ala Asn Ser Ser Phe Gln Arg His Ile Arg Lys
    275                 280                 285

Arg Arg Ser Thr Asp Phe Glu Phe Asp Pro His Ser Asn Phe Tyr His
290                 295                 300

Phe Thr Arg Pro Leu Ile Lys Pro Gln Cys Ala Ala Tyr Gly Lys Ala
305                 310                 315                 320

Leu Asp Leu Ser Leu Asn Ser Ile Phe
                325
```

<210> SEQ ID NO 17
<211> LENGTH: 1543
<212> TYPE: DNA
<213> ORGANISM: Homo sapiens
<220> FEATURE:
<221> NAME/KEY: CDS
<222> LOCATION: (1)..(513)
<223> OTHER INFORMATION:

<400> SEQUENCE: 17

-continued

| | | |
|---|---|---|
| cag tct ctt tcc aca tcc caa act ttc tat gat gct tac att tct tat<br>Gln Ser Leu Ser Thr Ser Gln Thr Phe Tyr Asp Ala Tyr Ile Ser Tyr<br>1               5                   10                  15 | | 48 |
| gac acc aaa gat gcc tct gtt act gac tgg gtg ata aat gag ctg cgc<br>Asp Thr Lys Asp Ala Ser Val Thr Asp Trp Val Ile Asn Glu Leu Arg<br>            20                  25                  30 | | 96 |
| tac cac ctt gaa gag agc cga gac aaa aac gtt ctc ctt tgt cta gag<br>Tyr His Leu Glu Glu Ser Arg Asp Lys Asn Val Leu Leu Cys Leu Glu<br>        35                  40                  45 | | 144 |
| gag agg gat tgg gac ccg gga ttg gcc atc atc gac aac ctc atg cag<br>Glu Arg Asp Trp Asp Pro Gly Leu Ala Ile Ile Asp Asn Leu Met Gln<br>    50                  55                  60 | | 192 |
| agc atc aac caa agc aag aaa aca gta ttt gtt tta acc aaa aaa tat<br>Ser Ile Asn Gln Ser Lys Lys Thr Val Phe Val Leu Thr Lys Lys Tyr<br>65                  70                  75                  80 | | 240 |
| gca aaa agc tgg aac ttt aaa aca gct ttt tac ttg gsc ttg cag agg<br>Ala Lys Ser Trp Asn Phe Lys Thr Ala Phe Tyr Leu Xaa Leu Gln Arg<br>                85                  90                  95 | | 288 |
| cta atg ggt gag aac atg gat gtg att ata ttt atc ctg ctg gag cca<br>Leu Met Gly Glu Asn Met Asp Val Ile Ile Phe Ile Leu Leu Glu Pro<br>            100                 105                 110 | | 336 |
| gtg tta cag cat tct ccg tat ttg agg cta cgg cag cgg atc tgt aag<br>Val Leu Gln His Ser Pro Tyr Leu Arg Leu Arg Gln Arg Ile Cys Lys<br>        115                 120                 125 | | 384 |
| agc tcc atc ctc cag tgg cct gac aac ccg aag gca gaa agg ttg ttt<br>Ser Ser Ile Leu Gln Trp Pro Asp Asn Pro Lys Ala Glu Arg Leu Phe<br>    130                 135                 140 | | 432 |
| tgg caa act ctg wga aat gtg gtc ttg act gaa aat gat tca cgg tat<br>Trp Gln Thr Leu Xaa Asn Val Val Leu Thr Glu Asn Asp Ser Arg Tyr<br>145                 150                 155                 160 | | 480 |
| aac aat atg tat gtc gat tcc att aag caa tac taactgacgt taagtcatga<br>Asn Asn Met Tyr Val Asp Ser Ile Lys Gln Tyr<br>                165                 170 | | 533 |
| tttcgcgcca taataaagat gcaaaggaat gacatttcgt attagttatc tattgctagg | | 593 |
| taacaaatta tcccaaaaac ttagtggttt aaaacaacac atttgctggc ccacagtttt | | 653 |
| tgagggtcag gagtccaggc ccagcataac tgggtcttct gcttcagggt gtctcagagg | | 713 |
| ctgcaatgta ggtgttcacc agagacatag gcatcactgg ggtcacactc atgtggttgt | | 773 |
| tttctggatt caattcctcc tgggctattg gccaaaggct atactcatgt aagccatgcg | | 833 |
| agcctatccc acaaggcagc ttgcttcatc agagctagca aaaagagag gttgctagca | | 893 |
| agatgaagtc acaatctttt gtaatcgaat caaaaaagtg atatctcatc actttggcca | | 953 |
| tattctattt gttagaagta aaccacaggt cccaccagct ccatgggagt gaccacctca | 1013 |
| gtccagggaa aacagctgaa gaccaagatg gtgagctctg attgcttcag ttggtcatca | 1073 |
| actattttcc cttgactgct gtcctgggat ggccggctat cttgatggat agattgtgaa | 1133 |
| tatcaggagg ccagggatca ctgtggacca tcttagcagt tgacctaaca catcttcttt | 1193 |
| tcaatatcta agaactttg ccactgtgac taatggtcct aatattaagc tgttgtttat | 1253 |
| atttatcata tatctatggc tacatggtta tattatgctg tggttgcgtt cggttttatt | 1313 |
| tacagttgct tttacaaata tttgctgtaa catttgactt ctaaggttta gatgccattt | 1373 |
| aagaactgag atggatagct tttaaagcat cttttacttc ttaccatttt ttaaaagtat | 1433 |
| gcagctaaat tcgaagcttt tggtctatat tgttaattgc cattgctgta aatcttaaaa | 1493 |
| tgaatgaata aaaatgtttc attttaaaaa aaaaaaaaa aaaaaaaaa | 1543 |

```
<210> SEQ ID NO 18
<211> LENGTH: 171
<212> TYPE: PRT
<213> ORGANISM: Homo sapiens
<220> FEATURE:
<221> NAME/KEY: misc_feature
<222> LOCATION: (93)..(93)
<223> OTHER INFORMATION: The 'Xaa' at location 93 stands for Gly, or
      Ala.
<220> FEATURE:
<221> NAME/KEY: misc_feature
<222> LOCATION: (149)..(149)
<223> OTHER INFORMATION: The 'Xaa' at location 149 stands for Arg, or a
      stop codon.

<400> SEQUENCE: 18

Gln Ser Leu Ser Thr Ser Gln Thr Phe Tyr Asp Ala Tyr Ile Ser Tyr
1               5                   10                  15

Asp Thr Lys Asp Ala Ser Val Thr Asp Trp Val Ile Asn Glu Leu Arg
            20                  25                  30

Tyr His Leu Glu Glu Ser Arg Asp Lys Asn Val Leu Leu Cys Leu Glu
        35                  40                  45

Glu Arg Asp Trp Asp Pro Gly Leu Ala Ile Ile Asp Asn Leu Met Gln
    50                  55                  60

Ser Ile Asn Gln Ser Lys Lys Thr Val Phe Val Leu Thr Lys Lys Tyr
65                  70                  75                  80

Ala Lys Ser Trp Asn Phe Lys Thr Ala Phe Tyr Leu Xaa Leu Gln Arg
                85                  90                  95

Leu Met Gly Glu Asn Met Asp Val Ile Ile Phe Ile Leu Leu Glu Pro
            100                 105                 110

Val Leu Gln His Ser Pro Tyr Leu Arg Leu Arg Gln Arg Ile Cys Lys
        115                 120                 125

Ser Ser Ile Leu Gln Trp Pro Asp Asn Pro Lys Ala Glu Arg Leu Phe
    130                 135                 140

Trp Gln Thr Leu Xaa Asn Val Val Leu Thr Glu Asn Asp Ser Arg Tyr
145                 150                 155                 160

Asn Asn Met Tyr Val Asp Ser Ile Lys Gln Tyr
                165                 170

<210> SEQ ID NO 19
<211> LENGTH: 629
<212> TYPE: DNA
<213> ORGANISM: Homo sapiens
<220> FEATURE:
<221> NAME/KEY: CDS
<222> LOCATION: (1)..(486)
<223> OTHER INFORMATION:

<400> SEQUENCE: 19 aat gaa ttg atc ccc aat cta gag aag gaa gat ggt tct atc ttg att      48
Asn Glu Leu Ile Pro Asn Leu Glu Lys Glu Asp Gly Ser Ile Leu Ile
1               5                   10                  15 tgc ctt tat gaa agc tac ttt gac cct ggc aaa agc att agt gaa aat      96
Cys Leu Tyr Glu Ser Tyr Phe Asp Pro Gly Lys Ser Ile Ser Glu Asn
            20                  25                  30 att gta agc ttc att gag aaa agc tat aag tcc atc ttt gtt ttg tcy     144
Ile Val Ser Phe Ile Glu Lys Ser Tyr Lys Ser Ile Phe Val Leu Xaa
        35                  40                  45 ccc aac ttt gtc cag aat gag tgg tgc cat tat gaa ttc tac ttt gcc     192
Pro Asn Phe Val Gln Asn Glu Trp Cys His Tyr Glu Phe Tyr Phe Ala
    50                  55                  60 cac cac aat ctc ttc cat gaa aat tct gat cay ata att ctt atc tta     240
```

```
His His Asn Leu Phe His Glu Asn Ser Asp His Ile Ile Leu Ile Leu
 65                  70                  75                  80 ctg gaa ccc att cca ttc tat tgc att ccc acc agg tat cat aaa ctg     288
Leu Glu Pro Ile Pro Phe Tyr Cys Ile Pro Thr Arg Tyr His Lys Leu
                 85                  90                  95 gaa gct ctc ctg gaa aaa aaa gca tac ttg gaa tgg ccc aag gat agg     336
Glu Ala Leu Leu Glu Lys Lys Ala Tyr Leu Glu Trp Pro Lys Asp Arg
            100                 105                 110 cgt aaa tgt ggg ctt ttc tgg gca aac ctt cga gct gct gtt aat gtt     384
Arg Lys Cys Gly Leu Phe Trp Ala Asn Leu Arg Ala Ala Val Asn Val
        115                 120                 125 aat gta tta gcc acc aga gaa atg tat gaa ctg cag aca ttc aca gag     432
Asn Val Leu Ala Thr Arg Glu Met Tyr Glu Leu Gln Thr Phe Thr Glu
    130                 135                 140 tta aat gaa gag tct cga ggt tct aca atc tct ctg atg aga aca gac     480
Leu Asn Glu Glu Ser Arg Gly Ser Thr Ile Ser Leu Met Arg Thr Asp
145                 150                 155                 160 tgt cta taaaatccca cagtccttgg gaagttgggg accacataca ctgttgggat      536
Cys Leu gtacattgat acaaccttta tgatggcaat ttgacaatat ttattaaaat aaaaaatggt   596
tattcccttc aaaaaaaaaa aaaaaaaaaa aaa                                629

<210> SEQ ID NO 20
<211> LENGTH: 162
<212> TYPE: PRT
<213> ORGANISM: Homo sapiens
<220> FEATURE:
<221> NAME/KEY: misc_feature
<222> LOCATION: (48)..(48)
<223> OTHER INFORMATION: The 'Xaa' at location 48 stands for Ser.

<400> SEQUENCE: 20

Asn Glu Leu Ile Pro Asn Leu Glu Lys Glu Asp Gly Ser Ile Leu Ile
  1               5                  10                  15

Cys Leu Tyr Glu Ser Tyr Phe Asp Pro Gly Lys Ser Ile Ser Glu Asn
             20                  25                  30

Ile Val Ser Phe Ile Glu Lys Ser Tyr Lys Ser Ile Phe Val Leu Xaa
         35                  40                  45

Pro Asn Phe Val Gln Asn Glu Trp Cys His Tyr Glu Phe Tyr Phe Ala
     50                  55                  60

His His Asn Leu Phe His Glu Asn Ser Asp His Ile Ile Leu Ile Leu
 65                  70                  75                  80

Leu Glu Pro Ile Pro Phe Tyr Cys Ile Pro Thr Arg Tyr His Lys Leu
                 85                  90                  95

Glu Ala Leu Leu Glu Lys Lys Ala Tyr Leu Glu Trp Pro Lys Asp Arg
            100                 105                 110

Arg Lys Cys Gly Leu Phe Trp Ala Asn Leu Arg Ala Ala Val Asn Val
        115                 120                 125

Asn Val Leu Ala Thr Arg Glu Met Tyr Glu Leu Gln Thr Phe Thr Glu
    130                 135                 140

Leu Asn Glu Glu Ser Arg Gly Ser Thr Ile Ser Leu Met Arg Thr Asp
145                 150                 155                 160

Cys Leu

<210> SEQ ID NO 21
<211> LENGTH: 427
<212> TYPE: DNA
<213> ORGANISM: Homo sapiens
```

```
<220> FEATURE:
<221> NAME/KEY: CDS
<222> LOCATION: (1)..(426)
<223> OTHER INFORMATION:

<400> SEQUENCE: 21 aag aac tcc aaa gaa aac ctc cag ttt cat gct ttt att tca tat agt      48
Lys Asn Ser Lys Glu Asn Leu Gln Phe His Ala Phe Ile Ser Tyr Ser
1               5                   10                  15 gaa cat gat tct gcc tgg gtg aaa agt gaa ttg gta cct tac cta gaa      96
Glu His Asp Ser Ala Trp Val Lys Ser Glu Leu Val Pro Tyr Leu Glu
            20                  25                  30 aaa gaa gat ata cag att tgt ctt cat gag aga aac ttt gtc cct ggc     144
Lys Glu Asp Ile Gln Ile Cys Leu His Glu Arg Asn Phe Val Pro Gly
        35                  40                  45 aag agc att gtg gaa aat atc atc aac tgc att gag aag agt tac aag     192
Lys Ser Ile Val Glu Asn Ile Ile Asn Cys Ile Glu Lys Ser Tyr Lys
    50                  55                  60 tcc atc ttt gtt ttg tct ccc aac ttt gtc cag agt gag tgg tgc cat     240
Ser Ile Phe Val Leu Ser Pro Asn Phe Val Gln Ser Glu Trp Cys His
65                  70                  75                  80 tac gaa ctc tat ttt gcc cat cac aat ctc ttt cat gaa gga tct aat     288
Tyr Glu Leu Tyr Phe Ala His His Asn Leu Phe His Glu Gly Ser Asn
                85                  90                  95 aac tta atc ctc atc tta ctg gaa ccc att cca cag aac agc att ccc     336
Asn Leu Ile Leu Ile Leu Leu Glu Pro Ile Pro Gln Asn Ser Ile Pro
            100                 105                 110 aac aag tac cac aag ctg aag gct ctc atg acg cag cgg act tat ttg     384
Asn Lys Tyr His Lys Leu Lys Ala Leu Met Thr Gln Arg Thr Tyr Leu
        115                 120                 125 cag tgg ccc aag gag aaa agc aaa cgt ggg ctc ttt tgg gct a           427
Gln Trp Pro Lys Glu Lys Ser Lys Arg Gly Leu Phe Trp Ala
    130                 135                 140

<210> SEQ ID NO 22
<211> LENGTH: 142
<212> TYPE: PRT
<213> ORGANISM: Homo sapiens

<400> SEQUENCE: 22

Lys Asn Ser Lys Glu Asn Leu Gln Phe His Ala Phe Ile Ser Tyr Ser
1               5                   10                  15

Glu His Asp Ser Ala Trp Val Lys Ser Glu Leu Val Pro Tyr Leu Glu
            20                  25                  30

Lys Glu Asp Ile Gln Ile Cys Leu His Glu Arg Asn Phe Val Pro Gly
        35                  40                  45

Lys Ser Ile Val Glu Asn Ile Ile Asn Cys Ile Glu Lys Ser Tyr Lys
    50                  55                  60

Ser Ile Phe Val Leu Ser Pro Asn Phe Val Gln Ser Glu Trp Cys His
65                  70                  75                  80

Tyr Glu Leu Tyr Phe Ala His His Asn Leu Phe His Glu Gly Ser Asn
                85                  90                  95

Asn Leu Ile Leu Ile Leu Leu Glu Pro Ile Pro Gln Asn Ser Ile Pro
            100                 105                 110

Asn Lys Tyr His Lys Leu Lys Ala Leu Met Thr Gln Arg Thr Tyr Leu
        115                 120                 125

Gln Trp Pro Lys Glu Lys Ser Lys Arg Gly Leu Phe Trp Ala
    130                 135                 140
```

```
<210> SEQ ID NO 23
<211> LENGTH: 662
<212> TYPE: DNA
<213> ORGANISM: Homo sapiens
<220> FEATURE:
<221> NAME/KEY: CDS
<222> LOCATION: (1)..(627)
<223> OTHER INFORMATION:
<220> FEATURE:
<221> NAME/KEY: misc_feature
<222> LOCATION: (316)..(316)
<223> OTHER INFORMATION: unknown nucleotide
<220> FEATURE:
<221> NAME/KEY: misc_feature
<222> LOCATION: (380)..(380)
<223> OTHER INFORMATION: unknown nucleotide
<220> FEATURE:
<221> NAME/KEY: misc_feature
<222> LOCATION: (407)..(407)
<223> OTHER INFORMATION: unknown nucleotide
<220> FEATURE:
<221> NAME/KEY: misc_feature
<222> LOCATION: (408)..(408)
<223> OTHER INFORMATION: unknown nucleotide

<400> SEQUENCE: 23
```

| | | | | | | | | | | | | | | | | |
|---|---|---|---|---|---|---|---|---|---|---|---|---|---|---|---|---|
| gct | tcc | acc | tgt | gcc | tgg | cct | ggc | ttc | cct | ggc | ggg | ggc | ggc | aaa | gtg | 48 |
| Ala | Ser | Thr | Cys | Ala | Trp | Pro | Gly | Phe | Pro | Gly | Gly | Gly | Gly | Lys | Val | |
| 1 | | | | 5 | | | | | 10 | | | | | 15 | | |
| ggc | gar | atg | agg | atg | ccc | tgc | cct | acg | atg | cct | tcg | tgg | tct | tcg | aca | 96 |
| Gly | Glu | Met | Arg | Met | Pro | Cys | Pro | Thr | Met | Pro | Ser | Trp | Ser | Ser | Thr | |
| | | | 20 | | | | | 25 | | | | | 30 | | | |
| aaa | cgc | rga | gcg | cag | tgg | cag | act | ggt | tgt | aca | acg | agc | ttc | ggg | ggc | 144 |
| Lys | Arg | Xaa | Ala | Gln | Trp | Gln | Thr | Gly | Cys | Thr | Thr | Ser | Phe | Gly | Gly | |
| | | 35 | | | | | 40 | | | | | 45 | | | | |
| agc | tgg | agg | agt | gcc | gtg | ggc | gct | ggg | cac | tcc | gcc | tgt | gcc | tgg | agg | 192 |
| Ser | Trp | Arg | Ser | Ala | Val | Gly | Ala | Gly | His | Ser | Ala | Cys | Ala | Trp | Arg | |
| | 50 | | | | | 55 | | | | | 60 | | | | | |
| aac | gcg | act | ggc | tgc | ctg | gca | aaa | ccc | tct | ttg | aga | acc | tgt | ggg | cct | 240 |
| Asn | Ala | Thr | Gly | Cys | Leu | Ala | Lys | Pro | Ser | Leu | Arg | Thr | Cys | Gly | Pro | |
| 65 | | | | 70 | | | | | 75 | | | | | 80 | | |
| cgg | tct | atg | gca | gcc | gca | aga | cgc | tgt | ttg | tgc | tgg | ccc | aca | cgg | acc | 288 |
| Arg | Ser | Met | Ala | Ala | Ala | Arg | Arg | Cys | Leu | Cys | Trp | Pro | Thr | Arg | Thr | |
| | | | 85 | | | | | 90 | | | | | 95 | | | |
| ggg | tca | gtg | gtc | tct | tgc | gcg | cca | ktt | ntc | ctg | ctg | gcc | cag | cag | cgc | 336 |
| Gly | Ser | Val | Val | Ser | Cys | Ala | Pro | Xaa | Xaa | Leu | Leu | Ala | Gln | Gln | Arg | |
| | | 100 | | | | | 105 | | | | | 110 | | | | |
| ctg | ctg | gar | gac | cgc | aag | gac | gtc | gtg | gtg | ctg | gtg | atc | cta | ang | cct | 384 |
| Leu | Leu | Glu | Asp | Arg | Lys | Asp | Val | Val | Val | Leu | Val | Ile | Leu | Xaa | Pro | |
| | 115 | | | | | 120 | | | | | 125 | | | | | |
| gac | ggc | caa | gcc | tcc | cga | cta | cnn | gat | gcg | ctg | acc | agc | gcc | tct | gcc | 432 |
| Asp | Gly | Gln | Ala | Ser | Arg | Leu | Xaa | Asp | Ala | Leu | Thr | Ser | Ala | Ser | Ala | |
| | 130 | | | | | 135 | | | | | 140 | | | | | |
| gcc | aga | gtg | tcc | tcc | tct | ggc | ccc | acc | agc | cca | gtg | gtc | gcg | cag | ctt | 480 |
| Ala | Arg | Val | Ser | Ser | Ser | Gly | Pro | Thr | Ser | Pro | Val | Val | Ala | Gln | Leu | |
| 145 | | | | 150 | | | | | 155 | | | | | 160 | | |
| ctg | agg | cca | gca | tgc | atg | gcc | ctg | acc | agg | gac | aac | cac | cac | ttc | tat | 528 |
| Leu | Arg | Pro | Ala | Cys | Met | Ala | Leu | Thr | Arg | Asp | Asn | His | His | Phe | Tyr | |
| | | | 165 | | | | | 170 | | | | | 175 | | | |
| aac | cgg | aac | ttc | tgc | cag | gga | acc | cac | ggc | cga | ata | gcc | gtg | agc | cgg | 576 |
| Asn | Arg | Asn | Phe | Cys | Gln | Gly | Thr | His | Gly | Arg | Ile | Ala | Val | Ser | Arg | |
| | | 180 | | | | | 185 | | | | | 190 | | | | |
| aat | cct | gca | cgg | tgc | cac | ctc | cac | aca | cac | cta | aca | tat | gcc | tgc | ctg | 624 |
| Asn | Pro | Ala | Arg | Cys | His | Leu | His | Thr | His | Leu | Thr | Tyr | Ala | Cys | Leu | |
| | 195 | | | | | 200 | | | | | 205 | | | | | |

```
atc tgaccaacac atgctcgcca ccctcaccac acacc                662
Ile
```

<210> SEQ ID NO 24
<211> LENGTH: 209
<212> TYPE: PRT
<213> ORGANISM: Homo sapiens
<220> FEATURE:
<221> NAME/KEY: misc_feature
<222> LOCATION: (35)..(35)
<223> OTHER INFORMATION: The 'Xaa' at location 35 stands for Gly, or Arg.
<220> FEATURE:
<221> NAME/KEY: misc_feature
<222> LOCATION: (105)..(105)
<223> OTHER INFORMATION: The 'Xaa' at location 105 stands for Val, or Phe.
<220> FEATURE:
<221> NAME/KEY: misc_feature
<222> LOCATION: (106)..(106)
<223> OTHER INFORMATION: The 'Xaa' at location 106 stands for Ile, Val, Leu, or Phe.
<220> FEATURE:
<221> NAME/KEY: misc_feature
<222> LOCATION: (127)..(127)
<223> OTHER INFORMATION: The 'Xaa' at location 127 stands for Lys, Arg, Thr, or Met.
<220> FEATURE:
<221> NAME/KEY: misc_feature
<222> LOCATION: (136)..(136)
<223> OTHER INFORMATION: The 'Xaa' at location 136 stands for Gln, His, Arg, Pro, or Leu.
<220> FEATURE:
<221> NAME/KEY: misc_feature
<222> LOCATION: (316)..(316)
<223> OTHER INFORMATION: unknown nucleotide
<220> FEATURE:
<221> NAME/KEY: misc_feature
<222> LOCATION: (380)..(380)
<223> OTHER INFORMATION: unknown nucleotide
<220> FEATURE:
<221> NAME/KEY: misc_feature
<222> LOCATION: (407)..(407)
<223> OTHER INFORMATION: unknown nucleotide
<220> FEATURE:
<221> NAME/KEY: misc_feature
<222> LOCATION: (408)..(408)
<223> OTHER INFORMATION: unknown nucleotide

<400> SEQUENCE: 24

```
Ala Ser Thr Cys Ala Trp Pro Gly Phe Pro Gly Gly Gly Lys Val
1               5                  10                  15

Gly Glu Met Arg Met Pro Cys Pro Thr Met Pro Ser Trp Ser Thr
            20                  25                  30

Lys Arg Xaa Ala Gln Trp Gln Thr Gly Cys Thr Thr Ser Phe Gly Gly
        35                  40                  45

Ser Trp Arg Ser Ala Val Gly Ala Gly His Ser Ala Cys Ala Trp Arg
    50                  55                  60

Asn Ala Thr Gly Cys Leu Ala Lys Pro Ser Leu Arg Thr Cys Gly Pro
65                  70                  75                  80

Arg Ser Met Ala Ala Ala Arg Arg Cys Leu Cys Trp Pro Thr Arg Thr
                85                  90                  95

Gly Ser Val Val Ser Cys Ala Pro Xaa Xaa Leu Leu Ala Gln Gln Arg
            100                 105                 110

Leu Leu Glu Asp Arg Lys Asp Val Val Leu Val Ile Leu Xaa Pro
        115                 120                 125

Asp Gly Gln Ala Ser Arg Leu Xaa Asp Ala Leu Thr Ser Ala Ser Ala
    130                 135                 140
```

```
Ala Arg Val Ser Ser Ser Gly Pro Thr Ser Pro Val Val Ala Gln Leu
145                 150                 155                 160

Leu Arg Pro Ala Cys Met Ala Leu Thr Arg Asp Asn His His Phe Tyr
            165                 170                 175

Asn Arg Asn Phe Cys Gln Gly Thr His Gly Arg Ile Ala Val Ser Arg
        180                 185                 190

Asn Pro Ala Arg Cys His Leu His Thr His Leu Thr Tyr Ala Cys Leu
    195                 200                 205

Ile

<210> SEQ ID NO 25
<211> LENGTH: 4865
<212> TYPE: DNA
<213> ORGANISM: Homo sapiens
<220> FEATURE:
<221> NAME/KEY: CDS
<222> LOCATION: (107)..(2617)
<223> OTHER INFORMATION:
<220> FEATURE:
<221> NAME/KEY: mat_peptide
<222> LOCATION: (173)..()
<223> OTHER INFORMATION:

<400> SEQUENCE: 25
aaaatactcc cttgcctcaa aaactgctcg gtcaaacggt gatagcaaac cacgcattca      60
cagggccact gctgctcaca aaaccagtga ggatgatgcc aggatg atg tct gcc       115
                                              Met Met Ser Ala
                                                          -20 tcg cgc ctg gct ggg act ctg atc cca gcc atg gcc ttc ctc tcc tgc      163
Ser Arg Leu Ala Gly Thr Leu Ile Pro Ala Met Ala Phe Leu Ser Cys
            -15                 -10                  -5 gtg aga cca gaa agc tgg gag ccc tgc gtg gag gtt cct aat att act      211
Val Arg Pro Glu Ser Trp Glu Pro Cys Val Glu Val Pro Asn Ile Thr
         -1   1               5                  10 tat caa tgc atg gag ctg aat ttc tac aaa atc ccc gac aac ctc ccc      259
Tyr Gln Cys Met Glu Leu Asn Phe Tyr Lys Ile Pro Asp Asn Leu Pro
     15                  20                  25 ttc tca acc aag aac ctg gac ctg agc ttt aat ccc ctg agg cat tta      307
Phe Ser Thr Lys Asn Leu Asp Leu Ser Phe Asn Pro Leu Arg His Leu
 30                  35                  40                  45 ggc agc tat agc ttc ttc agt ttc cca gaa ctg cag gtg ctg gat tta      355
Gly Ser Tyr Ser Phe Phe Ser Phe Pro Glu Leu Gln Val Leu Asp Leu
                 50                  55                  60 tcc agg tgt gaa atc cag aca att gaa gat ggg gca tat cag agc cta      403
Ser Arg Cys Glu Ile Gln Thr Ile Glu Asp Gly Ala Tyr Gln Ser Leu
             65                  70                  75 agc cac ctc tct acc tta ata ttg aca gga aac ccc atc cag agt tta      451
Ser His Leu Ser Thr Leu Ile Leu Thr Gly Asn Pro Ile Gln Ser Leu
         80                  85                  90 gcc ctg gga gcc ttt tct gga cta tca agt tta cag aag ctg gtg gct      499
Ala Leu Gly Ala Phe Ser Gly Leu Ser Ser Leu Gln Lys Leu Val Ala
     95                 100                 105 gtg gag aca aat cta gca tct cta gag aac ttc ccc att gga cat ctc      547
Val Glu Thr Asn Leu Ala Ser Leu Glu Asn Phe Pro Ile Gly His Leu
110                 115                 120                 125 aaa act ttg aaa gaa ctt aat gtg gct cac aat ctt atc caa tct ttc      595
Lys Thr Leu Lys Glu Leu Asn Val Ala His Asn Leu Ile Gln Ser Phe
                130                 135                 140 aaa tta cct gag tat ttt tct aat ctg acc aat cta gag cac ttg gac      643
Lys Leu Pro Glu Tyr Phe Ser Asn Leu Thr Asn Leu Glu His Leu Asp
            145                 150                 155
```

-continued

| | |
|---|---|
| ctt tcc agc aac aag att caa agt att tat tgc aca gac ttg cgg gtt<br>Leu Ser Ser Asn Lys Ile Gln Ser Ile Tyr Cys Thr Asp Leu Arg Val<br>         160                   165                170 | 691 |
| cta cat caa atg ccc cta ctc aat ctc tct tta gac ctg tcc ctg aac<br>Leu His Gln Met Pro Leu Leu Asn Leu Ser Leu Asp Leu Ser Leu Asn<br>175                   180                   185 | 739 |
| cct atg aac ttt atc caa cca ggt gca ttt aaa gaa att agg ctt cat<br>Pro Met Asn Phe Ile Gln Pro Gly Ala Phe Lys Glu Ile Arg Leu His<br>190                   195                 200               205 | 787 |
| aag ctg act tta aga aat aat ttt gat agt tta aat gta atg aaa act<br>Lys Leu Thr Leu Arg Asn Asn Phe Asp Ser Leu Asn Val Met Lys Thr<br>                 210                   215               220 | 835 |
| tgt att caa ggt ctg gct ggt tta gaa gtc cat cgt ttg gtt ctg gga<br>Cys Ile Gln Gly Leu Ala Gly Leu Glu Val His Arg Leu Val Leu Gly<br>         225                   230                   235 | 883 |
| gaa ttt aga aat gaa gga aac ttg gaa aag ttt gac aaa tct gct cta<br>Glu Phe Arg Asn Glu Gly Asn Leu Glu Lys Phe Asp Lys Ser Ala Leu<br>             240                   245               250 | 931 |
| gag ggc ctg tgc aat ttg acc att gaa gaa ttc cga tta gca tac tta<br>Glu Gly Leu Cys Asn Leu Thr Ile Glu Glu Phe Arg Leu Ala Tyr Leu<br>         255                   260                   265 | 979 |
| gac tac tac ctc gat gat att att gac tta ttt aat tgt ttg aca aat<br>Asp Tyr Tyr Leu Asp Asp Ile Ile Asp Leu Phe Asn Cys Leu Thr Asn<br>270                   275                   280               285 | 1027 |
| gtt tct tca ttt tcc ctg gtg agt gtg act att gaa agg gta aaa gac<br>Val Ser Ser Phe Ser Leu Val Ser Val Thr Ile Glu Arg Val Lys Asp<br>                 290                   295               300 | 1075 |
| ttt tct tat aat ttc gga tgg caa cat tta gaa tta gtt aac tgt aaa<br>Phe Ser Tyr Asn Phe Gly Trp Gln His Leu Glu Leu Val Asn Cys Lys<br>                 305                   310               315 | 1123 |
| ttt gga cag ttt ccc aca ttg aaa ctc aaa tct ctc aaa agg ctt act<br>Phe Gly Gln Phe Pro Thr Leu Lys Leu Lys Ser Leu Lys Arg Leu Thr<br>         320                   325                   330 | 1171 |
| ttc act tcc aac aaa ggt ggg aat gct ttt tca gaa gtt gat cta cca<br>Phe Thr Ser Asn Lys Gly Gly Asn Ala Phe Ser Glu Val Asp Leu Pro<br>335                   340                   345 | 1219 |
| agc ctt gag ttt cta gat ctc agt aga aat ggc ttg agt ttc aaa ggt<br>Ser Leu Glu Phe Leu Asp Leu Ser Arg Asn Gly Leu Ser Phe Lys Gly<br>350                   355                   360               365 | 1267 |
| tgc tgt tct caa agt gat ttt ggg aca acc agc cta aag tat tta gat<br>Cys Cys Ser Gln Ser Asp Phe Gly Thr Thr Ser Leu Lys Tyr Leu Asp<br>                 370                   375               380 | 1315 |
| ctg agc ttc aat ggt gtt att acc atg agt tca aac ttc ttg ggc tta<br>Leu Ser Phe Asn Gly Val Ile Thr Met Ser Ser Asn Phe Leu Gly Leu<br>         385                   390                   395 | 1363 |
| gaa caa cta gaa cat ctg gat ttc cag cat tcc aat ttg aaa caa atg<br>Glu Gln Leu Glu His Leu Asp Phe Gln His Ser Asn Leu Lys Gln Met<br>             400                   405               410 | 1411 |
| agt gag ttt tca gta ttc cta tca ctc aga aac ctc att tac ctt gac<br>Ser Glu Phe Ser Val Phe Leu Ser Leu Arg Asn Leu Ile Tyr Leu Asp<br>         415                   420                   425 | 1459 |
| att tct cat act cac acc aga gtt gct ttc aat ggc atc ttc aat ggc<br>Ile Ser His Thr His Thr Arg Val Ala Phe Asn Gly Ile Phe Asn Gly<br>430                   435                   440               445 | 1507 |
| ttg tcc agt ctc gaa gtc ttg aaa atg gct ggc aat tct ttc cag gaa<br>Leu Ser Ser Leu Glu Val Leu Lys Met Ala Gly Asn Ser Phe Gln Glu<br>                 450                   455               460 | 1555 |
| aac ttc ctt cca gat atc ttc aca gag ctg aga aac ttg acc ttc ctg<br>Asn Phe Leu Pro Asp Ile Phe Thr Glu Leu Arg Asn Leu Thr Phe Leu | 1603 |

-continued

|  |  |  |  |  |  |  |  |  |  |  |  |  |  |  |  |
|---|---|---|---|---|---|---|---|---|---|---|---|---|---|---|---|
|  |  |  | 465 |  |  |  | 470 |  |  |  | 475 |  |  |  |  |
| gac | ctc | tct | cag | tgt | caa | ctg | gag | cag | ttg | tct | cca | aca | gca | ttt | aac | 1651 |
| Asp | Leu | Ser | Gln | Cys | Gln | Leu | Glu | Gln | Leu | Ser | Pro | Thr | Ala | Phe | Asn |  |
|  |  |  | 480 |  |  |  | 485 |  |  |  | 490 |  |  |  |  |
| tca | ctc | tcc | agt | ctt | cag | gta | cta | aat | atg | agc | cac | aac | aac | ttc | ttt | 1699 |
| Ser | Leu | Ser | Ser | Leu | Gln | Val | Leu | Asn | Met | Ser | His | Asn | Asn | Phe | Phe |  |
|  | 495 |  |  |  | 500 |  |  |  | 505 |  |  |  |  |  |  |
| tca | ttg | gat | acg | ttt | cct | tat | aag | tgt | ctg | aac | tcc | ctc | cag | gtt | ctt | 1747 |
| Ser | Leu | Asp | Thr | Phe | Pro | Tyr | Lys | Cys | Leu | Asn | Ser | Leu | Gln | Val | Leu |  |
| 510 |  |  |  |  | 515 |  |  |  | 520 |  |  |  |  | 525 |  |  |
| gat | tac | agt | ctc | aat | cac | ata | atg | act | tcc | aaa | aaa | cag | gaa | cta | cag | 1795 |
| Asp | Tyr | Ser | Leu | Asn | His | Ile | Met | Thr | Ser | Lys | Lys | Gln | Glu | Leu | Gln |  |
|  |  |  |  | 530 |  |  |  |  | 535 |  |  |  |  | 540 |  |  |
| cat | ttt | cca | agt | agt | cta | gct | ttc | tta | aat | ctt | act | cag | aat | gac | ttt | 1843 |
| His | Phe | Pro | Ser | Ser | Leu | Ala | Phe | Leu | Asn | Leu | Thr | Gln | Asn | Asp | Phe |  |
|  |  |  |  | 545 |  |  |  |  | 550 |  |  |  |  | 555 |  |  |
| gct | tgt | act | tgt | gaa | cac | cag | agt | ttc | ctg | caa | tgg | atc | aag | gac | cag | 1891 |
| Ala | Cys | Thr | Cys | Glu | His | Gln | Ser | Phe | Leu | Gln | Trp | Ile | Lys | Asp | Gln |  |
|  |  |  |  | 560 |  |  |  |  | 565 |  |  |  |  | 570 |  |  |
| agg | cag | ctc | ttg | gtg | gaa | gtt | gaa | cga | atg | gaa | tgt | gca | aca | cct | tca | 1939 |
| Arg | Gln | Leu | Leu | Val | Glu | Val | Glu | Arg | Met | Glu | Cys | Ala | Thr | Pro | Ser |  |
|  | 575 |  |  |  | 580 |  |  |  | 585 |  |  |  |  |  |  |
| gat | aag | cag | ggc | atg | cct | gtg | ctg | agt | ttg | aat | atc | acc | tgt | cag | atg | 1987 |
| Asp | Lys | Gln | Gly | Met | Pro | Val | Leu | Ser | Leu | Asn | Ile | Thr | Cys | Gln | Met |  |
| 590 |  |  |  |  | 595 |  |  |  | 600 |  |  |  |  | 605 |  |  |
| aat | aag | acc | atc | att | ggt | gtg | tcg | gtc | ctc | agt | gtg | ctt | gta | gta | tct | 2035 |
| Asn | Lys | Thr | Ile | Ile | Gly | Val | Ser | Val | Leu | Ser | Val | Leu | Val | Val | Ser |  |
|  |  |  |  | 610 |  |  |  |  | 615 |  |  |  |  | 620 |  |  |
| gtt | gta | gca | gtt | ctg | gtc | tat | aag | ttc | tat | ttt | cac | ctg | atg | ctt | ctt | 2083 |
| Val | Val | Ala | Val | Leu | Val | Tyr | Lys | Phe | Tyr | Phe | His | Leu | Met | Leu | Leu |  |
|  |  |  | 625 |  |  |  |  | 630 |  |  |  |  | 635 |  |  |  |
| gct | ggc | tgc | ata | aag | tat | ggt | aga | ggt | gaa | aac | atc | tat | gat | gcc | ttt | 2131 |
| Ala | Gly | Cys | Ile | Lys | Tyr | Gly | Arg | Gly | Glu | Asn | Ile | Tyr | Asp | Ala | Phe |  |
|  |  |  | 640 |  |  |  |  | 645 |  |  |  |  | 650 |  |  |  |
| gtt | atc | tac | tca | agc | cag | gat | gag | gac | tgg | gta | agg | aat | gag | cta | gta | 2179 |
| Val | Ile | Tyr | Ser | Ser | Gln | Asp | Glu | Asp | Trp | Val | Arg | Asn | Glu | Leu | Val |  |
|  | 655 |  |  |  | 660 |  |  |  | 665 |  |  |  |  |  |  |
| aag | aat | tta | gaa | gaa | ggg | gtg | cct | cca | ttt | cag | ctc | tgc | ctt | cac | tac | 2227 |
| Lys | Asn | Leu | Glu | Glu | Gly | Val | Pro | Pro | Phe | Gln | Leu | Cys | Leu | His | Tyr |  |
| 670 |  |  |  |  | 675 |  |  |  | 680 |  |  |  |  | 685 |  |  |
| aga | gac | ttt | att | ccc | ggt | gtg | gcc | att | gct | gcc | aac | atc | atc | cat | gaa | 2275 |
| Arg | Asp | Phe | Ile | Pro | Gly | Val | Ala | Ile | Ala | Ala | Asn | Ile | Ile | His | Glu |  |
|  |  |  |  | 690 |  |  |  |  | 695 |  |  |  |  | 700 |  |  |
| ggt | ttc | cat | aaa | agc | cga | aag | gtg | att | gtt | gtg | gtg | tcc | cag | cac | ttc | 2323 |
| Gly | Phe | His | Lys | Ser | Arg | Lys | Val | Ile | Val | Val | Val | Ser | Gln | His | Phe |  |
|  |  |  | 705 |  |  |  |  | 710 |  |  |  |  | 715 |  |  |  |
| atc | cag | agc | cgc | tgg | tgt | atc | ttt | gaa | tat | gag | att | gct | cag | acc | tgg | 2371 |
| Ile | Gln | Ser | Arg | Trp | Cys | Ile | Phe | Glu | Tyr | Glu | Ile | Ala | Gln | Thr | Trp |  |
|  |  | 720 |  |  |  |  | 725 |  |  |  |  | 730 |  |  |  |  |
| cag | ttt | ctg | agc | agt | cgt | gct | ggt | atc | atc | ttc | att | gtc | ctg | cag | aag | 2419 |
| Gln | Phe | Leu | Ser | Ser | Arg | Ala | Gly | Ile | Ile | Phe | Ile | Val | Leu | Gln | Lys |  |
|  | 735 |  |  |  |  | 740 |  |  |  |  | 745 |  |  |  |  |
| gtg | gag | aag | acc | ctg | ctc | agg | cag | cag | gtg | gag | ctg | tac | cgc | ctt | ctc | 2467 |
| Val | Glu | Lys | Thr | Leu | Leu | Arg | Gln | Gln | Val | Glu | Leu | Tyr | Arg | Leu | Leu |  |
| 750 |  |  |  |  | 755 |  |  |  | 760 |  |  |  |  | 765 |  |  |
| agc | agg | aac | act | tac | ctg | gag | tgg | gag | gac | agt | gtc | ctg | ggg | cgg | cac | 2515 |
| Ser | Arg | Asn | Thr | Tyr | Leu | Glu | Trp | Glu | Asp | Ser | Val | Leu | Gly | Arg | His |  |
|  |  |  | 770 |  |  |  |  | 775 |  |  |  |  | 780 |  |  |  |
| atc | ttc | tgg | aga | cga | ctc | aga | aaa | gcc | ctg | ctg | gat | ggt | aaa | tca | tgg | 2563 |

```
Ile Phe Trp Arg Arg Leu Arg Lys Ala Leu Leu Asp Gly Lys Ser Trp
            785                 790                 795 aat cca gaa gga aca gtg ggt aca gga tgc aat tgg cag gaa gca aca      2611
Asn Pro Glu Gly Thr Val Gly Thr Gly Cys Asn Trp Gln Glu Ala Thr
        800                 805                 810 tct atc tgaagaggaa aaataaaaac ctcctgaggc atttcttgcc cagctgggtc       2667
Ser Ile
    815 caacacttgt tcagttaata agtattaaat gctgccacat gtcaggcctt atgctaaggg    2727 tgagtaattc catggtgcac tagatatgca gggctgctaa tctcaaggag cttccagtgc    2787 agagggaata aatgctagac taaaatacag agtcttccag gtgggcattt caaccaactc    2847 agtcaaggaa cccatgacaa agaaagtcat ttcaactctt acctcatcaa gttgaataaa    2907 gacagagaaa acagaaagag acattgttct tttcctgagt cttttgaatg gaaattgtat    2967 tatgttatag ccatcataaa accattttgg tagttttgac tgaactgggt gttcactttt    3027 tccttttga ttgaatacaa tttaaattct acttgatgac tgcagtcgtc aaggggctcc     3087 tgatgcaaga tgccccttcc attttaagtc tgtctcctta cagaggttaa agtctaatgg    3147 ctaattccta aggaaacctg attaacacat gctcacaacc atcctggtca ttctcgaaca    3207 tgttctattt tttaactaat caccoctgat atatttttat tttatatat ccagttttca     3267 ttttttacg tcttgcctat aagctaatat cataaataag gttgtttaag acgtgcttca     3327 aatatccata ttaaccacta tttttcaagg aagtatggaa agtacactc tgtcactttg     3387 tcactcgatg tcattccaaa gttattgcct actaagtaat gactgtcatg aaagcagcat    3447 tgaaataatt tgtttaaagg gggcactctt ttaaacggga agaaaatttc cgcttcctgg    3507 tcttatcatg gacaatttgg gctagaggca ggaaggaagt gggatgacct caggaagtca    3567 cctttcttg attccagaaa catatgggct gataaacccg gggtgacctc atgaaatgag     3627 ttgcagcaga agtttatttt tttcagaaca agtgatgttt gatggacctc tgaatctctt    3687 tagggagaca cagatggctg ggatccctcc cctgtaccct tctcactgcc aggagaacta    3747 cgtgtgaagg tattcaaggc agggagtata cattgctgtt tcctgttggg caatgctcct    3807 tgaccacatt ttgggaagag tggatgttat cattgagaaa acaatgtgtc tggaattaat    3867 ggggttctta taagaaggt tcccagaaaa gaatgttcat tccagcttct tcaggaaaca    3927 ggaacattca aggaaaagga caatcaggat gtcatcaggg aaatgaaaat aaaaaccaca    3987 atgagatatc accttatacc aggtagatgg ctactataaa aaaatgaagt gtcatcaagg    4047 atatagagaa attggaaccc ttcttcactg ctggagggaa tggaaaatgg tgtagccgtt    4107 atgaaaaaca gtacggaggt ttctcaaaaa ttaaaaatag aactgctata tgatccagca    4167 atctcacttc tgtatatata cccaaaataa ttgaaatcag aatttcaaga aaatatttac    4227 actcccatgt tcattgtggc actcttcaca atcactgttt ccaaagttat ggaaacaacc    4287 caaatttcca ttggaaaata aatggacaaa ggaaatgtgc ataacgta caatggggat      4347 attattcagc ctaaaaaaag gggggatcct gttatttatg acaacatgaa taaacccgga    4407 ggccattatg ctatgtaaaa tgagcaagta acagaaagac aaatactgcc tgatttcatt    4467 tatatgaggt tctaaaatag tcaaactcat agaagcagag aatagaacag tggttcctag    4527 ggaaaaggag gaagggagaa atgaggaaat agggagttgt ctaattggta taaaattata    4587 gtatgcaaga tgaattagct ctaaagatca gctgtatagc agagttcgta taatgaacaa    4647 tactgtatta tgcacttaac atttttgttaa gagggtacct ctcatgttaa gtgttcttac    4707
```

```
catatacata tacacaagga agcttttgga ggtgatggat atatttatta ccttgattgt    4767
ggtgatggtt tgacaggtat gtgactatgt ctaaactcat caaattgtat acattaaata    4827
tatgcagttt tataatatca aaaaaaaaaa aaaaaaa                             4865
```

<210> SEQ ID NO 26
<211> LENGTH: 837
<212> TYPE: PRT
<213> ORGANISM: Homo sapiens

<400> SEQUENCE: 26

```
Met Ser Ala Ser Arg Leu Ala Gly Thr Leu Ile Pro Ala Met Ala Phe
        -20                 -15                 -10

Leu Ser Cys Val Arg Pro Glu Ser Trp Glu Pro Cys Val Glu Val Pro
         -5              -1   1               5                  10

Asn Ile Thr Tyr Gln Cys Met Glu Leu Asn Phe Tyr Lys Ile Pro Asp
                 15                  20                  25

Asn Leu Pro Phe Ser Thr Lys Asn Leu Asp Leu Ser Phe Asn Pro Leu
             30                  35                  40

Arg His Leu Gly Ser Tyr Ser Phe Phe Ser Pro Glu Leu Gln Val
         45                  50                  55

Leu Asp Leu Ser Arg Cys Glu Ile Gln Thr Ile Glu Asp Gly Ala Tyr
60                  65                  70

Gln Ser Leu Ser His Leu Ser Thr Leu Ile Leu Thr Gly Asn Pro Ile
75                  80                  85                  90

Gln Ser Leu Ala Leu Gly Ala Phe Ser Gly Leu Ser Ser Leu Gln Lys
             95                 100                 105

Leu Val Ala Val Glu Thr Asn Leu Ala Ser Leu Glu Asn Phe Pro Ile
             110                 115                 120

Gly His Leu Lys Thr Leu Lys Glu Leu Asn Val Ala His Asn Leu Ile
         125                 130                 135

Gln Ser Phe Lys Leu Pro Glu Tyr Phe Ser Asn Leu Thr Asn Leu Glu
     140                 145                 150

His Leu Asp Leu Ser Ser Asn Lys Ile Gln Ser Ile Tyr Cys Thr Asp
155                 160                 165                 170

Leu Arg Val Leu His Gln Met Pro Leu Leu Asn Leu Ser Leu Asp Leu
             175                 180                 185

Ser Leu Asn Pro Met Asn Phe Ile Gln Pro Gly Ala Phe Lys Glu Ile
             190                 195                 200

Arg Leu His Lys Leu Thr Leu Arg Asn Asn Phe Asp Ser Leu Asn Val
         205                 210                 215

Met Lys Thr Cys Ile Gln Gly Leu Ala Gly Leu Glu Val His Arg Leu
     220                 225                 230

Val Leu Gly Glu Phe Arg Asn Glu Gly Asn Leu Glu Lys Phe Asp Lys
235                 240                 245                 250

Ser Ala Leu Glu Gly Leu Cys Asn Leu Thr Ile Glu Glu Phe Arg Leu
             255                 260                 265

Ala Tyr Leu Asp Tyr Tyr Leu Asp Asp Ile Ile Asp Leu Phe Asn Cys
             270                 275                 280

Leu Thr Asn Val Ser Ser Phe Ser Leu Val Ser Val Thr Ile Glu Arg
         285                 290                 295

Val Lys Asp Phe Ser Tyr Asn Phe Gly Trp Gln His Leu Glu Leu Val
     300                 305                 310

Asn Cys Lys Phe Gly Gln Phe Pro Thr Leu Lys Leu Lys Ser Leu Lys
315                 320                 325                 330
```

-continued

```
Arg Leu Thr Phe Thr Ser Asn Lys Gly Gly Asn Ala Phe Ser Glu Val
            335                 340                 345

Asp Leu Pro Ser Leu Glu Phe Leu Asp Leu Ser Arg Asn Gly Leu Ser
        350                 355                 360

Phe Lys Gly Cys Cys Ser Gln Ser Asp Phe Gly Thr Thr Ser Leu Lys
    365                 370                 375

Tyr Leu Asp Leu Ser Phe Asn Gly Val Ile Thr Met Ser Ser Asn Phe
380                 385                 390

Leu Gly Leu Glu Gln Leu Glu His Leu Asp Phe Gln His Ser Asn Leu
395                 400                 405                 410

Lys Gln Met Ser Glu Phe Ser Val Phe Leu Ser Leu Arg Asn Leu Ile
            415                 420                 425

Tyr Leu Asp Ile Ser His Thr His Thr Arg Val Ala Phe Asn Gly Ile
        430                 435                 440

Phe Asn Gly Leu Ser Ser Leu Glu Val Leu Lys Met Ala Gly Asn Ser
    445                 450                 455

Phe Gln Glu Asn Phe Leu Pro Asp Ile Phe Thr Glu Leu Arg Asn Leu
460                 465                 470

Thr Phe Leu Asp Leu Ser Gln Cys Gln Leu Glu Gln Leu Ser Pro Thr
475                 480                 485                 490

Ala Phe Asn Ser Leu Ser Ser Leu Gln Val Leu Asn Met Ser His Asn
            495                 500                 505

Asn Phe Phe Ser Leu Asp Thr Phe Pro Tyr Lys Cys Leu Asn Ser Leu
        510                 515                 520

Gln Val Leu Asp Tyr Ser Leu Asn His Ile Met Thr Ser Lys Lys Gln
    525                 530                 535

Glu Leu Gln His Phe Pro Ser Ser Leu Ala Phe Leu Asn Leu Thr Gln
    540                 545                 550

Asn Asp Phe Ala Cys Thr Cys Glu His Gln Ser Phe Leu Gln Trp Ile
555                 560                 565                 570

Lys Asp Gln Arg Gln Leu Leu Val Glu Val Glu Arg Met Glu Cys Ala
            575                 580                 585

Thr Pro Ser Asp Lys Gln Gly Met Pro Val Leu Ser Leu Asn Ile Thr
        590                 595                 600

Cys Gln Met Asn Lys Thr Ile Ile Gly Val Ser Val Leu Ser Val Leu
    605                 610                 615

Val Val Ser Val Val Ala Val Leu Val Tyr Lys Phe Tyr Phe His Leu
620                 625                 630

Met Leu Leu Ala Gly Cys Ile Lys Tyr Gly Arg Gly Glu Asn Ile Tyr
635                 640                 645                 650

Asp Ala Phe Val Ile Tyr Ser Ser Gln Asp Glu Asp Trp Val Arg Asn
            655                 660                 665

Glu Leu Val Lys Asn Leu Glu Glu Gly Val Pro Pro Phe Gln Leu Cys
        670                 675                 680

Leu His Tyr Arg Asp Phe Ile Pro Gly Val Ala Ile Ala Ala Asn Ile
    685                 690                 695

Ile His Glu Gly Phe His Lys Ser Arg Lys Val Ile Val Val Val Ser
700                 705                 710

Gln His Phe Ile Gln Ser Arg Trp Cys Ile Phe Glu Tyr Glu Ile Ala
715                 720                 725                 730

Gln Thr Trp Gln Phe Leu Ser Ser Arg Ala Gly Ile Ile Phe Ile Val
            735                 740                 745
```

```
Leu Gln Lys Val Glu Lys Thr Leu Leu Arg Gln Gln Val Glu Leu Tyr
            750                 755                 760

Arg Leu Leu Ser Arg Asn Thr Tyr Leu Glu Trp Glu Asp Ser Val Leu
        765                 770                 775

Gly Arg His Ile Phe Trp Arg Leu Arg Lys Ala Leu Leu Asp Gly
    780                 785                 790

Lys Ser Trp Asn Pro Glu Gly Thr Val Gly Thr Gly Cys Asn Trp Gln
795                 800                 805                 810

Glu Ala Thr Ser Ile
                815

<210> SEQ ID NO 27
<211> LENGTH: 300
<212> TYPE: DNA
<213> ORGANISM: Mus musculus
<220> FEATURE:
<221> NAME/KEY: CDS
<222> LOCATION: (1)..(300)
<223> OTHER INFORMATION:

<400> SEQUENCE: 27 tcc tat tct atg gaa aaa gat gct ttc cta ttt atg aga aat ttg aag      48
Ser Tyr Ser Met Glu Lys Asp Ala Phe Leu Phe Met Arg Asn Leu Lys
1               5                   10                  15 gtt ctc tca cta aaa gat aac aat gtc aca gct gtc ccc acc act ttg      96
Val Leu Ser Leu Lys Asp Asn Asn Val Thr Ala Val Pro Thr Thr Leu
            20                  25                  30 cca cct aat tta cta gag ctc tat ctt tat aac aat atc att aag aaa     144
Pro Pro Asn Leu Leu Glu Leu Tyr Leu Tyr Asn Asn Ile Ile Lys Lys
        35                  40                  45 atc caa gaa aat gat ttc aat aac ctc aat gag ttg caa gtc ctt gac     192
Ile Gln Glu Asn Asp Phe Asn Asn Leu Asn Glu Leu Gln Val Leu Asp
    50                  55                  60 cta cgt gga aat tgc cct cga tgt cat aat gtc cca tat ccg tgt aca     240
Leu Arg Gly Asn Cys Pro Arg Cys His Asn Val Pro Tyr Pro Cys Thr
65                  70                  75                  80 ccg tgt gaa aat aat tcc ccc tta cag atc cat gac aat gct ttc aat     288
Pro Cys Glu Asn Asn Ser Pro Leu Gln Ile His Asp Asn Ala Phe Asn
                85                  90                  95 tca tcg aca gac                                                     300
Ser Ser Thr Asp
            100

<210> SEQ ID NO 28
<211> LENGTH: 100
<212> TYPE: PRT
<213> ORGANISM: Mus musculus

<400> SEQUENCE: 28

Ser Tyr Ser Met Glu Lys Asp Ala Phe Leu Phe Met Arg Asn Leu Lys
1               5                   10                  15

Val Leu Ser Leu Lys Asp Asn Asn Val Thr Ala Val Pro Thr Thr Leu
            20                  25                  30

Pro Pro Asn Leu Leu Glu Leu Tyr Leu Tyr Asn Asn Ile Ile Lys Lys
        35                  40                  45

Ile Gln Glu Asn Asp Phe Asn Asn Leu Asn Glu Leu Gln Val Leu Asp
    50                  55                  60

Leu Arg Gly Asn Cys Pro Arg Cys His Asn Val Pro Tyr Pro Cys Thr
65                  70                  75                  80

Pro Cys Glu Asn Asn Ser Pro Leu Gln Ile His Asp Asn Ala Phe Asn
```

```
                85                 90                 95
Ser Ser Thr Asp
            100

<210> SEQ ID NO 29
<211> LENGTH: 1756
<212> TYPE: DNA
<213> ORGANISM: Mus musculus
<220> FEATURE:
<221> NAME/KEY: CDS
<222> LOCATION: (1)..(1182)
<223> OTHER INFORMATION:

<400> SEQUENCE: 29 tct cca gaa att ccc tgg aat tcc ttg cct cct gag gtt ttt gag ggt      48
Ser Pro Glu Ile Pro Trp Asn Ser Leu Pro Pro Glu Val Phe Glu Gly
1               5                  10                  15 atg ccg cca aat cta aag aat ctc tcc ttg gcc aaa aat ggg ctc aaa      96
Met Pro Pro Asn Leu Lys Asn Leu Ser Leu Ala Lys Asn Gly Leu Lys
            20                  25                  30 tct ttc ttt tgg gac aga ctc cag tta ctg aag cat ttg gaa att ttg     144
Ser Phe Phe Trp Asp Arg Leu Gln Leu Leu Lys His Leu Glu Ile Leu
        35                  40                  45 gac ctc agc cat aac cag ctg aca aaa gta cct gag aga ttg gcc aac     192
Asp Leu Ser His Asn Gln Leu Thr Lys Val Pro Glu Arg Leu Ala Asn
    50                  55                  60 tgt tcc aaa agt ctc aca aca ctg att ctt aag cat aat caa atc agg     240
Cys Ser Lys Ser Leu Thr Thr Leu Ile Leu Lys His Asn Gln Ile Arg
65                  70                  75                  80 caa ttg aca aaa tat ttt cta gaa gat gct ttg caa ttg cgc tat cta     288
Gln Leu Thr Lys Tyr Phe Leu Glu Asp Ala Leu Gln Leu Arg Tyr Leu
                85                  90                  95 gac atc agt tca aat aaa atc cag gtc att cag aag act agc ttc cca     336
Asp Ile Ser Ser Asn Lys Ile Gln Val Ile Gln Lys Thr Ser Phe Pro
            100                 105                 110 gaa aat gtc ctc aac aat ctg gag atg ttg gtt tta cat cac aat cgc     384
Glu Asn Val Leu Asn Asn Leu Glu Met Leu Val Leu His His Asn Arg
        115                 120                 125 ttt ctt tgc aac tgt gat gct gtg tgg ttt gtc tgg tgg gtt aac cat     432
Phe Leu Cys Asn Cys Asp Ala Val Trp Phe Val Trp Trp Val Asn His
    130                 135                 140 aca gat gtt act att cca tac ctg gcc act gat gtg act tgt gta ggt     480
Thr Asp Val Thr Ile Pro Tyr Leu Ala Thr Asp Val Thr Cys Val Gly
145                 150                 155                 160 cca gga gca cac aaa ggt caa agt gtc ata tcc ctt gat ctg tat acg     528
Pro Gly Ala His Lys Gly Gln Ser Val Ile Ser Leu Asp Leu Tyr Thr
                165                 170                 175 tgt gag tta gat ctc aca aac ctg att ctg ttc tca gtt tcc ata tca     576
Cys Glu Leu Asp Leu Thr Asn Leu Ile Leu Phe Ser Val Ser Ile Ser
            180                 185                 190 tca gtc ctc ttt ctt atg gta gtt atg aca aca agt cac ctc ttt ttc     624
Ser Val Leu Phe Leu Met Val Val Met Thr Thr Ser His Leu Phe Phe
        195                 200                 205 tgg gat atg tgg tac att tat tat ttt tgg aaa gca aag ata aag ggg     672
Trp Asp Met Trp Tyr Ile Tyr Tyr Phe Trp Lys Ala Lys Ile Lys Gly
    210                 215                 220 tat cca gca tct gca atc cca tgg agt cct tgt tat gat gct ttt att     720
Tyr Pro Ala Ser Ala Ile Pro Trp Ser Pro Cys Tyr Asp Ala Phe Ile
225                 230                 235                 240 gtg tat gac act aaa aac tca gct gtg aca gaa tgg gtt ttg cag gag     768
Val Tyr Asp Thr Lys Asn Ser Ala Val Thr Glu Trp Val Leu Gln Glu
```

|   |   |
|---|---|
| ctg gtg gca aaa ttg gaa gat cca aga gaa aaa cac ttc aat ttg tgt<br>Leu Val Ala Lys Leu Glu Asp Pro Arg Glu Lys His Phe Asn Leu Cys<br>           260                    265                    270 | 816 |
| cta gaa gaa aga gac tgg cta cca gga cag cca gtt cta gaa aac ctt<br>Leu Glu Glu Arg Asp Trp Leu Pro Gly Gln Pro Val Leu Glu Asn Leu<br>    275                    280                    285 | 864 |
| tcc cag agc ata cag ctc agc aaa aag aca gtg ttt gtg atg aca cag<br>Ser Gln Ser Ile Gln Leu Ser Lys Lys Thr Val Phe Val Met Thr Gln<br>290                    295                    300 | 912 |
| aaa tat gct aag act gag agt ttt aag atg gca ttt tat ttg tct cat<br>Lys Tyr Ala Lys Thr Glu Ser Phe Lys Met Ala Phe Tyr Leu Ser His<br>305                    310                    315                    320 | 960 |
| cag agg ctc ctg gat gaa aaa gtg gat gtg att atc ttg ata ttc ttg<br>Gln Arg Leu Leu Asp Glu Lys Val Asp Val Ile Ile Leu Ile Phe Leu<br>           325                    330                    335 | 1008 |
| gaa aga cct ctt cag aag tct aag ttt ctt cag ctc agg aag aga ctc<br>Glu Arg Pro Leu Gln Lys Ser Lys Phe Leu Gln Leu Arg Lys Arg Leu<br>    340                    345                    350 | 1056 |
| tgc agg agc tct gtc ctt gag tgg cct gca aat cca cag gct cac cca<br>Cys Arg Ser Ser Val Leu Glu Trp Pro Ala Asn Pro Gln Ala His Pro<br>           355                    360                    365 | 1104 |
| tac ttc tgg cag tgc ctg aaa aat gcc ctg acc aca gac aat cat gtg<br>Tyr Phe Trp Gln Cys Leu Lys Asn Ala Leu Thr Thr Asp Asn His Val<br>370                    375                    380 | 1152 |
| gct tat agt caa atg ttc aag gaa aca gtc tagctctctg aagaatgtca<br>Ala Tyr Ser Gln Met Phe Lys Glu Thr Val<br>385                    390 | 1202 |
| ccacctagga catgccttgg tacctgaagt tttcataaag gtttccataa atgaaggtct | 1262 |
| gaattttttcc taacagttgt catggctcag attggtggga aatcatcaat atatggctaa | 1322 |
| gaaattaaga aggggagact gatagaagat aatttctttc ttcatgtgcc atgctcagtt | 1382 |
| aaatatttcc cctagctcaa atctgaaaaa ctgtgcctag gagacaacac aaggctttga | 1442 |
| tttatctgca tacaattgat aagagccaca catctgccct gaagaagtac tagtagtttt | 1502 |
| agtagtaggg taaaaattac acaagctttc tctctctctg atactgaact gtaccagagt | 1562 |
| tcaatgaaat aaaagcccag agaacttctc agtaaatggt ttcattatca tgtagtatcc | 1622 |
| accatgcaat atgccacaaa accgctactg gtacaggaca gctggtagct gcttcaaggc | 1682 |
| ctcttatcat tttcttgggg cccatggagg ggttctctgg gaaaaaggga aggttttttt | 1742 |
| tggccatcca tgaa | 1756 |

<210> SEQ ID NO 30
<211> LENGTH: 394
<212> TYPE: PRT
<213> ORGANISM: Mus musculus

<400> SEQUENCE: 30

Ser Pro Glu Ile Pro Trp Asn Ser Leu Pro Pro Glu Val Phe Glu Gly
1               5                    10                  15

Met Pro Pro Asn Leu Lys Asn Leu Ser Leu Ala Lys Asn Gly Leu Lys
                20                    25                    30

Ser Phe Phe Trp Asp Arg Leu Gln Leu Leu Lys His Leu Glu Ile Leu
                     35                    40                    45

Asp Leu Ser His Asn Gln Leu Thr Lys Val Pro Glu Arg Leu Ala Asn
    50                    55                    60

Cys Ser Lys Ser Leu Thr Thr Leu Ile Leu Lys His Asn Gln Ile Arg

```
                65                  70                  75                  80
Gln Leu Thr Lys Tyr Phe Leu Glu Asp Ala Leu Gln Leu Arg Tyr Leu
                        85                  90                  95
Asp Ile Ser Ser Asn Lys Ile Gln Val Ile Gln Lys Thr Ser Phe Pro
                100                 105                 110
Glu Asn Val Leu Asn Asn Leu Glu Met Leu Val Leu His His Asn Arg
                115                 120                 125
Phe Leu Cys Asn Cys Asp Ala Val Trp Phe Val Trp Trp Val Asn His
            130                 135                 140
Thr Asp Val Thr Ile Pro Tyr Leu Ala Thr Val Thr Cys Val Gly
145                 150                 155                 160
Pro Gly Ala His Lys Gly Gln Ser Val Ile Ser Leu Asp Leu Tyr Thr
                    165                 170                 175
Cys Glu Leu Asp Leu Thr Asn Leu Ile Leu Phe Ser Val Ser Ile Ser
                180                 185                 190
Ser Val Leu Phe Leu Met Val Val Met Thr Thr Ser His Leu Phe Phe
                195                 200                 205
Trp Asp Met Trp Tyr Ile Tyr Tyr Phe Trp Lys Ala Lys Ile Lys Gly
        210                 215                 220
Tyr Pro Ala Ser Ala Ile Pro Trp Ser Pro Cys Tyr Asp Ala Phe Ile
225                 230                 235                 240
Val Tyr Asp Thr Lys Asn Ser Ala Val Thr Glu Trp Val Leu Gln Glu
                245                 250                 255
Leu Val Ala Lys Leu Glu Asp Pro Arg Glu Lys His Phe Asn Leu Cys
                260                 265                 270
Leu Glu Glu Arg Asp Trp Leu Pro Gly Gln Pro Val Leu Glu Asn Leu
                275                 280                 285
Ser Gln Ser Ile Gln Leu Ser Lys Lys Thr Val Phe Val Met Thr Gln
                290                 295                 300
Lys Tyr Ala Lys Thr Glu Ser Phe Lys Met Ala Phe Tyr Leu Ser His
305                 310                 315                 320
Gln Arg Leu Leu Asp Glu Lys Val Asp Val Ile Ile Leu Ile Phe Leu
                325                 330                 335
Glu Arg Pro Leu Gln Lys Ser Lys Phe Leu Gln Leu Arg Lys Arg Leu
                340                 345                 350
Cys Arg Ser Ser Val Leu Glu Trp Pro Ala Asn Pro Gln Ala His Pro
            355                 360                 365
Tyr Phe Trp Gln Cys Leu Lys Asn Ala Leu Thr Thr Asp Asn His Val
        370                 375                 380
Ala Tyr Ser Gln Met Phe Lys Glu Thr Val
385                 390
```

<210> SEQ ID NO 31
<211> LENGTH: 999
<212> TYPE: DNA
<213> ORGANISM: Homo sapiens
<220> FEATURE:
<221> NAME/KEY: CDS
<222> LOCATION: (2)..(847)
<223> OTHER INFORMATION:

<400> SEQUENCE: 31

```
c tcc gat gcc aag att cgg cac cag gca tat tca gag gtc atg atg gtt      49
  Ser Asp Ala Lys Ile Arg His Gln Ala Tyr Ser Glu Val Met Met Val
  1               5                   10                  15 gga tgg tca gat tca tac acc tgt gaa tac cct tta aac cta agg gga        97
```

```
                Gly Trp Ser Asp Ser Tyr Thr Cys Glu Tyr Pro Leu Asn Leu Arg Gly
                         20                  25                  30 act agg tta aaa gac gtt cat ctc cac gaa tta tct tgc aac aca gct            145
Thr Arg Leu Lys Asp Val His Leu His Glu Leu Ser Cys Asn Thr Ala
         35                  40                  45 ctg ttg att gtc acc att gtg gtt att atg cta gtt ctg ggg ttg gct            193
Leu Leu Ile Val Thr Ile Val Val Ile Met Leu Val Leu Gly Leu Ala
 50                  55                  60 gtg gcc ttc tgc tgt ctc cac ttt gat ctg ccc tgg tat ctc agg atg            241
Val Ala Phe Cys Cys Leu His Phe Asp Leu Pro Trp Tyr Leu Arg Met
 65                  70                  75                  80 cta ggt caa tgc aca caa aca tgg cac agg gtt agg aaa aca acc caa            289
Leu Gly Gln Cys Thr Gln Thr Trp His Arg Val Arg Lys Thr Thr Gln
                 85                  90                  95 gaa caa ctc aag aga aat gtc cga ttc cac gca ttt att tca tac agt            337
Glu Gln Leu Lys Arg Asn Val Arg Phe His Ala Phe Ile Ser Tyr Ser
             100                 105                 110 gaa cat gat tct ctg tgg gtg aag aat gaa ttg atc ccc aat cta gag            385
Glu His Asp Ser Leu Trp Val Lys Asn Glu Leu Ile Pro Asn Leu Glu
         115                 120                 125 aag gaa gat ggt tct atc ttg att tgc ctt tat gaa agc tac ttt gac            433
Lys Glu Asp Gly Ser Ile Leu Ile Cys Leu Tyr Glu Ser Tyr Phe Asp
     130                 135                 140 cct ggc aaa agc att agt gaa aat att gta agc ttc att gag aaa agc            481
Pro Gly Lys Ser Ile Ser Glu Asn Ile Val Ser Phe Ile Glu Lys Ser
145                 150                 155                 160 tat aag tcc atc ttt gtt ttg tct ccc aac ttt gtc cag aat gag tgg            529
Tyr Lys Ser Ile Phe Val Leu Ser Pro Asn Phe Val Gln Asn Glu Trp
                 165                 170                 175 tgc cat tat gaa ttc tac ttt gcc cac cac aat ctc ttc cat gaa aat            577
Cys His Tyr Glu Phe Tyr Phe Ala His His Asn Leu Phe His Glu Asn
             180                 185                 190 tct gat cac ata att ctt atc tta ctg gaa ccc att cca ttc tat tgc            625
Ser Asp His Ile Ile Leu Ile Leu Leu Glu Pro Ile Pro Phe Tyr Cys
         195                 200                 205 att ccc acc agg tat cat aaa ctg gaa gct ctc ctg gaa aaa aaa gca            673
Ile Pro Thr Arg Tyr His Lys Leu Glu Ala Leu Leu Glu Lys Lys Ala
     210                 215                 220 tac ttg gaa tgg ccc aag gat agg cgt aaa tgt ggg ctt ttc tgg gca            721
Tyr Leu Glu Trp Pro Lys Asp Arg Arg Lys Cys Gly Leu Phe Trp Ala
225                 230                 235                 240 aac ctt cga gct gct gtt aat gtt aat gta tta gcc acc aga gaa atg            769
Asn Leu Arg Ala Ala Val Asn Val Asn Val Leu Ala Thr Arg Glu Met
                 245                 250                 255 tat gaa ctg cag aca ttc aca gag tta aat gaa gag tct cga ggt tct            817
Tyr Glu Leu Gln Thr Phe Thr Glu Leu Asn Glu Glu Ser Arg Gly Ser
             260                 265                 270 aca atc tct ctg atg aga aca gac tgt cta taaaatccca cagtccttgg              867
Thr Ile Ser Leu Met Arg Thr Asp Cys Leu
         275                 280 gaagttgggg accacataca ctgttgggat gtacattgat acaacctta tgatggcaat           927 ttgacaatat ttattaaaat aaaaaatggt tattcccttc aaaaaaaaaa aaaaaaaaaa          987
aaaaaaaaaa aa                                                              999

<210> SEQ ID NO 32
<211> LENGTH: 282
<212> TYPE: PRT
<213> ORGANISM: Homo sapiens
```

```
<400> SEQUENCE: 32

Ser Asp Ala Lys Ile Arg His Gln Ala Tyr Ser Glu Val Met Met Val
1               5                   10                  15

Gly Trp Ser Asp Ser Tyr Thr Cys Glu Tyr Pro Leu Asn Leu Arg Gly
            20                  25                  30

Thr Arg Leu Lys Asp Val His Leu His Glu Leu Ser Cys Asn Thr Ala
        35                  40                  45

Leu Leu Ile Val Thr Ile Val Val Ile Met Leu Val Leu Gly Leu Ala
    50                  55                  60

Val Ala Phe Cys Cys Leu His Phe Asp Leu Pro Trp Tyr Leu Arg Met
65              70                  75                  80

Leu Gly Gln Cys Thr Gln Thr Trp His Arg Val Arg Lys Thr Thr Gln
                85                  90                  95

Glu Gln Leu Lys Arg Asn Val Arg Phe His Ala Phe Ile Ser Tyr Ser
            100                 105                 110

Glu His Asp Ser Leu Trp Val Lys Asn Glu Leu Ile Pro Asn Leu Glu
        115                 120                 125

Lys Glu Asp Gly Ser Ile Leu Ile Cys Leu Tyr Glu Ser Tyr Phe Asp
    130                 135                 140

Pro Gly Lys Ser Ile Ser Glu Asn Ile Val Ser Phe Ile Glu Lys Ser
145                 150                 155                 160

Tyr Lys Ser Ile Phe Val Leu Ser Pro Asn Phe Val Gln Asn Glu Trp
                165                 170                 175

Cys His Tyr Glu Phe Tyr Phe Ala His His Asn Leu Phe His Glu Asn
            180                 185                 190

Ser Asp His Ile Ile Leu Ile Leu Leu Glu Pro Ile Pro Phe Tyr Cys
        195                 200                 205

Ile Pro Thr Arg Tyr His Lys Leu Glu Ala Leu Leu Glu Lys Lys Ala
    210                 215                 220

Tyr Leu Glu Trp Pro Lys Asp Arg Arg Lys Cys Gly Leu Phe Trp Ala
225                 230                 235                 240

Asn Leu Arg Ala Ala Val Asn Val Asn Val Leu Ala Thr Arg Glu Met
                245                 250                 255

Tyr Glu Leu Gln Thr Phe Thr Glu Leu Asn Glu Glu Ser Arg Gly Ser
            260                 265                 270

Thr Ile Ser Leu Met Arg Thr Asp Cys Leu
        275                 280

<210> SEQ ID NO 33
<211> LENGTH: 1173
<212> TYPE: DNA
<213> ORGANISM: Homo sapiens
<220> FEATURE:
<221> NAME/KEY: CDS
<222> LOCATION: (1)..(1008)
<223> OTHER INFORMATION:

<400> SEQUENCE: 33 ctg cct gct ggc acc cgg ctc cgg agg ctg gat gtc agc tgc aac agc    48
Leu Pro Ala Gly Thr Arg Leu Arg Arg Leu Asp Val Ser Cys Asn Ser
1               5                   10                  15 atc agc ttc gtg gcc ccc ggc ttc ttt tcc aag gcc aag gag ctg cga    96
Ile Ser Phe Val Ala Pro Gly Phe Phe Ser Lys Ala Lys Glu Leu Arg
            20                  25                  30 gag ctc aac ctt agc gcc aac gcc ctc aag aca gtg gac cac tcc tgg   144
Glu Leu Asn Leu Ser Ala Asn Ala Leu Lys Thr Val Asp His Ser Trp
        35                  40                  45
```

```
                                                    -continued ttt ggg ccc ctg gcg agt gcc ctg caa ata cta gat gta agc gcc aac        192
Phe Gly Pro Leu Ala Ser Ala Leu Gln Ile Leu Asp Val Ser Ala Asn
 50                  55                  60 cct ctg cac tgc gcc tgt ggg gcg gcc ttt atg gac ttc ctg ctg gag        240
Pro Leu His Cys Ala Cys Gly Ala Ala Phe Met Asp Phe Leu Leu Glu
 65                  70                  75                  80 gtg cag gct gcc gtg ccc ggt ctg ccc agc cgg gtg aag tgt ggc agt        288
Val Gln Ala Ala Val Pro Gly Leu Pro Ser Arg Val Lys Cys Gly Ser
                 85                  90                  95 ccg ggc cag ctc cag ggc ctc agc atc ttt gca cag gac ctg cgc ctc        336
Pro Gly Gln Leu Gln Gly Leu Ser Ile Phe Ala Gln Asp Leu Arg Leu
            100                 105                 110 tgc ctg gat gag gcc ctc tcc tgg gac tgt ttc gcc ctc tcg ctg ctg        384
Cys Leu Asp Glu Ala Leu Ser Trp Asp Cys Phe Ala Leu Ser Leu Leu
        115                 120                 125 gct gtg gct ctg ggc ctg ggt gtg ccc atg ctg cat cac ctc tgt ggc        432
Ala Val Ala Leu Gly Leu Gly Val Pro Met Leu His His Leu Cys Gly
    130                 135                 140 tgg gac ctc tgg tac tgc ttc cac ctg tgc ctg gcc tgg ctt ccc tgg        480
Trp Asp Leu Trp Tyr Cys Phe His Leu Cys Leu Ala Trp Leu Pro Trp
145                 150                 155                 160 cgg ggg cgg caa agt ggg cga gat gag gat gcc ctg ccc tac gat gcc        528
Arg Gly Arg Gln Ser Gly Arg Asp Glu Asp Ala Leu Pro Tyr Asp Ala
                165                 170                 175 ttc gtg gtc ttc gac aaa acg cag agc gca gtg gca gac tgg gtg tac        576
Phe Val Val Phe Asp Lys Thr Gln Ser Ala Val Ala Asp Trp Val Tyr
            180                 185                 190 aac gag ctt cgg ggg cag ctg gag gag tgc cgt ggg cgc tgg gca ctc        624
Asn Glu Leu Arg Gly Gln Leu Glu Glu Cys Arg Gly Arg Trp Ala Leu
        195                 200                 205 cgc ctg tgc ctg gag gaa cgc gac tgg ctg cct ggc aaa acc ctc ttt        672
Arg Leu Cys Leu Glu Glu Arg Asp Trp Leu Pro Gly Lys Thr Leu Phe
    210                 215                 220 gag aac ctg tgg gcc tcg gtc tat ggc agc cgc aag acg ctg ttt gtg        720
Glu Asn Leu Trp Ala Ser Val Tyr Gly Ser Arg Lys Thr Leu Phe Val
225                 230                 235                 240 ctg gcc cac acg gac cgg gtc agt ggt ctc ttg cgc gcc agc ttc ctg        768
Leu Ala His Thr Asp Arg Val Ser Gly Leu Leu Arg Ala Ser Phe Leu
                245                 250                 255 ctg gcc cag cag cgc ctg ctg gag gac cgc aag gac gtc gtg gtg ctg        816
Leu Ala Gln Gln Arg Leu Leu Glu Asp Arg Lys Asp Val Val Val Leu
            260                 265                 270 gtg atc ctg agc cct gac ggc cgc cgc tcc cgc tac gag cgg ctg cgc        864
Val Ile Leu Ser Pro Asp Gly Arg Arg Ser Arg Tyr Glu Arg Leu Arg
        275                 280                 285 cag cgc ctc tgc cgc cag agt gtc ctc ctc tgg ccc cac cag ccc agt        912
Gln Arg Leu Cys Arg Gln Ser Val Leu Leu Trp Pro His Gln Pro Ser
    290                 295                 300 ggt cag cgc agc ttc tgg gcc cag ctg ggc atg gcc ctg acc agg gac        960
Gly Gln Arg Ser Phe Trp Ala Gln Leu Gly Met Ala Leu Thr Arg Asp
305                 310                 315                 320 aac cac cac ttc tat aac cgg aac ttc tgc cag gga ccc acg gcc gaa       1008
Asn His His Phe Tyr Asn Arg Asn Phe Cys Gln Gly Pro Thr Ala Glu
                325                 330                 335 tagccgtgag ccggaatcct gcacggtgcc acctccacac tcacctcacc tctgcctgcc       1068
tggtctgacc ctcccctgct cgcctccctc accccacacc tgacacagag caggcactca       1128
ataaatgcta ccgaaggcta aaaaaaaaaa aaaaaaaaa aacca                        1173
```

<210> SEQ ID NO 34
<211> LENGTH: 336
<212> TYPE: PRT
<213> ORGANISM: Homo sapiens

<400> SEQUENCE: 34

```
Leu Pro Ala Gly Thr Arg Leu Arg Arg Leu Asp Val Ser Cys Asn Ser
1               5                   10                  15

Ile Ser Phe Val Ala Pro Gly Phe Phe Ser Lys Ala Lys Glu Leu Arg
            20                  25                  30

Glu Leu Asn Leu Ser Ala Asn Ala Leu Lys Thr Val Asp His Ser Trp
        35                  40                  45

Phe Gly Pro Leu Ala Ser Ala Leu Gln Ile Leu Asp Val Ser Ala Asn
    50                  55                  60

Pro Leu His Cys Ala Cys Gly Ala Ala Phe Met Asp Phe Leu Leu Glu
65                  70                  75                  80

Val Gln Ala Ala Val Pro Gly Leu Pro Ser Arg Val Lys Cys Gly Ser
                85                  90                  95

Pro Gly Gln Leu Gln Gly Leu Ser Ile Phe Ala Gln Asp Leu Arg Leu
            100                 105                 110

Cys Leu Asp Glu Ala Leu Ser Trp Asp Cys Phe Ala Leu Ser Leu Leu
        115                 120                 125

Ala Val Ala Leu Gly Leu Gly Val Pro Met Leu His His Leu Cys Gly
    130                 135                 140

Trp Asp Leu Trp Tyr Cys Phe His Leu Cys Leu Ala Trp Leu Pro Trp
145                 150                 155                 160

Arg Gly Arg Gln Ser Gly Arg Asp Glu Asp Ala Leu Pro Tyr Asp Ala
                165                 170                 175

Phe Val Val Phe Asp Lys Thr Gln Ser Ala Val Ala Asp Trp Val Tyr
            180                 185                 190

Asn Glu Leu Arg Gly Gln Leu Glu Glu Cys Arg Gly Arg Trp Ala Leu
        195                 200                 205

Arg Leu Cys Leu Glu Glu Arg Asp Trp Leu Pro Gly Lys Thr Leu Phe
    210                 215                 220

Glu Asn Leu Trp Ala Ser Val Tyr Gly Ser Arg Lys Thr Leu Phe Val
225                 230                 235                 240

Leu Ala His Thr Asp Arg Val Ser Gly Leu Leu Arg Ala Ser Phe Leu
                245                 250                 255

Leu Ala Gln Gln Arg Leu Leu Glu Asp Arg Lys Asp Val Val Val Leu
            260                 265                 270

Val Ile Leu Ser Pro Asp Gly Arg Arg Ser Arg Tyr Glu Arg Leu Arg
        275                 280                 285

Gln Arg Leu Cys Arg Gln Ser Val Leu Leu Trp Pro His Gln Pro Ser
    290                 295                 300

Gly Gln Arg Ser Phe Trp Ala Gln Leu Gly Met Ala Leu Thr Arg Asp
305                 310                 315                 320

Asn His His Phe Tyr Asn Arg Asn Phe Cys Gln Gly Pro Thr Ala Glu
                325                 330                 335
```

<210> SEQ ID NO 35
<211> LENGTH: 497
<212> TYPE: DNA
<213> ORGANISM: Mus musculus

<400> SEQUENCE: 35

-continued

```
tggcccacac ggaccgcgtc agtggcctcc tgcgcaccag cttcctgctg gctcagcagc    60
gcctgttgga agaccgcaag gacgtggtgg tgttggtgat cctgcgtccg gatgccccac   120
cgtcccgcta tgtgcgactg cgccagcgtc tctgccgcca gagtgtgctc ttctggcccc   180
agcgacccaa cgggcagggg ggcttctggg cccagctgag tacagccctg actagggaca   240
accgccactt ctataaccag aacttctgcc ggggacctac agcagaatag ctcagagcaa   300
cagctggaaa cagctgcatc ttcatgtctg gttcccgagt tgctctgcct gccttgctct   360
gtcttactac accgctattt ggcaagtgcg caatatatgc taccaagcca ccaggcccac   420
ggagcaaagg ttggctgtaa agggtagttt tcttcccatg catctttcag gagagtgaag   480
atagacacca aacccac                                                  497
```

<210> SEQ ID NO 36
<211> LENGTH: 3099
<212> TYPE: DNA
<213> ORGANISM: Homo sapiens
<220> FEATURE:
<221> NAME/KEY: CDS
<222> LOCATION: (1)..(3096)
<223> OTHER INFORMATION:
<220> FEATURE:
<221> NAME/KEY: mat_peptide
<222> LOCATION: (52)..()
<223> OTHER INFORMATION:

<400> SEQUENCE: 36

```
atg ctg acc tgc att ttc ctg cta ata tct ggt tcc tgt gag tta tgc     48
Met Leu Thr Cys Ile Phe Leu Leu Ile Ser Gly Ser Cys Glu Leu Cys
    -15                 -10                  -5 gcc gaa gaa aat ttt tct aga agc tat cct tgt gat gag aaa aag caa     96
Ala Glu Glu Asn Phe Ser Arg Ser Tyr Pro Cys Asp Glu Lys Lys Gln
-1   1               5                  10                  15 aat gac tca gtt att gca gag tgc agc aat cgt cga cta cag gaa gtt    144
Asn Asp Ser Val Ile Ala Glu Cys Ser Asn Arg Arg Leu Gln Glu Val
                20                  25                  30 ccc caa acg gtg ggc aaa tat gtg aca gaa cta gac ctg tct gat aat    192
Pro Gln Thr Val Gly Lys Tyr Val Thr Glu Leu Asp Leu Ser Asp Asn
            35                  40                  45 ttc atc aca cac ata acg aat gaa tca ttt caa ggg ctg caa aat ctc    240
Phe Ile Thr His Ile Thr Asn Glu Ser Phe Gln Gly Leu Gln Asn Leu
        50                  55                  60 act aaa ata aat cta aac cac aac ccc aat gta cag cac cag aac gga    288
Thr Lys Ile Asn Leu Asn His Asn Pro Asn Val Gln His Gln Asn Gly
    65                  70                  75 aat ccc ggt ata caa tca aat ggc ttg aat atc aca gac ggg gca ttc    336
Asn Pro Gly Ile Gln Ser Asn Gly Leu Asn Ile Thr Asp Gly Ala Phe
80                  85                  90                  95 ctc aac cta aaa aac cta agg gag tta ctg ctt gaa gac aac cag tta    384
Leu Asn Leu Lys Asn Leu Arg Glu Leu Leu Leu Glu Asp Asn Gln Leu
                100                 105                 110 ccc caa ata ccc tct ggt ttg cca gag tct ttg aca gaa ctt agt cta    432
Pro Gln Ile Pro Ser Gly Leu Pro Glu Ser Leu Thr Glu Leu Ser Leu
            115                 120                 125 att caa aac aat ata tac aac ata act aaa gag ggc att tca aga ctt    480
Ile Gln Asn Asn Ile Tyr Asn Ile Thr Lys Glu Gly Ile Ser Arg Leu
        130                 135                 140 ata aac ttg aaa aat ctc tat ttg gcc tgg aac tgc tat ttt aac aaa    528
Ile Asn Leu Lys Asn Leu Tyr Leu Ala Trp Asn Cys Tyr Phe Asn Lys
    145                 150                 155 gtt tgc gag aaa act aac ata gaa gat gga gta ttt gaa acg ctg aca    576
Val Cys Glu Lys Thr Asn Ile Glu Asp Gly Val Phe Glu Thr Leu Thr
```

|   |   |   |   |   |   |   |   |   |   |   |   |   |   |   |   |     |
|---|---|---|---|---|---|---|---|---|---|---|---|---|---|---|---|-----|
| Val | Cys | Glu | Lys | Thr | Asn | Ile | Glu | Asp | Gly | Val | Phe | Glu | Thr | Leu | Thr | |
| 160 |   |   |   | 165 |   |   |   | 170 |   |   |   | 175 |   |   |   | |
| aat | ttg | gag | ttg | cta | tca | cta | tct | ttc | aat | tct | ctt | tca | cat | gtg | cca | 624 |
| Asn | Leu | Glu | Leu | Leu | Ser | Leu | Ser | Phe | Asn | Ser | Leu | Ser | His | Val | Pro | |
|   |   |   |   | 180 |   |   |   | 185 |   |   |   | 190 |   |   |   | |
| ccc | aaa | ctg | cca | agc | tcc | cta | cgc | aaa | ctt | ttt | ctg | agc | aac | acc | cag | 672 |
| Pro | Lys | Leu | Pro | Ser | Ser | Leu | Arg | Lys | Leu | Phe | Leu | Ser | Asn | Thr | Gln | |
|   |   |   | 195 |   |   |   |   | 200 |   |   |   |   | 205 |   |   | |
| atc | aaa | tac | att | agt | gaa | gat | ttc | aag | gga | ttg | ata | aat | tta | aca | | 720 |
| Ile | Lys | Tyr | Ile | Ser | Glu | Glu | Asp | Phe | Lys | Gly | Leu | Ile | Asn | Leu | Thr | |
|   |   | 210 |   |   |   |   | 215 |   |   |   |   | 220 |   |   |   | |
| tta | cta | gat | tta | agc | ggg | aac | tgt | ccg | agg | tgc | ttc | aat | gcc | cca | ttt | 768 |
| Leu | Leu | Asp | Leu | Ser | Gly | Asn | Cys | Pro | Arg | Cys | Phe | Asn | Ala | Pro | Phe | |
|   | 225 |   |   |   |   | 230 |   |   |   |   | 235 |   |   |   |   | |
| cca | tgc | gtg | cct | tgt | gat | ggt | ggt | gct | tca | att | aat | ata | gat | cgt | ttt | 816 |
| Pro | Cys | Val | Pro | Cys | Asp | Gly | Gly | Ala | Ser | Ile | Asn | Ile | Asp | Arg | Phe | |
| 240 |   |   |   |   | 245 |   |   |   |   | 250 |   |   |   |   | 255 | |
| gct | ttt | caa | aac | ttg | acc | caa | ctt | cga | tac | cta | aac | ctc | tct | agc | act | 864 |
| Ala | Phe | Gln | Asn | Leu | Thr | Gln | Leu | Arg | Tyr | Leu | Asn | Leu | Ser | Ser | Thr | |
|   |   |   |   | 260 |   |   |   |   | 265 |   |   |   |   | 270 |   | |
| tcc | ctc | agg | aag | att | aat | gct | gcc | tgg | ttt | aaa | aat | atg | cct | cat | ctg | 912 |
| Ser | Leu | Arg | Lys | Ile | Asn | Ala | Ala | Trp | Phe | Lys | Asn | Met | Pro | His | Leu | |
|   |   |   | 275 |   |   |   |   | 280 |   |   |   |   | 285 |   |   | |
| aag | gtg | ctg | gat | ctt | gaa | ttc | aac | tat | tta | gtg | gga | gaa | ata | gcc | tct | 960 |
| Lys | Val | Leu | Asp | Leu | Glu | Phe | Asn | Tyr | Leu | Val | Gly | Glu | Ile | Ala | Ser | |
|   |   | 290 |   |   |   |   | 295 |   |   |   |   | 300 |   |   |   | |
| ggg | gca | ttt | tta | acg | atg | ctg | ccc | cgc | tta | gaa | ata | ctt | gac | ttg | tct | 1008 |
| Gly | Ala | Phe | Leu | Thr | Met | Leu | Pro | Arg | Leu | Glu | Ile | Leu | Asp | Leu | Ser | |
|   | 305 |   |   |   |   | 310 |   |   |   |   | 315 |   |   |   |   | |
| ttt | aac | tat | ata | aag | ggg | agt | tat | cca | cag | cat | att | aat | att | tcc | aga | 1056 |
| Phe | Asn | Tyr | Ile | Lys | Gly | Ser | Tyr | Pro | Gln | His | Ile | Asn | Ile | Ser | Arg | |
| 320 |   |   |   |   | 325 |   |   |   |   | 330 |   |   |   |   | 335 | |
| aac | ttc | tct | aaa | ctt | ttg | tct | cta | cgg | gca | ttg | cat | tta | aga | ggt | tat | 1104 |
| Asn | Phe | Ser | Lys | Leu | Leu | Ser | Leu | Arg | Ala | Leu | His | Leu | Arg | Gly | Tyr | |
|   |   |   |   | 340 |   |   |   |   | 345 |   |   |   |   | 350 |   | |
| gtg | ttc | cag | gaa | ctc | aga | gaa | gat | gat | ttc | cag | ccc | ctg | atg | cag | ctt | 1152 |
| Val | Phe | Gln | Glu | Leu | Arg | Glu | Asp | Asp | Phe | Gln | Pro | Leu | Met | Gln | Leu | |
|   |   |   | 355 |   |   |   |   | 360 |   |   |   |   | 365 |   |   | |
| cca | aac | tta | tcg | act | atc | aac | ttg | ggt | att | aat | ttt | att | aag | caa | atc | 1200 |
| Pro | Asn | Leu | Ser | Thr | Ile | Asn | Leu | Gly | Ile | Asn | Phe | Ile | Lys | Gln | Ile | |
|   |   | 370 |   |   |   |   | 375 |   |   |   |   | 380 |   |   |   | |
| gat | ttc | aaa | ctt | ttc | caa | aat | ttc | tcc | aat | ctg | gaa | att | att | tac | ttg | 1248 |
| Asp | Phe | Lys | Leu | Phe | Gln | Asn | Phe | Ser | Asn | Leu | Glu | Ile | Ile | Tyr | Leu | |
| 385 |   |   |   |   | 390 |   |   |   |   | 395 |   |   |   |   |   | |
| tca | gaa | aac | aga | ata | tca | ccg | ttg | gta | aaa | gat | acc | cgg | cag | agt | tat | 1296 |
| Ser | Glu | Asn | Arg | Ile | Ser | Pro | Leu | Val | Lys | Asp | Thr | Arg | Gln | Ser | Tyr | |
| 400 |   |   |   | 405 |   |   |   |   | 410 |   |   |   |   | 415 |   | |
| gca | aat | agt | tcc | tct | ttt | caa | cgt | cat | atc | cgg | aaa | cga | cgc | tca | aca | 1344 |
| Ala | Asn | Ser | Ser | Ser | Phe | Gln | Arg | His | Ile | Arg | Lys | Arg | Arg | Ser | Thr | |
|   |   |   | 420 |   |   |   |   | 425 |   |   |   |   | 430 |   |   | |
| gat | ttt | gag | ttt | gac | cca | cat | tcg | aac | ttt | tat | cat | ttc | acc | cgt | cct | 1392 |
| Asp | Phe | Glu | Phe | Asp | Pro | His | Ser | Asn | Phe | Tyr | His | Phe | Thr | Arg | Pro | |
|   |   | 435 |   |   |   |   | 440 |   |   |   |   | 445 |   |   |   | |
| tta | ata | aag | cca | caa | tgt | gct | gct | tat | gga | aaa | gcc | tta | gat | tta | agc | 1440 |
| Leu | Ile | Lys | Pro | Gln | Cys | Ala | Ala | Tyr | Gly | Lys | Ala | Leu | Asp | Leu | Ser | |
|   | 450 |   |   |   |   | 455 |   |   |   |   | 460 |   |   |   |   | |
| ctc | aac | agt | att | ttc | ttc | att | ggg | cca | aac | caa | ttt | gaa | aat | ctt | cct | 1488 |
| Leu | Asn | Ser | Ile | Phe | Phe | Ile | Gly | Pro | Asn | Gln | Phe | Glu | Asn | Leu | Pro | |
| 465 |   |   |   |   | 470 |   |   |   |   | 475 |   |   |   |   |   | |

-continued

```
gac att gcc tgt tta aat ctg tct gca aat agc aat gct caa gtg tta        1536
Asp Ile Ala Cys Leu Asn Leu Ser Ala Asn Ser Asn Ala Gln Val Leu
480                 485                 490                 495 agt gga act gaa ttt tca gcc att cct cat gtc aaa tat ttg gat ttg        1584
Ser Gly Thr Glu Phe Ser Ala Ile Pro His Val Lys Tyr Leu Asp Leu
                500                 505                 510 aca aac aat aga cta gac ttt gat aat gct agt gct ctt act gaa ttg        1632
Thr Asn Asn Arg Leu Asp Phe Asp Asn Ala Ser Ala Leu Thr Glu Leu
        515                 520                 525 tcc gac ttg gaa gtt cta gat ctc agc tat aat tca cac tat ttc aga        1680
Ser Asp Leu Glu Val Leu Asp Leu Ser Tyr Asn Ser His Tyr Phe Arg
    530                 535                 540 ata gca ggc gta aca cat cat cta gaa ttt att caa aat ttc aca aat        1728
Ile Ala Gly Val Thr His His Leu Glu Phe Ile Gln Asn Phe Thr Asn
545                 550                 555 cta aaa gtt tta aac ttg agc cac aac aac att tat act tta aca gat        1776
Leu Lys Val Leu Asn Leu Ser His Asn Asn Ile Tyr Thr Leu Thr Asp
560                 565                 570                 575 aag tat aac ctg gaa agc aag tcc ctg gta gaa tta gtt ttc agt ggc        1824
Lys Tyr Asn Leu Glu Ser Lys Ser Leu Val Glu Leu Val Phe Ser Gly
                580                 585                 590 aat cgc ctt gac att ttg tgg aat gat gat gac aac agg tat atc tcc        1872
Asn Arg Leu Asp Ile Leu Trp Asn Asp Asp Asp Asn Arg Tyr Ile Ser
        595                 600                 605 att ttc aaa ggt ctc aag aat ctg aca cgt ctg gat tta tcc ctt aat        1920
Ile Phe Lys Gly Leu Lys Asn Leu Thr Arg Leu Asp Leu Ser Leu Asn
    610                 615                 620 agg ctc aag cac atc cca aat gaa gca ttc ctt aat ttg cca gcg agt        1968
Arg Leu Lys His Ile Pro Asn Glu Ala Phe Leu Asn Leu Pro Ala Ser
625                 630                 635 ctc act gaa cta cat ata aat gat aat atg tta aag ttt ttt aac tgg        2016
Leu Thr Glu Leu His Ile Asn Asp Asn Met Leu Lys Phe Phe Asn Trp
640                 645                 650                 655 aca tta ctc cag cag ttt cct cgt ctc gag ttg ctt gac tta cgt gga        2064
Thr Leu Leu Gln Gln Phe Pro Arg Leu Glu Leu Leu Asp Leu Arg Gly
                660                 665                 670 aac aaa cta ctc ttt tta act gat agc cta tct gac ttt aca tct tcc        2112
Asn Lys Leu Leu Phe Leu Thr Asp Ser Leu Ser Asp Phe Thr Ser Ser
        675                 680                 685 ctt cgg aca ctg ctg agt cat aac agg att tcc cac cta ccc tct        2160
Leu Arg Thr Leu Leu Leu Ser His Asn Arg Ile Ser His Leu Pro Ser
    690                 695                 700 ggc ttt ctt tct gaa gtc agt agt ctg aag cac ctc gat tta agt tcc        2208
Gly Phe Leu Ser Glu Val Ser Ser Leu Lys His Leu Asp Leu Ser Ser
705                 710                 715 aat ctg cta aaa aca atm aac aaa tcc gca ctt gaa act aag acc acc        2256
Asn Leu Leu Lys Thr Xaa Asn Lys Ser Ala Leu Glu Thr Lys Thr Thr
720                 725                 730                 735 acc aaa tta tct atg ttg gaa cta cac gga aac ccc ttt gaa tgc acc        2304
Thr Lys Leu Ser Met Leu Glu Leu His Gly Asn Pro Phe Glu Cys Thr
                740                 745                 750 tgt gac att gga gat ttc cga aga tgg atg gat gaa cat ctg aat gtc        2352
Cys Asp Ile Gly Asp Phe Arg Arg Trp Met Asp Glu His Leu Asn Val
        755                 760                 765 aaa att ccc aga ctg gta gat gtc att tgt gcc agt cct ggg gat caa        2400
Lys Ile Pro Arg Leu Val Asp Val Ile Cys Ala Ser Pro Gly Asp Gln
    770                 775                 780 aga ggg aag agt att gtg agt ctg gag cta aca act tgt gtt tca gat        2448
Arg Gly Lys Ser Ile Val Ser Leu Glu Leu Thr Thr Cys Val Ser Asp
785                 790                 795
```

-continued

| | | |
|---|---|---|
| gtc act gca gtg ata tta ttt ttc ttc acg ttc ttt atc acc acc atg<br>Val Thr Ala Val Ile Leu Phe Phe Phe Thr Phe Phe Ile Thr Thr Met<br>800                       805                        810                  815 | | 2496 |
| gtt atg ttg gct gcc ctg gct cac cat ttg ttt tac tgg gat gtt tgg<br>Val Met Leu Ala Ala Leu Ala His His Leu Phe Tyr Trp Asp Val Trp<br>              820                        825                        830 | | 2544 |
| ttt ata tat aat gtg tgt tta gct aag tta aaa ggc tac agg tct ctt<br>Phe Ile Tyr Asn Val Cys Leu Ala Lys Leu Lys Gly Tyr Arg Ser Leu<br>                  835                        840                        845 | | 2592 |
| tcc aca tcc caa act ttc tat gat gct tac att tct tat gac acc aaa<br>Ser Thr Ser Gln Thr Phe Tyr Asp Ala Tyr Ile Ser Tyr Asp Thr Lys<br>850                       855                        860 | | 2640 |
| gat gcc tct gtt act gac tgg gtg ata aat gag ctg cgc tac cac ctt<br>Asp Ala Ser Val Thr Asp Trp Val Ile Asn Glu Leu Arg Tyr His Leu<br>865                       870                        875 | | 2688 |
| gaa gag agc cga gac aaa aac gtt ctc ctt tgt cta gag gag agg gat<br>Glu Glu Ser Arg Asp Lys Asn Val Leu Leu Cys Leu Glu Glu Arg Asp<br>880                       885                        890                        895 | | 2736 |
| tgg gac ccg gga ttg gcc atc atc gac aac ctc atg cag agc atc aac<br>Trp Asp Pro Gly Leu Ala Ile Ile Asp Asn Leu Met Gln Ser Ile Asn<br>              900                        905                        910 | | 2784 |
| caa agc aag aaa aca gta ttt gtt tta acc aaa aaa tat gca aaa agc<br>Gln Ser Lys Lys Thr Val Phe Val Leu Thr Lys Lys Tyr Ala Lys Ser<br>                915                        920                        925 | | 2832 |
| tgg aac ttt aaa aca gct ttt tac ttg gcc ttg cag agg cta atg ggt<br>Trp Asn Phe Lys Thr Ala Phe Tyr Leu Ala Leu Gln Arg Leu Met Gly<br>              930                        935                        940 | | 2880 |
| gag aac atg gat gtg att ata ttt atc ctg ctg gag cca gtg tta cag<br>Glu Asn Met Asp Val Ile Ile Phe Ile Leu Leu Glu Pro Val Leu Gln<br>945                       950                        955 | | 2928 |
| cat tct ccg tat ttg agg cta cgg cag cgg atc tgt aag agc tcc atc<br>His Ser Pro Tyr Leu Arg Leu Arg Gln Arg Ile Cys Lys Ser Ser Ile<br>960                       965                        970                        975 | | 2976 |
| ctc cag tgg cct gac aac ccg aag gca gaa ggc ttg ttt tgg caa act<br>Leu Gln Trp Pro Asp Asn Pro Lys Ala Glu Gly Leu Phe Trp Gln Thr<br>              980                        985                        990 | | 3024 |
| ctg aga aat gtg gtc ttg act gaa aat gat tca cgg tat aac aat atg<br>Leu Arg Asn Val Val Leu Thr Glu Asn Asp Ser Arg Tyr Asn Asn Met<br>                995                      1000                      1005 | | 3072 |
| tat gtc gat tcc att aag caa tac taa<br>Tyr Val Asp Ser Ile Lys Gln Tyr<br>          1010                      1015 | | 3099 |

<210> SEQ ID NO 37
<211> LENGTH: 1032
<212> TYPE: PRT
<213> ORGANISM: Homo sapiens
<220> FEATURE:
<221> NAME/KEY: misc_feature
<222> LOCATION: (725)..(725)
<223> OTHER INFORMATION: The 'Xaa' at location 725 stands for Ile.

<400> SEQUENCE: 37

Met Leu Thr Cys Ile Phe Leu Leu Ile Ser Gly Ser Cys Glu Leu Cys
            -15                     -10                      -5

Ala Glu Glu Asn Phe Ser Arg Ser Tyr Pro Cys Asp Glu Lys Lys Gln
-1  1               5                    10                      15

Asn Asp Ser Val Ile Ala Glu Cys Ser Asn Arg Arg Leu Gln Glu Val
                  20                      25                      30

Pro Gln Thr Val Gly Lys Tyr Val Thr Glu Leu Asp Leu Ser Asp Asn

```
                35                  40                  45
Phe Ile Thr His Ile Thr Asn Glu Ser Phe Gln Gly Leu Gln Asn Leu
         50                  55                  60
Thr Lys Ile Asn Leu Asn His Asn Pro Asn Val Gln His Gln Asn Gly
 65                  70                  75
Asn Pro Gly Ile Gln Ser Asn Gly Leu Asn Ile Thr Asp Gly Ala Phe
 80                  85                  90                  95
Leu Asn Leu Lys Asn Leu Arg Glu Leu Leu Leu Glu Asp Asn Gln Leu
                100                 105                 110
Pro Gln Ile Pro Ser Gly Leu Pro Glu Ser Leu Thr Glu Leu Ser Leu
            115                 120                 125
Ile Gln Asn Asn Ile Tyr Asn Ile Thr Lys Glu Gly Ile Ser Arg Leu
        130                 135                 140
Ile Asn Leu Lys Asn Leu Tyr Leu Ala Trp Asn Cys Tyr Phe Asn Lys
    145                 150                 155
Val Cys Glu Lys Thr Asn Ile Glu Asp Gly Val Phe Glu Thr Leu Thr
160                 165                 170                 175
Asn Leu Glu Leu Leu Ser Leu Ser Phe Asn Ser Leu Ser His Val Pro
                180                 185                 190
Pro Lys Leu Pro Ser Ser Leu Arg Lys Leu Phe Leu Ser Asn Thr Gln
            195                 200                 205
Ile Lys Tyr Ile Ser Glu Glu Asp Phe Lys Gly Leu Ile Asn Leu Thr
        210                 215                 220
Leu Leu Asp Leu Ser Gly Asn Cys Pro Arg Cys Phe Asn Ala Pro Phe
    225                 230                 235
Pro Cys Val Pro Cys Asp Gly Gly Ala Ser Ile Asn Ile Asp Arg Phe
240                 245                 250                 255
Ala Phe Gln Asn Leu Thr Gln Leu Arg Tyr Leu Asn Leu Ser Ser Thr
                260                 265                 270
Ser Leu Arg Lys Ile Asn Ala Ala Trp Phe Lys Asn Met Pro His Leu
            275                 280                 285
Lys Val Leu Asp Leu Glu Phe Asn Tyr Leu Val Gly Glu Ile Ala Ser
        290                 295                 300
Gly Ala Phe Leu Thr Met Leu Pro Arg Leu Glu Ile Leu Asp Leu Ser
    305                 310                 315
Phe Asn Tyr Ile Lys Gly Ser Tyr Pro Gln His Ile Asn Ile Ser Arg
320                 325                 330                 335
Asn Phe Ser Lys Leu Leu Ser Leu Arg Ala Leu His Leu Arg Gly Tyr
                340                 345                 350
Val Phe Gln Glu Leu Arg Glu Asp Phe Gln Pro Leu Met Gln Leu
            355                 360                 365
Pro Asn Leu Ser Thr Ile Asn Leu Gly Ile Asn Phe Ile Lys Gln Ile
        370                 375                 380
Asp Phe Lys Leu Phe Gln Asn Phe Ser Asn Leu Glu Ile Ile Tyr Leu
    385                 390                 395
Ser Glu Asn Arg Ile Ser Pro Leu Val Lys Asp Thr Arg Gln Ser Tyr
400                 405                 410                 415
Ala Asn Ser Ser Phe Gln Arg His Ile Arg Lys Arg Arg Ser Thr
                420                 425                 430
Asp Phe Glu Phe Asp Pro His Ser Asn Phe Tyr His Phe Thr Arg Pro
            435                 440                 445
Leu Ile Lys Pro Gln Cys Ala Ala Tyr Gly Lys Ala Leu Asp Leu Ser
        450                 455                 460
```

```
Leu Asn Ser Ile Phe Phe Ile Gly Pro Asn Gln Phe Glu Asn Leu Pro
465                 470                 475

Asp Ile Ala Cys Leu Asn Leu Ser Ala Asn Ser Asn Ala Gln Val Leu
480                 485                 490                 495

Ser Gly Thr Glu Phe Ser Ala Ile Pro His Val Lys Tyr Leu Asp Leu
                500                 505                 510

Thr Asn Asn Arg Leu Asp Phe Asp Asn Ala Ser Ala Leu Thr Glu Leu
                515                 520                 525

Ser Asp Leu Glu Val Leu Asp Leu Ser Tyr Asn Ser His Tyr Phe Arg
                530                 535                 540

Ile Ala Gly Val Thr His His Leu Glu Phe Ile Gln Asn Phe Thr Asn
545                 550                 555

Leu Lys Val Leu Asn Leu Ser His Asn Asn Ile Tyr Thr Leu Thr Asp
560                 565                 570                 575

Lys Tyr Asn Leu Glu Ser Lys Ser Leu Val Glu Leu Val Phe Ser Gly
                580                 585                 590

Asn Arg Leu Asp Ile Leu Trp Asn Asp Asp Asn Arg Tyr Ile Ser
                595                 600                 605

Ile Phe Lys Gly Leu Lys Asn Leu Thr Arg Leu Asp Leu Ser Leu Asn
                610                 615                 620

Arg Leu Lys His Ile Pro Asn Glu Ala Phe Leu Asn Leu Pro Ala Ser
                625                 630                 635

Leu Thr Glu Leu His Ile Asn Asp Asn Met Leu Lys Phe Phe Asn Trp
640                 645                 650                 655

Thr Leu Leu Gln Gln Phe Pro Arg Leu Glu Leu Leu Asp Leu Arg Gly
                660                 665                 670

Asn Lys Leu Leu Phe Leu Thr Asp Ser Leu Ser Asp Phe Thr Ser Ser
                675                 680                 685

Leu Arg Thr Leu Leu Leu Ser His Asn Arg Ile Ser His Leu Pro Ser
                690                 695                 700

Gly Phe Leu Ser Glu Val Ser Ser Leu Lys His Leu Asp Leu Ser Ser
                705                 710                 715

Asn Leu Leu Lys Thr Xaa Asn Lys Ser Ala Leu Glu Thr Lys Thr Thr
720                 725                 730                 735

Thr Lys Leu Ser Met Leu Glu Leu His Gly Asn Pro Phe Glu Cys Thr
                740                 745                 750

Cys Asp Ile Gly Asp Phe Arg Arg Trp Met Asp Glu His Leu Asn Val
                755                 760                 765

Lys Ile Pro Arg Leu Val Asp Val Ile Cys Ala Ser Pro Gly Asp Gln
                770                 775                 780

Arg Gly Lys Ser Ile Val Ser Leu Glu Leu Thr Thr Cys Val Ser Asp
785                 790                 795

Val Thr Ala Val Ile Leu Phe Phe Thr Phe Phe Ile Thr Thr Met
800                 805                 810                 815

Val Met Leu Ala Ala Leu Ala His His Leu Phe Tyr Trp Asp Val Trp
                820                 825                 830

Phe Ile Tyr Asn Val Cys Leu Ala Lys Leu Lys Gly Tyr Arg Ser Leu
                835                 840                 845

Ser Thr Ser Gln Thr Phe Tyr Asp Ala Tyr Ile Ser Tyr Asp Thr Lys
                850                 855                 860

Asp Ala Ser Val Thr Asp Trp Val Ile Asn Glu Leu Arg Tyr His Leu
865                 870                 875
```

-continued

```
Glu Glu Ser Arg Asp Lys Asn Val Leu Leu Cys Leu Glu Glu Arg Asp
880             885                 890                 895

Trp Asp Pro Gly Leu Ala Ile Ile Asp Asn Leu Met Gln Ser Ile Asn
        900                 905                 910

Gln Ser Lys Lys Thr Val Phe Val Leu Thr Lys Lys Tyr Ala Lys Ser
            915                 920                 925

Trp Asn Phe Lys Thr Ala Phe Tyr Leu Ala Leu Gln Arg Leu Met Gly
        930                 935                 940

Glu Asn Met Asp Val Ile Ile Phe Ile Leu Leu Glu Pro Val Leu Gln
    945                 950                 955

His Ser Pro Tyr Leu Arg Leu Arg Gln Arg Ile Cys Lys Ser Ser Ile
960                 965                 970                 975

Leu Gln Trp Pro Asp Asn Pro Lys Ala Glu Gly Leu Phe Trp Gln Thr
            980                 985                 990

Leu Arg Asn Val Val Leu Thr Glu Asn Asp Ser Arg Tyr Asn Asn Met
            995                 1000                1005

Tyr Val Asp Ser Ile Lys Gln Tyr
        1010                1015
```

```
<210> SEQ ID NO 38
<211> LENGTH: 3046
<212> TYPE: DNA
<213> ORGANISM: Homo sapiens
<220> FEATURE:
<221> NAME/KEY: CDS
<222> LOCATION: (111)..(2543)
<223> OTHER INFORMATION:
<220> FEATURE:
<221> NAME/KEY: mat_peptide
<222> LOCATION: (168)..()
<223> OTHER INFORMATION:

<400> SEQUENCE: 38
gaatcatcca cgcacctgca gctctgctga gagagtgcaa gccgtggggg ttttgagctc        60
atcttcatca ttcatatgag gaaataagtg gtaaaatcct tggaaataca atg aga         116
                                                         Met Arg ctc atc aga aac att tac ata ttt tgt agt att gtt atg aca gca gag        164
Leu Ile Arg Asn Ile Tyr Ile Phe Cys Ser Ile Val Met Thr Ala Glu
    -15                 -10                  -5 ggt gat gct cca gag ctg cca gaa gaa agg gaa ctg atg acc aac tgc        212
Gly Asp Ala Pro Glu Leu Pro Glu Glu Arg Glu Leu Met Thr Asn Cys
 -1   1               5                  10                  15 tcc aac atg tct cta aga aag gtt ccc gca gac ttg acc cca gcc aca        260
Ser Asn Met Ser Leu Arg Lys Val Pro Ala Asp Leu Thr Pro Ala Thr
                20                  25                  30 acg aca ctg gat tta tcc tat aac ctc ctt ttt caa ctc cag agt tca        308
Thr Thr Leu Asp Leu Ser Tyr Asn Leu Leu Phe Gln Leu Gln Ser Ser
            35                  40                  45 gat ttt cat tct gtc tcc aaa ctg aga gtt ttg att cta tgc cat aac        356
Asp Phe His Ser Val Ser Lys Leu Arg Val Leu Ile Leu Cys His Asn
        50                  55                  60 aga att caa cag ctg gat ctc aaa acc ttt gaa ttc aac aag gag tta        404
Arg Ile Gln Gln Leu Asp Leu Lys Thr Phe Glu Phe Asn Lys Glu Leu
    65                  70                  75 aga tat tta gat ttg tct aat aac aga ctg aag agt gta act tgg tat        452
Arg Tyr Leu Asp Leu Ser Asn Asn Arg Leu Lys Ser Val Thr Trp Tyr
 80                  85                  90                  95 tta ctg gca ggt ctc agg tat tta gat ctt tct ttt aat gac ttt gac        500
Leu Leu Ala Gly Leu Arg Tyr Leu Asp Leu Ser Phe Asn Asp Phe Asp
                100                 105                 110
```

-continued

| | | |
|---|---|---|
| acc atg cct atc tgt gag gaa gct ggc aac atg tca cac ctg gaa atc<br>Thr Met Pro Ile Cys Glu Glu Ala Gly Asn Met Ser His Leu Glu Ile<br>            115                    120                    125 | 548 |
| cta ggt ttg agt ggg gca aaa ata caa aaa tca gat ttc cag aaa att<br>Leu Gly Leu Ser Gly Ala Lys Ile Gln Lys Ser Asp Phe Gln Lys Ile<br>        130                    135                    140 | 596 |
| gct cat ctg cat cta aat act gtc ttc tta gga ttc aga act ctt cct<br>Ala His Leu His Leu Asn Thr Val Phe Leu Gly Phe Arg Thr Leu Pro<br>145                    150                    155 | 644 |
| cat tat gaa gaa ggt agc ctg ccc atc tta aac aca aca aaa ctg cac<br>His Tyr Glu Glu Gly Ser Leu Pro Ile Leu Asn Thr Thr Lys Leu His<br>160                    165                    170                    175 | 692 |
| att gtt tta cca atg gac aca aat ttc tgg gtt ctt ttg cgt gat gga<br>Ile Val Leu Pro Met Asp Thr Asn Phe Trp Val Leu Leu Arg Asp Gly<br>                180                    185                    190 | 740 |
| atc aag act tca aaa ata tta gaa atg aca aat ata gat ggc aaa agc<br>Ile Lys Thr Ser Lys Ile Leu Glu Met Thr Asn Ile Asp Gly Lys Ser<br>        195                    200                    205 | 788 |
| caa ttt gta agt tat gaa atg caa cga aat ctt agt tta gaa aat gct<br>Gln Phe Val Ser Tyr Glu Met Gln Arg Asn Leu Ser Leu Glu Asn Ala<br>            210                    215                    220 | 836 |
| aag aca tcg gtt cta ttg ctt aat aaa gtt gat tta ctc tgg gac gac<br>Lys Thr Ser Val Leu Leu Leu Asn Lys Val Asp Leu Leu Trp Asp Asp<br>225                    230                    235 | 884 |
| ctt ttc ctt atc tta caa ttt gtt tgg cat aca tca gtg gaa cac ttt<br>Leu Phe Leu Ile Leu Gln Phe Val Trp His Thr Ser Val Glu His Phe<br>240                    245                    250                    255 | 932 |
| cag atc cga aat gtg act ttt ggt ggt aag gct tat ctt gac cac aat<br>Gln Ile Arg Asn Val Thr Phe Gly Gly Lys Ala Tyr Leu Asp His Asn<br>                260                    265                    270 | 980 |
| tca ttt gac tac tca aat act gta atg aga act ata aaa ttg gag cat<br>Ser Phe Asp Tyr Ser Asn Thr Val Met Arg Thr Ile Lys Leu Glu His<br>        275                    280                    285 | 1028 |
| gta cat ttc aga gtg ttt tac att caa cag gat aaa atc tat ttg ctt<br>Val His Phe Arg Val Phe Tyr Ile Gln Gln Asp Lys Ile Tyr Leu Leu<br>            290                    295                    300 | 1076 |
| ttg acc aaa atg gac ata gaa aac ctg aca ata tca aat gca caa atg<br>Leu Thr Lys Met Asp Ile Glu Asn Leu Thr Ile Ser Asn Ala Gln Met<br>305                    310                    315 | 1124 |
| cca cac atg ctt ttc ccg aat tat cct acg aaa ttc caa tat tta aat<br>Pro His Met Leu Phe Pro Asn Tyr Pro Thr Lys Phe Gln Tyr Leu Asn<br>320                    325                    330                    335 | 1172 |
| ttt gcc aat aat atc tta aca gac gag ttg ttt aaa aga act atc caa<br>Phe Ala Asn Asn Ile Leu Thr Asp Glu Leu Phe Lys Arg Thr Ile Gln<br>                340                    345                    350 | 1220 |
| ctg cct cac ttg aaa act ctc att ttg aat ggc aat aaa ctg gag aca<br>Leu Pro His Leu Lys Thr Leu Ile Leu Asn Gly Asn Lys Leu Glu Thr<br>        355                    360                    365 | 1268 |
| ctt tct tta gta agt tgc ttt gct aac aac aca ccc ttg gaa cac ttg<br>Leu Ser Leu Val Ser Cys Phe Ala Asn Asn Thr Pro Leu Glu His Leu<br>            370                    375                    380 | 1316 |
| gat ctg agt caa aat cta tta caa cat aaa aat gat gaa aat tgc tca<br>Asp Leu Ser Gln Asn Leu Leu Gln His Lys Asn Asp Glu Asn Cys Ser<br>385                    390                    395 | 1364 |
| tgg cca gaa act gtg gtc aat atg aat ctg tca tac aat aaa ttg tct<br>Trp Pro Glu Thr Val Val Asn Met Asn Leu Ser Tyr Asn Lys Leu Ser<br>400                    405                    410                    415 | 1412 |
| gat tct gtc ttc agg tgc ttg ccc aaa agt att caa ata ctt gac cta<br>Asp Ser Val Phe Arg Cys Leu Pro Lys Ser Ile Gln Ile Leu Asp Leu | 1460 |

-continued

```
                420                 425                 430
aat aat aac caa atc caa act gta cct aaa gag act att cat ctg atg      1508
Asn Asn Asn Gln Ile Gln Thr Val Pro Lys Glu Thr Ile His Leu Met
            435                 440                 445 gcc tta cga gaa cta aat att gca ttt aat ttt cta act gat ctc cct      1556
Ala Leu Arg Glu Leu Asn Ile Ala Phe Asn Phe Leu Thr Asp Leu Pro
            450                 455                 460 gga tgc agt cat ttc agt aga ctt tca gtt ctg aac att gaa atg aac      1604
Gly Cys Ser His Phe Ser Arg Leu Ser Val Leu Asn Ile Glu Met Asn
465                 470                 475 ttc att ctc agc cca tct ctg gat ttt gtt cag agc tgc cag gaa gtt      1652
Phe Ile Leu Ser Pro Ser Leu Asp Phe Val Gln Ser Cys Gln Glu Val
480                 485                 490                 495 aaa act cta aat gcg gga aga aat cca ttc cgg tgt acc tgt gaa tta      1700
Lys Thr Leu Asn Ala Gly Arg Asn Pro Phe Arg Cys Thr Cys Glu Leu
            500                 505                 510 aaa aat ttc att cag ctt gaa aca tat tca gag gtc atg atg gtt gga      1748
Lys Asn Phe Ile Gln Leu Glu Thr Tyr Ser Glu Val Met Met Val Gly
            515                 520                 525 tgg tca gat tca tac acc tgt gaa tac cct tta aac cta agg gga act      1796
Trp Ser Asp Ser Tyr Thr Cys Glu Tyr Pro Leu Asn Leu Arg Gly Thr
            530                 535                 540 agg tta aaa gac gtt cat ctc cac gaa tta tct tgc aac aca gct ctg      1844
Arg Leu Lys Asp Val His Leu His Glu Leu Ser Cys Asn Thr Ala Leu
545                 550                 555 ttg att gtc acc att gtg gtt att atg cta gtt ctg ggg ttg gct gtg      1892
Leu Ile Val Thr Ile Val Val Ile Met Leu Val Leu Gly Leu Ala Val
560                 565                 570                 575 gcc ttc tgc tgt ctc cac ttt gat ctg ccc tgg tat ctc agg atg cta      1940
Ala Phe Cys Cys Leu His Phe Asp Leu Pro Trp Tyr Leu Arg Met Leu
            580                 585                 590 ggt caa tgc aca caa aca tgg cac agg gtt agg aaa aca acc caa gaa      1988
Gly Gln Cys Thr Gln Thr Trp His Arg Val Arg Lys Thr Thr Gln Glu
            595                 600                 605 caa ctc aag aga aat gtc cga ttc cac gca ttt att tca tac agt gaa      2036
Gln Leu Lys Arg Asn Val Arg Phe His Ala Phe Ile Ser Tyr Ser Glu
            610                 615                 620 cat gat tct ctg tgg gtg aag aat gaa ttg atc ccc aat cta gag aag      2084
His Asp Ser Leu Trp Val Lys Asn Glu Leu Ile Pro Asn Leu Glu Lys
625                 630                 635 gaa gat ggt tct atc ttg att tgc ctt tat gaa agc tac ttt gac cct      2132
Glu Asp Gly Ser Ile Leu Ile Cys Leu Tyr Glu Ser Tyr Phe Asp Pro
640                 645                 650                 655 ggc aaa agc att agt gaa aat att gta agc ttc att gag aaa agc tat      2180
Gly Lys Ser Ile Ser Glu Asn Ile Val Ser Phe Ile Glu Lys Ser Tyr
            660                 665                 670 aag tcc atc ttt gtt ttg tct ccc aac ttt gtc cag aat gag tgg tgc      2228
Lys Ser Ile Phe Val Leu Ser Pro Asn Phe Val Gln Asn Glu Trp Cys
            675                 680                 685 cat tat gaa ttc tac ttt gcc cac cac aat ctc ttc cat gaa aat tct      2276
His Tyr Glu Phe Tyr Phe Ala His His Asn Leu Phe His Glu Asn Ser
            690                 695                 700 gat cat ata att ctt atc tta ctg gaa ccc att cca ttc tat tgc att      2324
Asp His Ile Ile Leu Ile Leu Leu Glu Pro Ile Pro Phe Tyr Cys Ile
705                 710                 715 ccc acc agg tat cat aaa ctg aaa gct ctc ctg gaa aaa aaa gca tac      2372
Pro Thr Arg Tyr His Lys Leu Lys Ala Leu Leu Glu Lys Lys Ala Tyr
720                 725                 730                 735 ttg gaa tgg ccc aag gat agg cgt aaa tgt ggg ctt ttc tgg gca aac      2420
```

-continued

```
Leu Glu Trp Pro Lys Asp Arg Arg Lys Cys Gly Leu Phe Trp Ala Asn
            740                 745                 750 ctt cga gct gct att aat gtt aat gta tta gcc acc aga gaa atg tat      2468
Leu Arg Ala Ala Ile Asn Val Asn Val Leu Ala Thr Arg Glu Met Tyr
            755                 760                 765 gaa ctg cag aca ttc aca gag tta aat gaa gag tct cga ggt tct aca      2516
Glu Leu Gln Thr Phe Thr Glu Leu Asn Glu Glu Ser Arg Gly Ser Thr
            770                 775                 780 atc tct ctg atg aga aca gat tgt cta taaaatccca cagtccttgg            2563
Ile Ser Leu Met Arg Thr Asp Cys Leu
            785                 790 gaagttgggg accacataca ctgttgggat gtacattgat acaaccttta tgatggcaat    2623
ttgacaatat ttattaaaat aaaaaatggt tattcccttc atatcagttt ctagaaggat    2683
ttctaagaat gtatcctata gaaacacctt cacaagttta taagggctta tggaaaaagg   2743
tgttcatccc aggattgttt ataatcatga aaaatgtggc caggtgcagt ggctcactct    2803
tgtaatccca gcactatggg aggccaaggt gggtgaccca cgaggtcaag agatggagac    2863
catcctggcc aacatggtga aaccctgtct ctactaaaaa tacaaaaatt agctgggcgt    2923
gatggtgcac gcctgtagtc ccagctactt gggaggctga ggcaggagaa tcgcttgaac    2983
ccgggaggtg gcagttgcag tgagctgaga tcgagccact gcactccagc ctggtgacag    3043
agc                                                                    3046
```

<210> SEQ ID NO 39
<211> LENGTH: 811
<212> TYPE: PRT
<213> ORGANISM: Homo sapiens

<400> SEQUENCE: 39

```
Met Arg Leu Ile Arg Asn Ile Tyr Ile Phe Cys Ser Ile Val Met Thr
                -15                 -10                  -5

Ala Glu Gly Asp Ala Pro Glu Leu Pro Glu Glu Arg Glu Leu Met Thr
            -1   1               5                  10

Asn Cys Ser Asn Met Ser Leu Arg Lys Val Pro Ala Asp Leu Thr Pro
     15                  20                  25

Ala Thr Thr Thr Leu Asp Leu Ser Tyr Asn Leu Leu Phe Gln Leu Gln
30                   35                  40                  45

Ser Ser Asp Phe His Ser Val Ser Lys Leu Arg Val Leu Ile Leu Cys
                50                  55                  60

His Asn Arg Ile Gln Gln Leu Asp Leu Lys Thr Phe Glu Phe Asn Lys
                65                  70                  75

Glu Leu Arg Tyr Leu Asp Leu Ser Asn Asn Arg Leu Lys Ser Val Thr
            80                  85                  90

Trp Tyr Leu Ala Gly Leu Arg Tyr Leu Asp Leu Ser Phe Asn Asp
        95                 100                 105

Phe Asp Thr Met Pro Ile Cys Glu Glu Ala Gly Asn Met Ser His Leu
110                 115                 120                 125

Glu Ile Leu Gly Leu Ser Gly Ala Lys Ile Gln Lys Ser Asp Phe Gln
                130                 135                 140

Lys Ile Ala His Leu His Leu Asn Thr Val Phe Leu Gly Phe Arg Thr
                145                 150                 155

Leu Pro His Tyr Glu Glu Gly Ser Leu Pro Ile Leu Asn Thr Thr Lys
            160                 165                 170

Leu His Ile Val Leu Pro Met Asp Thr Asn Phe Trp Val Leu Leu Arg
    175                 180                 185
```

-continued

```
Asp Gly Ile Lys Thr Ser Lys Ile Leu Glu Met Thr Asn Ile Asp Gly
190                 195                 200                 205

Lys Ser Gln Phe Val Ser Tyr Glu Met Gln Arg Asn Leu Ser Leu Glu
            210                 215                 220

Asn Ala Lys Thr Ser Val Leu Leu Asn Lys Val Asp Leu Leu Trp
            225                 230                 235

Asp Asp Leu Phe Leu Ile Leu Gln Phe Val Trp His Thr Ser Val Glu
            240                 245                 250

His Phe Gln Ile Arg Asn Val Thr Phe Gly Gly Lys Ala Tyr Leu Asp
            255                 260                 265

His Asn Ser Phe Asp Tyr Ser Asn Thr Val Met Arg Thr Ile Lys Leu
270                 275                 280                 285

Glu His Val His Phe Arg Val Phe Tyr Ile Gln Gln Asp Lys Ile Tyr
                290                 295                 300

Leu Leu Leu Thr Lys Met Asp Ile Glu Asn Leu Thr Ile Ser Asn Ala
                305                 310                 315

Gln Met Pro His Met Leu Phe Pro Asn Tyr Pro Thr Lys Phe Gln Tyr
            320                 325                 330

Leu Asn Phe Ala Asn Asn Ile Leu Thr Asp Glu Leu Phe Lys Arg Thr
            335                 340                 345

Ile Gln Leu Pro His Leu Lys Thr Leu Ile Leu Asn Gly Asn Lys Leu
350                 355                 360                 365

Glu Thr Leu Ser Leu Val Ser Cys Phe Ala Asn Asn Thr Pro Leu Glu
                370                 375                 380

His Leu Asp Leu Ser Gln Asn Leu Leu Gln His Lys Asn Asp Glu Asn
                385                 390                 395

Cys Ser Trp Pro Glu Thr Val Val Asn Met Asn Leu Ser Tyr Asn Lys
            400                 405                 410

Leu Ser Asp Ser Val Phe Arg Cys Leu Pro Lys Ser Ile Gln Ile Leu
            415                 420                 425

Asp Leu Asn Asn Asn Gln Ile Gln Thr Val Pro Lys Glu Thr Ile His
430                 435                 440                 445

Leu Met Ala Leu Arg Glu Leu Asn Ile Ala Phe Asn Phe Leu Thr Asp
                450                 455                 460

Leu Pro Gly Cys Ser His Phe Ser Arg Leu Ser Val Leu Asn Ile Glu
            465                 470                 475

Met Asn Phe Ile Leu Ser Pro Ser Leu Asp Phe Val Gln Ser Cys Gln
            480                 485                 490

Glu Val Lys Thr Leu Asn Ala Gly Arg Asn Pro Phe Arg Cys Thr Cys
            495                 500                 505

Glu Leu Lys Asn Phe Ile Gln Leu Glu Thr Tyr Ser Glu Val Met Met
510                 515                 520                 525

Val Gly Trp Ser Asp Ser Tyr Thr Cys Glu Tyr Pro Leu Asn Leu Arg
            530                 535                 540

Gly Thr Arg Leu Lys Asp Val His Leu His Glu Leu Ser Cys Asn Thr
            545                 550                 555

Ala Leu Leu Ile Val Thr Ile Val Ile Met Leu Val Leu Gly Leu
            560                 565                 570

Ala Val Ala Phe Cys Cys Leu His Phe Asp Leu Pro Trp Tyr Leu Arg
            575                 580                 585

Met Leu Gly Gln Cys Thr Gln Thr Trp His Arg Val Arg Lys Thr Thr
590                 595                 600                 605
```

-continued

```
Gln Glu Gln Leu Lys Arg Asn Val Arg Phe His Ala Phe Ile Ser Tyr
            610                 615                 620

Ser Glu His Asp Ser Leu Trp Val Lys Asn Glu Leu Ile Pro Asn Leu
            625                 630                 635

Glu Lys Glu Asp Gly Ser Ile Leu Ile Cys Leu Tyr Glu Ser Tyr Phe
            640                 645                 650

Asp Pro Gly Lys Ser Ile Ser Glu Asn Ile Val Ser Phe Ile Glu Lys
            655                 660                 665

Ser Tyr Lys Ser Ile Phe Val Leu Ser Pro Asn Phe Val Gln Asn Glu
670                 675                 680                 685

Trp Cys His Tyr Glu Phe Tyr Phe Ala His Asn Leu Phe His Glu
                    690                 695                 700

Asn Ser Asp His Ile Ile Leu Ile Leu Leu Glu Pro Ile Pro Phe Tyr
            705                 710                 715

Cys Ile Pro Thr Arg Tyr His Lys Leu Lys Ala Leu Leu Glu Lys Lys
            720                 725                 730

Ala Tyr Leu Glu Trp Pro Lys Asp Arg Arg Lys Cys Gly Leu Phe Trp
735                 740                 745

Ala Asn Leu Arg Ala Ala Ile Asn Val Asn Val Leu Ala Thr Arg Glu
750                 755                 760                 765

Met Tyr Glu Leu Gln Thr Phe Thr Glu Leu Asn Glu Glu Ser Arg Gly
                    770                 775                 780

Ser Thr Ile Ser Leu Met Arg Thr Asp Cys Leu
            785                 790
```

<210> SEQ ID NO 40
<211> LENGTH: 2760
<212> TYPE: DNA
<213> ORGANISM: Homo sapiens
<220> FEATURE:
<221> NAME/KEY: CDS
<222> LOCATION: (68)..(2455)
<223> OTHER INFORMATION:
<220> FEATURE:
<221> NAME/KEY: mat_peptide
<222> LOCATION: (161)..()
<223> OTHER INFORMATION:
<220> FEATURE:
<221> NAME/KEY: misc_feature
<222> LOCATION: (2529)..(2529)
<223> OTHER INFORMATION: unknown nucleotide

<400> SEQUENCE: 40

```
aagaatttgg actcatatca agatgctctg aagaagaaca acccttttagg atagccactg        60 caacatc atg acc aaa gac aaa gaa cct att gtt aaa agc ttc cat ttt          109
        Met Thr Lys Asp Lys Glu Pro Ile Val Lys Ser Phe His Phe
            -30                 -25                 -20 gtt tgc ctt atg atc ata ata gtt gga acc aga atc cag ttc tcc gac          157
Val Cys Leu Met Ile Ile Ile Val Gly Thr Arg Ile Gln Phe Ser Asp
    -15                 -10                  -5 gga aat gaa ttt gca gta gac aag tca aaa aga ggt ctt att cat gtt          205
Gly Asn Glu Phe Ala Val Asp Lys Ser Lys Arg Gly Leu Ile His Val
 -1  1                   5                  10                  15 cca aaa gac cta ccg ctg aaa acc aaa gtc tta gat atg tct cag aac          253
Pro Lys Asp Leu Pro Leu Lys Thr Lys Val Leu Asp Met Ser Gln Asn
                    20                  25                  30 tac atc gct gag ctt cag gtc tct gac atg agc ttt cta tca gag ttg          301
Tyr Ile Ala Glu Leu Gln Val Ser Asp Met Ser Phe Leu Ser Glu Leu
        35                  40                  45 aca gtt ttg aga ctt tcc cat aac aga atc cag cta ctt gat tta agt          349
```

```
                                                                                    -continued Thr Val Leu Arg Leu Ser His Asn Arg Ile Gln Leu Leu Asp Leu Ser
         50                  55                  60 gtt ttc aag ttc aac cag gat tta gaa tat ttg gat tta tct cat aat      397
Val Phe Lys Phe Asn Gln Asp Leu Glu Tyr Leu Asp Leu Ser His Asn
 65                  70                  75 cag ttg caa aag ata tcc tgc cat cct att gtg agt ttc agg cat tta      445
Gln Leu Gln Lys Ile Ser Cys His Pro Ile Val Ser Phe Arg His Leu
 80                  85                  90                  95 gat ctc tca ttc aat gat ttc aag gcc ctg ccc atc tgt aag gaa ttt      493
Asp Leu Ser Phe Asn Asp Phe Lys Ala Leu Pro Ile Cys Lys Glu Phe
                    100                 105                 110 ggc aac tta tca caa ctg aat ttc ttg gga ttg agt gct atg aag ctg      541
Gly Asn Leu Ser Gln Leu Asn Phe Leu Gly Leu Ser Ala Met Lys Leu
                115                 120                 125 caa aaa tta gat ttg ctg cca att gct cac ttg cat cta agt tat atc      589
Gln Lys Leu Asp Leu Leu Pro Ile Ala His Leu His Leu Ser Tyr Ile
            130                 135                 140 ctt ctg gat tta aga aat tat tat ata aaa gaa aat gag aca gaa agt      637
Leu Leu Asp Leu Arg Asn Tyr Tyr Ile Lys Glu Asn Glu Thr Glu Ser
        145                 150                 155 cta caa att ctg aat gca aaa acc ctt cac ctt gtt ttt cac cca act      685
Leu Gln Ile Leu Asn Ala Lys Thr Leu His Leu Val Phe His Pro Thr
160                 165                 170                 175 agt tta ttc gct atc caa gtg aac ata tca gtt aat act tta ggg tgc      733
Ser Leu Phe Ala Ile Gln Val Asn Ile Ser Val Asn Thr Leu Gly Cys
                    180                 185                 190 tta caa ctg act aat att aaa ttg aat gat gac aac tgt caa gtt ttc      781
Leu Gln Leu Thr Asn Ile Lys Leu Asn Asp Asp Asn Cys Gln Val Phe
                195                 200                 205 att aaa ttt tta tca gaa ctc acc aga ggt cca acc tta ctg aat ttt      829
Ile Lys Phe Leu Ser Glu Leu Thr Arg Gly Pro Thr Leu Leu Asn Phe
            210                 215                 220 acc ctc aac cac ata gaa acg act tgg aaa tgc ctg gtc aga gtc ttt      877
Thr Leu Asn His Ile Glu Thr Thr Trp Lys Cys Leu Val Arg Val Phe
        225                 230                 235 caa ttt ctt tgg ccc aaa cct gtg gaa tat ctc aat att tac aat tta      925
Gln Phe Leu Trp Pro Lys Pro Val Glu Tyr Leu Asn Ile Tyr Asn Leu
240                 245                 250                 255 aca ata att gaa agc att cgt gaa gaa gat ttt act tat tct aaa acg      973
Thr Ile Ile Glu Ser Ile Arg Glu Glu Asp Phe Thr Tyr Ser Lys Thr
                    260                 265                 270 aca ttg aaa gca ttg aca ata gaa cat atc acg aac caa gtt ttt ctg     1021
Thr Leu Lys Ala Leu Thr Ile Glu His Ile Thr Asn Gln Val Phe Leu
                275                 280                 285 ttt tca cag aca gct ttg tac acc gtg ttt tct gag atg aac att atg     1069
Phe Ser Gln Thr Ala Leu Tyr Thr Val Phe Ser Glu Met Asn Ile Met
            290                 295                 300 atg tta acc att tca gat aca cct ttt ata cac atg ctg tgt cct cat     1117
Met Leu Thr Ile Ser Asp Thr Pro Phe Ile His Met Leu Cys Pro His
        305                 310                 315 gca cca agc aca ttc aag ttt ttg aac ttt acc cag aac gtt ttc aca     1165
Ala Pro Ser Thr Phe Lys Phe Leu Asn Phe Thr Gln Asn Val Phe Thr
320                 325                 330                 335 gat agt att ttt gaa aaa tgt tcc acg tta gtt aaa ttg gag aca ctt     1213
Asp Ser Ile Phe Glu Lys Cys Ser Thr Leu Val Lys Leu Glu Thr Leu
                    340                 345                 350 atc tta caa aag aat gga tta aaa gac ctt ttc aaa gta ggt ctc atg     1261
Ile Leu Gln Lys Asn Gly Leu Lys Asp Leu Phe Lys Val Gly Leu Met
                355                 360                 365
```

```
acg aag gat atg cct tct ttg gaa ata ctg gat gtt agc tgg aat tct      1309
Thr Lys Asp Met Pro Ser Leu Glu Ile Leu Asp Val Ser Trp Asn Ser
        370                 375                 380 ttg gaa tct ggt aga cat aaa gaa aac tgc act tgg gtt gag agt ata      1357
Leu Glu Ser Gly Arg His Lys Glu Asn Cys Thr Trp Val Glu Ser Ile
385                 390                 395 gtg gtg tta aat ttg tct tca aat atg ctt act gac tct gtt ttc aga      1405
Val Val Leu Asn Leu Ser Ser Asn Met Leu Thr Asp Ser Val Phe Arg
400                 405                 410                 415 tgt tta cct ccc agg atc aag gta ctt gat ctt cac agc aat aaa ata      1453
Cys Leu Pro Pro Arg Ile Lys Val Leu Asp Leu His Ser Asn Lys Ile
            420                 425                 430 aag agc gtt cct aaa caa gtc gta aaa ctg gaa gct ttg caa gaa ctc      1501
Lys Ser Val Pro Lys Gln Val Val Lys Leu Glu Ala Leu Gln Glu Leu
                435                 440                 445 aat gtt gct ttc aat tct tta act gac ctt cct gga tgt ggc agc ttt      1549
Asn Val Ala Phe Asn Ser Leu Thr Asp Leu Pro Gly Cys Gly Ser Phe
            450                 455                 460 agc agc ctt tct gta ttg atc att gat cac aat tca gtt tcc cac cca      1597
Ser Ser Leu Ser Val Leu Ile Ile Asp His Asn Ser Val Ser His Pro
465                 470                 475 tcg gct gat ttc ttc cag agc tgc cag aag atg agg tca ata aaa gca      1645
Ser Ala Asp Phe Phe Gln Ser Cys Gln Lys Met Arg Ser Ile Lys Ala
480                 485                 490                 495 ggg gac aat cca ttc caa tgt acc tgt gag cta aga gaa ttt gtc aaa      1693
Gly Asp Asn Pro Phe Gln Cys Thr Cys Glu Leu Arg Glu Phe Val Lys
            500                 505                 510 aat ata gac caa gta tca agt gaa gtg tta gag ggc tgg cct gat tct      1741
Asn Ile Asp Gln Val Ser Ser Glu Val Leu Glu Gly Trp Pro Asp Ser
                515                 520                 525 tat aag tgt gac tac cca gaa agt tat aga gga agc cca cta aag gac      1789
Tyr Lys Cys Asp Tyr Pro Glu Ser Tyr Arg Gly Ser Pro Leu Lys Asp
            530                 535                 540 ttt cac atg tct gaa tta tcc tgc aac ata act ctg ctg atc gtc acc      1837
Phe His Met Ser Glu Leu Ser Cys Asn Ile Thr Leu Leu Ile Val Thr
545                 550                 555 atc ggt gcc acc atg ctg gtg ttg gct gtg act gtg acc tcc ctc tgc      1885
Ile Gly Ala Thr Met Leu Val Leu Ala Val Thr Val Thr Ser Leu Cys
560                 565                 570                 575 atc tac ttg gat ctg ccc tgg tat ctc agg atg gtg tgc cag tgg acc      1933
Ile Tyr Leu Asp Leu Pro Trp Tyr Leu Arg Met Val Cys Gln Trp Thr
            580                 585                 590 cag act cgg cgc agg gcc agg aac ata ccc tta gaa gaa ctc caa aga      1981
Gln Thr Arg Arg Arg Ala Arg Asn Ile Pro Leu Glu Glu Leu Gln Arg
            595                 600                 605 aac ctc cag ttt cat gct ttt att tca tat agt gaa cat gat tct gcc      2029
Asn Leu Gln Phe His Ala Phe Ile Ser Tyr Ser Glu His Asp Ser Ala
        610                 615                 620 tgg gtg aaa agt gaa ttg gta cct tac cta gaa aaa gaa gat ata cag      2077
Trp Val Lys Ser Glu Leu Val Pro Tyr Leu Glu Lys Glu Asp Ile Gln
625                 630                 635 att tgt ctt cat gag agg aac ttt gtc cct ggc aag agc att gtg gaa      2125
Ile Cys Leu His Glu Arg Asn Phe Val Pro Gly Lys Ser Ile Val Glu
640                 645                 650                 655 aat atc atc aac tgc att gag aag agt tac aag tcc atc ttt gtt ttg      2173
Asn Ile Ile Asn Cys Ile Glu Lys Ser Tyr Lys Ser Ile Phe Val Leu
                660                 665                 670 tct ccc aac ttt gtc cag agt gag tgg tgc cat tac gaa ctc tat ttt      2221
Ser Pro Asn Phe Val Gln Ser Glu Trp Cys His Tyr Glu Leu Tyr Phe
            675                 680                 685
```

-continued

```
gcc cat cac aat ctc ttt cat gaa gga tct aat aac tta atc ctc atc      2269
Ala His His Asn Leu Phe His Glu Gly Ser Asn Asn Leu Ile Leu Ile
        690                 695                 700 tta ctg gaa ccc att cca cag aac agc att ccc aac aag tac cac aag      2317
Leu Leu Glu Pro Ile Pro Gln Asn Ser Ile Pro Asn Lys Tyr His Lys
705                 710                 715 ctg aag gct ctc atg acg cag cgg act tat ttg cag tgg ccc aag gag      2365
Leu Lys Ala Leu Met Thr Gln Arg Thr Tyr Leu Gln Trp Pro Lys Glu
720                 725                 730                 735 aaa agc aaa cgt ggg ctc ttt tgg gct aac att aga gcc gct ttt aat      2413
Lys Ser Lys Arg Gly Leu Phe Trp Ala Asn Ile Arg Ala Ala Phe Asn
                740                 745                 750 atg aaa tta aca cta gtc act gaa aat aat gat gtg aaa tct              2455
Met Lys Leu Thr Leu Val Thr Glu Asn Asn Asp Val Lys Ser
        755                 760                 765 taaaaaaatt taggaaattc aacttaagaa accattattt acttggatga tggtgaatag    2515
tacagtcgta agtnactgtc tggaggtgcc tccattatcc tcatgccttc aggaaagact    2575
taacaaaaac aatgtttcat ctggggaact gagctaggcg gtgaggttag cctgccagtt    2635
agagacagcc cagtctcttc tggtttaatc attatgtttc aaattgaaac agtctctttt    2695
gagtaaatgc tcagtttttc agctcctctc cactctgctt tcccaaatgg attctgttgg    2755
tgaag                                                                2760
```

<210> SEQ ID NO 41
<211> LENGTH: 796
<212> TYPE: PRT
<213> ORGANISM: Homo sapiens
<220> FEATURE:
<221> NAME/KEY: misc_feature
<222> LOCATION: (2529)..(2529)
<223> OTHER INFORMATION: unknown nucleotide

<400> SEQUENCE: 41

```
Met Thr Lys Asp Lys Glu Pro Ile Val Lys Ser Phe His Phe Val Cys
        -30                 -25                 -20

Leu Met Ile Ile Ile Val Gly Thr Arg Ile Gln Phe Ser Asp Gly Asn
-15                 -10                  -5                  -1  1

Glu Phe Ala Val Asp Lys Ser Lys Arg Gly Leu Ile His Val Pro Lys
                 5                  10                  15

Asp Leu Pro Leu Lys Thr Lys Val Leu Asp Met Ser Gln Asn Tyr Ile
            20                  25                  30

Ala Glu Leu Gln Val Ser Asp Met Ser Phe Leu Ser Glu Leu Thr Val
        35                  40                  45

Leu Arg Leu Ser His Asn Arg Ile Gln Leu Leu Asp Leu Ser Val Phe
50                  55                  60                  65

Lys Phe Asn Gln Asp Leu Glu Tyr Leu Asp Leu Ser His Asn Gln Leu
                70                  75                  80

Gln Lys Ile Ser Cys His Pro Ile Val Ser Phe Arg His Leu Asp Leu
            85                  90                  95

Ser Phe Asn Asp Phe Lys Ala Leu Pro Ile Cys Lys Glu Phe Gly Asn
        100                 105                 110

Leu Ser Gln Leu Asn Phe Leu Gly Leu Ser Ala Met Lys Leu Gln Lys
    115                 120                 125

Leu Asp Leu Leu Pro Ile Ala His Leu His Leu Ser Tyr Ile Leu Leu
130                 135                 140                 145

Asp Leu Arg Asn Tyr Tyr Ile Lys Glu Asn Glu Thr Glu Ser Leu Gln
```

-continued

```
                        150                 155                 160
Ile Leu Asn Ala Lys Thr Leu His Leu Val Phe His Pro Thr Ser Leu
                165                 170                 175
Phe Ala Ile Gln Val Asn Ile Ser Val Asn Thr Leu Gly Cys Leu Gln
            180                 185                 190
Leu Thr Asn Ile Lys Leu Asn Asp Asp Asn Cys Gln Val Phe Ile Lys
        195                 200                 205
Phe Leu Ser Glu Leu Thr Arg Gly Pro Thr Leu Leu Asn Phe Thr Leu
210                 215                 220                 225
Asn His Ile Glu Thr Thr Trp Lys Cys Leu Val Arg Val Phe Gln Phe
                230                 235                 240
Leu Trp Pro Lys Pro Val Glu Tyr Leu Asn Ile Tyr Asn Leu Thr Ile
                245                 250                 255
Ile Glu Ser Ile Arg Glu Glu Asp Phe Thr Tyr Ser Lys Thr Thr Leu
            260                 265                 270
Lys Ala Leu Thr Ile Glu His Ile Thr Asn Gln Val Phe Leu Phe Ser
        275                 280                 285
Gln Thr Ala Leu Tyr Thr Val Phe Ser Glu Met Asn Ile Met Met Leu
290                 295                 300                 305
Thr Ile Ser Asp Thr Pro Phe Ile His Met Leu Cys Pro His Ala Pro
                310                 315                 320
Ser Thr Phe Lys Phe Leu Asn Phe Thr Gln Asn Val Phe Thr Asp Ser
                325                 330                 335
Ile Phe Glu Lys Cys Ser Thr Leu Val Lys Leu Glu Thr Leu Ile Leu
            340                 345                 350
Gln Lys Asn Gly Leu Lys Asp Leu Phe Lys Val Gly Leu Met Thr Lys
        355                 360                 365
Asp Met Pro Ser Leu Glu Ile Leu Asp Val Ser Trp Asn Ser Leu Glu
370                 375                 380                 385
Ser Gly Arg His Lys Glu Asn Cys Thr Trp Val Glu Ser Ile Val Val
                390                 395                 400
Leu Asn Leu Ser Ser Asn Met Leu Thr Asp Ser Val Phe Arg Cys Leu
                405                 410                 415
Pro Pro Arg Ile Lys Val Leu Asp Leu His Ser Asn Lys Ile Lys Ser
            420                 425                 430
Val Pro Lys Gln Val Val Lys Leu Glu Ala Leu Gln Glu Leu Asn Val
        435                 440                 445
Ala Phe Asn Ser Leu Thr Asp Leu Pro Gly Cys Gly Ser Phe Ser Ser
450                 455                 460                 465
Leu Ser Val Leu Ile Ile Asp His Asn Ser Val Ser His Pro Ser Ala
                470                 475                 480
Asp Phe Phe Gln Ser Cys Gln Lys Met Arg Ser Ile Lys Ala Gly Asp
                485                 490                 495
Asn Pro Phe Gln Cys Thr Cys Glu Leu Arg Glu Phe Val Lys Asn Ile
            500                 505                 510
Asp Gln Val Ser Ser Glu Val Leu Glu Gly Trp Pro Asp Ser Tyr Lys
        515                 520                 525
Cys Asp Tyr Pro Glu Ser Tyr Arg Gly Ser Pro Leu Lys Asp Phe His
530                 535                 540                 545
Met Ser Glu Leu Ser Cys Asn Ile Thr Leu Leu Ile Val Thr Ile Gly
                550                 555                 560
Ala Thr Met Leu Val Leu Ala Val Thr Val Thr Ser Leu Cys Ile Tyr
                565                 570                 575
```

-continued

```
Leu Asp Leu Pro Trp Tyr Leu Arg Met Val Cys Gln Trp Thr Gln Thr
        580                 585                 590

Arg Arg Arg Ala Arg Asn Ile Pro Leu Glu Glu Leu Gln Arg Asn Leu
    595                 600                 605

Gln Phe His Ala Phe Ile Ser Tyr Ser Glu His Asp Ser Ala Trp Val
610                 615                 620                 625

Lys Ser Glu Leu Val Pro Tyr Leu Glu Lys Glu Asp Ile Gln Ile Cys
                630                 635                 640

Leu His Glu Arg Asn Phe Val Pro Gly Lys Ser Ile Val Glu Asn Ile
            645                 650                 655

Ile Asn Cys Ile Glu Lys Ser Tyr Lys Ser Ile Phe Val Leu Ser Pro
        660                 665                 670

Asn Phe Val Gln Ser Glu Trp Cys His Tyr Glu Leu Tyr Phe Ala His
    675                 680                 685

His Asn Leu Phe His Glu Gly Ser Asn Asn Leu Ile Leu Ile Leu Leu
690                 695                 700                 705

Glu Pro Ile Pro Gln Asn Ser Ile Pro Asn Lys Tyr His Lys Leu Lys
                710                 715                 720

Ala Leu Met Thr Gln Arg Thr Tyr Leu Gln Trp Pro Lys Glu Lys Ser
            725                 730                 735

Lys Arg Gly Leu Phe Trp Ala Asn Ile Arg Ala Ala Phe Asn Met Lys
        740                 745                 750

Leu Thr Leu Val Thr Glu Asn Asn Asp Val Lys Ser
    755                 760                 765

<210> SEQ ID NO 42
<211> LENGTH: 3168
<212> TYPE: DNA
<213> ORGANISM: Homo sapiens
<220> FEATURE:
<221> NAME/KEY: CDS
<222> LOCATION: (1)..(3165)
<223> OTHER INFORMATION:
<220> FEATURE:
<221> NAME/KEY: mat_peptide
<222> LOCATION: (145)..()
<223> OTHER INFORMATION:

<400> SEQUENCE: 42 atg ccc atg aag tgg agt ggg tgg agg tgg agc tgg ggg ccg gcc act      48
Met Pro Met Lys Trp Ser Gly Trp Arg Trp Ser Trp Gly Pro Ala Thr
            -45                 -40                 -35 cac aca gcc ctc cca ccc cca cag ggt ttc tgc cgc agc gcc ctg cac      96
His Thr Ala Leu Pro Pro Pro Gln Gly Phe Cys Arg Ser Ala Leu His
        -30                 -25                 -20 ccg ctg tct ctc ctg gtg cag gcc atc atg ctg gcc atg acc ctg gcc     144
Pro Leu Ser Leu Leu Val Gln Ala Ile Met Leu Ala Met Thr Leu Ala
    -15                 -10                 -5                  -1 ctg ggt acc ttg cct gcc ttc cta ccc tgt gag ctc cag ccc cac ggc     192
Leu Gly Thr Leu Pro Ala Phe Leu Pro Cys Glu Leu Gln Pro His Gly
1               5                   10                  15 ctg gtg aac tgc aac tgg ctg ttc ctg aag tct gtg ccc cac ttc tcc     240
Leu Val Asn Cys Asn Trp Leu Phe Leu Lys Ser Val Pro His Phe Ser
            20                  25                  30 atg gca gca ccc cgt ggc aat gtc acc agc ctt tcc ttg tcc tcc aac     288
Met Ala Ala Pro Arg Gly Asn Val Thr Ser Leu Ser Leu Ser Ser Asn
        35                  40                  45 cgc atc cac cac ctc cat gat tct gac ttt gcc cac ctg ccc agc ctg     336
Arg Ile His His Leu His Asp Ser Asp Phe Ala His Leu Pro Ser Leu
```

|  |  |
|---|---|
| cgg cat ctc aac ctc aag tgg aac tgc ccg ccg gtt ggc ctc agc ccc<br>Arg His Leu Asn Leu Lys Trp Asn Cys Pro Pro Val Gly Leu Ser Pro<br>65                       70                       75                      80 | 384 |
| atg cac ttc ccc tgc cac atg acc atc gag ccc agc acc ttc ttg gct<br>Met His Phe Pro Cys His Met Thr Ile Glu Pro Ser Thr Phe Leu Ala<br>                  85                       90                       95 | 432 |
| gtg ccc acc ctg gaa gag cta aac ctg agc tac aac aac atc atg act<br>Val Pro Thr Leu Glu Glu Leu Asn Leu Ser Tyr Asn Asn Ile Met Thr<br>                100                    105                    110 | 480 |
| gtg cct gcg ctg ccc aaa tcc ctc ata tcc ctg tcc ctc agc cat acc<br>Val Pro Ala Leu Pro Lys Ser Leu Ile Ser Leu Ser Leu Ser His Thr<br>             115                    120                    125 | 528 |
| aac atc ctg atg cta gac tct gcc agc ctc gcc ggc ctg cat gcc ctg<br>Asn Ile Leu Met Leu Asp Ser Ala Ser Leu Ala Gly Leu His Ala Leu<br>130                      135                    140 | 576 |
| cgc ttc cta ttc atg gac ggc aac tgt tat tac aag aac ccc tgc agg<br>Arg Phe Leu Phe Met Asp Gly Asn Cys Tyr Tyr Lys Asn Pro Cys Arg<br>145                      150                    155                    160 | 624 |
| cag gca ctg gag gtg gcc ccg ggt gcc ctc ctt ggc ctg ggc aac ctc<br>Gln Ala Leu Glu Val Ala Pro Gly Ala Leu Leu Gly Leu Gly Asn Leu<br>                  165                    170                    175 | 672 |
| acc cac ctg tca ctc aag tac aac aac ctc act gtg gtg ccc cgc aac<br>Thr His Leu Ser Leu Lys Tyr Asn Asn Leu Thr Val Val Pro Arg Asn<br>             180                    185                    190 | 720 |
| ctg cct tcc agc ctg gag tat ctg ctg ttg tcc tac aac cgc atc gtc<br>Leu Pro Ser Ser Leu Glu Tyr Leu Leu Leu Ser Tyr Asn Arg Ile Val<br>                  195                    200                    205 | 768 |
| aaa ctg gcg cct gag gac ctg gcc aat ctg acc gcc ctg cgt gtg ctc<br>Lys Leu Ala Pro Glu Asp Leu Ala Asn Leu Thr Ala Leu Arg Val Leu<br>210                      215                    220 | 816 |
| gat gtg ggc gga aat tgc cgc cgc tgc gac cac gct ccc aac ccc tgc<br>Asp Val Gly Gly Asn Cys Arg Arg Cys Asp His Ala Pro Asn Pro Cys<br>225                      230                    235                    240 | 864 |
| atg gag tgc cct cgt cac ttc ccc cag cta cat ccc gat acc ttc agc<br>Met Glu Cys Pro Arg His Phe Pro Gln Leu His Pro Asp Thr Phe Ser<br>                  245                    250                    255 | 912 |
| cac ctg agc cgt ctt gaa ggc ctg gtg ttg aag gac agt tct ctc tcc<br>His Leu Ser Arg Leu Glu Gly Leu Val Leu Lys Asp Ser Ser Leu Ser<br>             260                    265                    270 | 960 |
| tgg ctg aat gcc agt tgg ttc cgt ggg ctg gga aac ctc cga gtg ctg<br>Trp Leu Asn Ala Ser Trp Phe Arg Gly Leu Gly Asn Leu Arg Val Leu<br>                  275                    280                    285 | 1008 |
| gac ctg agt gag aac ttc ctc tac aaa tgc atc act aaa acc aag gcc<br>Asp Leu Ser Glu Asn Phe Leu Tyr Lys Cys Ile Thr Lys Thr Lys Ala<br>290                      295                    300 | 1056 |
| ttc cag ggc cta aca cag ctg cgc aag ctt aac ctg tcc ttc aat tac<br>Phe Gln Gly Leu Thr Gln Leu Arg Lys Leu Asn Leu Ser Phe Asn Tyr<br>305                      310                    315                    320 | 1104 |
| caa aag agg gtg tcc ttt gcc cac ctg tct ctg gcc cct tcc ttc ggg<br>Gln Lys Arg Val Ser Phe Ala His Leu Ser Leu Ala Pro Ser Phe Gly<br>                  325                    330                    335 | 1152 |
| agc ctg gtc gcc ctg aag gag ctg gac atg cac ggc atc ttc ttc cgc<br>Ser Leu Val Ala Leu Lys Glu Leu Asp Met His Gly Ile Phe Phe Arg<br>             340                    345                    350 | 1200 |
| tca ctc gat gag acc acg ctc cgg cca ctg gcc cgc ctg ccc atg ctc<br>Ser Leu Asp Glu Thr Thr Leu Arg Pro Leu Ala Arg Leu Pro Met Leu<br>                  355                    360                    365 | 1248 |
| cag act ctg cgt ctg cag atg aac ttc atc aac cag gcc cag ctc ggc | 1296 |

-continued

```
Gln Thr Leu Arg Leu Gln Met Asn Phe Ile Asn Gln Ala Gln Leu Gly
    370                 375                 380 atc ttc agg gcc ttc cct ggc ctg cgc tac gtg gac ctg tcg gac aac    1344
Ile Phe Arg Ala Phe Pro Gly Leu Arg Tyr Val Asp Leu Ser Asp Asn
385                 390                 395                 400 cgc atc agc gga gct tcg gag ctg aca gcc acc atg ggg gag gca gat    1392
Arg Ile Ser Gly Ala Ser Glu Leu Thr Ala Thr Met Gly Glu Ala Asp
                405                 410                 415 gga ggg gag aag gtc tgg ctg cag cct ggg gac ctt gct ccg gcc cca    1440
Gly Gly Glu Lys Val Trp Leu Gln Pro Gly Asp Leu Ala Pro Ala Pro
            420                 425                 430 gtg gac act ccc agc tct gaa gac ttc agg ccc aac tgc agc acc ctc    1488
Val Asp Thr Pro Ser Ser Glu Asp Phe Arg Pro Asn Cys Ser Thr Leu
        435                 440                 445 aac ttc acc ttg gat ctg tca cgg aac aac ctg gtg acc gtg cag ccg    1536
Asn Phe Thr Leu Asp Leu Ser Arg Asn Asn Leu Val Thr Val Gln Pro
    450                 455                 460 gag atg ttt gcc cag ctc tcg cac ctg cag tgc ctg cgc ctg agc cac    1584
Glu Met Phe Ala Gln Leu Ser His Leu Gln Cys Leu Arg Leu Ser His
465                 470                 475                 480 aac tgc atc tcg cag gca gtc aat ggc tcc cag ttc ctg ccg ctg acc    1632
Asn Cys Ile Ser Gln Ala Val Asn Gly Ser Gln Phe Leu Pro Leu Thr
                485                 490                 495 ggt ctg cag gtg cta gac ctg tcc cac aat aag ctg gac ctc tac cac    1680
Gly Leu Gln Val Leu Asp Leu Ser His Asn Lys Leu Asp Leu Tyr His
            500                 505                 510 gag cac tca ttc acg gag cta cca cga ctg gag gcc ctg gac ctc agc    1728
Glu His Ser Phe Thr Glu Leu Pro Arg Leu Glu Ala Leu Asp Leu Ser
        515                 520                 525 tac aac agc cag ccc ttt ggc atg cag ggc gtg ggc cac aac ttc agc    1776
Tyr Asn Ser Gln Pro Phe Gly Met Gln Gly Val Gly His Asn Phe Ser
    530                 535                 540 ttc gtg gct cac ctg cgc acc ctg cgc cac ctc agc ctg gcc cac aac    1824
Phe Val Ala His Leu Arg Thr Leu Arg His Leu Ser Leu Ala His Asn
545                 550                 555                 560 aac atc cac agc caa gtg tcc cag cag ctc tgc agt acg tcg ctg cgg    1872
Asn Ile His Ser Gln Val Ser Gln Gln Leu Cys Ser Thr Ser Leu Arg
                565                 570                 575 gcc ctg gac ttc agc ggc aat gca ctg ggc cat atg tgg gcc gag gga    1920
Ala Leu Asp Phe Ser Gly Asn Ala Leu Gly His Met Trp Ala Glu Gly
            580                 585                 590 gac ctc tat ctg cac ttc ttc caa ggc ctg agc ggt ttg atc tgg ctg    1968
Asp Leu Tyr Leu His Phe Phe Gln Gly Leu Ser Gly Leu Ile Trp Leu
        595                 600                 605 gac ttg tcc cag aac cgc ctg cac acc ctc ctg ccc caa acc ctg cgc    2016
Asp Leu Ser Gln Asn Arg Leu His Thr Leu Leu Pro Gln Thr Leu Arg
    610                 615                 620 aac ctc ccc aag agc cta cag gtg ctg cgt ctc cgt gac aat tac ctg    2064
Asn Leu Pro Lys Ser Leu Gln Val Leu Arg Leu Arg Asp Asn Tyr Leu
625                 630                 635                 640 gcc ttc ttt aag tgg tgg agc ctc cac ttc ctg ccc aaa ctg gaa gtc    2112
Ala Phe Phe Lys Trp Trp Ser Leu His Phe Leu Pro Lys Leu Glu Val
                645                 650                 655 ctc gac ctg gca gga aac cag ctg aag gcc ctg acc aat ggc agc ctg    2160
Leu Asp Leu Ala Gly Asn Gln Leu Lys Ala Leu Thr Asn Gly Ser Leu
            660                 665                 670 cct gct ggc acc cgg ctc cgg agg ctg gat gtc agc tgc aac agc atc    2208
Pro Ala Gly Thr Arg Leu Arg Arg Leu Asp Val Ser Cys Asn Ser Ile
        675                 680                 685
```

```
agc ttc gtg gcc ccc ggc ttc ttt tcc aag gcc aag gag ctg cga gag    2256
Ser Phe Val Ala Pro Gly Phe Phe Ser Lys Ala Lys Glu Leu Arg Glu
690                 695                 700 ctc aac ctt agc gcc aac gcc ctc aag aca gtg gac cac tcc tgg ttt    2304
Leu Asn Leu Ser Ala Asn Ala Leu Lys Thr Val Asp His Ser Trp Phe
705                 710                 715                 720 ggg ccc ctg gcg agt gcc ctg caa ata cta gat gta agc gcc aac cct    2352
Gly Pro Leu Ala Ser Ala Leu Gln Ile Leu Asp Val Ser Ala Asn Pro
                725                 730                 735 ctg cac tgc gcc tgt ggg gcg gcc ttt atg gac ttc ctg ctg gag gtg    2400
Leu His Cys Ala Cys Gly Ala Ala Phe Met Asp Phe Leu Leu Glu Val
                740                 745                 750 cag gct gcc gtg ccc ggt ctg ccc agc cgg gtg aag tgt ggc agt ccg    2448
Gln Ala Ala Val Pro Gly Leu Pro Ser Arg Val Lys Cys Gly Ser Pro
            755                 760                 765 ggc cag ctc cag ggc ctc agc atc ttt gca cag gac ctg cgc ctc tgc    2496
Gly Gln Leu Gln Gly Leu Ser Ile Phe Ala Gln Asp Leu Arg Leu Cys
770                 775                 780 ctg gat gag gcc ctc tcc tgg gac tgt ttc gcc ctc tcg ctg ctg gct    2544
Leu Asp Glu Ala Leu Ser Trp Asp Cys Phe Ala Leu Ser Leu Leu Ala
785                 790                 795                 800 gtg gct ctg ggc ctg ggt gtg ccc atg ctg cat cac ctc tgt ggc tgg    2592
Val Ala Leu Gly Leu Gly Val Pro Met Leu His His Leu Cys Gly Trp
                805                 810                 815 gac ctc tgg tac tgc ttc cac ctg tgc ctg gcc tgg ctt ccc tgg cgg    2640
Asp Leu Trp Tyr Cys Phe His Leu Cys Leu Ala Trp Leu Pro Trp Arg
                820                 825                 830 ggg cgg caa agt ggg cga gat gag gat gcc ctg ccc tac gat gcc ttc    2688
Gly Arg Gln Ser Gly Arg Asp Glu Asp Ala Leu Pro Tyr Asp Ala Phe
                835                 840                 845 gtg gtc ttc gac aaa acg cag agc gca gtg gca gac tgg gtg tac aac    2736
Val Val Phe Asp Lys Thr Gln Ser Ala Val Ala Asp Trp Val Tyr Asn
850                 855                 860 gag ctt cgg ggg cag ctg gag gag tgc cgt ggg cgc tgg gca ctc cgc    2784
Glu Leu Arg Gly Gln Leu Glu Glu Cys Arg Gly Arg Trp Ala Leu Arg
865                 870                 875                 880 ctg tgc ctg gag gaa cgc gac tgg ctg cct ggc aaa acc ctc ttt gag    2832
Leu Cys Leu Glu Glu Arg Asp Trp Leu Pro Gly Lys Thr Leu Phe Glu
                885                 890                 895 aac ctg tgg gcc tcg gtc tat ggc agc cgc aag acg ctg ttt gtg ctg    2880
Asn Leu Trp Ala Ser Val Tyr Gly Ser Arg Lys Thr Leu Phe Val Leu
                900                 905                 910 gcc cac acg gac cgg gtc agt ggt ctc ttg cgc gcc agc ttc ctg ctg    2928
Ala His Thr Asp Arg Val Ser Gly Leu Leu Arg Ala Ser Phe Leu Leu
                915                 920                 925 gcc cag cag cgc ctg ctg gag gac cgc aag gac gtc gtg gtg ctg gtg    2976
Ala Gln Gln Arg Leu Leu Glu Asp Arg Lys Asp Val Val Val Leu Val
930                 935                 940 atc ctg agc cct gac ggc cgc cgc tcc cgc tat gtg cgg ctg cgc cag    3024
Ile Leu Ser Pro Asp Gly Arg Arg Ser Arg Tyr Val Arg Leu Arg Gln
945                 950                 955                 960 cgc ctc tgc cgc cag agt gtc ctc ctc tgg ccc cac cag ccc agt ggt    3072
Arg Leu Cys Arg Gln Ser Val Leu Leu Trp Pro His Gln Pro Ser Gly
                965                 970                 975 cag cgc agc ttc tgg gcc cag ctg ggc atg gcc ctg acc agg gac aac    3120
Gln Arg Ser Phe Trp Ala Gln Leu Gly Met Ala Leu Thr Arg Asp Asn
                980                 985                 990 cac cac ttc tat aac cgg aac ttc tgc cag gga ccc acg gcc gaa tag    3168
His His Phe Tyr Asn Arg Asn Phe Cys Gln Gly Pro Thr Ala Glu
                995                 1000                1005
```

<210> SEQ ID NO 43
<211> LENGTH: 1055
<212> TYPE: PRT
<213> ORGANISM: Homo sapiens

<400> SEQUENCE: 43

```
Met Pro Met Lys Trp Ser Gly Trp Arg Trp Ser Trp Gly Pro Ala Thr
        -45                 -40                 -35

His Thr Ala Leu Pro Pro Gln Gly Phe Cys Arg Ser Ala Leu His
        -30             -25                 -20

Pro Leu Ser Leu Leu Val Gln Ala Ile Met Leu Ala Met Thr Leu Ala
        -15             -10                 -5                  -1

Leu Gly Thr Leu Pro Ala Phe Leu Pro Cys Glu Leu Gln Pro His Gly
1                5                   10                  15

Leu Val Asn Cys Asn Trp Leu Phe Leu Lys Ser Val Pro His Phe Ser
            20                  25                  30

Met Ala Ala Pro Arg Gly Asn Val Thr Ser Leu Ser Leu Ser Ser Asn
        35                  40                  45

Arg Ile His His Leu His Asp Ser Asp Phe Ala His Leu Pro Ser Leu
50                  55                  60

Arg His Leu Asn Leu Lys Trp Asn Cys Pro Pro Val Gly Leu Ser Pro
65                  70                  75                  80

Met His Phe Pro Cys His Met Thr Ile Glu Pro Ser Thr Phe Leu Ala
            85                  90                  95

Val Pro Thr Leu Glu Glu Leu Asn Leu Ser Tyr Asn Asn Ile Met Thr
            100                 105                 110

Val Pro Ala Leu Pro Lys Ser Leu Ile Ser Leu Ser Leu Ser His Thr
            115                 120                 125

Asn Ile Leu Met Leu Asp Ser Ala Ser Leu Ala Gly Leu His Ala Leu
130                 135                 140

Arg Phe Leu Phe Met Asp Gly Asn Cys Tyr Tyr Lys Asn Pro Cys Arg
145                 150                 155                 160

Gln Ala Leu Glu Val Ala Pro Gly Ala Leu Leu Gly Leu Gly Asn Leu
            165                 170                 175

Thr His Leu Ser Leu Lys Tyr Asn Asn Leu Thr Val Val Pro Arg Asn
            180                 185                 190

Leu Pro Ser Ser Leu Glu Tyr Leu Leu Leu Ser Tyr Asn Arg Ile Val
            195                 200                 205

Lys Leu Ala Pro Glu Asp Leu Ala Asn Leu Thr Ala Leu Arg Val Leu
210                 215                 220

Asp Val Gly Gly Asn Cys Arg Arg Cys Asp His Ala Pro Asn Pro Cys
225                 230                 235                 240

Met Glu Cys Pro Arg His Phe Pro Gln Leu His Pro Asp Thr Phe Ser
            245                 250                 255

His Leu Ser Arg Leu Glu Gly Leu Val Leu Lys Asp Ser Ser Leu Ser
            260                 265                 270

Trp Leu Asn Ala Ser Trp Phe Arg Gly Leu Gly Asn Leu Arg Val Leu
            275                 280                 285

Asp Leu Ser Glu Asn Phe Leu Tyr Lys Cys Ile Thr Lys Thr Lys Ala
290                 295                 300

Phe Gln Gly Leu Thr Gln Leu Arg Lys Leu Asn Leu Ser Phe Asn Tyr
305                 310                 315                 320

Gln Lys Arg Val Ser Phe Ala His Leu Ser Leu Ala Pro Ser Phe Gly
```

-continued

```
            325                 330                 335
Ser Leu Val Ala Leu Lys Glu Leu Asp Met His Gly Ile Phe Phe Arg
            340                 345                 350
Ser Leu Asp Glu Thr Thr Leu Arg Pro Leu Ala Arg Leu Pro Met Leu
            355                 360                 365
Gln Thr Leu Arg Leu Gln Met Asn Phe Ile Asn Gln Ala Gln Leu Gly
            370                 375                 380
Ile Phe Arg Ala Phe Pro Gly Leu Arg Tyr Val Asp Leu Ser Asp Asn
385                 390                 395                 400
Arg Ile Ser Gly Ala Ser Glu Leu Thr Ala Thr Met Gly Glu Ala Asp
            405                 410                 415
Gly Gly Glu Lys Val Trp Leu Gln Pro Gly Asp Leu Ala Pro Ala Pro
            420                 425                 430
Val Asp Thr Pro Ser Ser Glu Asp Phe Arg Pro Asn Cys Ser Thr Leu
            435                 440                 445
Asn Phe Thr Leu Asp Leu Ser Arg Asn Asn Leu Val Thr Val Gln Pro
            450                 455                 460
Glu Met Phe Ala Gln Leu Ser His Leu Gln Cys Leu Arg Leu Ser His
465                 470                 475                 480
Asn Cys Ile Ser Gln Ala Val Asn Gly Ser Gln Phe Leu Pro Leu Thr
            485                 490                 495
Gly Leu Gln Val Leu Asp Leu Ser His Asn Lys Leu Asp Leu Tyr His
            500                 505                 510
Glu His Ser Phe Thr Glu Leu Pro Arg Leu Glu Ala Leu Asp Leu Ser
            515                 520                 525
Tyr Asn Ser Gln Pro Phe Gly Met Gln Gly Val Gly His Asn Phe Ser
            530                 535                 540
Phe Val Ala His Leu Arg Thr Leu Arg His Leu Ser Leu Ala His Asn
545                 550                 555                 560
Asn Ile His Ser Gln Val Ser Gln Gln Leu Cys Ser Thr Ser Leu Arg
            565                 570                 575
Ala Leu Asp Phe Ser Gly Asn Ala Leu Gly His Met Trp Ala Glu Gly
            580                 585                 590
Asp Leu Tyr Leu His Phe Phe Gln Gly Leu Ser Gly Leu Ile Trp Leu
            595                 600                 605
Asp Leu Ser Gln Asn Arg Leu His Thr Leu Leu Pro Gln Thr Leu Arg
            610                 615                 620
Asn Leu Pro Lys Ser Leu Gln Val Leu Arg Leu Arg Asp Asn Tyr Leu
625                 630                 635                 640
Ala Phe Phe Lys Trp Trp Ser Leu His Phe Leu Pro Lys Leu Glu Val
            645                 650                 655
Leu Asp Leu Ala Gly Asn Gln Leu Lys Ala Leu Thr Asn Gly Ser Leu
            660                 665                 670
Pro Ala Gly Thr Arg Leu Arg Arg Leu Asp Val Ser Cys Asn Ser Ile
            675                 680                 685
Ser Phe Val Ala Pro Gly Phe Phe Ser Lys Ala Lys Glu Leu Arg Glu
            690                 695                 700
Leu Asn Leu Ser Ala Asn Ala Leu Lys Thr Val Asp His Ser Trp Phe
705                 710                 715                 720
Gly Pro Leu Ala Ser Ala Leu Gln Ile Leu Asp Val Ser Ala Asn Pro
            725                 730                 735
Leu His Cys Ala Cys Gly Ala Ala Phe Met Asp Phe Leu Leu Glu Val
            740                 745                 750
```

```
Gln Ala Ala Val Pro Gly Leu Pro Ser Arg Val Lys Cys Gly Ser Pro
        755                 760                 765
Gly Gln Leu Gln Gly Leu Ser Ile Phe Ala Gln Asp Leu Arg Leu Cys
        770                 775                 780
Leu Asp Glu Ala Leu Ser Trp Asp Cys Phe Ala Leu Ser Leu Leu Ala
785                 790                 795                 800
Val Ala Leu Gly Leu Gly Val Pro Met Leu His His Leu Cys Gly Trp
                805                 810                 815
Asp Leu Trp Tyr Cys Phe His Leu Cys Leu Ala Trp Leu Pro Trp Arg
                820                 825                 830
Gly Arg Gln Ser Gly Arg Asp Glu Asp Ala Leu Pro Tyr Asp Ala Phe
        835                 840                 845
Val Val Phe Asp Lys Thr Gln Ser Ala Val Ala Asp Trp Val Tyr Asn
        850                 855                 860
Glu Leu Arg Gly Gln Leu Glu Glu Cys Arg Gly Arg Trp Ala Leu Arg
865                 870                 875                 880
Leu Cys Leu Glu Glu Arg Asp Trp Leu Pro Gly Lys Thr Leu Phe Glu
                885                 890                 895
Asn Leu Trp Ala Ser Val Tyr Gly Ser Arg Lys Thr Leu Phe Val Leu
                900                 905                 910
Ala His Thr Asp Arg Val Ser Gly Leu Leu Arg Ala Ser Phe Leu Leu
        915                 920                 925
Ala Gln Gln Arg Leu Leu Glu Asp Arg Lys Asp Val Val Leu Val
        930                 935                 940
Ile Leu Ser Pro Asp Gly Arg Arg Ser Arg Tyr Val Arg Leu Arg Gln
945                 950                 955                 960
Arg Leu Cys Arg Gln Ser Val Leu Leu Trp Pro His Gln Pro Ser Gly
                965                 970                 975
Gln Arg Ser Phe Trp Ala Gln Leu Gly Met Ala Leu Thr Arg Asp Asn
        980                 985                 990
His His Phe Tyr Asn Arg Asn Phe  Cys Gln Gly Pro Thr  Ala Glu
        995                 1000                1005
```

```
<210> SEQ ID NO 44
<211> LENGTH: 2289
<212> TYPE: DNA
<213> ORGANISM: Mus musculus
<220> FEATURE:
<221> NAME/KEY: CDS
<222> LOCATION: (1)..(2079)
<223> OTHER INFORMATION:

<400> SEQUENCE: 44
```

| | | | | | | | | | | | | | | | | |
|---|---|---|---|---|---|---|---|---|---|---|---|---|---|---|---|---|
| aac | ctg | tcc | ttc | aat | tac | cgc | aag | aag | gta | tcc | ttt | gcc | cgc | ctc | cac | 48 |
| Asn | Leu | Ser | Phe | Asn | Tyr | Arg | Lys | Lys | Val | Ser | Phe | Ala | Arg | Leu | His | |
| 1 | | | | 5 | | | | | 10 | | | | | 15 | | |
| ctg | gca | agt | tcc | ttt | aag | aac | ctg | gtg | tca | ctg | cag | gag | ctg | aac | atg | 96 |
| Leu | Ala | Ser | Ser | Phe | Lys | Asn | Leu | Val | Ser | Leu | Gln | Glu | Leu | Asn | Met | |
| | | | 20 | | | | | 25 | | | | | 30 | | | |
| aac | ggc | atc | ttc | ttc | cgc | ttg | ctc | aac | aag | tac | acg | ctc | aga | tgg | ctg | 144 |
| Asn | Gly | Ile | Phe | Phe | Arg | Leu | Leu | Asn | Lys | Tyr | Thr | Leu | Arg | Trp | Leu | |
| | | 35 | | | | | 40 | | | | | 45 | | | | |
| gcc | gat | ctg | ccc | aaa | ctc | cac | act | ctg | cat | ctt | caa | atg | aac | ttc | atc | 192 |
| Ala | Asp | Leu | Pro | Lys | Leu | His | Thr | Leu | His | Leu | Gln | Met | Asn | Phe | Ile | |
| | 50 | | | | | 55 | | | | | 60 | | | | | |
| aac | cag | gca | cag | ctc | agc | atc | ttt | ggt | acc | ttc | cga | gcc | ctt | cgc | ttt | 240 |
| Asn | Gln | Ala | Gln | Leu | Ser | Ile | Phe | Gly | Thr | Phe | Arg | Ala | Leu | Arg | Phe | |

```
                65                  70                  75                  80
gtg gac ttg tca gac aat cgc atc agt ggg cct tca acg ctg tca gaa    288
Val Asp Leu Ser Asp Asn Arg Ile Ser Gly Pro Ser Thr Leu Ser Glu
             85                  90                  95 gcc acc cct gaa gag gca gat gat gca gag cag gag gag ctg ttg tct    336
Ala Thr Pro Glu Glu Ala Asp Asp Ala Glu Gln Glu Glu Leu Leu Ser
            100                 105                 110 gcg gat cct cac cca gct ccg ctg agc acc cct gct tct aag aac ttc    384
Ala Asp Pro His Pro Ala Pro Leu Ser Thr Pro Ala Ser Lys Asn Phe
            115                 120                 125 atg gac agg tgt aag aac ttc aag ttc aac atg gac ctg tct cgg aac    432
Met Asp Arg Cys Lys Asn Phe Lys Phe Asn Met Asp Leu Ser Arg Asn
        130                 135                 140 aac ctg gtg act atc aca gca gag atg ttt gta aat ctc tca cgc ctc    480
Asn Leu Val Thr Ile Thr Ala Glu Met Phe Val Asn Leu Ser Arg Leu
145                 150                 155                 160 cag tgt ctt agc ctg agc cac aac tca att gca cag gct gtc aat ggc    528
Gln Cys Leu Ser Leu Ser His Asn Ser Ile Ala Gln Ala Val Asn Gly
                165                 170                 175 tct cag ttc ctg ccg ctg acc ggt ctg cag gtg cta gac ctg tcc cac    576
Ser Gln Phe Leu Pro Leu Thr Gly Leu Gln Val Leu Asp Leu Ser His
            180                 185                 190 aat aag ctg gac ctc tac cac gag cac tca ttc acg gag cta cca cga    624
Asn Lys Leu Asp Leu Tyr His Glu His Ser Phe Thr Glu Leu Pro Arg
            195                 200                 205 ctg gag gcc ctg gac ctc agc tac aac agc cag ccc ttt agc atg aag    672
Leu Glu Ala Leu Asp Leu Ser Tyr Asn Ser Gln Pro Phe Ser Met Lys
        210                 215                 220 ggt ata ggc cac aat ttc agt ttt gtg acc cat ctg tcc atg cta cag    720
Gly Ile Gly His Asn Phe Ser Phe Val Thr His Leu Ser Met Leu Gln
225                 230                 235                 240 agc ctt agc ctg gca cac aat gac att cat acc cgt gtg tcc tca cat    768
Ser Leu Ser Leu Ala His Asn Asp Ile His Thr Arg Val Ser Ser His
                245                 250                 255 ctc aac agc aac tca gtg agg ttt ctt gac ttc agc ggc aac ggt atg    816
Leu Asn Ser Asn Ser Val Arg Phe Leu Asp Phe Ser Gly Asn Gly Met
            260                 265                 270 ggc cgc atg tgg gat gag ggg ggc ctt tat ctc cat ttc ttc caa ggc    864
Gly Arg Met Trp Asp Glu Gly Gly Leu Tyr Leu His Phe Phe Gln Gly
            275                 280                 285 ctg agt ggc gtg ctg aag ctg gac ctg tct caa aat aac ctg cat atc    912
Leu Ser Gly Val Leu Lys Leu Asp Leu Ser Gln Asn Asn Leu His Ile
        290                 295                 300 ctc cgg ccc cag aac ctt gac aac ctc ccc aag agc ctg aag ctg ctg    960
Leu Arg Pro Gln Asn Leu Asp Asn Leu Pro Lys Ser Leu Lys Leu Leu
305                 310                 315                 320 agc ctc cga gac aac tac cta tct ttc ttt aac tgg acc agt ctg tcc   1008
Ser Leu Arg Asp Asn Tyr Leu Ser Phe Phe Asn Trp Thr Ser Leu Ser
                325                 330                 335 ttc cta ccc aac ctg gaa gtc cta gac ctg gca ggc aac cag cta aag   1056
Phe Leu Pro Asn Leu Glu Val Leu Asp Leu Ala Gly Asn Gln Leu Lys
            340                 345                 350 gcc ctg acc aat ggc acc ctg cct aat ggc acc ctc ctc cag aaa ctc   1104
Ala Leu Thr Asn Gly Thr Leu Pro Asn Gly Thr Leu Leu Gln Lys Leu
            355                 360                 365 gat gtc agt agc aac agt atc gtc tct gtg gcc ccc ggc ttc ttt tcc   1152
Asp Val Ser Ser Asn Ser Ile Val Ser Val Ala Pro Gly Phe Phe Ser
            370                 375                 380 aag gcc aag gag ctg cga gag ctc aac ctt agc gcc aac gcc ctc aag   1200
```

```
Lys Ala Lys Glu Leu Arg Glu Leu Asn Leu Ser Ala Asn Ala Leu Lys
385                 390                 395                 400 aca gtg gac cac tcc tgg ttt ggg ccc att gtg atg aac ctg aca gtt    1248
Thr Val Asp His Ser Trp Phe Gly Pro Ile Val Met Asn Leu Thr Val
                405                 410                 415 cta gac gtg aga agc aac cct ctg cac tgt gcc tgt ggg gca gcc ttc    1296
Leu Asp Val Arg Ser Asn Pro Leu His Cys Ala Cys Gly Ala Ala Phe
                420                 425                 430 gta gac tta ctg ttg gag gtg cag acc aag gtg cct ggc ctg gct aat    1344
Val Asp Leu Leu Leu Glu Val Gln Thr Lys Val Pro Gly Leu Ala Asn
            435                 440                 445 ggt gtg aag tgt ggc agc ccc ggc cag ctg cag ggc cgt agc atc ttc    1392
Gly Val Lys Cys Gly Ser Pro Gly Gln Leu Gln Gly Arg Ser Ile Phe
        450                 455                 460 gcg cag gac ctg cgg ctg tgc ctg gat gag gtc ctc tct tgg gac tgc    1440
Ala Gln Asp Leu Arg Leu Cys Leu Asp Glu Val Leu Ser Trp Asp Cys
465                 470                 475                 480 ttt ggc ctt tca ctc ttg gct gtg gcc gtg ggc atg gtg gtg cct ata    1488
Phe Gly Leu Ser Leu Leu Ala Val Ala Val Gly Met Val Val Pro Ile
                485                 490                 495 ctg cac cat ctc tgc ggc tgg gac gtc tgg tac tgt ttt cat ctg tgc    1536
Leu His His Leu Cys Gly Trp Asp Val Trp Tyr Cys Phe His Leu Cys
                500                 505                 510 ctg gca tgg cta cct ttg cta gcc cgc agc cga cgc agc gcc caa act    1584
Leu Ala Trp Leu Pro Leu Leu Ala Arg Ser Arg Arg Ser Ala Gln Thr
            515                 520                 525 ctc cct tat gat gcc ttc gtg gtg ttc gat aag gca cag agc gca gtt    1632
Leu Pro Tyr Asp Ala Phe Val Val Phe Asp Lys Ala Gln Ser Ala Val
530                 535                 540 gcc gac tgg gtg tat aac gag ctg cgg gtg cgg ctg gag gag cgc cgc    1680
Ala Asp Trp Val Tyr Asn Glu Leu Arg Val Arg Leu Glu Glu Arg Arg
545                 550                 555                 560 ggc cgc tgg gca ctc cgc ctg tgc ctg gag gac cga gat tgg ctg cct    1728
Gly Arg Trp Ala Leu Arg Leu Cys Leu Glu Asp Arg Asp Trp Leu Pro
                565                 570                 575 ggc cag acg ctc ttc gag aac ctc tgg gct tcc atc tat ggg agc cgc    1776
Gly Gln Thr Leu Phe Glu Asn Leu Trp Ala Ser Ile Tyr Gly Ser Arg
                580                 585                 590 aag act cta ttt gtg ctg gcc cac acg gac cgc gtc agt ggc ctc ctg    1824
Lys Thr Leu Phe Val Leu Ala His Thr Asp Arg Val Ser Gly Leu Leu
                595                 600                 605 cgc acc agc ttc ctg ctg gct cag cag cgc ctg ttg gaa gac cgc aag    1872
Arg Thr Ser Phe Leu Leu Ala Gln Gln Arg Leu Leu Glu Asp Arg Lys
            610                 615                 620 gac gtg gtg gtg ttg gtg atc ctg cgt ccg gat gcc cac cgc tcc cgc    1920
Asp Val Val Val Leu Val Ile Leu Arg Pro Asp Ala His Arg Ser Arg
625                 630                 635                 640 tat gtg cga ctg cgc cag cgt ctc tgc cgc cag agt gtg ctc ttc tgg    1968
Tyr Val Arg Leu Arg Gln Arg Leu Cys Arg Gln Ser Val Leu Phe Trp
                645                 650                 655 ccc cag cag ccc aac ggg cag ggg ggc ttc tgg gcc cag ctg agt aca    2016
Pro Gln Gln Pro Asn Gly Gln Gly Gly Phe Trp Ala Gln Leu Ser Thr
                660                 665                 670 gcc ctg act agg gac aac cgc cac ttc tat aac cag aac ttc tgc cgg    2064
Ala Leu Thr Arg Asp Asn Arg His Phe Tyr Asn Gln Asn Phe Cys Arg
                675                 680                 685 gga cct aca gca gaa tagctcagag caacagctgg aaacagctgc atcttcatgt    2119
Gly Pro Thr Ala Glu
        690
```

```
ctggttcccg agttgctctg cctgccttgc tctgtcttac tacaccgcta tttggcaagt    2179
gcgcaatata tgctaccaag ccaccaggcc cacggagcaa aggttggctg taaagggtag    2239
ttttcttccc atgcatcttt caggagagtg aagatagaca ccaaacccac               2289
```

<210> SEQ ID NO 45
<211> LENGTH: 693
<212> TYPE: PRT
<213> ORGANISM: Mus musculus

<400> SEQUENCE: 45

```
Asn Leu Ser Phe Asn Tyr Arg Lys Lys Val Ser Phe Ala Arg Leu His
  1               5                  10                  15

Leu Ala Ser Ser Phe Lys Asn Leu Val Ser Leu Gln Glu Leu Asn Met
             20                  25                  30

Asn Gly Ile Phe Phe Arg Leu Leu Asn Lys Tyr Thr Leu Arg Trp Leu
         35                  40                  45

Ala Asp Leu Pro Lys Leu His Thr Leu His Leu Gln Met Asn Phe Ile
     50                  55                  60

Asn Gln Ala Gln Leu Ser Ile Phe Gly Thr Phe Arg Ala Leu Arg Phe
 65                  70                  75                  80

Val Asp Leu Ser Asp Asn Arg Ile Ser Gly Pro Ser Thr Leu Ser Glu
                 85                  90                  95

Ala Thr Pro Glu Glu Ala Asp Asp Ala Glu Gln Glu Glu Leu Leu Ser
            100                 105                 110

Ala Asp Pro His Pro Ala Pro Leu Ser Thr Pro Ala Ser Lys Asn Phe
        115                 120                 125

Met Asp Arg Cys Lys Asn Phe Lys Phe Asn Met Asp Leu Ser Arg Asn
    130                 135                 140

Asn Leu Val Thr Ile Thr Ala Glu Met Phe Val Asn Leu Ser Arg Leu
145                 150                 155                 160

Gln Cys Leu Ser Leu Ser His Asn Ser Ile Ala Gln Ala Val Asn Gly
                165                 170                 175

Ser Gln Phe Leu Pro Leu Thr Gly Leu Gln Val Leu Asp Leu Ser His
            180                 185                 190

Asn Lys Leu Asp Leu Tyr His Glu His Ser Phe Thr Glu Leu Pro Arg
        195                 200                 205

Leu Glu Ala Leu Asp Leu Ser Tyr Asn Ser Gln Pro Phe Ser Met Lys
    210                 215                 220

Gly Ile Gly His Asn Phe Ser Phe Val Thr His Leu Ser Met Leu Gln
225                 230                 235                 240

Ser Leu Ser Leu Ala His Asn Asp Ile His Thr Arg Val Ser Ser His
                245                 250                 255

Leu Asn Ser Asn Ser Val Arg Phe Leu Asp Phe Ser Gly Asn Gly Met
            260                 265                 270

Gly Arg Met Trp Asp Glu Gly Gly Leu Tyr Leu His Phe Phe Gln Gly
        275                 280                 285

Leu Ser Gly Val Leu Lys Leu Asp Leu Ser Gln Asn Asn Leu His Ile
    290                 295                 300
```

-continued

```
Leu Arg Pro Gln Asn Leu Asp Asn Leu Pro Lys Ser Leu Lys Leu Leu
305                 310                 315                 320

Ser Leu Arg Asp Asn Tyr Leu Ser Phe Phe Asn Trp Thr Ser Leu Ser
                325                 330                 335

Phe Leu Pro Asn Leu Glu Val Leu Asp Leu Ala Gly Asn Gln Leu Lys
            340                 345                 350

Ala Leu Thr Asn Gly Thr Leu Pro Asn Gly Thr Leu Leu Gln Lys Leu
        355                 360                 365

Asp Val Ser Ser Asn Ser Ile Val Ser Val Ala Pro Gly Phe Phe Ser
370                 375                 380

Lys Ala Lys Glu Leu Arg Glu Leu Asn Leu Ser Ala Asn Ala Leu Lys
385                 390                 395                 400

Thr Val Asp His Ser Trp Phe Gly Pro Ile Val Met Asn Leu Thr Val
                405                 410                 415

Leu Asp Val Arg Ser Asn Pro Leu His Cys Ala Cys Gly Ala Ala Phe
            420                 425                 430

Val Asp Leu Leu Leu Glu Val Gln Thr Lys Val Pro Gly Leu Ala Asn
        435                 440                 445

Gly Val Lys Cys Gly Ser Pro Gly Gln Leu Gln Gly Arg Ser Ile Phe
    450                 455                 460

Ala Gln Asp Leu Arg Leu Cys Leu Asp Glu Val Leu Ser Trp Asp Cys
465                 470                 475                 480

Phe Gly Leu Ser Leu Leu Ala Val Ala Val Gly Met Val Val Pro Ile
                485                 490                 495

Leu His His Leu Cys Gly Trp Asp Val Trp Tyr Cys Phe His Leu Cys
            500                 505                 510

Leu Ala Trp Leu Pro Leu Leu Ala Arg Ser Arg Arg Ser Ala Gln Thr
        515                 520                 525

Leu Pro Tyr Asp Ala Phe Val Val Phe Asp Lys Ala Gln Ser Ala Val
    530                 535                 540

Ala Asp Trp Val Tyr Asn Glu Leu Arg Val Arg Leu Glu Glu Arg Arg
545                 550                 555                 560

Gly Arg Trp Ala Leu Arg Leu Cys Leu Glu Asp Arg Asp Trp Leu Pro
                565                 570                 575

Gly Gln Thr Leu Phe Glu Asn Leu Trp Ala Ser Ile Tyr Gly Ser Arg
            580                 585                 590

Lys Thr Leu Phe Val Leu Ala His Thr Asp Arg Val Ser Gly Leu Leu
        595                 600                 605

Arg Thr Ser Phe Leu Leu Ala Gln Gln Arg Leu Leu Glu Asp Arg Lys
    610                 615                 620

Asp Val Val Val Leu Val Ile Leu Arg Pro Asp Ala His Arg Ser Arg
625                 630                 635                 640

Tyr Val Arg Leu Arg Gln Arg Leu Cys Arg Gln Ser Val Leu Phe Trp
                645                 650                 655

Pro Gln Gln Pro Asn Gly Gln Gly Gly Phe Trp Ala Gln Leu Ser Thr
            660                 665                 670

Ala Leu Thr Arg Asp Asn Arg His Phe Tyr Asn Gln Asn Phe Cys Arg
        675                 680                 685

Gly Pro Thr Ala Glu
    690
```